(12) United States Patent
Milder et al.

(10) Patent No.: US 11,905,314 B2
(45) Date of Patent: Feb. 20, 2024

(54) INFLUENZA VIRUS VACCINES AND USES THEREOF

(71) Applicant: JANSSEN VACCINES & PREVENTION B.V., Leiden (NL)

(72) Inventors: Ferdinand Jacobus Milder, Zwolle (NL); Tina Ritschel, Oegstgeest (NL); Boerries Brandenburg, Utrecht (NL); Mandy Antonia Catharina Jongeneelen, Leiden (NL); Daphné Truan, Cambridge (GB); Johannes Petrus Maria Langedijk, Amsterdam (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 43 days.

(21) Appl. No.: 17/814,871

(22) Filed: Jul. 26, 2022

(65) Prior Publication Data

US 2022/0411474 A1    Dec. 29, 2022

Related U.S. Application Data

(63) Continuation of application No. 16/964,089, filed as application No. PCT/EP2019/051532 on Jan. 22, 2019, now Pat. No. 11,447,526.

(30) Foreign Application Priority Data

Jan. 23, 2018 (EP) .................................... 18152991

(51) Int. Cl.
| | |
|---|---|
| *C07K 14/005* | (2006.01) |
| *C07K 14/11* | (2006.01) |
| *C07K 16/10* | (2006.01) |
| *C07K 19/00* | (2006.01) |
| *A61K 39/145* | (2006.01) |
| *A61P 31/16* | (2006.01) |
| *C12N 7/00* | (2006.01) |

(52) U.S. Cl.
CPC .......... *C07K 14/005* (2013.01); *A61K 39/145* (2013.01); *A61P 31/16* (2018.01); *C12N 7/00* (2013.01); *C12N 2760/16122* (2013.01); *C12N 2760/16134* (2013.01)

(58) Field of Classification Search
CPC ........ A61P 31/16; A61P 31/14; A61K 39/145; A61K 39/12; A61K 39/00
See application file for complete search history.

(56) References Cited

U.S. PATENT DOCUMENTS

| | | |
|---|---|---|
| 5,057,540 A | 10/1991 | Kensil |
| 2010/0297174 A1 | 11/2010 | Garcia-Sastre |
| 2013/0129761 A1 | 5/2013 | Garcia-Sastre |
| 2014/0357845 A1 | 12/2014 | Meijberg |

FOREIGN PATENT DOCUMENTS

| | | |
|---|---|---|
| EP | 20110173953 | 7/2011 |
| WO | 9003184 A1 | 4/1990 |
| WO | 9014837 A1 | 12/1990 |
| WO | 9611711 A1 | 4/1996 |
| WO | 2004004762 A1 | 1/2004 |
| WO | 2005002620 A1 | 1/2005 |
| WO | 2008028946 | 3/2008 |
| WO | 2010117786 | 10/2010 |
| WO | 2010130636 | 11/2010 |
| WO | 2011123495 | 10/2011 |
| WO | 2013007770 A1 | 1/2013 |
| WO | 2013079473 A1 | 6/2013 |
| WO | 2014191435 | 12/2014 |
| WO | 2016005480 | 1/2016 |
| WO | 2016005482 | 1/2016 |

OTHER PUBLICATIONS

Alberini et al., "Pseudoparticle Neutralization is a Reliable Assay to Measure Immunity and Cross-Reactivity to H5N1 Influenza Viruses", Vaccine, vol. 27, pp. 5998-6003 (2009).
Atsmon et al., "Safety and Immunogenicity of Multimeric-001—a Novel Universal Influenza Vaccine", Journ. Clin. Immunol., vol. 32, pp. 595-603 (2012).
B. Ciani et al., "Molecular basis of coiled-coil oligomerization-state specificity," PNAS, vol. 107, No. 46, Nov. 16, 2010.
Bianchi et al., Universal influenza B vaccine based on the maturational cleavage site of the hemagglutinin precursor, Journal of Virology, The American Society for Microbiology, pp. 7380-7388, vol. 79, No. 12, 2005.
Bommakanti et al., "Design of an HA2-Based *Escherichia coli* Expressed Influenza Immunogen that Protects Mice from Pathogenic Challenge", Proc. of the Nat. Acad. of Sciences, vol. 107, No. 31, pp. 13701-13706 (Aug. 2010).
Cheng et al., "Development of a Robust Reporter-based ADCC Assay with Frozen, Thaw-and-use Cells to Measure Fc Effector Function of Therapeutic Antibodies", Journ. Immunol. Methods, vol. 414, pp. 69-81 (2014).
Coffman et al., "Vaccine Adjuvants" Putting Innate Immunity to Work, Immunity, vol. 33, pp. 492-503(Oct. 2010).
Degorce et al., "HTRF: A technology tailored for drug discovery—a review of theoretical aspects and recent applications," Curr. Chem. Genomics 3:22-32 (2009).
Devereux et al., "A Comprehensive Set of Sequence Analysis Programs for the VAX", Nucl. Acids Res., vol. 12, No. 1, pp. 387-395 (1984).
DiLillo et al., "Broadly Neutralizing Hemagglutinin Stalk-Specific Antibodies Require FcγR Interactions for Protection Against Influenza Virus in Vivo", Nat. Med., vol. 20, No. 2, pp. 143-153 (Feb. 2014).
Dopheide et al., "The Location of the Bromelain Cleavage Site in a Hong Kond Influenza Virus Haemagglutinin", Journ. Gen. Virol., vol. 52, pp. 367-370 (1981).
Dr. Gill et al., "Increased persistence of lung gene expression using plasmids containing the ubiquitin C or elongation Factor 1 promoter," Gene Therapy, vol. 8, pp. 1539-1546 (2001).

(Continued)

*Primary Examiner* — Barry A Chestnut
(74) *Attorney, Agent, or Firm* — Ice Miller LLP

(57) ABSTRACT

Provided herein are influenza hemagglutinin stem polypeptides, nucleic acids encoding said polypeptides, vectors comprising said nucleic acid and pharmaceutical compositions comprising the same, as well as methods of their use, in particular in the prevention and/or treatment of influenza virus infections.

16 Claims, 21 Drawing Sheets

Specification includes a Sequence Listing.

(56) References Cited

OTHER PUBLICATIONS

Eckert et al., Stalking influenza, Proceedings of the National Academy of Sciences of the United States of America, , pp. 13563-13564, vol. 107, No. 31, Aug. 3, 2010.
Ekiert Damian C et al, "Antibody Recognition of a Highly Conserved Influenza Virus Epitope", Science, American Association for the Advancement of Science, US, (Apr. 1, 2009), vol. 324, No. 5924, ISSN 0036-8075, pp. 246-251, XP009144786.
Ekiert et al, "A Highly Conserved Neutralizing Epitope on Group 2 Influenza A Viruses," Science, vol. 333, pp. 843-850(2011).
Ferguson et al., "Ecological and Immunological Determinants of Influenza Evolution", Nature, vol. 422, pp. 428-443 (Mar. 2003).
G. Bommakanti et al., "Design of *Escherichia coli*-Expressed Stalk Doman Immunogens of H1N1 Hemagglutinin That Protect Mice from Lethal Challenge," Journal of Virology, vol. 86, No. 24, Sep. 26, 2012.
G. Das et al., "SV 40 Promoters and Their Regulation," Progress in Nucleic Acid Research and Molecular Biology, vol. 32, 1985.
G. Winter et al., "Nucleotid sequence of the haemagglutinin gene of a human influenza virus H1 subtype," Nature, vol. 292, Jul. 2, 1981.
Gayathri Bommakanti et al, "Supporting Information. Bommakanti et al. 10.1073/pnas.1007465107", vol. 107, No. 31, doi:10.1073/PNAS.1007465107, ISSN 0027-8424, (Aug. 3, 2010), pp. 1-6, Proceedings of the National Academy of Sciences, National Academy of Sciences, URL: http://www.pnas.org/content/107/31/13701, (Jul. 6, 2010), XP002675046.
Ichihashi et al., "Cross-Protective Peptide Vaccine against Influenza A Viruses developed in HLA-A *2402 Human Immunity Model", PLoS One, vol. 6, Issue 9, pp. 1-9, Sep. 2011.
Int'l Search Report and Written Opinion dated Mar. 5, 2013 in Int'l Application No. PCT/EP2012/073706. (13 pages).
Int'l Search Report and Written Opinion dated Sep. 16, 2014 in Int'l Application No. PCT/EP2014/060997. (12 pages).
Int'l Search Report and Written Opinion dated Sep. 18, 2015 in Int'l Application No. PCT/EP2015/065661. (12 pages).
Int'l Search Report and Written Opinion dated Sep. 30, 2015 in Int'l Application No. PCT/EP2015/065663. (10 pages).
International Search Report dated Mar. 20, 2019 in International Application No. PCT/EP2019/051532.
John Steel et al, "Influenza Virus Vaccine Based on the Conserved Hemagglutinin Stalk Domain", MBIO, American Society for Microbiology, (May 18, 2010), vol. 1, No. 1, doi:10.1128/MBIO.00018-10, ISSN 2150-7511, pp. e00018-e00010, XP002675042.
Kang et al., Novel vaccines against influenza viruses, Virus Research, pp. 31-38, vol. 162, No. 1., Oct. 1, 2011.
Kodihalli et al., "Strategies for inducing protection against avian influenza A virus subtypes with DNA vaccines", Vaccine,18(23)2592-2599, 2000.
Lorieau et al., "The Complete Influenza Hemagglutinin Fusion Domain Adopts a Tight Helical Hairpin Arrangement at the Lipid: Water Interface", Proc. Natl. Acad. Sci., vol. 107, No. 25, pp. 11341-11346 (Jun. 2010).
Lu et al., "Production and Stabilization of the Trimeric Influenza Hemagglutinin Stem Domain for Potentially Broadly Protective Influenza Vaccines", Proc. of the Nat. Acad. of Sciences, pp. 1-27 (2013).
Mallajosyula et al., "Influenza Hemagglutinin Stem-Fragment Immunogen Elicts Broadly Neutralizing Antibodies and Confers Heterologous Protection", Proc. of the Nat. Acad. of Sciences, vol. 111, No. 25, pp. E2514-E2523 (Jun. 2014).
Parekh et al., "Development and Validation of an Antibody-Dependent Cell-Mediated Cytotoxicity-Reporter Gene Assay", mAbs, vol. 4, No. 3, pp. 310-318 (2012).
Peter S. Lee et al, "Design and Structure of an Engineered Disulfide-Stabilized Influenza Virus Hemagglutinin Trimer", Journal of Virology., US, (Apr. 29, 2015), vol. 89, No. 14, doi: 10.1128/JVI.00808-15, ISSN 0022-538X, pp. 7417-7420, XP055480679.
R. Kaufman, "Overview of Vector Design for Mammalian Gene Expression," Molecular Biotechnology, vol. 16, 2000).
S. Guthe et al., "Very Fast Folding and Association of a Trimerization Domain from Bacteriophase T4 Fibritin," J. Molecular Biology, vol. 337, pp. 905-915 (2004).
Safronetz et al., "Pandemic Swine-Origin H1N1 Influenza A Virus Isolates Show Heterogeneous Virulence in Macaques", Journ. of Virol., vol. 85, No. 3, pp. 1214-1223 (Feb. 2011).
Sagawa H et al, "The immunological activity of a deletion mutant of influenza virus haemagglutinin lacking the globular region", Journal of General Virology, (Jan. 1, 1996), vol. 77, No. 7, ISSN 0022-1317, pp. 1483-1487, XP002675043.
Schnueriger et al., "Development of a Quantitative, Cell-Line Based Assay to Measure ADCC Activity Mediated by Therapeutic Antibodies", Molec. Immun., vol. 48, pp. 1512-1517 (2011).
Sophie A. Valkenburg et al, "Stalking influenza by vaccination with pre-fusion headless HA mini-stem", Scientific Reports, (Mar. 7, 2016), vol. 6, No. 1, doi:10.1038/srep22666, XP055482479.
Steel et al., Live Attenuated Influenza Viruses Containing NS1 Truncations as Vaccine Candidates against H5N1 Highly Pathogenic Avian influenza, Journal of Virology, pp. 1742-1753, vol. 83, No. 4, Feb. 2009.
Stevens et al., "Structure and Receptor Specificity of the Hemagglutinin from an H5N1 Influenza Virus", Science, vol. 312, pp. 404-410 (Apr. 2006).
Stevens et al., "Structure of the Uncleaved Human H1 Hemagglutinin from the Extinct 1918 Influenza Virus", Science, vol. 303, pp. 1866-1870 (Mar. 2004).
Sun et al., "Modifications to the hemagglutinin cleavage site control the virulence of a neurotropic H1N1 influenza virus," Journ. of Virol., vol. 84, No. 17, pp. 8683-8690 (Sep. 2010).
Temperton et al., "A Sensitive Retroviral Pseudotype Assay for Influenza H5N1-Neutralizing Antibodies", Viruses, vol. 1, No. 3,, pp. 105-112 (2007).
Throsby et al, "Heterosubtypic Neutralizing Monoclonal Antibodes Cross-Protective Against H5N1 and H1N1 Recovered From Human IgM+ Memory B Cells," PLoS One, vol. 3, Issue 12, pp. e3942 (2008).
V. Letarov et al., "The Carboxy-Terminal Domain Initiates Trimerization of Bacteriophage T4 Fibritin," Biochemistry (Moscow), vol. 64, No. 7, pp. 817-823 (1999).
Wang et al., Vaccination with a synthetic peptide from the influenza virus hemagglutinin provides protection against distinct viral subtypes, Proceedings of the National Academy of Sciences of the United States of America, pp. 18979-18984, vol. 107, No. 44., Nov. 2010.
Wilson et al., "Structure of the Haemagglutinin Membrane Glycoprotein of Influenza Virus at 3 A Resolution", Nature, vol. 289, pp. 366-373 (Jan. 1981).
Written Opinion dated Mar. 20, 2019 in International Application No. PCT/EP2019/051532.
Zhirnov et al., "Cleavage of Influenza A Virus Hemagglutinin in Human Respiratory Epithelium is Cell Associated and Sensitive to Exogenous Antiproteases", Journal of Virology, vol. 76, No. 17, pp. 8682-8689, Sep. 2002.

| ID. | Strain | Expression |
|---|---|---|
| UFV180496 | H1 A/California/07/09 | 375 mg/L |
| UFV180497 | H1 A/Michigan/45/2015 | 367 mg/L |
| UFV180498 | H1 A/Puerto Rico/8/1934 | 244 mg/L |
| UFV180499 | H5 A/Hong Kong/156/97 | 133 mg/L |
| UFV180500 | H5 A/Vietnam/1203/04 | 42 mg/L |
| UFV180501 | H2 A/Singapore/1/57 | 229 mg/L |

B

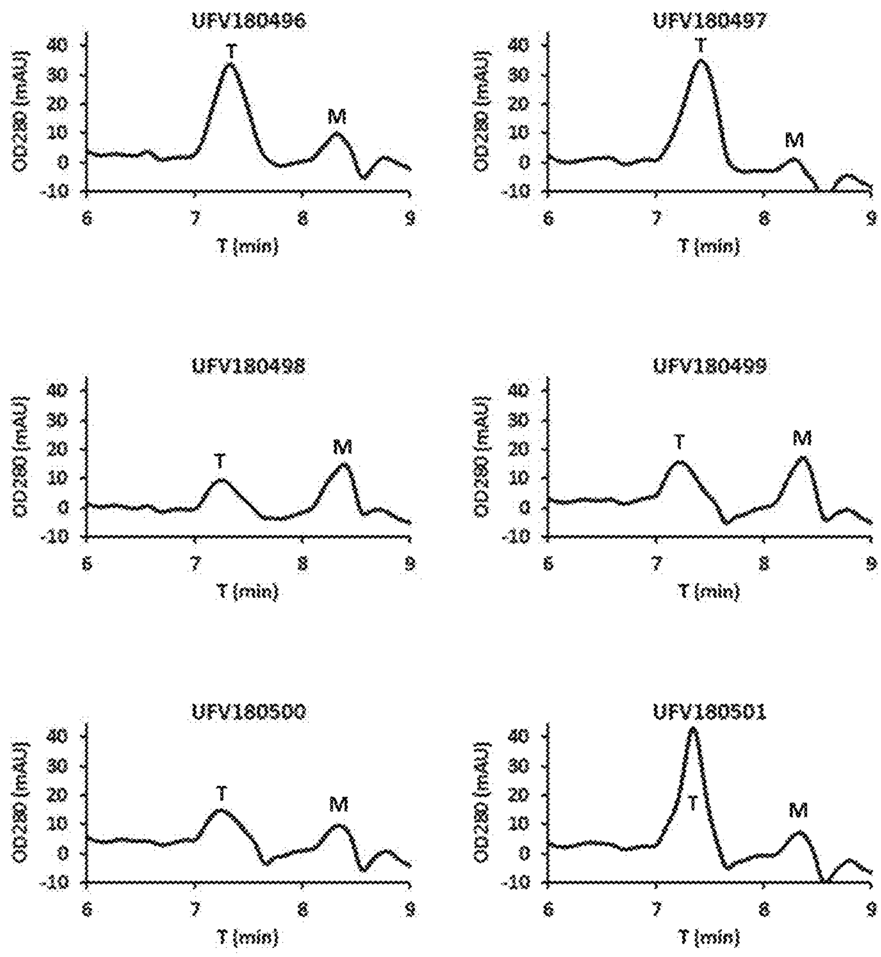

C
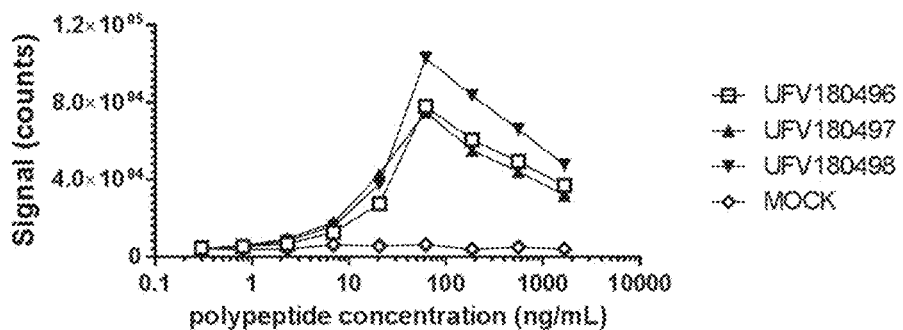
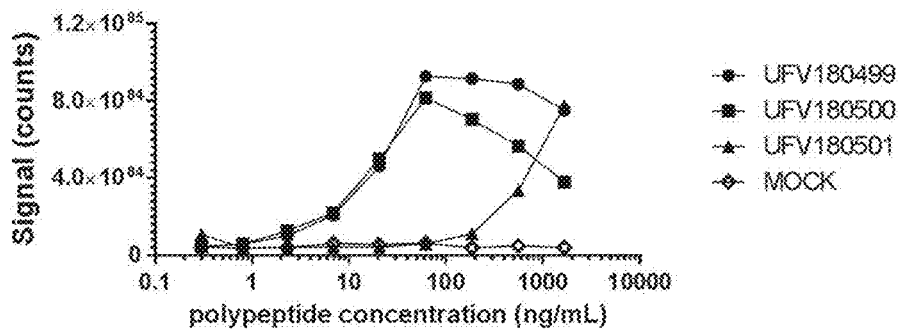
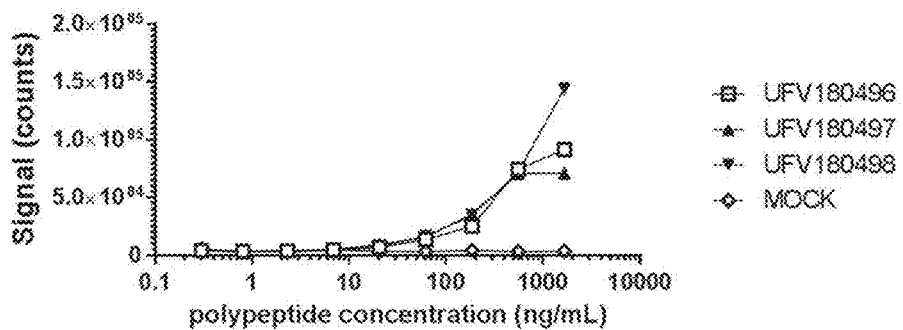
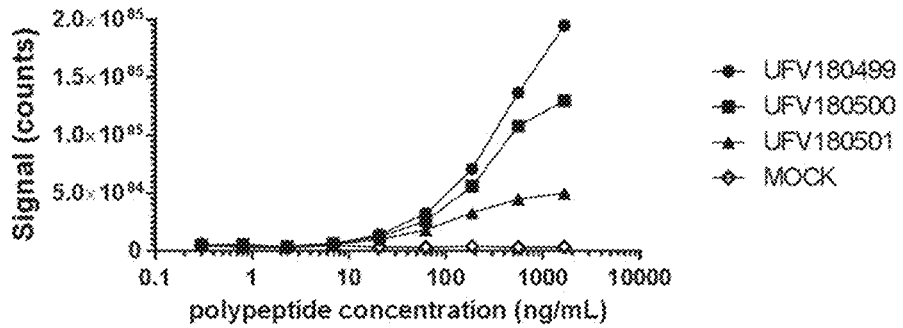
FIG. 28 - continued

SEQUENCE LISTING

```
Sequence total quantity: 154
SEQ ID NO: 1           moltype = AA  length = 565
FEATURE                Location/Qualifiers
REGION                 1..565
                       note = H1 Full length (A/Brisbane/59/2007)
source                 1..565
                       mol_type = protein
                       organism = synthetic construct
SEQUENCE: 1
MKVKLLVLLC TFTATYADTI CIGYHANNST DTVDTVLEKN VTVTHSVNLL ENSHNGKLCL  60
LKGIAPLQLG NCSVAGWILG NPECELLISK ESWSYIVEKP NPENGTCYPG HFADYEELRE  120
QLSSVSSFER FEIFPKESSW PNHTVTGVSA SCSHNGESSF YRNLLWLTGK NGLYPNLSKS  180
YANNKEKEVL VLWGVHHPPN IGDQKALYHT ENAYVSVVSS HYSRKFTPEI AKRPKVRDQE  240
GRINYYWTLL EPGDTIIFEA NGNLIAPRYA FALSRGFGSG IINSNAPMDK CDAKCQTPQG  300
AINSSLPFQN VHPVTIGECP KYVRSAKLRM VTGLRNIPSI QSRGLFGAIA GFIEGGWTGM  360
VDGWYGYHHQ NEQGSGYAAD QKSTQNAING ITNKVNSVIE KMNTQFTAVG KEFNKLERRM  420
ENLNKKVDDG FIDIWTYNAE LLVLLENERT LDFHDSNVKN LYEKVKSQLK NNAKEIGNGC  480
FEFYHKCNDE CMESVKNGTY DYPKYSEESK LNREKIDGVK LESMGVYQIL AIYSTVASSL  540
VLLVSLGAIS FWMCSNGSLQ CRICI                                      565

SEQ ID NO: 2           moltype = AA  length = 566
FEATURE                Location/Qualifiers
REGION                 1..566
                       note = H1 Full length (A/California/07/2009)
source                 1..566
                       mol_type = protein
                       organism = synthetic construct
SEQUENCE: 2
MKAILVVLLY TFATANADTL CIGYHANNST DTVDTVLEKN VTVTHSVNLL EDKHNGKLCK  60
LRGVAPLHLG KCNIAGWILG NPECESLSTA SSWSYIVETP SSDNGTCYPG DFIDYEELRE  120
QLSSVSSFER FEIFPKTSSW PNHDSNKGVT AACPHAGAKS FYKNLIWLVK KGNSYPKLSK  180
SYINDKGKEV LVLWGIHHPS TSADQQSLYQ NADAYVFVGS SRYSKKFKPE IAIRPKVRDQ  240
EGRMNYYWTL VEPGDKITFE ATGNLVVPRY AFAMERNAGS GIIISDTPVH DCNTTCQTPK  300
GAINTSLPFQ NIHPITIGKC PKYVKSTKLR LATGLRNIPS IQSRGLFGAI AGFIEGGWTG  360
MVDGWYGYHH QNEQGSGYAA DLKSTQNAID EITNKVNSVI EKMNTQFTAV GKEFNHLEKR  420
IENLNKKVDD GFLDIWTYNA ELLVLLENER TLDYHDSNVK NLYEKVRSQL KNNAKEIGNG  480
CFEFYHKCDN TCMESVKNGT YDYPKYSEEA KLNREEIDGV KLESTRIYQI LAIYSTVASS  540
LVLVVSLGAI SFWMCSNGSL QCRICI                                     566
```

-continued

```
SEQ ID NO: 3            moltype = AA  length = 565
FEATURE                 Location/Qualifiers
REGION                  1..565
                        note = A/Texas/UR06-0526/2007(H1N1)
source                  1..565
                        mol_type = protein
                        organism = synthetic construct
SEQUENCE: 3
MKVKLLVLLC TFTATYADTI CIGYHANNST DTVDTVLEKN VTVTHSVNLL EDSHNGKLCL  60
LKGTAPLQLG NCSVAGWILG NPECELLISK ESWSYIVETP NPENGTCYPG YFADYEELRE  120
QLSSVSSFER FEIFPKESSW PNHTVTGVSA SCSHNGKSSF YRNLLWLTGK NGLYPNLSKS  180
YANNKEKEVL VLWGVHHPPN IGDQRALYHT ENAYVSVVSS HYSRRFTPEI AKRPKVRDQE  240
GRINYYWTLL EPGDTIIFEA NGNLIAPRFA FALSRGFGSG IITSNAPMGE CDAKCQTPQG  300
AINSSLPFQN VHPVTIGECP KYVRSAKLRM VTGLRNIPSI QSRGLFGAIA GFIEGGWTGM  360
VDGWYGYHHQ NEQGSGYAAD QKSTQNAING ITNKVNSVIE KMNTQFTAVG KEFNKLERRM  420
ENLNKKVDDG FLDIWTYNAE LLVLLENERT LDFHDSNVKN LYEKVKNQLK NNAKEIGNGC  480
FEFYHKCNDE CMESVKNGTY DYPKYSEESK LNREKIDGVK LESMGVYQIL AIYSTVASSL  540
VLLISLGAIS FWMCSNGSLQ CRICI                                       565

SEQ ID NO: 4            moltype = AA  length = 566
FEATURE                 Location/Qualifiers
REGION                  1..566
                        note = A/NewYork/629/1995 (H1N1)
source                  1..566
                        mol_type = protein
                        organism = synthetic construct
SEQUENCE: 4
MKVKLLVLLC AFTATYADTI CIGYHANNST DTVDTVLEKN VTVTHSVNLL EDSHNGKLCR  60
LKGTAPLQLG NCSVAGWILG NPECESLFSK ESWSYIAETP NPENGTCYPG YFADYEELRE  120
QLSSVSSFER FEIFPKESSW PNHTVTKGVT ASCSHNGKSS FYKNLLWLTE KNGLYPNLSK  180
SYVNNKEKEV LVLWGVHHPS NIGDQRAIYH TENAYVSVVS SHYSRRFTPE IAKRPKVRDQ  240
EGRINYYWTL LEPGDTIIFE ANGNLIAPWY AFALSRGFGS GIITSNASMS ECDAKCQTPQ  300
GAINSSLPFQ NVHPVTIGEC PKYVRSTKLR MVTGLRNIPS IQSRGLFGAI AGFIEGGWTG  360
MIDGWYGYHH QNEQGSGYAA DQKSTQNAID GITNKVNSVI EKMNTQFTAV GKEFNKLERR  420
MENLNKKVDD GFLDIWTYNA ELLVLLENER TLDFHDSNVK NLYEKVKNQL KNNAKEIGNG  480
CFEFYHKCNN ECMESVKNGT YDYPKYSEES KLNREKIDGV KLESMGVYQI LAIYSTVASS  540
LVLLVSLGAI SFWMCSNGSL QCRICI                                      566

SEQ ID NO: 5            moltype = AA  length = 566
FEATURE                 Location/Qualifiers
REGION                  1..566
                        note = A/AA_Marton/1943 (H1N1)
source                  1..566
                        mol_type = protein
                        organism = synthetic construct
SEQUENCE: 5
MKARLLVLLC ALAATDADTI CIGYHANNST DTVDTVLEKN VTVTHSVNLL EDSHNGKLCR  60
LKGIAPLQLG KCNIAGWILG NPECESLLSE RSWSYIVETP NSENGTCYPG DFIDYEELRE  120
QLSSVSSFER FEIFSKESSW PKHNTTRGVT AACSHAGKSS FYRNLLWLTE KDGSYPNLNN  180
SYVNKKGKEV LVLWGVHHPS NIKDQQTLYQ KENAYVSVVS SNYNRRFTPE IAERPKVRGQ  240
AGRMNYYWTL LKPGDTIMFE ANGNLIAPWY AFALSRGFGS GIITSNASMH ECDTKCQTPQ  300
GAINSSLPFQ NIHPVTIGEC PKYVRSTKLR MVTGLRNIPS IQSRGLFGAI AGFIEGGWTG  360
MIDGWYGYHH QNEQGSGYAA DQKSTQNAIN GITNKVNSVI EKMNTQFTAV GKEFNNLEKR  420
MENLNKKVDD GFLDIWTYNA ELLVLLENER TLDFHDSNVK NLYEKVKNQL RNNAKEIGNG  480
CFEFYHKCNN ECMESVKNGT YDYPKYSEES KLNREKIDGV KLESMGVYQI LAIYSTVASS  540
LVLLVSLGAI SFWMCSNGSL QCRICI                                      566

SEQ ID NO: 6            moltype = AA  length = 562
FEATURE                 Location/Qualifiers
REGION                  1..562
                        note = A/Adachi/2/57 (H2N2)
source                  1..562
                        mol_type = protein
                        organism = synthetic construct
SEQUENCE: 6
MAIIYLILLF TAVRGDQICI GYHANNSTEK VDTILERNVT VTHAKDILEK THNGKLCKLN  60
GIPPLELGDC SIAGWLLGNP ECDRLLSVPE WSYIMEKENP RNGLCYPGSF NDYEELKHLL  120
SSVKHFEKVK ILPKDRWTQH TTTGGSQACA VSGNPSFFRN MVWLTKKGSD YPVAKGSYNN  180
TSGEQMLIIW GVHHPIDETE QRTLYQNVGT YVSVGTSTLN KRSTPEIATR PKVNGLGSRM  240
EFSWTLLDMW DTINFESTGN LIAPEYGFKI SKRGSSGIMK TEGTLENCET KCQTPLGAIN  300
TTLPFHNVHP LTIGECPKYV KSEKLVLATG LRNVPQIESR GLFGAIAGFI EGGWQGMVDG  360
WYGYHHSNDQ GSGYAADKES TQKAFDGITN KVNSVIEKMN TQFEAVGKEF GNLERRLENL  420
NKKMEDGFLD VWTYNAELLV LMENERTLDF HDSNVKNLYD KVRMQLRDNV KELGNGCFEF  480
YHKCDDECMN SVKNGTYDYP KYEEESKLNR NEIKGVKLSS MGVYQILAIY ATVAGSLSLA  540
IMMAGISFWM CSNGSLQCRI CI                                          562
```

-continued

```
SEQ ID NO: 7            moltype = AA  length = 562
FEATURE                 Location/Qualifiers
REGION                  1..562
                        note = A/Singapore/1/57 (H2N2)
source                  1..562
                        mol_type = protein
                        organism = synthetic construct
SEQUENCE: 7
MAIIYLILLF TAVRGDQICI GYHANNSTEK VDTILERNVT VTHAKDILEK THNGKLCKLN  60
GIPPLELGDC SIAGWLLGNP ECDRLLSVPE WSYIMEKENP RDGLCYPGSF NDYEELKHLL  120
SSVKHFEKVK ILPKDRWTQH TTTGGSRACA VSGNPSFFRN MVWLTEKGSN YPVAKGSYNN  180
TSGEQMLIIW GVHHPNDEKE QRTLYQNVGT YVSVGTSTLN KRSTPDIATR PKVNGLGSRM  240
EFSWTLLDMW DTINFESTGN LIAPEYGFKI SKRGSSGIMK TEGTLENCET KCQTPLGAIN  300
TTLPFHNVHP LTIGECPKYV KSEKLVLATG LRNVPQIESR GLFGAIAGFI EGGWQGMIDG  360
WYGYHHSNDQ GSGYAADKES TQKAFDGITN KVNSVIEKMN TQFEAVGKEF SNLERRLENL  420
NKKMEDGFLD VWTYNAELLV LMENERTLDF HDSNVKNLYD KVRMQLRDNV KELGNGCFEF  480
YHKCDDECMN SVKNGTYDYP KYEEESKLNR NEIKGVKLSS MGVYQILAIY ATVAGSLSLA  540
IMMAGISFWM CSNGSLQCRI CI                                          562

SEQ ID NO: 8            moltype = AA  length = 568
FEATURE                 Location/Qualifiers
REGION                  1..568
                        note = A/Viet Nam/1203/2004 H5N1)
source                  1..568
                        mol_type = protein
                        organism = synthetic construct
SEQUENCE: 8
MEKIVLLFAI VSLVKSDQIC IGYHANNSTE QVDTIMEKNV TVTHAQDILE KKHNGKLCDL  60
DGVKPLILRD CSVAGWLLGN PMCDEFINVP EWSYIVEKAN PVNDLCYPGD FNDYEELKHL  120
LSRINHFEKI QIIPKSSWSS HEASLGVSSA CPYQGKSSFF RNVVWLIKKN STYPTIKRSY  180
NNTNQEDLLV LWGIHHPNDA AEQTKLYQNP TTYISVGTST LNQRLVPRIA TRSKVNGQSG  240
RMEFFWTILK PNDAINFESN GNFIAPEYAY KIVKKGDSTI MKSELEYGNC NTKCQTPMGA  300
INSSMPFHNI HPLTIGECPK YVKSNRLVLA TGLRNSPQRE RRRKKRGLFG AIAGFIEGGW  360
QGMVDGWYGY HHSNEQGSGY AADKESTQKA IDGVTNKVNS IIDKMNTQFE AVGREFNNLE  420
RRIENLNKKM EDGFLDVWTY NAELLVLMEN ERTLDFHDSN VKNLYDKVRL QLRDNAKELG  480
NGCFEFYHKC DNECMESVRN GTYDYPQYSE EARLKREEIS GVKLESIGIY QILSIYSTVA  540
SSLALAIMVA GLSLWMCSNG SLQCRICI                                    568

SEQ ID NO: 9            moltype = AA  length = 121
FEATURE                 Location/Qualifiers
REGION                  1..121
                        note = CR9114 VH PROTEIN
source                  1..121
                        mol_type = protein
                        organism = synthetic construct
SEQUENCE: 9
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
S                                                                 121

SEQ ID NO: 10           moltype = AA  length = 110
FEATURE                 Location/Qualifiers
REGION                  1..110
                        note = CR9114 VL PROTEIN
source                  1..110
                        mol_type = protein
                        organism = synthetic construct
SEQUENCE: 10
SYVLTQPPAV SGTPGQRVTI SCSGSDSNIG RRSVNWYQQF PGTAPKLLIY SNDQRPSVVP  60
DRFSGSKSGT SASLAISGLQ SEDEAEYYCA AWDDSLKGAV FGGGTQLTVL            110

SEQ ID NO: 11           moltype = AA  length = 121
FEATURE                 Location/Qualifiers
REGION                  1..121
                        note = CR6261 VH PROTEIN
source                  1..121
                        mol_type = protein
                        organism = synthetic construct
SEQUENCE: 11
EVQLVESGAE VKKPGSSVKV SCKASGGPFR SYAISWVRQA PGQGPEWMGG IIPIFGTTKY  60
APKFQGRVTI TADDFAGTVY MELSSLRSED TAMYYCAKHM GYQVRETMDV WGKGTTVTVS  120
S                                                                 121

SEQ ID NO: 12           moltype = AA  length = 112
FEATURE                 Location/Qualifiers
REGION                  1..112
                        note = CR6261 VL PROTEIN
```

```
                    source          1..112
                                    mol_type = protein
                                    organism = synthetic construct
SEQUENCE: 12
QSVLTQPPSV SAAPGQKVTI SCSGSSSSNIG NDYVSWYQQL PGTAPKLLIY DNNKRPSGIP    60
DRFSGSKSGT SATLGITGLQ TGDEANYYCA TWDRRPTAYV VFGGGTKLTV LG            112

SEQ ID NO: 13                      moltype = AA  length = 153
FEATURE                            Location/Qualifiers
REGION                             1..153
                                   note = SD15016
source                             1..153
                                   mol_type = protein
                                   organism = synthetic construct
SEQUENCE: 13
EVQLVESGGG LVQAGGSLRL SCVASGMFFG IAAMGWYRQA PGKQRELVAN ITSDFSTNYA     60
DSVKDRFTIS RDNAENTVYL QMNSLKPEDT AVYYCAADSL GTGWRHYYYW GQGTQVTVSS    120
AAAWSHPQFE KGAAWSHPQF EKGAAWSHPQ FEK                                 153

SEQ ID NO: 14                      moltype = AA  length = 157
FEATURE                            Location/Qualifiers
REGION                             1..157
                                   note = SD15004
source                             1..157
                                   mol_type = protein
                                   organism = synthetic construct
SEQUENCE: 14
EVQLVESGGG LVQPGGSLRL SCAVSISIFD IYAMDWYRQA PGKQRDLVAT SFRDGSTNYA     60
DSVKGRFTIS RDNAKNTLYL QMNSLKPEDT AVYLCHVSLY RDPLGVAGGM GVYWGKGALV   120
TVSSAAAWSH PQFEKGAAWS HPQFEKGAAW SHPQFEK                            157

SEQ ID NO: 15                      moltype = AA  length = 550
FEATURE                            Location/Qualifiers
REGION                             1..550
                                   note = CAA24269.1 haemagglutinin (Influenza A
                                    virus(A/Aichi/2/1968(H3N2) (excluding signal sequence)
source                             1..550
                                   mol_type = protein
                                   organism = synthetic construct
SEQUENCE: 15
QDLPGNDNST ATLCLGHHAV PNGTLVKTIT DDQIEVTNAT ELVQSSSTGK ICNNPHRILD     60
GIDCTLIDAL LGDPHCDVFQ NETWDLFVER SKAFSNCYPY DVPDYASLRS LVASSGTLEF   120
ITEGFTWTGV TQNGGSNACK RGPGSGFFSR LNWLTKSGST YPVLNVTMPN NDNFDKLYIW   180
GIHHPSTNQE QTSLYVQASG RVTVSTRRSQ QTIIPNIGSR PWVRGLSSRI SIYWTIVKPG   240
DVLVINSNGN LIAPRGYFKM RTGKSSIMRS DAPIDTCISE CITPNGSIPN DKPFQNVNKI   300
TYGACPKYVK QNTLKLATGM RNVPEKQTRG LFGAIAGFIE NGWEGMIDGW YGFRHQNSEG   360
TGQAADLKST QAAIDQINGK LNRVIEKTNE KFHQIEKEFS EVEGRIQDLE KYVEDTKIDL   420
WSYNAELLVA LENQHTIDLT DSEMNKLFEK TRRQLRENAE EMGNGCFKIY HKCDNACIES   480
IRNGTYDHDV YRDEALNNRF QIKGVELKSG YKDWILWISF AISCFLLCVV LLGFIMWACQ   540
RGNIRCNICI                                                          550

SEQ ID NO: 16                      moltype = AA  length = 248
FEATURE                            Location/Qualifiers
REGION                             1..248
                                   note = UFV5367
source                             1..248
                                   mol_type = protein
                                   organism = synthetic construct
SEQUENCE: 16
DTICIGYHAN NSTDTVDTVL EKNVTVTHSV NLLENGGGGK YVCSAKLRMV TGLRNKPSKQ     60
SQGLFGAIAG FTEGGWTGMV DGWYGYHHQN EQGSGYAADQ KSTQNAINGI TNKVNSVIEK   120
MNTQYTAIGC EYNKSERCMK QIEDKIEEIE SKIWCYNAEL LVLLENERTL DFHDSNVKNL   180
YEKVKSQLKN NAKEIGNGCF EFYHKCNDEC MESVKNGTYD YPKYSEESKL NREKIDGVKL   240
ESMGVYQI                                                            248

SEQ ID NO: 17                      moltype = AA  length = 248
FEATURE                            Location/Qualifiers
REGION                             1..248
                                   note = UFV5369
source                             1..248
                                   mol_type = protein
                                   organism = synthetic construct
SEQUENCE: 17
DTLCIGYHAN NSTDTVDTVL EKNVTVTHSV NLLEDGGGGK YVCSTKLRLA TGLRNKPSKQ     60
SQGLFGAIAG FTEGGWTGMV DGWYGYHHQN EQGSGYAADL KSTQNAIDEI TNKVNSVIEK   120
MNTQYTAIGC EYNKSERCMK QIEDKIEEIE SKIWCYNAEL LVLLENERTL DYHDSNVKNL   180
YEKVRSQLKN NAKEIGNGCF EFYHKCDNTC MESVKNGTYD YPKYSEEAKL NREEIDGVKL   240
ESTRIYQI                                                            248
```

```
SEQ ID NO: 18           moltype = AA  length = 15
FEATURE                 Location/Qualifiers
REGION                  1..15
                        note = heterologous trimerization sequence
source                  1..15
                        mol_type = protein
                        organism = synthetic construct
SEQUENCE: 18
RMKQIEDKIE EIESK                                                    15

SEQ ID NO: 19           moltype = AA  length = 15
FEATURE                 Location/Qualifiers
REGION                  1..15
                        note = heterologous trimerization sequence
source                  1..15
                        mol_type = protein
                        organism = synthetic construct
SEQUENCE: 19
RIKQIEDKIE EIESK                                                    15

SEQ ID NO: 20           moltype = AA  length = 15
FEATURE                 Location/Qualifiers
REGION                  1..15
                        note = heterologous trimerization sequence
source                  1..15
                        mol_type = protein
                        organism = synthetic construct
SEQUENCE: 20
RMEALEKKVD DIEKK                                                    15

SEQ ID NO: 21           moltype = AA  length = 15
FEATURE                 Location/Qualifiers
REGION                  1..15
                        note = heterologous trimerization sequence
source                  1..15
                        mol_type = protein
                        organism = synthetic construct
SEQUENCE: 21
RIEALEKKVD DIEKK                                                    15

SEQ ID NO: 22           moltype = AA  length = 15
FEATURE                 Location/Qualifiers
REGION                  1..15
                        note = heterologous trimerization sequence
source                  1..15
                        mol_type = protein
                        organism = synthetic construct
SEQUENCE: 22
RMENLEKKVD DIEEK                                                    15

SEQ ID NO: 23           moltype = AA  length = 15
FEATURE                 Location/Qualifiers
REGION                  1..15
                        note = heterologous trimerization sequence
source                  1..15
                        mol_type = protein
                        organism = synthetic construct
SEQUENCE: 23
RIENLEKKVD DIEEK                                                    15

SEQ ID NO: 24           moltype = AA  length = 15
FEATURE                 Location/Qualifiers
REGION                  1..15
                        note = heterologous trimerization sequence
source                  1..15
                        mol_type = protein
                        organism = synthetic construct
SEQUENCE: 24
CMKQIEDKIE EIESK                                                    15

SEQ ID NO: 25           moltype = AA  length = 15
FEATURE                 Location/Qualifiers
REGION                  1..15
                        note = heterologous trimerization sequence
source                  1..15
                        mol_type = protein
                        organism = synthetic construct
SEQUENCE: 25
CIKQIEDKIE EIESK                                                    15
```

```
SEQ ID NO: 26          moltype = AA  length = 15
FEATURE                Location/Qualifiers
REGION                 1..15
                       note = heterologous trimerization sequence
source                 1..15
                       mol_type = protein
                       organism = synthetic construct
SEQUENCE: 26
CMEALEKKVD DIEKK                                                         15

SEQ ID NO: 27          moltype = AA  length = 15
FEATURE                Location/Qualifiers
REGION                 1..15
                       note = heterologous trimerization sequence
source                 1..15
                       mol_type = protein
                       organism = synthetic construct
SEQUENCE: 27
CIEALEKKVD DIEKK                                                         15

SEQ ID NO: 28          moltype = AA  length = 15
FEATURE                Location/Qualifiers
REGION                 1..15
                       note = heterologous trimerization sequence
source                 1..15
                       mol_type = protein
                       organism = synthetic construct
SEQUENCE: 28
RMECLEKKVD DIEKK                                                         15

SEQ ID NO: 29          moltype = AA  length = 15
FEATURE                Location/Qualifiers
REGION                 1..15
                       note = heterologous trimerization sequence
source                 1..15
                       mol_type = protein
                       organism = synthetic construct
SEQUENCE: 29
RIECLEKKVD DIEKK                                                         15

SEQ ID NO: 30          moltype = AA  length = 248
FEATURE                Location/Qualifiers
REGION                 1..248
                       note = UFV150558
source                 1..248
                       mol_type = protein
                       organism = synthetic construct
SEQUENCE: 30
DTLCIGYHAN NSTDTVDTVL EKNVTVTHSV NLLEDGGGGK YVCSTKLRLA TGLRNKPSKQ         60
SQGLFGAIAG FTEGGWTGMV DGWYGYHHQN EQGSGYAADL KSTQNAIDEI TNKVNSVIEK        120
MNTQPTAIGC EYNKSEQCMK QIEDKIEEIE SKIWCYNAEL LVLLENQRTL DYHDANVKNL        180
YEKVRSQLKN NAKEIGNGCF EFYHKCDNTC MESVKNGTYD YPKYSEEAKL NREEIDGVKL        240
ESTRIYQI                                                                248

SEQ ID NO: 31          moltype = AA  length = 248
FEATURE                Location/Qualifiers
REGION                 1..248
                       note = UFV150559
source                 1..248
                       mol_type = protein
                       organism = synthetic construct
SEQUENCE: 31
DTLCIGYHAN NSTDTVDTVL EKNVTVTHSV NLLEDGGGGK YVCSTKLRLA TGLRNKPSKQ         60
SQGLFGAIAG FTEGGWTGMV DGWYGYHHQN EQGSGYAADL KSTQNAIDEI TNKVNSVIEK        120
MNTQRTAIGC EFNKSEQCMK QIEDKIEEIE SKIWCYNAEL LVLLENQRTL DYHDSNVKNL        180
YEKVRSQLKN NAKEIGNGCF EFYHKCDNTC MESVKNGTYD YPKYSEEAKL NREEIDGVKL        240
ESTRIYQI                                                                248

SEQ ID NO: 32          moltype = AA  length = 252
FEATURE                Location/Qualifiers
REGION                 1..252
                       note = UFV150565
source                 1..252
                       mol_type = protein
                       organism = synthetic construct
SEQUENCE: 32
DTICIGYHAN NSTDTVDTVL EKNVTVTHSV NLLENGGGGK YVCSAKLRMV TGLRNKPSKQ         60
SQGLFGAIAG FTEGGWTGMV DGWYGYHHQN EQGSGYAADQ KSTQNAINGI TNKVNSVIEK        120
```

```
MNTQYTAIGC EYNKSERCMK QIEDKIEEIE SKIWCYNAEL LVLLENERTL DFHDSNVKNL    180
YEKVKSQLKN NAKEIGNGCF EFYHKCNDEC MESVKNGTYD YPKYSEESKL NREKIDGVKL    240
ESMGVYQILA IY                                                       252

SEQ ID NO: 33           moltype = AA  length = 250
FEATURE                 Location/Qualifiers
REGION                  1..250
                        note = UFV150566
source                  1..250
                        mol_type = protein
                        organism = synthetic construct
SEQUENCE: 33
DTICIGYHAN NSTDTVDTVL EKNVTVTHSV NLLENGGGGK YVCSAKLRMV TGLRNKPSKQ    60
SQGLFGAIAG FTEGGWTGMV DGWYGYHHQN EQGSGYAADQ KSTQNAINGI TNKVNSVIEK    120
MNTQYTAIGC EYNKSERCMK QIEDKIEEIE SKIWCYNAEL LVLLENERTL DFHDSNVKNL    180
YEKVKSQLKN NAKEIGNGCF EFYHKCNDEC MESVKNGTYD YPKYSEESKL NREKIDGVKL    240
ESMGVYQILA                                                          250

SEQ ID NO: 34           moltype = AA  length = 246
FEATURE                 Location/Qualifiers
REGION                  1..246
                        note = UFV150567
source                  1..246
                        mol_type = protein
                        organism = synthetic construct
SEQUENCE: 34
DTICIGYHAN NSTDTVDTVL EKNVTVTHSV NLLENGGGGK YVCSAKLRMV TGLRNKPSKQ    60
SQGLFGAIAG FTEGGWTGMV DGWYGYHHQN EQGSGYAADQ KSTQNAINGI TNKVNSVIEK    120
MNTQYTAIGC EYNKSERCMK QIEDKIEEIE SKIWCYNAEL LVLLENERTL DFHDSNVKNL    180
YEKVKSQLKN NAKEIGNGCF EFYHKCNDEC MESVKNGTYD YPKYSEESKL NREKIDGVKL    240
ESMGVY                                                              246

SEQ ID NO: 35           moltype = AA  length = 244
FEATURE                 Location/Qualifiers
REGION                  1..244
                        note = UFV150568
source                  1..244
                        mol_type = protein
                        organism = synthetic construct
SEQUENCE: 35
DTICIGYHAN NSTDTVDTVL EKNVTVTHSV NLLENGGGGK YVCSAKLRMV TGLRNKPSKQ    60
SQGLFGAIAG FTEGGWTGMV DGWYGYHHQN EQGSGYAADQ KSTQNAINGI TNKVNSVIEK    120
MNTQYTAIGC EYNKSERCMK QIEDKIEEIE SKIWCYNAEL LVLLENERTL DFHDSNVKNL    180
YEKVKSQLKN NAKEIGNGCF EFYHKCNDEC MESVKNGTYD YPKYSEESKL NREKIDGVKL    240
ESMG                                                                244

SEQ ID NO: 36           moltype = AA  length = 242
FEATURE                 Location/Qualifiers
REGION                  1..242
                        note = UFV150569
source                  1..242
                        mol_type = protein
                        organism = synthetic construct
SEQUENCE: 36
DTICIGYHAN NSTDTVDTVL EKNVTVTHSV NLLENGGGGK YVCSAKLRMV TGLRNKPSKQ    60
SQGLFGAIAG FTEGGWTGMV DGWYGYHHQN EQGSGYAADQ KSTQNAINGI TNKVNSVIEK    120
MNTQYTAIGC EYNKSERCMK QIEDKIEEIE SKIWCYNAEL LVLLENERTL DFHDSNVKNL    180
YEKVKSQLKN NAKEIGNGCF EFYHKCNDEC MESVKNGTYD YPKYSEESKL NREKIDGVKL    240
ES                                                                  242

SEQ ID NO: 37           moltype = AA  length = 240
FEATURE                 Location/Qualifiers
REGION                  1..240
                        note = UFV150570
source                  1..240
                        mol_type = protein
                        organism = synthetic construct
SEQUENCE: 37
DTICIGYHAN NSTDTVDTVL EKNVTVTHSV NLLENGGGGK YVCSAKLRMV TGLRNKPSKQ    60
SQGLFGAIAG FTEGGWTGMV DGWYGYHHQN EQGSGYAADQ KSTQNAINGI TNKVNSVIEK    120
MNTQYTAIGC EYNKSERCMK QIEDKIEEIE SKIWCYNAEL LVLLENERTL DFHDSNVKNL    180
YEKVKSQLKN NAKEIGNGCF EFYHKCNDEC MESVKNGTYD YPKYSEESKL NREKIDGVKL    240

SEQ ID NO: 38           moltype = AA  length = 238
FEATURE                 Location/Qualifiers
REGION                  1..238
                        note = UFV150571
```

```
source                          1..238
                                mol_type = protein
                                organism = synthetic construct
SEQUENCE: 38
DTICIGYHAN NSTDTVDTVL EKNVTVTHSV NLLENGGGGK YVCSAKLRMV TGLRNKPSKQ    60
SQGLFGAIAG FTEGGWTGMV DGWYGYHHQN EQGSGYAADQ KSTQNAINGI TNKVNSVIEK   120
MNTQYTAIGC EYNKSERCMK QIEDKIEEIE SKIWCYNAEL LVLLENERTL DFHDSNVKNL   180
YEKVKSQLKN NAKEIGNGCF EFYHKCNDEC MESVKNGTYD YPKYSEESKL NREKIDGV     238

SEQ ID NO: 39                   moltype = AA   length = 236
FEATURE                         Location/Qualifiers
REGION                          1..236
                                note = UFV150572
source                          1..236
                                mol_type = protein
                                organism = synthetic construct
SEQUENCE: 39
DTICIGYHAN NSTDTVDTVL EKNVTVTHSV NLLENGGGGK YVCSAKLRMV TGLRNKPSKQ    60
SQGLFGAIAG FTEGGWTGMV DGWYGYHHQN EQGSGYAADQ KSTQNAINGI TNKVNSVIEK   120
MNTQYTAIGC EYNKSERCMK QIEDKIEEIE SKIWCYNAEL LVLLENERTL DFHDSNVKNL   180
YEKVKSQLKN NAKEIGNGCF EFYHKCNDEC MESVKNGTYD YPKYSEESKL NREKID       236

SEQ ID NO: 40                   moltype = AA   length = 234
FEATURE                         Location/Qualifiers
REGION                          1..234
                                note = UFV150573
source                          1..234
                                mol_type = protein
                                organism = synthetic construct
SEQUENCE: 40
DTICIGYHAN NSTDTVDTVL EKNVTVTHSV NLLENGGGGK YVCSAKLRMV TGLRNKPSKQ    60
SQGLFGAIAG FTEGGWTGMV DGWYGYHHQN EQGSGYAADQ KSTQNAINGI TNKVNSVIEK   120
MNTQYTAIGC EYNKSERCMK QIEDKIEEIE SKIWCYNAEL LVLLENERTL DFHDSNVKNL   180
YEKVKSQLKN NAKEIGNGCF EFYHKCNDEC MESVKNGTYD YPKYSEESKL NREK         234

SEQ ID NO: 41                   moltype = AA   length = 232
FEATURE                         Location/Qualifiers
REGION                          1..232
                                note = UFV150574
source                          1..232
                                mol_type = protein
                                organism = synthetic construct
SEQUENCE: 41
DTICIGYHAN NSTDTVDTVL EKNVTVTHSV NLLENGGGGK YVCSAKLRMV TGLRNKPSKQ    60
SQGLFGAIAG FTEGGWTGMV DGWYGYHHQN EQGSGYAADQ KSTQNAINGI TNKVNSVIEK   120
MNTQYTAIGC EYNKSERCMK QIEDKIEEIE SKIWCYNAEL LVLLENERTL DFHDSNVKNL   180
YEKVKSQLKN NAKEIGNGCF EFYHKCNDEC MESVKNGTYD YPKYSEESKL NR           232

SEQ ID NO: 42                   moltype = AA   length = 252
FEATURE                         Location/Qualifiers
REGION                          1..252
                                note = UFV150575
source                          1..252
                                mol_type = protein
                                organism = synthetic construct
SEQUENCE: 42
DTLCIGYHAN NSTDTVDTVL EKNVTVTHSV NLLEDGGGGK YVCSTKLRLA TGLRNKPSKQ    60
SQGLFGAIAG FTEGGWTGMV DGWYGYHHQN EQGSGYAADL KSTQNAIDEI TNKVNSVIEK   120
MNTQYTAIGC EYNKSERCMK QIEDKIEEIE SKIWCYNAEL LVLLENERTL DYHDSNVKNL   180
YEKVRSQLKN NAKEIGNGCF EFYHKCDNTC MESVKNGTYD YPKYSEEAKL NREEIDGVKL   240
ESTRIYQILA IY                                                      252

SEQ ID NO: 43                   moltype = AA   length = 250
FEATURE                         Location/Qualifiers
REGION                          1..250
                                note = UFV150576
source                          1..250
                                mol_type = protein
                                organism = synthetic construct
SEQUENCE: 43
DTLCIGYHAN NSTDTVDTVL EKNVTVTHSV NLLEDGGGGK YVCSTKLRLA TGLRNKPSKQ    60
SQGLFGAIAG FTEGGWTGMV DGWYGYHHQN EQGSGYAADL KSTQNAIDEI TNKVNSVIEK   120
MNTQYTAIGC EYNKSERCMK QIEDKIEEIE SKIWCYNAEL LVLLENERTL DYHDSNVKNL   180
YEKVRSQLKN NAKEIGNGCF EFYHKCDNTC MESVKNGTYD YPKYSEEAKL NREEIDGVKL   240
ESTRIYQILA                                                         250
```

```
SEQ ID NO: 44            moltype = AA  length = 246
FEATURE                  Location/Qualifiers
REGION                   1..246
                         note = UFV150577
source                   1..246
                         mol_type = protein
                         organism = synthetic construct
SEQUENCE: 44
DTLCIGYHAN NSTDTVDTVL EKNVTVTHSV NLLEDGGGGK YVCSTKLRLA TGLRNKPSKQ    60
SQGLFGAIAG FTEGGWTGMV DGWYGYHHQN EQGSGYAADL KSTQNAIDEI TNKVNSVIEK   120
MNTQYTAIGC EYNKSERCMK QIEDKIEEIE SKIWCYNAEL LVLLENERTL DYHDSNVKNL   180
YEKVRSQLKN NAKEIGNGCF EFYHKCDNTC MESVKNGTYD YPKYSEEAKL NREEIDGVKL   240
ESTRIY                                                              246

SEQ ID NO: 45            moltype = AA  length = 244
FEATURE                  Location/Qualifiers
REGION                   1..244
                         note = UFV150578
source                   1..244
                         mol_type = protein
                         organism = synthetic construct
SEQUENCE: 45
DTLCIGYHAN NSTDTVDTVL EKNVTVTHSV NLLEDGGGGK YVCSTKLRLA TGLRNKPSKQ    60
SQGLFGAIAG FTEGGWTGMV DGWYGYHHQN EQGSGYAADL KSTQNAIDEI TNKVNSVIEK   120
MNTQYTAIGC EYNKSERCMK QIEDKIEEIE SKIWCYNAEL LVLLENERTL DYHDSNVKNL   180
YEKVRSQLKN NAKEIGNGCF EFYHKCDNTC MESVKNGTYD YPKYSEEAKL NREEIDGVKL   240
ESTR                                                                244

SEQ ID NO: 46            moltype = AA  length = 242
FEATURE                  Location/Qualifiers
REGION                   1..242
                         note = UFV150579
source                   1..242
                         mol_type = protein
                         organism = synthetic construct
SEQUENCE: 46
DTLCIGYHAN NSTDTVDTVL EKNVTVTHSV NLLEDGGGGK YVCSTKLRLA TGLRNKPSKQ    60
SQGLFGAIAG FTEGGWTGMV DGWYGYHHQN EQGSGYAADL KSTQNAIDEI TNKVNSVIEK   120
MNTQYTAIGC EYNKSERCMK QIEDKIEEIE SKIWCYNAEL LVLLENERTL DYHDSNVKNL   180
YEKVRSQLKN NAKEIGNGCF EFYHKCDNTC MESVKNGTYD YPKYSEEAKL NREEIDGVKL   240
ES                                                                  242

SEQ ID NO: 47            moltype = AA  length = 240
FEATURE                  Location/Qualifiers
REGION                   1..240
                         note = UFV150580
source                   1..240
                         mol_type = protein
                         organism = synthetic construct
SEQUENCE: 47
DTLCIGYHAN NSTDTVDTVL EKNVTVTHSV NLLEDGGGGK YVCSTKLRLA TGLRNKPSKQ    60
SQGLFGAIAG FTEGGWTGMV DGWYGYHHQN EQGSGYAADL KSTQNAIDEI TNKVNSVIEK   120
MNTQYTAIGC EYNKSERCMK QIEDKIEEIE SKIWCYNAEL LVLLENERTL DYHDSNVKNL   180
YEKVRSQLKN NAKEIGNGCF EFYHKCDNTC MESVKNGTYD YPKYSEEAKL NREEIDGVKL   240

SEQ ID NO: 48            moltype = AA  length = 238
FEATURE                  Location/Qualifiers
REGION                   1..238
                         note = UFV150581
source                   1..238
                         mol_type = protein
                         organism = synthetic construct
SEQUENCE: 48
DTLCIGYHAN NSTDTVDTVL EKNVTVTHSV NLLEDGGGGK YVCSTKLRLA TGLRNKPSKQ    60
SQGLFGAIAG FTEGGWTGMV DGWYGYHHQN EQGSGYAADL KSTQNAIDEI TNKVNSVIEK   120
MNTQYTAIGC EYNKSERCMK QIEDKIEEIE SKIWCYNAEL LVLLENERTL DYHDSNVKNL   180
YEKVRSQLKN NAKEIGNGCF EFYHKCDNTC MESVKNGTYD YPKYSEEAKL NREEIDGV     238

SEQ ID NO: 49            moltype = AA  length = 236
FEATURE                  Location/Qualifiers
REGION                   1..236
                         note = UFV150582
source                   1..236
                         mol_type = protein
                         organism = synthetic construct
SEQUENCE: 49
DTLCIGYHAN NSTDTVDTVL EKNVTVTHSV NLLEDGGGGK YVCSTKLRLA TGLRNKPSKQ    60
SQGLFGAIAG FTEGGWTGMV DGWYGYHHQN EQGSGYAADL KSTQNAIDEI TNKVNSVIEK   120
```

```
MNTQYTAIGC EYNKSERCMK QIEDKIEEIE SKIWCYNAEL LVLLENERTL DYHDSNVKNL   180
YEKVRSQLKN NAKEIGNGCF EFYHKCDNTC MESVKNGTYD YPKYSEEAKL NREEID       236

SEQ ID NO: 50            moltype = AA  length = 234
FEATURE                  Location/Qualifiers
REGION                   1..234
                         note = UFV150583
source                   1..234
                         mol_type = protein
                         organism = synthetic construct
SEQUENCE: 50
DTLCIGYHAN NSTDTVDTVL EKNVTVTHSV NLLEDGGGGK YVCSTKLRLA TGLRNKPSKQ   60
SQGLFGAIAG FTEGGWTGMV DGWYGYHHQN EQGSGYAADL KSTQNAIDEI TNKVNSVIEK   120
MNTQYTAIGC EYNKSERCMK QIEDKIEEIE SKIWCYNAEL LVLLENERTL DYHDSNVKNL   180
YEKVRSQLKN NAKEIGNGCF EFYHKCDNTC MESVKNGTYD YPKYSEEAKL NREE         234

SEQ ID NO: 51            moltype = AA  length = 232
FEATURE                  Location/Qualifiers
REGION                   1..232
                         note = UFV150584
source                   1..232
                         mol_type = protein
                         organism = synthetic construct
SEQUENCE: 51
DTLCIGYHAN NSTDTVDTVL EKNVTVTHSV NLLEDGGGGK YVCSTKLRLA TGLRNKPSKQ   60
SQGLFGAIAG FTEGGWTGMV DGWYGYHHQN EQGSGYAADL KSTQNAIDEI TNKVNSVIEK   120
MNTQYTAIGC EYNKSERCMK QIEDKIEEIE SKIWCYNAEL LVLLENERTL DYHDSNVKNL   180
YEKVRSQLKN NAKEIGNGCF EFYHKCDNTC MESVKNGTYD YPKYSEEAKL NR           232

SEQ ID NO: 52            moltype = AA  length = 248
FEATURE                  Location/Qualifiers
REGION                   1..248
                         note = UFV150849
source                   1..248
                         mol_type = protein
                         organism = synthetic construct
SEQUENCE: 52
DTICIGYHAN NSTDTVDTVL EKNVTVTHSV NLLENGGGGK YVCSAKLRMV TGLRNKPSKQ   60
SQGLFGAIAG FTEGGWTGMV DGWYGYHHQN EQGSGYAADQ KSTQNAINGI TNKVNSVIEK   120
MNTQRTAIGC EYNKSERCMK QIEDKIEEIE SKIWCYNAEL LVLLENQRTL EFHDSNVKNL   180
YEKVKSQLKN NAKEIGNGCF EFYHKCNDEC MESVKNGTYD YPKYSEESKL NREKIDGVKL   240
ESMGVYQI                                                            248

SEQ ID NO: 53            moltype = AA  length = 248
FEATURE                  Location/Qualifiers
REGION                   1..248
                         note = UFV150850
source                   1..248
                         mol_type = protein
                         organism = synthetic construct
SEQUENCE: 53
DTLCIGYHAN NSTDTVDTVL EKNVTVTHSV NLLEDGGGGK YVCSTKLRLA TGLRNKPSKQ   60
SQGLFGAIAG FTEGGWTGMV DGWYGYHHQN EQGSGYAADL KSTQNAIDEI TNKVNSVIEK   120
MNTQRTAIGC EYNKSERCMK QIEDKIEEIE SKIWCYNAEL LVLLENQRTL EYHDSNVKNL   180
YEKVRSQLKN NAKEIGNGCF EFYHKCDNTC MESVKNGTYD YPKYSEEAKL NREEIDGVKL   240
ESTRIYQI                                                            248

SEQ ID NO: 54            moltype = AA  length = 248
FEATURE                  Location/Qualifiers
REGION                   1..248
                         note = UFV150552
source                   1..248
                         mol_type = protein
                         organism = synthetic construct
SEQUENCE: 54
DTICIGYHAN NSTDTVDTVL EKNVTVTHSV NLLENGGGGK YVCSAKLRMV TGLRNKPSKQ   60
SQGLFGAIAG FTEGGWTGMV DGWYGYHHQN EQGSGYAADQ KSTQNAINGI TNKVNSVIEK   120
MNTQPTAIGC EYNKSEQCMK QIEDKIEEIE SKIWCYNAEL LVLLENQRTL DFHDANVKNL   180
YEKVKSQLKN NAKEIGNGCF EFYHKCNDEC MESVKNGTYD YPKYSEESKL NREKIDGVKL   240
ESMGVYQI                                                            248

SEQ ID NO: 55            moltype = AA  length = 248
FEATURE                  Location/Qualifiers
REGION                   1..248
                         note = UFV160088
source                   1..248
                         mol_type = protein
                         organism = synthetic construct
```

```
SEQUENCE: 55
DTICIGYHAN NSTDTVDTVL EKNVTVTHSV NLLENGGGGK YVCSAKLRMV TGLRNKPSKQ    60
SRGLFGAIAG FIEGGWTGMV DGWYGYHHQN EQGSGYAADQ KSTQNAINGI TNKVNSVIEK   120
MNTQRTAICK EYPKSEQRME CLEKKVDDIE KKIWCYNAEL LVLLENQRTL EFHDINVKNL   180
YEKVKSQLKN NAKEIGNGCF EFYHKCNDEC MESVKNGTYD YPKYSEESKL NREKIDGVKL   240
ESMGVYQI                                                           248

SEQ ID NO: 56           moltype = AA  length = 248
FEATURE                 Location/Qualifiers
REGION                  1..248
                        note = UFV160090
source                  1..248
                        mol_type = protein
                        organism = synthetic construct
SEQUENCE: 56
DTLCIGYHAN NSTDTVDTVL EKNVTVTHSV NLLEDGGGGK YVCSTKLRLA TGLRNKPSKQ    60
SQGLFGAIAG FTEGGWTGMV DGWYGYHHQN EQGSGYAADL KSTQNAIDEI TNKVNSVIEK   120
MNTQRTAIGC EYNKSERCIE ALEKKVDDIE KKIWCYNAEL LVLLENQRTL EYHDSNVKNL   180
YEKVRSQLKN NAKEIGNGCF EFYHKCDNTC MESVKNGTYD YPKYSEEAKL NREEIDGVKL   240
ESTRIYQI                                                           248

SEQ ID NO: 57           moltype = AA  length = 248
FEATURE                 Location/Qualifiers
REGION                  1..248
                        note = UFV160093
source                  1..248
                        mol_type = protein
                        organism = synthetic construct
SEQUENCE: 57
DTLCIGYHAN NSTDTVDTVL EKNVTVTHSV NLLEDGGGGK YVCSTKLRLA TGLRNKPSKQ    60
SQGLFGAIAG FTEGGWTGMV DGWYGYHHQN EQGSGYAADL KSTQNAIDEI TNKVNSVIEK   120
MNTQRTAIGK ECNKSERCIE ALEKKVDDIE KKIWCYNAEL LVLLENQRTL EYHDSNVKNL   180
YEKVRSQLKN NAKEIGNGCF EFYHKCDNTC MESVKNGTYD YPKYSEEAKL NREEIDGVKL   240
ESTRIYQI                                                           248

SEQ ID NO: 58           moltype = AA  length = 248
FEATURE                 Location/Qualifiers
REGION                  1..248
                        note = UFV160097
source                  1..248
                        mol_type = protein
                        organism = synthetic construct
SEQUENCE: 58
DTLCIGYHAN NSTDTVDTVL EKNVTVTHSV NLLEDGGGGK YVCSTKLRLA TGLRNKPSKQ    60
SQGLFGAIAG FTEGGWTGMV DGWYGYHHQN EQGSGYAADL KSTQNAIDEI TNKVNSVIEK   120
MNTQRTAIGC EYNKSERCMK QIEDKIEEIE SKIWCYNAEL LVLLENQRTL EYHDSNVKNL   180
YEKVRSQLKN NAKEIGNGCF EFYHKCDNTC MESVKNGTYD YPKYSEEAKL NREEIDGVKL   240
ESTRIYQI                                                           248

SEQ ID NO: 59           moltype = AA  length = 251
FEATURE                 Location/Qualifiers
REGION                  1..251
                        note = UFV160301
source                  1..251
                        mol_type = protein
                        organism = synthetic construct
SEQUENCE: 59
DTLCIGYHAN NSTDTVDTVL EKNVTVTHSV NLLEDGGGGK YVCSTKLRLA TGLRNKPSKQ    60
RRRKKGLFGA IAGFTEGGWT GMVDGWYGYH HQNEQGSGYA ADLKSTQNAI DEITNKVNSV   120
IEKMNTQRTA IGCEYNKSER CMKQIEDKIE EIESKIWCYN AELLVLLENQ RTLEYHDSNV   180
KNLYEKVRSQ LKNNAKEIGN GCFEFYHKCD NTCMESVKNG TYDYPKYSEE AKLNREEIDG   240
VKLESTRIYQ I                                                       251

SEQ ID NO: 60           moltype = AA  length = 248
FEATURE                 Location/Qualifiers
REGION                  1..248
                        note = UFV160302
source                  1..248
                        mol_type = protein
                        organism = synthetic construct
SEQUENCE: 60
DTLCIGYHAN NSTDTVDTVL EKNVTVTHSV NLLEDGGGGK YVCSTKLRLA TGLRNKPSKQ    60
SRGLFGAIAG FTEGGWTGMV DGWYGYHHQN EQGSGYAADL KSTQNAIDEI TNKVNSVIEK   120
MNTQRTAIGC EYNKSERCMK QIEDKIEEIE SKIWCYNAEL LVLLENQRTL EYHDSNVKNL   180
YEKVRSQLKN NAKEIGNGCF EFYHKCDNTC MESVKNGTYD YPKYSEEAKL NREEIDGVKL   240
ESTRIYQI                                                           248

SEQ ID NO: 61           moltype = AA  length = 248
FEATURE                 Location/Qualifiers
```

| | | | |
|---|---|---|---|
| REGION | 1..248 | | |
| | note = UFV160303 | | |
| source | 1..248 | | |
| | mol_type = protein | | |
| | organism = synthetic construct | | |

SEQUENCE: 61
```
DTLCIGYHAN NSTDTVDTVL EKNVTVTHSV NLLEDGGGGK YVCSTKLRLA TGLRNKPSKQ   60
SRGLFGAIAG FTEGGWTGMV DGWYGYHHQN EQGSGYAADL KSTQNAIDEI TNKVNSVIEK  120
MNTQRTAIGC EYNKSERCMK QIEDKIEEIE SKIWCYNAEL LVLLENQRTL DYHDSNVKNL  180
YEKVRSQLKN NAKEIGNGCF EFYHKCDNTC MESVKNGTYD YPKYSEEAKL NREEIDGVKL  240
ESTRIYQI                                                          248
```

| | | | |
|---|---|---|---|
| SEQ ID NO: 62 | moltype = AA length = 248 | | |
| FEATURE | Location/Qualifiers | | |
| REGION | 1..248 | | |
| | note = UFV160304 | | |
| source | 1..248 | | |
| | mol_type = protein | | |
| | organism = synthetic construct | | |

SEQUENCE: 62
```
DTLCIGYHAN NSTDTVDTVL EKNVTVTHSV NLLEDGGGGK YVCSTKLRLA TGLRNKPSKQ   60
SRGLFGAIAG FTEGGWTGMV DGWYGYHHQN EQGSGYAADL KSTQNAIDEI TNKVNSVIEK  120
MNTQYTAIGC EYNKSERCMK QIEDKIEEIE SKIWCYNAEL LVLLENQRTL EYHDSNVKNL  180
YEKVRSQLKN NAKEIGNGCF EFYHKCDNTC MESVKNGTYD YPKYSEEAKL NREEIDGVKL  240
ESTRIYQI                                                          248
```

| | | | |
|---|---|---|---|
| SEQ ID NO: 63 | moltype = AA length = 248 | | |
| FEATURE | Location/Qualifiers | | |
| REGION | 1..248 | | |
| | note = UFV160360 | | |
| source | 1..248 | | |
| | mol_type = protein | | |
| | organism = synthetic construct | | |

SEQUENCE: 63
```
DTLCIGYHAN NSTDTVDTVL EKNVTVTHSV NLLEDGGGGK YVCSTKLRLA TGLRNKPSKQ   60
SQGLFGAIAG FTEGGWTGMV DGWYGYHHQN EQGSGYAADL KSTQNAIDEI TNKVNSVIEK  120
MNTQPTAIGC EYNKSEQCMK QIEDKIEEIE SKIWCYNAEL LVLLENQRTL DYHDANVKNL  180
YEKVRSQLKN NAKEIGNGCF EFYHKCDNTC MESVKNGTYD YPKYSEEAKL NREEIDGVKL  240
ESTRIYQI                                                          248
```

| | | | |
|---|---|---|---|
| SEQ ID NO: 64 | moltype = AA length = 244 | | |
| FEATURE | Location/Qualifiers | | |
| REGION | 1..244 | | |
| | note = UFV160361 | | |
| source | 1..244 | | |
| | mol_type = protein | | |
| | organism = synthetic construct | | |

SEQUENCE: 64
```
DTLCIGYHAN NSTDTVDTVL EKNVTVTHSV NLLEDKYVCS TKLRLATGLR NKPSKQSQGL   60
FGAIAGFTEG GWTGMVDGWY GYHHQNEQGS GYAADLKSTQ NAIDEITNKV NSVIEKMNTQ  120
PTAIGCEYNK SEQCMKQIED KIEEIESKIW CYNAELLVLL ENQRTLDYHD ANVKNLYEKV  180
RSQLKNNAKE IGNGCFEFYH KCDNTCMESV KNGTYDYPKY SEEAKLNREE IDGVKLESTR  240
IYQI                                                              244
```

| | | | |
|---|---|---|---|
| SEQ ID NO: 65 | moltype = AA length = 245 | | |
| FEATURE | Location/Qualifiers | | |
| REGION | 1..245 | | |
| | note = UFV160362 | | |
| source | 1..245 | | |
| | mol_type = protein | | |
| | organism = synthetic construct | | |

SEQUENCE: 65
```
DTLCIGYHAN NSTDTVDTVL EKNVTVTHSV NLLEDKKYVC STKLRLATGL RNKPSKQSQG   60
LFGAIAGFTE GGWTGMVDGW YGYHHQNEQG SGYAADLKST QNAIDEITNK VNSVIEKMNT  120
QPTAIGCEYN KSEQCMKQIE DKIEEIESKI WCYNAELLVL LENQRTLDYH DANVKNLYEK  180
VRSQLKNNAK EIGNGCFEFY HKCDNTCMES VKNGTYDYPK YSEEAKLNRE EIDGVKLEST  240
RIYQI                                                             245
```

| | | | |
|---|---|---|---|
| SEQ ID NO: 66 | moltype = AA length = 246 | | |
| FEATURE | Location/Qualifiers | | |
| REGION | 1..246 | | |
| | note = UFV160363 | | |
| source | 1..246 | | |
| | mol_type = protein | | |
| | organism = synthetic construct | | |

SEQUENCE: 66
```
DTLCIGYHAN NSTDTVDTVL EKNVTVTHSV NLLEDKHKYV CSTKLRLATG LRNKPSKQSQ   60
GLFGAIAGFT EGGWTGMVDG WYGYHHQNEQ GSGYAADLKS TQNAIDEITN KVNSVIEKMN  120
TQPTAIGCEY NKSEQCMKQI EDKIEEIESK IWCYNAELLV LLENQRTLDY HDANVKNLYE  180
```

```
KVRSQLKNNA KEIGNGCFEF YHKCDNTCME SVKNGTYDYP KYSEEAKLNR EEIDGVKLES   240
TRIYQI                                                              246

SEQ ID NO: 67           moltype = AA  length = 247
FEATURE                 Location/Qualifiers
REGION                  1..247
                        note = UFV160364
source                  1..247
                        mol_type = protein
                        organism = synthetic construct
SEQUENCE: 67
DTLCIGYHAN NSTDTVDTVL EKNVTVTHSV NLLEDKHNKY VCSTKLRLAT GLRNKPSKQS   60
QGLFGAIAGF TEGGWTGMVD GWYGYHHQNE QGSGYAADLK STQNAIDEIT NKVNSVIEKM   120
NTQPTAIGCE YNKSEQCMKQ IEDKIEEIES KIWCYNAELL VLLENQRTLD YHDANVKNLY   180
EKVRSQLKNN AKEIGNGCFE FYHKCDNTCM ESVKNGTYDY PKYSEEAKLN REEIDGVKLE   240
STRIYQI                                                             247

SEQ ID NO: 68           moltype = AA  length = 248
FEATURE                 Location/Qualifiers
REGION                  1..248
                        note = UFV160365
source                  1..248
                        mol_type = protein
                        organism = synthetic construct
SEQUENCE: 68
DTLCIGYHAN NSTDTVDTVL EKNVTVTHSV NLLEDKHNGK YVCSTKLRLA TGLRNKPSKQ   60
SQGLFGAIAG FTEGGWTGMV DGWYGYHHQN EQGSGYAADL KSTQNAIDEI TNKVNSVIEK   120
MNTQPTAIGC EYNKSEQCMK QIEDKIEEIE SKIWCYNAEL LVLLENQRTL DYHDANVKNL   180
YEKVRSQLKN NAKEIGNGCF EFYHKCDNTC MESVKNGTYD YPKYSEEAKL NREEIDGVKL   240
ESTRIYQI                                                            248

SEQ ID NO: 69           moltype = AA  length = 249
FEATURE                 Location/Qualifiers
REGION                  1..249
                        note = UFV160366
source                  1..249
                        mol_type = protein
                        organism = synthetic construct
SEQUENCE: 69
DTLCIGYHAN NSTDTVDTVL EKNVTVTHSV NLLEDKHNGK KYVCSTKLRL ATGLRNKPSK   60
QSQGLFGAIA GFTEGGWTGM VDGWYGYHHQ NEQGSGYAAD LKSTQNAIDE ITNKVNSVIE   120
KMNTQPTAIG CEYNKSEQCM KQIEDKIEEI ESKIWCYNAE LLVLLENQRT LDYHDANVKN   180
LYEKVRSQLK NNAKEIGNGC FEFYHKCDNT CMESVKNGTY DYPKYSEEAK LNREEIDGVK   240
LESTRIYQI                                                           249

SEQ ID NO: 70           moltype = AA  length = 250
FEATURE                 Location/Qualifiers
REGION                  1..250
                        note = UFV160367
source                  1..250
                        mol_type = protein
                        organism = synthetic construct
SEQUENCE: 70
DTLCIGYHAN NSTDTVDTVL EKNVTVTHSV NLLEDKHNGK LKYVCSTKLR LATGLRNKPS   60
KQSQGLFGAI AGFTEGGWTG MVDGWYGYHH QNEQGSGYAA DLKSTQNAID EITNKVNSVI   120
EKMNTQPTAI GCEYNKSEQC MKQIEDKIEE IESKIWCYNA ELLVLLENQR TLDYHDANVK   180
NLYEKVRSQL KNNAKEIGNG CFEFYHKCDN TCMESVKNGT YDYPKYSEEA KLNREEIDGV   240
KLESTRIYQI                                                          250

SEQ ID NO: 71           moltype = AA  length = 251
FEATURE                 Location/Qualifiers
REGION                  1..251
                        note = UFV160368
source                  1..251
                        mol_type = protein
                        organism = synthetic construct
SEQUENCE: 71
DTLCIGYHAN NSTDTVDTVL EKNVTVTHSV NLLEDKHNGK LGKYVCSTKL RLATGLRNKP   60
SKQSQGLFGA IAGFTEGGWT GMVDGWYGYH HQNEQGSGYA ADLKSTQNAI DEITNKVNSV   120
IEKMNTQPTA IGCEYNKSEQ CMKQIEDKIE EIESKIWCYN AELLVLLENQ RTLDYHDANV   180
KNLYEKVRSQ LKNNAKEIGN GCFEFYHKCD NTCMESVKNG TYDYPKYSEE AKLNREEIDG   240
VKLESTRIYQ I                                                        251

SEQ ID NO: 72           moltype = AA  length = 252
FEATURE                 Location/Qualifiers
REGION                  1..252
                        note = UFV160369
```

-continued

```
source                  1..252
                        mol_type = protein
                        organism = synthetic construct
SEQUENCE: 72
DTLCIGYHAN NSTDTVDTVL EKNVTVTHSV NLLEDKHNGK LGPKYVCSTK LRLATGLRNK   60
PSKQSQGLFG AIAGFTEGGW TGMVDGWYGY HHQNEQGSGY AADLKSTQNA IDEITNKVNS  120
VIEKMNTQPT AIGCEYNKSE QCMKQIEDKI EEIESKIWCY NAELLVLLEN QRTLDYHDAN  180
VKNLYEKVRS QLKNNAKEIG NGCFEFYHKC DNTCMESVKN GTYDYPKYSE EAKLNREEID  240
GVKLESTRIY QI                                                     252

SEQ ID NO: 73           moltype = AA  length = 248
FEATURE                 Location/Qualifiers
REGION                  1..248
                        note = UFV160370
source                  1..248
                        mol_type = protein
                        organism = synthetic construct
SEQUENCE: 73
DTLCIGYHAN NSTDTVDTVL EKNVTVTHSV NLLEDKHGPK YVCSTKLRLA TGLRNKPSKQ   60
SQGLFGAIAG FTEGGWTGMV DGWYGYHHQN EQGSGYAADL KSTQNAIDEI TNKVNSVIEK  120
MNTQPTAIGC EYNKSEQCMK QIEDKIEEIE SKIWCYNAEL LVLLENQRTL DYHDANVKNL  180
YEKVRSQLKN NAKEIGNGCF EFYHKCDNTC MESVKNGTYD YPKYSEEAKL NREEIDGVKL  240
ESTRIYQI                                                          248

SEQ ID NO: 74           moltype = AA  length = 248
FEATURE                 Location/Qualifiers
REGION                  1..248
                        note = UFV160371
source                  1..248
                        mol_type = protein
                        organism = synthetic construct
SEQUENCE: 74
DTLCIGYHAN NSTDTVDTVL EKNVTVTHSV NLLEDGEGPK YVCSTKLRLA TGLRNKPSKQ   60
SQGLFGAIAG FTEGGWTGMV DGWYGYHHQN EQGSGYAADL KSTQNAIDEI TNKVNSVIEK  120
MNTQPTAIGC EYNKSEQCMK QIEDKIEEIE SKIWCYNAEL LVLLENQRTL DYHDANVKNL  180
YEKVRSQLKN NAKEIGNGCF EFYHKCDNTC MESVKNGTYD YPKYSEEAKL NREEIDGVKL  240
ESTRIYQI                                                          248

SEQ ID NO: 75           moltype = AA  length = 242
FEATURE                 Location/Qualifiers
REGION                  1..242
                        note = UFV160372
source                  1..242
                        mol_type = protein
                        organism = synthetic construct
SEQUENCE: 75
DTLCIGYHAN NSTDTVDTVL EKNVTVTHSV NLLEDVCSTK LRLATGLRNK PSKQSQGLFG   60
AIAGFTEGGW TGMVDGWYGY HHQNEQGSGY AADLKSTQNA IDEITNKVNS VIEKMNTQPT  120
AIGCEYNKSE QCMKQIEDKI EEIESKIWCY NAELLVLLEN QRTLDYHDAN VKNLYEKVRS  180
QLKNNAKEIG NGCFEFYHKC DNTCMESVKN GTYDYPKYSE EAKLNREEID GVKLESTRIY  240
QI                                                                242

SEQ ID NO: 76           moltype = AA  length = 243
FEATURE                 Location/Qualifiers
REGION                  1..243
                        note = UFV160373
source                  1..243
                        mol_type = protein
                        organism = synthetic construct
SEQUENCE: 76
DTLCIGYHAN NSTDTVDTVL EKNVTVTHSV NLLEDKVCST KLRLATGLRN KPSKQSQGLF   60
GAIAGFTEGG WTGMVDGWYG YHHQNEQGSG YAADLKSTQN AIDEITNKVN SVIEKMNTQP  120
TAIGCEYNKS EQCMKQIEDK IEEIESKIWC YNAELLVLLE NQRTLDYHDA NVKNLYEKVR  180
SQLKNNAKEI GNGCFEFYHK CDNTCMESVK NGTYDYPKYS EEAKLNREEI DGVKLESTRI  240
YQI                                                               243

SEQ ID NO: 77           moltype = AA  length = 244
FEATURE                 Location/Qualifiers
REGION                  1..244
                        note = UFV160374
source                  1..244
                        mol_type = protein
                        organism = synthetic construct
SEQUENCE: 77
DTLCIGYHAN NSTDTVDTVL EKNVTVTHSV NLLEDKHVCS TKLRLATGLR NKPSKQSQGL   60
FGAIAGFTEG GWTGMVDGWY GYHHQNEQGS GYAADLKSTQ NAIDEITNKV NSVIEKMNTQ  120
PTAIGCEYNK SEQCMKQIED KIEEIESKIW CYNAELLVLL ENQRTLDYHD ANVKNLYEKV  180
RSQLKNNAKE IGNGCFEFYH KCDNTCMESV KNGTYDYPKY SEEAKLNREE IDGVKLESTR  240
IYQI                                                              244
```

```
SEQ ID NO: 78               moltype = AA  length = 245
FEATURE                     Location/Qualifiers
REGION                      1..245
                            note = UFV160375
source                      1..245
                            mol_type = protein
                            organism = synthetic construct
SEQUENCE: 78
DTLCIGYHAN NSTDTVDTVL EKNVTVTHSV NLLEDKHNVC STKLRLATGL RNKPSKQSQG      60
LFGAIAGFTE GGWTGMVDGW YGYHHQNEQG SGYAADLKST QNAIDEITNK VNSVIEKMNT     120
QPTAIGCEYN KSEQCMKQIE DKIEEIESKI WCYNAELLVL LENQRTLDYH DANVKNLYEK     180
VRSQLKNNAK EIGNGCFEFY HKCDNTCMES VKNGTYDYPK YSEEAKLNRE EIDGVKLEST     240
RIYQI                                                                 245

SEQ ID NO: 79               moltype = AA  length = 246
FEATURE                     Location/Qualifiers
REGION                      1..246
                            note = UFV160376
source                      1..246
                            mol_type = protein
                            organism = synthetic construct
SEQUENCE: 79
DTLCIGYHAN NSTDTVDTVL EKNVTVTHSV NLLEDKHNGV CSTKLRLATG LRNKPSKQSQ      60
GLFGAIAGFT EGGWTGMVDG WYGYHHQNEQ GSGYAADLKS TQNAIDEITN KVNSVIEKMN     120
TQPTAIGCEY NKSEQCMKQI EDKIEEIESK IWCYNAELLV LLENQRTLDY HDANVKNLYE     180
KVRSQLKNNA KEIGNGCFEF YHKCDNTCME SVKNGTYDYP KYSEEAKLNR EEIDGVKLES     240
TRIYQI                                                                246

SEQ ID NO: 80               moltype = AA  length = 247
FEATURE                     Location/Qualifiers
REGION                      1..247
                            note = UFV160377
source                      1..247
                            mol_type = protein
                            organism = synthetic construct
SEQUENCE: 80
DTLCIGYHAN NSTDTVDTVL EKNVTVTHSV NLLEDKHNGK VCSTKLRLAT GLRNKPSKQS      60
QGLFGAIAGF TEGGWTGMVD GWYGYHHQNE QGSGYAADLK STQNAIDEIT NKVNSVIEKM     120
NTQPTAIGCE YNKSEQCMKQ IEDKIEEIES KIWCYNAELL VLLENQRTLD YHDANVKNLY     180
EKVRSQLKNN AKEIGNGCFE FYHKCDNTCM ESVKNGTYDY PKYSEEAKLN REEIDGVKLE     240
STRIYQI                                                               247

SEQ ID NO: 81               moltype = AA  length = 248
FEATURE                     Location/Qualifiers
REGION                      1..248
                            note = UFV160378
source                      1..248
                            mol_type = protein
                            organism = synthetic construct
SEQUENCE: 81
DTLCIGYHAN NSTDTVDTVL EKNVTVTHSV NLLEDKHNGK LVCSTKLRLA TGLRNKPSKQ      60
SQGLFGAIAG FTEGGWTGMV DGWYGYHHQN EQGSGYAADL KSTQNAIDEI TNKVNSVIEK     120
MNTQPTAIGC EYNKSEQCMK QIEDKIEEIE SKIWCYNAEL LVLLENQRTL DYHDANVKNL     180
YEKVRSQLKN NAKEIGNGCF EFYHKCDNTC MESVKNGTYD YPKYSEEAKL NREEIDGVKL     240
ESTRIYQI                                                              248

SEQ ID NO: 82               moltype = AA  length = 249
FEATURE                     Location/Qualifiers
REGION                      1..249
                            note = UFV160379
source                      1..249
                            mol_type = protein
                            organism = synthetic construct
SEQUENCE: 82
DTLCIGYHAN NSTDTVDTVL EKNVTVTHSV NLLEDKHNGK LGVCSTKLRL ATGLRNKPSK      60
QSQGLFGAIA GFTEGGWTGM VDGWYGYHHQ NEQGSGYAADL KSTQNAIDE ITNKVNSVIE     120
KMNTQPTAIG CEYNKSEQCM KQIEDKIEEI ESKIWCYNAE LLVLLENQRT LDYHDANVKN     180
LYEKVRSQLK NNAKEIGNGC FEFYHKCDNT CMESVKNGTY DYPKYSEEAK LNREEIDGVK     240
LESTRIYQI                                                             249

SEQ ID NO: 83               moltype = AA  length = 248
FEATURE                     Location/Qualifiers
REGION                      1..248
                            note = UFV160380
source                      1..248
                            mol_type = protein
                            organism = synthetic construct
```

```
SEQUENCE: 83
DTLCIGYHAN NSTDTVDTVL EKNVTVTHSV NLLEDAGSGK YVCSTKLRLA TGLRNKPSKQ    60
SQGLFGAIAG FTEGGWTGMV DGWYGYHHQN EQGSGYAADL KSTQNAIDEI TNKVNSVIEK   120
MNTQPTAIGC EYNKSEQCMK QIEDKIEEIE SKIWCYNAEL LVLLENQRTL DYHDANVKNL   180
YEKVRSQLKN NAKEIGNGCF EFYHKCDNTC MESVKNGTYD YPKYSEEAKL NREEIDGVKL   240
ESTRIYQI                                                           248

SEQ ID NO: 84           moltype = AA  length = 247
FEATURE                 Location/Qualifiers
REGION                  1..247
                        note = UFV160381
source                  1..247
                        mol_type = protein
                        organism = synthetic construct
SEQUENCE: 84
DTLCIGYHAN NSTDTVDTVL EKNVTVTHSV NLLEDAGSKY VCSTKLRLAT GLRNKPSKQS    60
QGLFGAIAGF TEGGWTGMVD GWYGYHHQNE QGSGYAADLK STQNAIDEIT NKVNSVIEKM   120
NTQPTAIGCE YNKSEQCMKQ IEDKIEEIES KIWCYNAELL VLLENQRTLD YHDANVKNLY   180
EKVRSQLKNN AKEIGNGCFE FYHKCDNTCM ESVKNGTYDY PKYSEEAKLN REEIDGVKLE   240
STRIYQI                                                            247

SEQ ID NO: 85           moltype = AA  length = 249
FEATURE                 Location/Qualifiers
REGION                  1..249
                        note = UFV160382
source                  1..249
                        mol_type = protein
                        organism = synthetic construct
SEQUENCE: 85
DTLCIGYHAN NSTDTVDTVL EKNVTVTHSV NLLEDAGSGI KYVCSTKLRL ATGLRNKPSK    60
QSQGLFGAIA GFTEGGWTGM VDGWYGYHHQ NEQGSGYAAD LKSTQNAIDE ITNKVNSVIE   120
KMNTQPTAIG CEYNKSEQCM KQIEDKIEEI ESKIWCYNAE LLVLLENQRT LDYHDANVKN   180
LYEKVRSQLK NNAKEIGNGC FEFYHKCDNT CMESVKNGTY DYPKYSEEAK LNREEIDGVK   240
LESTRIYQI                                                          249

SEQ ID NO: 86           moltype = AA  length = 247
FEATURE                 Location/Qualifiers
REGION                  1..247
                        note = UFV160383
source                  1..247
                        mol_type = protein
                        organism = synthetic construct
SEQUENCE: 86
DTLCIGYHAN NSTDTVDTVL EKNVTVTHSV NLLEDAGSGI VCSTKLRLAT GLRNKPSKQS    60
QGLFGAIAGF TEGGWTGMVD GWYGYHHQNE QGSGYAADLK STQNAIDEIT NKVNSVIEKM   120
NTQPTAIGCE YNKSEQCMKQ IEDKIEEIES KIWCYNAELL VLLENQRTLD YHDANVKNLY   180
EKVRSQLKNN AKEIGNGCFE FYHKCDNTCM ESVKNGTYDY PKYSEEAKLN REEIDGVKLE   240
STRIYQI                                                            247

SEQ ID NO: 87           moltype = AA  length = 248
FEATURE                 Location/Qualifiers
REGION                  1..248
                        note = UFV160384
source                  1..248
                        mol_type = protein
                        organism = synthetic construct
SEQUENCE: 87
DTLCIGYHAN NSTDTVDTVL EKNVTVTHSV NLLEDGSGIK YVCSTKLRLA TGLRNKPSKQ    60
SQGLFGAIAG FTEGGWTGMV DGWYGYHHQN EQGSGYAADL KSTQNAIDEI TNKVNSVIEK   120
MNTQPTAIGC EYNKSEQCMK QIEDKIEEIE SKIWCYNAEL LVLLENQRTL DYHDANVKNL   180
YEKVRSQLKN NAKEIGNGCF EFYHKCDNTC MESVKNGTYD YPKYSEEAKL NREEIDGVKL   240
ESTRIYQI                                                           248

SEQ ID NO: 88           moltype = AA  length = 247
FEATURE                 Location/Qualifiers
REGION                  1..247
                        note = UFV160385
source                  1..247
                        mol_type = protein
                        organism = synthetic construct
SEQUENCE: 88
DTLCIGYHAN NSTDTVDTVL EKNVTVTHSV NLLEDGSGKY VCSTKLRLAT GLRNKPSKQS    60
QGLFGAIAGF TEGGWTGMVD GWYGYHHQNE QGSGYAADLK STQNAIDEIT NKVNSVIEKM   120
NTQPTAIGCE YNKSEQCMKQ IEDKIEEIES KIWCYNAELL VLLENQRTLD YHDANVKNLY   180
EKVRSQLKNN AKEIGNGCFE FYHKCDNTCM ESVKNGTYDY PKYSEEAKLN REEIDGVKLE   240
STRIYQI                                                            247

SEQ ID NO: 89           moltype = AA  length = 248
FEATURE                 Location/Qualifiers
```

```
REGION                     1..248
                           note = UFV160386
source                     1..248
                           mol_type = protein
                           organism = synthetic construct
SEQUENCE: 89
DTLCIGYHAN NSTDTVDTVL EKNVTVTHSV NLLEDHAGAK YVCSTKLRLA TGLRNKPSKQ    60
SQGLFGAIAG FTEGGWTGMV DGWYGYHHQN EQGSGYAADL KSTQNAIDEI TNKVNSVIEK   120
MNTQPTAIGC EYNKSEQCMK QIEDKIEEIE SKIWCYNAEL LVLLENQRTL DYHDANVKNL   180
YEKVRSQLKN NAKEIGNGCF EFYHKCDNTC MESVKNGTYD YPKYSEEAKL NREEIDGVKL   240
ESTRIYQI                                                            248

SEQ ID NO: 90              moltype = AA  length = 248
FEATURE                    Location/Qualifiers
REGION                     1..248
                           note = UFV160387
source                     1..248
                           mol_type = protein
                           organism = synthetic construct
SEQUENCE: 90
DTLCIGYHAN NSTDTVDTVL EKNVTVTHSV NLLEDDQEGK YVCSTKLRLA TGLRNKPSKQ    60
SQGLFGAIAG FTEGGWTGMV DGWYGYHHQN EQGSGYAADL KSTQNAIDEI TNKVNSVIEK   120
MNTQPTAIGC EYNKSEQCMK QIEDKIEEIE SKIWCYNAEL LVLLENQRTL DYHDANVKNL   180
YEKVRSQLKN NAKEIGNGCF EFYHKCDNTC MESVKNGTYD YPKYSEEAKL NREEIDGVKL   240
ESTRIYQI                                                            248

SEQ ID NO: 91              moltype = AA  length = 248
FEATURE                    Location/Qualifiers
REGION                     1..248
                           note = UFV160388
source                     1..248
                           mol_type = protein
                           organism = synthetic construct
SEQUENCE: 91
DTLCIGYHAN NSTDTVDTVL EKNVTVTHSV NLLEDDTPVK YVCSTKLRLA TGLRNKPSKQ    60
SQGLFGAIAG FTEGGWTGMV DGWYGYHHQN EQGSGYAADL KSTQNAIDEI TNKVNSVIEK   120
MNTQPTAIGC EYNKSEQCMK QIEDKIEEIE SKIWCYNAEL LVLLENQRTL DYHDANVKNL   180
YEKVRSQLKN NAKEIGNGCF EFYHKCDNTC MESVKNGTYD YPKYSEEAKL NREEIDGVKL   240
ESTRIYQI                                                            248

SEQ ID NO: 92              moltype = AA  length = 248
FEATURE                    Location/Qualifiers
REGION                     1..248
                           note = UFV160389
source                     1..248
                           mol_type = protein
                           organism = synthetic construct
SEQUENCE: 92
DTLCIGYHAN NSTDTVDTVL EKNVTVTHSV NLLEDFPKTK YVCSTKLRLA TGLRNKPSKQ    60
SQGLFGAIAG FTEGGWTGMV DGWYGYHHQN EQGSGYAADL KSTQNAIDEI TNKVNSVIEK   120
MNTQPTAIGC EYNKSEQCMK QIEDKIEEIE SKIWCYNAEL LVLLENQRTL DYHDANVKNL   180
YEKVRSQLKN NAKEIGNGCF EFYHKCDNTC MESVKNGTYD YPKYSEEAKL NREEIDGVKL   240
ESTRIYQI                                                            248

SEQ ID NO: 93              moltype = AA  length = 248
FEATURE                    Location/Qualifiers
REGION                     1..248
                           note = UFV160390
source                     1..248
                           mol_type = protein
                           organism = synthetic construct
SEQUENCE: 93
DTLCIGYHAN NSTDTVDTVL EKNVTVTHSV NLLEDEPGDK YVCSTKLRLA TGLRNKPSKQ    60
SQGLFGAIAG FTEGGWTGMV DGWYGYHHQN EQGSGYAADL KSTQNAIDEI TNKVNSVIEK   120
MNTQPTAIGC EYNKSEQCMK QIEDKIEEIE SKIWCYNAEL LVLLENQRTL DYHDANVKNL   180
YEKVRSQLKN NAKEIGNGCF EFYHKCDNTC MESVKNGTYD YPKYSEEAKL NREEIDGVKL   240
ESTRIYQI                                                            248

SEQ ID NO: 94              moltype = AA  length = 247
FEATURE                    Location/Qualifiers
REGION                     1..247
                           note = UFV160391
source                     1..247
                           mol_type = protein
                           organism = synthetic construct
SEQUENCE: 94
DTLCIGYHAN NSTDTVDTVL EKNVTVTHSV NLLEDEPGKY VCSTKLRLAT GLRNKPSKQS    60
QGLFGAIAGF TEGGWTGMVD GWYGYHHQNE QGSGYAADLK STQNAIDEIT NKVNSVIEKM   120
NTQPTAIGCE YNKSEQCMKQ IEDKIEEIES KIWCYNAELL VLLENQRTLD YHDANVKNLY   180
```

EKVRSQLKNN AKEIGNGCFE FYHKCDNTCM ESVKNGTYDY PKYSEEAKLN REEIDGVKLE    240
STRIYQI                                                              247

SEQ ID NO: 95           moltype = AA  length = 248
FEATURE                 Location/Qualifiers
REGION                  1..248
                        note = UFV160392
source                  1..248
                        mol_type = protein
                        organism = synthetic construct
SEQUENCE: 95
DTLCIGYHAN NSTDTVDTVL EKNVTVTHSV NLLEDTGNLK YVCSTKLRLA TGLRNKPSKQ    60
SQGLFGAIAG FTEGGWTGMV DGWYGYHHQN EQGSGYAADL KSTQNAIDEI TNKVNSVIEK    120
MNTQPTAIGC EYNKSEQCMK QIEDKIEEIE SKIWCYNAEL LVLLENQRTL DYHDANVKNL    180
YEKVRSQLKN NAKEIGNGCF EFYHKCDNTC MESVKNGTYD YPKYSEEAKL NREEIDGVKL    240
ESTRIYQI                                                             248

SEQ ID NO: 96           moltype = AA  length = 248
FEATURE                 Location/Qualifiers
REGION                  1..248
                        note = UFV160393
source                  1..248
                        mol_type = protein
                        organism = synthetic construct
SEQUENCE: 96
DTLCIGYHAN NSTDTVDTVL EKNVTVTHSV NLLEDTPSSK YVCSTKLRLA TGLRNKPSKQ    60
SQGLFGAIAG FTEGGWTGMV DGWYGYHHQN EQGSGYAADL KSTQNAIDEI TNKVNSVIEK    120
MNTQPTAIGC EYNKSEQCMK QIEDKIEEIE SKIWCYNAEL LVLLENQRTL DYHDANVKNL    180
YEKVRSQLKN NAKEIGNGCF EFYHKCDNTC MESVKNGTYD YPKYSEEAKL NREEIDGVKL    240
ESTRIYQI                                                             248

SEQ ID NO: 97           moltype = AA  length = 247
FEATURE                 Location/Qualifiers
REGION                  1..247
                        note = UFV160394
source                  1..247
                        mol_type = protein
                        organism = synthetic construct
SEQUENCE: 97
DTLCIGYHAN NSTDTVDTVL EKNVTVTHSV NLLEDTPSKY VCSTKLRLAT GLRNKPSKQS    60
QGLFGAIAGF TEGGWTGMVD GWYGYHHQNE QGSGYAADLK STQNAIDEIT NKVNSVIEKM    120
NTQPTAIGCE YNKSEQCMKQ IEDKIEEIES KIWCYNAELL VLLENQRTLD YHDANVKNLY    180
EKVRSQLKNN AKEIGNGCFE FYHKCDNTCM ESVKNGTYDY PKYSEEAKLN REEIDGVKLE    240
STRIYQI                                                              247

SEQ ID NO: 98           moltype = AA  length = 248
FEATURE                 Location/Qualifiers
REGION                  1..248
                        note = UFV160395
source                  1..248
                        mol_type = protein
                        organism = synthetic construct
SEQUENCE: 98
DTLCIGYHAN NSTDTVDTVL EKNVTVTHSV NLLEDATGNK YVCSTKLRLA TGLRNKPSKQ    60
SQGLFGAIAG FTEGGWTGMV DGWYGYHHQN EQGSGYAADL KSTQNAIDEI TNKVNSVIEK    120
MNTQPTAIGC EYNKSEQCMK QIEDKIEEIE SKIWCYNAEL LVLLENQRTL DYHDANVKNL    180
YEKVRSQLKN NAKEIGNGCF EFYHKCDNTC MESVKNGTYD YPKYSEEAKL NREEIDGVKL    240
ESTRIYQI                                                             248

SEQ ID NO: 99           moltype = AA  length = 248
FEATURE                 Location/Qualifiers
REGION                  1..248
                        note = UFV160396
source                  1..248
                        mol_type = protein
                        organism = synthetic construct
SEQUENCE: 99
DTLCIGYHAN NSTDTVDTVL EKNVTVTHSV NLLEDYPGDK YVCSTKLRLA TGLRNKPSKQ    60
SQGLFGAIAG FTEGGWTGMV DGWYGYHHQN EQGSGYAADL KSTQNAIDEI TNKVNSVIEK    120
MNTQPTAIGC EYNKSEQCMK QIEDKIEEIE SKIWCYNAEL LVLLENQRTL DYHDANVKNL    180
YEKVRSQLKN NAKEIGNGCF EFYHKCDNTC MESVKNGTYD YPKYSEEAKL NREEIDGVKL    240
ESTRIYQI                                                             248

SEQ ID NO: 100          moltype = AA  length = 246
FEATURE                 Location/Qualifiers
REGION                  1..246
                        note = UFV160397

| source | 1..246 |
| --- | --- |
| | mol_type = protein |
| | organism = synthetic construct |

SEQUENCE: 100

```
DTLCIGYHAN NSTDTVDTVL EKNVTVTHSV NLLEDYPGDV CSTKLRLATG LRNKPSKQSQ    60
GLFGAIAGFT EGGWTGMVDG WYGYHHQNEQ GSGYAADLKS TQNAIDEITN KVNSVIEKMN   120
TQPTAIGCEY NKSEQCMKQI EDKIEEIESK IWCYNAELLV LLENQRTLDY HDANVKNLYE   180
KVRSQLKNNA KEIGNGCFEF YHKCDNTCME SVKNGTYDYP KYSEEAKLNR EEIDGVKLES   240
TRIYQI                                                             246
```

| SEQ ID NO: 101 | moltype = AA   length = 251 |
| --- | --- |
| FEATURE | Location/Qualifiers |
| REGION | 1..251 |
| | note = UFV160503 |
| source | 1..251 |
| | mol_type = protein |
| | organism = synthetic construct |

SEQUENCE: 101

```
DTLCIGYHAN NSTDTVDTVL EKNVTVTHSV NLLEDGGGGK YVCSTKLRLA TGLRNKPSKQ    60
SRKRRGLFGA IAGFTEGGWT GMVDGWYGYH HQNEQGSGYA ADLKSTQNAI DEITNKVNSV   120
IEKMNTQRTA IGCEYNKSER CMKQIEDKIE EIESKIWCYN AELLVLLENQ RTLEYHDSNV   180
KNLYEKVRSQ LKNNAKEIGN GCFEFYHKCD NTCMESVKNG TYDYPKYSEE AKLNREEIDG   240
VKLESTRIYQ I                                                       251
```

| SEQ ID NO: 102 | moltype = AA   length = 252 |
| --- | --- |
| FEATURE | Location/Qualifiers |
| REGION | 1..252 |
| | note = UFV160504 |
| source | 1..252 |
| | mol_type = protein |
| | organism = synthetic construct |

SEQUENCE: 102

```
DTLCIGYHAN NSTDTVDTVL EKNVTVTHSV NLLEDGGGGK YVCSTKLRLA TGLRNKPQRE    60
RRRKKRGLFG AIAGFTEGGW TGMVDGWYGY HHQNEQGSGY AADLKSTQNA IDEITNKVNS   120
VIEKMNTQRT AIGCEYNKSE RCMKQIEDKI EEIESKIWCY NAELLVLLEN QRTLEYHDSN   180
VKNLYEKVRS QLKNNAKEIG NGCFEFYHKC DNTCMESVKN GTYDYPKYSE EAKLNREEID   240
GVKLESTRIY QI                                                      252
```

| SEQ ID NO: 103 | moltype = AA   length = 245 |
| --- | --- |
| FEATURE | Location/Qualifiers |
| REGION | 1..245 |
| | note = UFV160655 |
| source | 1..245 |
| | mol_type = protein |
| | organism = synthetic construct |

SEQUENCE: 103

```
DTICIGYHAN NSTDTVDTVL EKNVTVTHSV NLLENSKYVC SAKLRMVTGL RNKPSKQSQG    60
LFGAIAGFTE GGWTGMVDGW YGYHHQNEQG SGYAADQKST QNAINGITNK VNSVIEKMNT   120
QPTAIGCEYN KSEQCMKQIE DKIEEIESKI WCYNAELLVL LENQRTLDFH DANVKNLYEK   180
VKSQLKNNAK EIGNGCFEFY HKCNDECMES VKNGTYDYPK YSEESKLNRE KIDGVKLESM   240
GVYQI                                                              245
```

| SEQ ID NO: 104 | moltype = AA   length = 245 |
| --- | --- |
| FEATURE | Location/Qualifiers |
| REGION | 1..245 |
| | note = UFV160656 |
| source | 1..245 |
| | mol_type = protein |
| | organism = synthetic construct |

SEQUENCE: 104

```
DTLCIGYHAN NSTDTVDTVL EKNVTVTHSV NLLEDKKYVC STKLRLATGL RNKPSKQSQG    60
LFGAIAGFTE GGWTGMVDGW YGYHHQNEQG SGYAADLKST QNAIDEITNK VNSVIEKMNT   120
QPTAIGCEYN KSEQCMKQIE DKIEEIESKI WCYNAELLVL LENQRTLDYH DANVKNLYEK   180
VRSQLKNNAK EIGNGCFEFY HKCDNTCMES VKNGTYDYPK YSEEAKLNRE EIDGVKLEST   240
RIYQI                                                              245
```

| SEQ ID NO: 105 | moltype = AA   length = 251 |
| --- | --- |
| FEATURE | Location/Qualifiers |
| REGION | 1..251 |
| | note = UFV160657 |
| source | 1..251 |
| | mol_type = protein |
| | organism = synthetic construct |

SEQUENCE: 105

```
DTLCIGYHAN NSTDTVDTVL EKNVTVTHSV NLLEDKHNGK LGKYVCSTKL RLATGLRNKP    60
SKQSQGLFGA IAGFTEGGWT GMVDGWYGYH HQNEQGSGYA ADLKSTQNAI DEITNKVNSV   120
IEKMNTQPTA IGCEYNKSEQ CMKQIEDKIE EIESKIWCYN AELLVLLENQ RTLDYHDANV   180
KNLYEKVRSQ LKNNAKEIGN GCFEFYHKCD NTCMESVKNG TYDYPKYSEE AKLNREEIDG   240
VKLESTRIYQ I                                                       251
```

```
SEQ ID NO: 106          moltype = AA  length = 245
FEATURE                 Location/Qualifiers
REGION                  1..245
                        note = UFV160658
source                  1..245
                        mol_type = protein
                        organism = synthetic construct
SEQUENCE: 106
DTLCIGYHAN NSTDTVDTVL EKNVTVTHSV NLLEDKKYVC STKLRLATGL RNKPSKQSQG    60
LFGAIAGFTE GGWTGMVDGW YGYHHQNEQG SGYAADLKST QNAIDEITNK VNSVIEKMNT   120
QRTAIGCEYN KSERCMKQIE DKIEEIESKI WCYNAELLVL LENQRTLEYH DSNVKNLYEK   180
VRSQLKNNAK EIGNGCFEFY HKCDNTCMES VKNGTYDYPK YSEEAKLNRE EIDGVKLEST   240
RIYQI                                                               245

SEQ ID NO: 107          moltype = AA  length = 251
FEATURE                 Location/Qualifiers
REGION                  1..251
                        note = UFV160659
source                  1..251
                        mol_type = protein
                        organism = synthetic construct
SEQUENCE: 107
DTLCIGYHAN NSTDTVDTVL EKNVTVTHSV NLLEDKHNGK LGKYVCSTKL RLATGLRNKP    60
SKQSQGLFGA IAGFTEGGWT GMVDGWYGYH HQNEQGSGYA ADLKSTQNAI DEITNKVNSV   120
IEKMNTQRTA IGCEYNKSER CMKQIEDKIE EIESKIWCYN AELLVLLENQ RTLEYHDSNV   180
KNLYEKVRSQ LKNNAKEIGN GCFEFYHKCD NTCMESVKNG TYDYPKYSEE AKLNREEIDG   240
VKLESTRIYQ I                                                        251

SEQ ID NO: 108          moltype = AA  length = 248
FEATURE                 Location/Qualifiers
REGION                  1..248
                        note = UFV160663
source                  1..248
                        mol_type = protein
                        organism = synthetic construct
SEQUENCE: 108
DTLCIGYHAN NSTDTVDTVL EKNVTVTHSV NLLEDGGGGK YVCSTKLRLA TGLRNKPSKQ    60
SQGLFGAIAG FTEGGWTGMV DGWYGYHHQN EQGSGYAADL KSTQNAIDEI TNKVNSVIEK   120
MNTQRTAIGC EYNKSERCMK QIEDKIEEIE SKIWCYNAEL LVLLENQRTL DYHDSNVKNL   180
YEKVRSQLKN NAKEIGNGCF EFYHKCDNTC MESVKNGTYD YPKYSEEAKL NREEIDGVKL   240
ESTRIYQI                                                            248

SEQ ID NO: 109          moltype = AA  length = 245
FEATURE                 Location/Qualifiers
REGION                  1..245
                        note = UFV160664
source                  1..245
                        mol_type = protein
                        organism = synthetic construct
SEQUENCE: 109
DTLCIGYHAN NSTDTVDTVL EKNVTVTHSV NLLEDKKYVC STKLRLATGL RNKPSKQSQG    60
LFGAIAGFTE GGWTGMVDGW YGYHHQNEQG SGYAADLKST QNAIDEITNK VNSVIEKMNT   120
QRTAIGCEYN KSERCMKQIE DKIEEIESKI WCYNAELLVL LENQRTLDYH DSNVKNLYEK   180
VRSQLKNNAK EIGNGCFEFY HKCDNTCMES VKNGTYDYPK YSEEAKLNRE EIDGVKLEST   240
RIYQI                                                               245

SEQ ID NO: 110          moltype = AA  length = 245
FEATURE                 Location/Qualifiers
REGION                  1..245
                        note = UFV160665
source                  1..245
                        mol_type = protein
                        organism = synthetic construct
SEQUENCE: 110
DTLCIGYHAN NSTDTVDTVL EKNVTVTHSV NLLEDKKYVC STKLRLATGL RNKPSKQSQG    60
LFGAIAGFTE GGWTGMVDGW YGYHHQNEQG SGYAADLKST QNAIDEITNK VNSVIEKMNT   120
QPTAIGCEYN KSERCMKQIE DKIEEIESKI WCYNAELLVL LENQRTLDYH DSNVKNLYEK   180
VRSQLKNNAK EIGNGCFEFY HKCDNTCMES VKNGTYDYPK YSEEAKLNRE EIDGVKLEST   240
RIYQI                                                               245

SEQ ID NO: 111          moltype = AA  length = 251
FEATURE                 Location/Qualifiers
REGION                  1..251
                        note = UFV160666
source                  1..251
                        mol_type = protein
                        organism = synthetic construct
```

```
SEQUENCE: 111
DTLCIGYHAN NSTDTVDTVL EKNVTVTHSV NLLEDKHNGK LGKYVCSTKL RLATGLRNKP    60
SKQSQGLFGA IAGFTEGGWT GMVDGWYGYH HQNEQGSGYA ADLKSTQNAI DEITNKVNSV   120
IEKMNTQRTA IGCEYNKSER CMKQIEDKIE EIESKIWCYN AELLVLLENQ RTLDYHDSNV   180
KNLYEKVRSQ LKNNAKEIGN GCFEFYHKCD NTCMESVKNG TYDYPKYSEE AKLNREEIDG   240
VKLESTRIYQ I                                                       251

SEQ ID NO: 112         moltype = AA  length = 251
FEATURE                Location/Qualifiers
REGION                 1..251
                       note = UFV160667
source                 1..251
                       mol_type = protein
                       organism = synthetic construct
SEQUENCE: 112
DTLCIGYHAN NSTDTVDTVL EKNVTVTHSV NLLEDKHNGK LGKYVCSTKL RLATGLRNKP    60
SKQSQGLFGA IAGFTEGGWT GMVDGWYGYH HQNEQGSGYA ADLKSTQNAI DEITNKVNSV   120
IEKMNTQPTA IGCEYNKSER CMKQIEDKIE EIESKIWCYN AELLVLLENQ RTLDYHDSNV   180
KNLYEKVRSQ LKNNAKEIGN GCFEFYHKCD NTCMESVKNG TYDYPKYSEE AKLNREEIDG   240
VKLESTRIYQ I                                                       251

SEQ ID NO: 113         moltype = AA  length = 6
FEATURE                Location/Qualifiers
REGION                 1..6
                       note = His-tag
source                 1..6
                       mol_type = protein
                       organism = synthetic construct
SEQUENCE: 113
HHHHHH                                                               6

SEQ ID NO: 114         moltype = AA  length = 7
FEATURE                Location/Qualifiers
REGION                 1..7
                       note = His-tag
source                 1..7
                       mol_type = protein
                       organism = synthetic construct
SEQUENCE: 114
HHHHHHH                                                              7

SEQ ID NO: 115         moltype = AA  length = 8
FEATURE                Location/Qualifiers
REGION                 1..8
                       note = FLAG tag
source                 1..8
                       mol_type = protein
                       organism = synthetic construct
SEQUENCE: 115
DYKDDDDK                                                             8

SEQ ID NO: 116         moltype = AA  length = 4
FEATURE                Location/Qualifiers
REGION                 1..4
                       note = proteolytic cleavage site
source                 1..4
                       mol_type = protein
                       organism = synthetic construct
SEQUENCE: 116
IEGR                                                                 4

SEQ ID NO: 117         moltype = AA  length = 6
FEATURE                Location/Qualifiers
REGION                 1..6
                       note = proteolytic cleavage site
source                 1..6
                       mol_type = protein
                       organism = synthetic construct
SEQUENCE: 117
LVPRGS                                                               6

SEQ ID NO: 118         moltype = AA  length = 27
FEATURE                Location/Qualifiers
REGION                 1..27
                       note = foldon
source                 1..27
                       mol_type = protein
                       organism = synthetic construct
```

```
SEQUENCE: 118
GYIPEAPRDG QAYVRKDGEW VLLSTFL                                          27

SEQ ID NO: 119          moltype = AA  length = 54
FEATURE                 Location/Qualifiers
REGION                  1..54
                        note = Flag - Foldon - His tag
source                  1..54
                        mol_type = protein
                        organism = synthetic construct
SEQUENCE: 119
SGRDYKDDDD KLVPRGSPGS GYIPEAPRDG QAYVRKDGEW VLLSTFLGHH HHHH             54

SEQ ID NO: 120          moltype = AA  length = 53
FEATURE                 Location/Qualifiers
REGION                  1..53
                        note = FLAG- GS linker - His tag
source                  1..53
                        mol_type = protein
                        organism = synthetic construct
SEQUENCE: 120
SGRDYKDDDD KPGGGGSGGG GSGGGGSGGG GSGGGGSGGG GSGGGGSHHH HHH              53

SEQ ID NO: 121          moltype = AA  length = 218
FEATURE                 Location/Qualifiers
REGION                  1..218
                        note = Nanoluc - Strep tag
source                  1..218
                        mol_type = protein
                        organism = synthetic construct
SEQUENCE: 121
EGRAAAGGSG GGGSMVFTLE DFVGDWRQTA GYNLDQVLEQ GGVSSLFQNL GVSVTPIQRI       60
VLSGENGLKI DIHVIIPYEG LSGDQMGQIE KIFKVVYPVD DHHFKVILHY GTLVIDGVTP      120
NMIDYFGRPY EGIAVFDGKK ITVTGTLWNG NKIIDERLIN PDGSLLFRVT INGVTGWRLC      180
ERILAAAAWS HPQFEKGAAW SHPQFEKGAA WSHPQFEK                              218

SEQ ID NO: 122          moltype = AA  length = 192
FEATURE                 Location/Qualifiers
REGION                  1..192
                        note = Nanoluc - C tag
source                  1..192
                        mol_type = protein
                        organism = synthetic construct
SEQUENCE: 122
EGRAAAGGSG GGGSMVFTLE DFVGDWRQTA GYNLDQVLEQ GGVSSLFQNL GVSVTPIQRI       60
VLSGENGLKI DIHVIIPYEG LSGDQMGQIE KIFKVVYPVD DHHFKVILHY GTLVIDGVTP      120
NMIDYFGRPY EGIAVFDGKK ITVTGTLWNG NKIIDERLIN PDGSLLFRVT INGVTGWRLC      180
ERILAGAAEP EA                                                          192

SEQ ID NO: 123          moltype = AA  length = 19
FEATURE                 Location/Qualifiers
REGION                  1..19
                        note = Sortase - C tag
source                  1..19
                        mol_type = protein
                        organism = synthetic construct
SEQUENCE: 123
EGRAAALPET GGGAAEPEA                                                    19

SEQ ID NO: 124          moltype = AA  length = 77
FEATURE                 Location/Qualifiers
REGION                  1..77
                        note = FLAG - GS linker - Strep tag
source                  1..77
                        mol_type = protein
                        organism = synthetic construct
SEQUENCE: 124
SGRDYKDDDD KPGGGGSGGG GSGGGGSGGG GSGGGGSGGG GSGGGGSWSH PQFEKGAAWS       60
HPQFEKGAAW SHPQFEK                                                      77

SEQ ID NO: 125          moltype = AA  length = 81
FEATURE                 Location/Qualifiers
REGION                  1..81
                        note = Myc tag - GS linker - Strep tag
source                  1..81
                        mol_type = protein
                        organism = synthetic construct
```

```
SEQUENCE: 125
EGRAAAEQKL ISEEDLGGGG SGGGGSGGGG SGGGGSGGGG SGGGGSGGGG SWSHPQFEKG    60
AAWSHPQFEK GAAWSHPQFE K                                              81

SEQ ID NO: 126          moltype = AA  length = 20
FEATURE                 Location/Qualifiers
REGION                  1..20
                        note = B-loop
source                  1..20
                        mol_type = protein
                        organism = synthetic construct
SEQUENCE: 126
IEKMNTQYTA IGKEYNKSER                                                20

SEQ ID NO: 127          moltype = AA  length = 20
FEATURE                 Location/Qualifiers
REGION                  1..20
                        note = B-loop
source                  1..20
                        mol_type = protein
                        organism = synthetic construct
SEQUENCE: 127
IEKMNTQYTA IGCEYNKSER                                                20

SEQ ID NO: 128          moltype = AA  length = 20
FEATURE                 Location/Qualifiers
REGION                  1..20
                        note = B-loop
source                  1..20
                        mol_type = protein
                        organism = synthetic construct
SEQUENCE: 128
IEKMNTQPTA IGCEYNKSEQ                                                20

SEQ ID NO: 129          moltype = AA  length = 20
FEATURE                 Location/Qualifiers
REGION                  1..20
                        note = B-loop
source                  1..20
                        mol_type = protein
                        organism = synthetic construct
SEQUENCE: 129
IEKMNTQRTA IGCEFNKSEQ                                                20

SEQ ID NO: 130          moltype = AA  length = 20
FEATURE                 Location/Qualifiers
REGION                  1..20
                        note = B-loop
source                  1..20
                        mol_type = protein
                        organism = synthetic construct
SEQUENCE: 130
IEKMNTQPTA IGCEYNKSER                                                20

SEQ ID NO: 131          moltype = AA  length = 20
FEATURE                 Location/Qualifiers
REGION                  1..20
                        note = B-loop
source                  1..20
                        mol_type = protein
                        organism = synthetic construct
SEQUENCE: 131
IEKMNTQPTA IGCEFNKSEQ                                                20

SEQ ID NO: 132          moltype = AA  length = 20
FEATURE                 Location/Qualifiers
REGION                  1..20
                        note = B-loop
source                  1..20
                        mol_type = protein
                        organism = synthetic construct
SEQUENCE: 132
IEKMNTQRTA IGCEYNKSER                                                20

SEQ ID NO: 133          moltype = AA  length = 20
FEATURE                 Location/Qualifiers
REGION                  1..20
                        note = B-loop
```

```
source                  1..20
                        mol_type = protein
                        organism = synthetic construct
SEQUENCE: 133
IEKMNTQRTA ICKEYPKSEQ                                                    20

SEQ ID NO: 134          moltype = AA  length = 20
FEATURE                 Location/Qualifiers
REGION                  1..20
                        note = B-loop
source                  1..20
                        mol_type = protein
                        organism = synthetic construct
SEQUENCE: 134
IEKMNTQRTA IGKECNKSER                                                    20

SEQ ID NO: 135          moltype = AA  length = 248
FEATURE                 Location/Qualifiers
REGION                  1..248
                        note = UFV150553
source                  1..248
                        mol_type = protein
                        organism = synthetic construct
SEQUENCE: 135
DTICIGYHAN NSTDTVDTVL EKNVTVTHSV NLLENGGGGK YVCSAKLRMV TGLRNKPSKQ          60
SQGLFGAIAG FTEGGWTGMV DGWYGYHHQN EQGSGYAADQ KSTQNAINGI TNKVNSVIEK         120
MNTQRTAIGC EFNKSEQCMK QIEDKIEEIE SKIWCYNAEL LVLLENQRTL DFHDSNVKNL         180
YEKVKSQLKN NAKEIGNGCF EFYHKCNDEC MESVKNGTYD YPKYSEESKL NREKIDGVKL         240
ESMGVYQI                                                                248

SEQ ID NO: 136          moltype = AA  length = 19
FEATURE                 Location/Qualifiers
REGION                  1..19
                        note = signal peptide
source                  1..19
                        mol_type = protein
                        organism = synthetic construct
SEQUENCE: 136
MGSTAILGLL LAVLQGVCA                                                     19

SEQ ID NO: 137          moltype = AA  length = 21
FEATURE                 Location/Qualifiers
REGION                  1..21
                        note = signal peptide
source                  1..21
                        mol_type = protein
                        organism = synthetic construct
SEQUENCE: 137
MGMTSALLAL LALALKPGAW A                                                  21

SEQ ID NO: 138          moltype = DNA  length = 792
FEATURE                 Location/Qualifiers
misc_feature            1..792
                        note = UFV160655
source                  1..792
                        mol_type = other DNA
                        organism = synthetic construct
SEQUENCE: 138
atgaaagtca aactgctggt cctgctgtgc accttcaccg ccacttacgc cgacaccatc         60
tgtattgggt accacgctaa caactccacc gacacagtgg ataccgtgct ggagaagaac        120
gtgaccgtga cacactctgt gaaccctctg gagaattcca agtacgtctg cagcgccaag        180
ctgaggatgg tgacaggcct gagaaataag cccagcaagc agtcccaggg cctgttcgga        240
gcaatcgcag gctttaccga gggaggatgg acaggaatgg tggacggatg gtacggctat        300
caccaccaga acgagcaggg ctccggctat gccgccgatc agaagtctac ccagaacgcc        360
atcaatggca tcacaaacaa ggtcaatagc gtgatcgaga gatgaacac ccagcctaca        420
gccatcggct gcgagtacaa taagtccgag cagtgcatga agcagatcga ggacaagatc        480
gaggagatcg agtctaagat ctggtgctat aacgccgagc tgctggtgct gctcgagaat        540
cagaggaccc tggacttcca cgatgccaac gtgaagaatc tgtacgagaa ggtgaagtcc        600
cagctgaaga caatgccaa ggagatcggc aacggctgtt tcgagtttta ccacaagtgc        660
aacgacgagt gtatggagtc cgtgaagaat ggcacatacg attatcctaa gtattctgag        720
gagagcaaac tgaatcggga aaaaatcgat ggcgtgaaac tggaatcaat ggggggtgtat        780
cagatctaat aa                                                            792

SEQ ID NO: 139          moltype = DNA  length = 792
FEATURE                 Location/Qualifiers
misc_feature            1..792
                        note = UFV160656
```

| | | |
|---|---|---|
| source | 1..792 | |
| | mol_type = other DNA | |
| | organism = synthetic construct | |

SEQUENCE: 139
```
atgaaggcca tcctggtggt gctgctgtac accttcgcca cagccaacgc cgacaccctg   60
tgcatcgggt accacgccaa caattccacc gacacagtgg atacagtgct ggagaagaat  120
gtgaccgtga cacactccgt gaacctgctg gaggataaga agtacgtctg cagcaccaag  180
ctgaggctgg ccacaggcct gagaaacaag ccaagcaagc agtcccaggg cctgttcgga  240
gccatcgccg gctttaccga gggaggatgg acaggaatgg tggacggatg gtacggctat  300
caccaccaga acgagcaggg cagcggatac gccgccgacc tgaagtccac ccagaatgcc  360
atcgacgaga ttaccaacaa ggtcaatagc gtgattgaga agatgaacac ccagcccaca  420
gccatcggct gcgagtacaa taagagcgag cagtgtatga agcagattga ggataagatt  480
gaggagattg agtccaagat ttggtgctat aacgccgagc tgctggtgct gctcgagaat  540
cagaggaccc tggactacca cgatgccaac gtgaagaatc tgtatgagaa ggtgaggagc  600
cagctgaaga acaatgccaa ggagattggc aacggctgtt tcgagtttta ccacaagtgc  660
gacaacacct gtatggagtc tgtgaagaat ggcacatacg attatcccaa gtatagcgag  720
gaggccaagc tgaatcggga ggaaatcgat ggcgtgaagc tggagagcac ccgcatctac  780
cagatctaat aa                                                      792
```

| | | |
|---|---|---|
| SEQ ID NO: 140 | moltype = DNA   length = 792 | |
| FEATURE | Location/Qualifiers | |
| misc_feature | 1..792 | |
| | note = UFV160664 | |
| source | 1..792 | |
| | mol_type = other DNA | |
| | organism = synthetic construct | |

SEQUENCE: 140
```
atgaaggcca tcctggtcgt cctgctgtac actttcgcca ccgccaacgc tgataccctg   60
tgcatcgggt accacgctaa caactctacc gacacagtgg ataccgtgct ggagaagaac  120
gtgaccgtga cacactctgt gaatctgctg gaggataaga agtacgtctg cagcaccaag  180
ctgaggctgg ccacaggcct gagaaacaag cccagcaagc agagccaggg cctgtttgga  240
gcaattgcag gctttaccga gggcggctgg acaggcatgg tggatggctg gtacggctat  300
caccaccaga atgagcaggg atctggatat gctgctgacc tgaagtctac ccagaatgcc  360
attgatgaga tcacaaacaa ggtcaatagc gtgatcgaga agatgaacac ccagcggaca  420
gccatcggct gcgagtacaa taagtccgag aggtgcatga agcagatcga ggacaagatc  480
gaggagatcg agtctaagat ctggtgctat aacgccgagc tgctggtgct gctcgagaat  540
cagcggaccc tggactacca cgacagcaac gtgaagaatc tgtatgagaa ggtgcgctcc  600
cagctgaaga acaatgccaa ggagatcggc aacggctgtt tcgagtttta ccacaagtgc  660
gacaacacct gtatggagtc tgtgaagaat ggcacatacg attatcccaa gtatagcgag  720
gaggccaagc tgaatgggga ggaaatcgat ggcgtgaagc tggagtctac aagaatctac  780
cagatctaat aa                                                      792
```

| | | |
|---|---|---|
| SEQ ID NO: 141 | moltype = DNA   length = 792 | |
| FEATURE | Location/Qualifiers | |
| misc_feature | 1..792 | |
| | note = UFV160665 | |
| source | 1..792 | |
| | mol_type = other DNA | |
| | organism = synthetic construct | |

SEQUENCE: 141
```
atgaaggcca tcctggtcgt cctgctgtac actttcgcca ccgccaacgc tgataccctg   60
tgcatcgggt accacgctaa caactctacc gacacagtgg ataccgtgct ggagaagaac  120
gtgaccgtga cacactctgt gaatctgctg gaggataaga agtacgtctg cagcaccaag  180
ctgaggctgg ccacaggcct gagaaacaag cccagcaagc agagccaggg cctgtttgga  240
gcaattgcag gctttaccga gggcggctgg acaggcatgg tggatggctg gtacggctat  300
caccaccaga atgagcaggg atctggatat gctgctgacc tgaagtctac ccagaatgcc  360
attgatgaga tcacaaacaa ggtcaatagc gtgatcgaga agatgaacac ccagcctaca  420
gccatcggct gcgagtacaa taagtccgag aggtgcatga agcagatcga ggacaagatc  480
gaggagatcg agtctaagat ctggtgctat aacgccgagc tgctggtgct gctcgagaat  540
cagcggaccc tggactacca cgacagcaac gtgaagaatc tgtatgagaa ggtgcgctcc  600
cagctgaaga acaatgccaa ggagatcggc aacggctgtt tcgagtttta ccacaagtgc  660
gacaacacct gtatggagtc tgtgaagaat ggcacatacg attatcccaa gtatagcgag  720
gaggccaagc tgaataggga ggaaatcgat ggcgtgaagc tggagtctac aagaatctac  780
cagatctaat aa                                                      792
```

| | | |
|---|---|---|
| SEQ ID NO: 142 | moltype = DNA   length = 900 | |
| FEATURE | Location/Qualifiers | |
| misc_feature | 1..900 | |
| | note = UFV171588 | |
| source | 1..900 | |
| | mol_type = other DNA | |
| | organism = synthetic construct | |

SEQUENCE: 142
```
atgaaggtca aactgctggt cctgctgtgc acttttactg ccacctacgc tgacactatc   60
tgtatcgggt accacgcaaa caactcaacc gacacagtgg ataccgtgct ggagaagaac  120
gtgaccgtga cacactccgt gaacctgctg gagaatagca agtacgtctg cagcgccaag  180
ctgcggatgt gcacaggcct gagaaataag ccctctaagc agagccaggg actgttcgga  240
gcaatcgcag gctttaccga gggaggatgg acaggaatgg tggacggatg gtacggctat  300
caccaccaga acgagcaggg cagcggctat gccgccgatc agagtccac ccagaacgcc  360
```

```
atcaatggca tcacaaacaa ggtgaacagc gtgatcgaga agatgaacac ccagcctaca   420
gccatcggct gcgagtataa taagagcgag cagtgtatga agcagatcga ggacaagatc   480
gaggagatcg agtccaagat ctggtgctac aacgccgagc tgctggtgct gctggagaat   540
cagcgcaccc tggacttcca cgatgccaac gtgaagaatc tgtatgagaa ggtgaagagc   600
cagctgaaga acaatgccaa ggagatcggc aacggctgtt tcgagtttta ccacaagtgc   660
aacgacgagt gtatggagag cgtgaagaat ggcacctacg attatcctaa gtattccgag   720
gagtctaagc tgaatcggga gaaaatcgat ggcgtgaagc tggagtccat gggcgtgtac   780
cagatcctgg ccatctattc tacagtggcc agctccctgg tgctgctggt gagcctgggg   840
gctatttcat tctggatgtg ctctaacggc tctctccagt gtcgcatttg tatctgataa   900

SEQ ID NO: 143           moltype = DNA  length = 900
FEATURE                  Location/Qualifiers
misc_feature             1..900
                         note = UFV171589
source                   1..900
                         mol_type = other DNA
                         organism = synthetic construct
SEQUENCE: 143
atgaaggcca ttctggtcgt gctgctgtac actttcgcca ccgctaacgc tgacaccctg   60
tgcatcgggt accacgccaa taactccacc gacacagtgg ataccgtgct ggagaagaac   120
gtgaccgtga cacactctgt gaatctgctg gaggacaaga agtacgtctg cagcaccaag   180
ctgaggctgg ccacaggcct gagaaacaag ccctctaagc agagccaggg cctgttcgga   240
gcaatcgcag gctttaccga gggaggatgg acaggcatgg tggatggctg gtacggctat   300
caccaccaga acgagcaggg atccggatat gccgccgacc tgaagtctac ccagaatgcc   360
atcgacgaga tcacaaacaa ggtcaattct gtgatcgaga agatgaacac ccagcctaca   420
gccatcggct gcgagtacaa taagagcgag cagtgtatga agcagatcga ggacaagatc   480
gaggagatcg agtccaagat ctggtgctat aacgccgagc tgctggtgct gctggagaat   540
cagaggaccc tggactacca cgatgccaac gtgaagaatc tgtatgagaa ggtgcggtcc   600
cagctgaaga acaatgccaa ggagatcggc aacggctgtt tcgagtttta ccacaagtgc   660
gacaacacct gtatggagtc cgtgaagaat ggcacatacg attatcccaa gtattccgag   720
gaggccaagc tgaatcggga ggaaatcgat ggcgtgaagc tggagtctac ccgcatctac   780
cagatcctgg ccatctatag cacagtggcc agctccctgg tgctggtggt gtccctgggg   840
gctatctctt tctggatgtg ctcaaatggg tccctccagt gtcgcatctg tatctgataa   900

SEQ ID NO: 144           moltype = DNA  length = 900
FEATURE                  Location/Qualifiers
misc_feature             1..900
                         note = UFV171590
source                   1..900
                         mol_type = other DNA
                         organism = synthetic construct
SEQUENCE: 144
atgaaggcca ttctggtcgt gctgctgtac actttcgcca ccgctaacgc tgacaccctg   60
tgcatcgggt accacgccaa taactccacc gacacagtgg ataccgtgct ggagaagaac   120
gtgaccgtga cacactctgt gaatctgctg gaggacaaga agtacgtctg cagcaccaag   180
ctgaggctgg ccacaggcct gagaaacaag ccctctaagc agagccaggg cctgttcgga   240
gcaatcgcag gctttaccga gggaggatgg acaggcatgg tggatggctg gtacggctat   300
caccaccaga acgagcaggg atccggatat gccgccgacc tgaagtctac ccagaatgcc   360
atcgacgaga tcacaaacaa ggtcaattct gtgatcgaga agatgaacac ccagaggaca   420
gccatcggct gcgagtacaa taagagcgag aggtgtatga agcagatcga ggacaagatc   480
gaggagatcg agtccaagat ctggtgctat aacgccgagc tgctggtgct gctggagaat   540
cagaggaccc tggactacca cgatagcaac gtgaagaatc tgtatgagaa ggtgcggtcc   600
cagctgaaga acaatgccaa ggagatcggc aacggctgtt tcgagtttta ccacaagtgc   660
gacaacacct gtatggagtc cgtgaagaat ggcacatacg attatcccaa gtattctgag   720
gaggccaagc tgaatcggga ggaaatcgat ggcgtgaagc tggagtctac ccgcatctac   780
cagatcctgg ccatctatag cacagtggcc agctccctgg tgctggtggt gtccctgggg   840
gctatctctt tctggatgtg ctcaaatggg tccctccagt gtcgcatctg tatctgataa   900

SEQ ID NO: 145           moltype = DNA  length = 900
FEATURE                  Location/Qualifiers
misc_feature             1..900
                         note = UFV171591
source                   1..900
                         mol_type = other DNA
                         organism = synthetic construct
SEQUENCE: 145
atgaaggcca ttctggtcgt gctgctgtac actttcgcca ccgctaacgc tgacaccctg   60
tgcatcgggt accacgccaa taactccacc gacacagtgg ataccgtgct ggagaagaac   120
gtgaccgtga cacactctgt gaatctgctg gaggacaaga agtacgtctg cagcaccaag   180
ctgaggctgg ccacaggcct gagaaacaag ccctctaagc agagccaggg cctgttcgga   240
gcaatcgcag gctttaccga gggaggatgg acaggcatgg tggatggctg gtacggctat   300
caccaccaga acgagcaggg atccggatat gccgccgacc tgaagtctac ccagaatgcc   360
atcgacgaga tcacaaacaa ggtcaattct gtgatcgaga agatgaacac ccagcctaca   420
gccatcggct gcgagtacaa taagagcgag aggtgtatga agcagatcga ggacaagatc   480
gaggagatcg agtccaagat ctggtgctat aacgccgagc tgctggtgct gctggagaat   540
cagaggaccc tggactacca cgatagcaac gtgaagaatc tgtatgagaa ggtgcggtcc   600
cagctgaaga acaatgccaa ggagatcggc aacggctgtt tcgagtttta ccacaagtgc   660
gacaacacct gtatggagtc cgtgaagaat ggcacatacg attatcccaa gtattctgag   720
gaggccaagc tgaatcggga ggaaatcgat ggcgtgaagc tggagtctac ccgcatctac   780
```

```
cagatcctgg ccatctatag cacagtggcc agctccctgg tgctggtggt gtccctgggg    840
gctatctctt tctggatgtg ctcaaatggg tccctccagt gtcgcatctg tatctgataa    900

SEQ ID NO: 146           moltype = AA  length = 749
FEATURE                  Location/Qualifiers
REGION                   1..749
                         note = MD3606
source                   1..749
                         mol_type = protein
                         organism = synthetic construct
SEQUENCE: 146
EVQLVESGGG LVQPGGSLRL SCAVSISIFD IYAMDWYRQA PGKQRDLVAT SFRDGSTNYA     60
DSVKGRFTIS RDNAKNTLYL QMNSLKPEDT AVYLCHVSLY RDPLGVAGGM GVYWGKGALV    120
TVSSGGGGSG GGGSEVQLVE SGGGLVQAGG SLKLSCAASG RTYAMGWFRQ APGKEREFVA    180
HINALGTRTY YSDSVKGRFT ISRDNAKNTE YLEMNNLKPE DTAVYYCTAQ GQWRAAPVAV    240
AAEYEFWGQG TQVTVSSGGG GSGGGGSEVQ LVESGGGLVQ PGGSLRLSCA ATGFTLENKA    300
IGWFRQTPGS EREGVLCISK SGSWTYYTDS MRGRFTISRD NAENTVYLQM DSLKPEDTAV    360
YYCATTTAGG GLCWDGTTFS RLASSWGQGT QVTVSSGGGG GGGSEVQL VESGGGLVQP      420
GGSLKLSCAA SGFTFSTSWM YWLRQAPGKG LEWVSVINTD GGTYYADSVK DRFTISRDNA    480
KDTLYLQMSS LKSEDTAVYY CAKDWGGPEP TRGQGTQVTV SSDKTHTCPP CPAPELLGGP    540
SVFLFPPKPK DTLMISRTPE VTCVVVDVSH EDPEVKFNWY VDGVEVHNAK TKPREEQYNS    600
TYRVVSVLTV LHQDWLNGKE YKCKVSNKAL PAPIEKTISK AKGQPREPQV YTLPPSREEM    660
TKNQVSLTCL VKGFYPSDIA VEWESNGQPE NNYKTTPPVL DSDGSFFLYS KLTVDKSRWQ    720
QGNVFSCSVM HEALHNHYTQ KSLSLSPGK                                     749

SEQ ID NO: 147           moltype = AA  length = 268
FEATURE                  Location/Qualifiers
REGION                   1..268
                         note = UFV180496 H1 A/California/07/09
source                   1..268
                         mol_type = protein
                         organism = synthetic construct
SEQUENCE: 147
MKAILVVLLY TFATANADTL CIGYHANNST DTVDTVLEKN VTVTHSVNLL EDKKYVCSTK     60
LRLATGLRNK PSKQSQGLFG AIAGFTEGGW TGMVDGWYGY HHQNEQGSGY AADLKSTQNA    120
IDEITNKVNS VIEKMNTQRT AIGCEYNKSE RCMKQIEDKI EEIESKIWCY NAELLVLLEN    180
QRTLDYHDSN VKNLYEKVRS QLKNNAKEIG NGCFEFYHKC DNTCMESVKN GTYDYPKYSE    240
EAKLNREEID GVKLESTRIY QIHHHHHH                                      268

SEQ ID NO: 148           moltype = AA  length = 268
FEATURE                  Location/Qualifiers
REGION                   1..268
                         note = UFV180497 H1 A/Michigan/45/2015
source                   1..268
                         mol_type = protein
                         organism = synthetic construct
SEQUENCE: 148
MKAILVVLLY TFTTANADTL CIGYHANNST DTVDTVLEKN VTVTHSVNLL EDKKYVCSTK     60
LRLATGLRNK PSKQSQGLFG AIAGFTEGGW TGMVDGWYGY HHQNEQGSGY AADLKSTQNA    120
IDKITNKVNS VIEKMNTQRT AIGCEYNKSE KCMKQIEDKI EEIESKIWCY NAELLVLLEN    180
QRTLDYHDSN VKNLYEKVRN QLKNNAKEIG NGCFEFYHKC DNTCMESVKN GTYDYPKYSE    240
EAKLNREKID GVKLESTRIY QIHHHHHH                                      268

SEQ ID NO: 149           moltype = AA  length = 268
FEATURE                  Location/Qualifiers
REGION                   1..268
                         note = UFV180498 H1 A/Puerto Rico/8/1934
source                   1..268
                         mol_type = protein
                         organism = synthetic construct
SEQUENCE: 149
MKANLLVLLC ALAAADADTI CIGYHANNST DTVDTVLEKN VTVTHSVNLL EDSKYVCSAK     60
LRMVTGLRNK PSKQSQGLFG AIAGFTEGGW TGMIDGWYGY HHQNEQGSGY AADQKSTQNA    120
INGITNKVNS VIEKMNIQRT AIGCEYNKSE KCMKQIEDKI EEIESKIWCY NAELLVLMEN    180
QRTLDFHDSN VKNLYEKVKS QLKNNAKEIG NGCFEFYHKC DNECMESVRN GTYDYPKYSE    240
ESKLNREKVD GVKLESMGIY QIHHHHHH                                      268

SEQ ID NO: 150           moltype = AA  length = 267
FEATURE                  Location/Qualifiers
REGION                   1..267
                         note = UFV180499 H5 A/Hong Kong/156/97
source                   1..267
                         mol_type = protein
                         organism = synthetic construct
SEQUENCE: 150
MEKTVLLLAT VSLVKSDQIC IGYHANNSTE QVDTIMEKNV TVTHAQDILE RTKYVCSNRL     60
VLATGLRNKP QKESQGLFGA IAGFTEGGWQ GMVDGWYGYH HSNEQGSGYA ADKESTQKAI    120
DGVTNKVNSI INKMNTQREA IGCEYNKSER CMKQIEDKIE EIESKVWCYN AELLVLMENQ    180
RTLDFHDSNV KNLYDKVRLQ LRDNAKELGN GCFEFYHKCD NECMESVKNG TYDPQYSEE     240
```

-continued

```
ARLNREEISG VKLESMGTYQ IHHHHHH                                267

SEQ ID NO: 151          moltype = AA  length = 267
FEATURE                 Location/Qualifiers
REGION                  1..267
                        note = UFV180500 H5 A/Vietnam/1203/04
source                  1..267
                        mol_type = protein
                        organism = synthetic construct
SEQUENCE: 151
MEKIVLLFAI VSLVKSDQIC IGYHANNSTE QVDTIMEKNV TVTHAQDILE KKKYVCSNRL  60
VLATGLRNKP QKESQGLFGA IAGFTEGGWQ GMVDGWYGYH HSNEQGSGYA ADKESTQKAI  120
DGVTNKVNSI IDKMNTQREA IGCEYNKSER CMKQIEDKIE EIESKVWCYN AELLVLMENQ  180
RTLDFHDSNV KNLYDKVRLQ LRDNAKELGN GCFEFYHKCD NECMESVRNG TYDYPQYSEE  240
ARLKREEISG VKLESIGIYQ IHHHHHH                                267

SEQ ID NO: 152          moltype = AA  length = 266
FEATURE                 Location/Qualifiers
REGION                  1..266
                        note = UFV180501 H2 A/Singapore/1/57
source                  1..266
                        mol_type = protein
                        organism = synthetic construct
SEQUENCE: 152
MAIIYLILLF TAVRGDQICI GYHANNSTEK VDTILERNVT VTHAKDILEK TKYVCSEKLV  60
LATGLRNKPQ KESQGLFGAI AGFTEGGWQG MVDGWYGYHH SNDQGSGYAA DKESTQKAFD  120
GITNKVNSVI EKMNTQREAI GCEYSKSERC MKQIEDKIEE IESKVWCYNA ELLVLMENQR  180
TLDFHDSNVK NLYDKVRMQL RDNVKELGNG CFEFYHKCDD ECMNSVKNGT YDYPKYEEES  240
KLNRNEIKGV KLSSMGVYQI HHHHHH                                 266

SEQ ID NO: 153          moltype = AA  length = 298
FEATURE                 Location/Qualifiers
REGION                  1..298
                        note = UFV171590 (UFV160664+TM)
source                  1..298
                        mol_type = protein
                        organism = synthetic construct
SEQUENCE: 153
MKAILVVLLY TFATANADTL CIGYHANNST DTVDTVLEKN VTVTHSVNLL EDKKYVCSTK  60
LRLATGLRNK PSKQSQGLFG AIAGFTEGGW TGMVDGWYGY HHQNEQGSGY AADLKSTQNA  120
IDEITNKVNS VIEKMNTQRT AIGCEYNKSE RCMKQIEDKI EEIESKIWCY NAELLVLLEN  180
QRTLDYHDSN VKNLYEKVRS QLKNNAKEIG NGCFEFYHKC DNTCMESVKN GTYDYPKYSE  240
EAKLNREEID GVKLESTRIY QILAIYSTVA SSLVLVVSLG AISFWMCSNG SLQCRICI    298

SEQ ID NO: 154          moltype = AA  length = 36
FEATURE                 Location/Qualifiers
REGION                  1..36
                        note = Strep tag
source                  1..36
                        mol_type = protein
                        organism = synthetic construct
SEQUENCE: 154
EGRAAAWSHP QFEKGAAWSH PQFEKGAAWS HPQFEK                      36
```

INFLUENZA VIRUS VACCINES AND USES THEREOF

CROSS-REFERENCE TO RELATED APPLICATION

This application is a Section 371 of International Application No. PCT/EP2019/051532, filed Jan. 22, 2019, which was published in the English language on Aug. 1, 2019, under International Publication No. WO 2019/145310 A1, which claims priority under 35 U.S.C. § 119(b) to EP Application No. 18152991.8, filed Jan. 23, 2018, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing" and a creation date of Jun. 30, 2020 and having a size of 283 kb. The sequence listing submitted via EFS-Web is part of the specification and is herein incorporated by reference in its entirety.

INTRODUCTION

The invention relates to the field of medicine. Provided herein are influenza A hemagglutinin (HA) stem domain polypeptides, nucleic acids encoding said polypeptides, pharmaceutical compositions comprising the same, and methods of their use.

BACKGROUND

Influenza viruses are major human pathogens, causing a respiratory disease (commonly referred to as "influenza" or "the flu") that ranges in severity from sub-clinical infection to primary viral pneumonia which can result in death. The clinical effects of infection vary with the virulence of the influenza strain and the exposure, history, age, and immune status of the host. Every year it is estimated that approximately 1 billion people worldwide undergo infection with influenza virus, leading to severe illness in 3-5 million cases and an estimated 300,000 to 500,000 of influenza related deaths. The bulk of these infections can be attributed to influenza A viruses carrying H1 or H3 hemagglutinin subtypes, with a smaller contribution from Influenza B viruses, and therefore representatives of these are typically included in the seasonal vaccine. The current immunization practice relies on early identification of circulating influenza viruses to allow for timely production of an effective seasonal influenza vaccine. Apart from the inherent difficulties in predicting the strains that will be dominant during the next season, antiviral resistance and immune escape also play a role in failure of current vaccines to prevent morbidity and mortality. In addition, the possibility of a pandemic caused by a highly virulent viral strain originating from animal reservoirs and reassorted to increase human to human spread, still poses a significant and realistic threat to global health.

Influenza viruses are enveloped RNA viruses that belong to the family of Orthomyxoviridae. Their genomes consist of eight single-stranded RNA segments that code for 11 different proteins, one nucleoprotein (NP), three polymerase proteins (PA, PB1, and PB2), two matrix proteins (M1 and M2), three non-structural proteins (NS1, NS2, and PB1-F2), and two external glycoproteins: hemagglutinin (HA) and neuraminidase (NA).

Influenza A viruses are widely distributed in nature and can infect a variety of birds and mammals. The viruses are classified on the basis of differences in antigenic structure of the HA and NA proteins, with their different combinations representing unique virus subtypes that are further classified into specific influenza virus strains. Although all known subtypes can be found in birds, currently circulating human influenza A subtypes are H1N1 and H3N2. Phylogenetic analysis of influenza A viruses has demonstrated a subdivision of hemagglutinins into two main, so-called phylogenetic groups: inter alia the H1, H2, H5 and H9 subtypes in phylogenetic group 1 (the group 1 viruses) and inter alia the H3, H4 and H7 subtypes in phylogenetic group 2 (group 2 viruses).

The influenza type B virus strains are strictly human. The antigenic variation in HA within the influenza type B virus strains is smaller than those observed within the type A strains. Two genetically and antigenically distinct lineages of influenza B virus are circulating in humans, as represented by the B/Yamagata/16/88 (also referred to as B/Yamagata) and B/Victoria/2/87 (B/Victoria) lineages. Although the spectrum of disease caused by influenza B viruses is generally milder than that caused by influenza A viruses, severe illness requiring hospitalization is still frequently observed with influenza B infection.

It is known that antibodies that neutralize the influenza virus are primarily directed against hemagglutinin (HA). Hemagglutinin or HA is a trimeric glycoprotein that is anchored in the viral membrane and has a dual function: it is responsible for binding to the cell surface receptor sialic acid and, after uptake, it mediates the fusion of viral and endosomal membrane leading to the release of viral RNA into the cytosol of the target cell. HA comprises a large head domain and a smaller stem domain. The stem domain is anchored in to the viral membrane via a C-terminal transmembrane domain sequence. The protein is post-translationally cleaved to yield two HA polypeptides, HA1 and HA2 (the full sequence is referred to as HA0) (FIG. 1A). The membrane distal head region is mainly derived from HA1 and the membrane proximal stem region primarily from HA2. Cleavage of the HA precursor molecule HA0 is required to activate virus infectivity, and the distribution of activating proteases in the host is one of the determinants of pathogenicity of the influenza virus. The HAs of mammalian and nonpathogenic avian viruses are cleaved extracellularly, which limits their spread in hosts to tissues where the appropriate proteases are encountered. On the other hand, the HAs of pathogenic viruses are cleaved intracellularly by ubiquitously occurring proteases and therefore have the capacity to infect various cell types and cause systemic infections.

The reason that the seasonal influenza vaccine must be updated every year is the large variability of the virus. In the HA protein this variation is particularly manifested in the head domain where antigenic drift and shift have resulted in a large number of different variants. Since this is also the area that is immunodominant, most neutralizing antibodies are directed against this domain and act by interfering with receptor binding. The combination of immunodominance and large variation of the head domain explains why infection with a particular strain does not lead to immunity to other strains: the antibodies elicited by the first infection only recognize a limited number of strains closely related to the virus of the primary infection.

Recently, influenza hemagglutinin stem polypeptides, lacking the complete influenza hemagglutinin globular head domain or a substantial part of it, have been described and have been used to generate an immune response to one or more conserved epitopes of the stem domain polypeptide. It is believed that epitopes of the stem polypeptide are less immunogenic than the highly immunogenic regions of a globular head domain, and that the absence of a globular head domain in the stem polypeptide might allow an immune response against one or more epitopes of the stem polypeptide to develop (Steel et al., 2010). Steel et al. thus created an influenza HA stem polypeptide by deleting amino acid residue 53 to 276 from the HA1 domain of the A/Puerto Rico/8/1934 (H1N1) and A/Hong Kong/1968 (H3N2) strains and replacing the deleted sequence by a short flexible linking sequence GGGG. Vaccination of mice with the H3 HK68 construct did not elicit antisera that were cross-reactive with group 1 HAs. In addition, as shown in WO2013/079473, the stem polypeptides were unstable and did not adopt the correct conformation as proven by the lack of binding of antibodies that were shown to bind to conserved epitopes in the stem region.

Bommakanti et al. (2010) described an HA2 based polypeptide comprising amino acid residues 330-501 (HA2), a 7-amino acid linker (GSAGSAG), amino acid residues 16-55 of HAL a 6-amino acid linker GSAGSA, followed by residues 290-321 of HAL with the mutations V297T, I300E, Y302T and C305T in HAL The design was based on the sequence of H3 HA (A/Hong Kong/1968). The polypeptide did only provide cross-protection against another influenza virus strain within the H3 subtype (A/Phil/2/82 but not against an H1 subtype (A/PR/8/34). In a more recent paper by Bommakanti et al. (2012), a stem polypeptide based on HA from H1N1 A/Puerto Rico/8/1934 (H1HA0HA6) was described. In this polypeptide, the equivalent of amino acid residues 48 to 288 have been deleted and mutations I297T, V300T, I302N, C305S, F392D, F395T, and L402D have been made. Both the H3 and H1 based polypeptides were expressed in *E. coli* and therefore lack the glycans that are part of the naturally occurring HA proteins.

More recently, Lu et al. (2014) also described soluble stem polypeptides derived from the HA of H1N1 A/California/05/2009. In the final design, the amino acid residues from 52 to 277 were deleted (the leader sequence is also not present) and two mutations were introduced in the B-loop of the protein, i.e. F392D, and L402D. Furthermore, the polypeptide contained a C-terminal trimerization domain (foldon). In addition, two intermonomer disulfide bridges were introduced, one in the area of the trimeric foldon domain, and one at position 416 and 417 (i.e. G416C and F417C in H3 numbering). The polypeptide was produced in an *E. coli* based cell free system, (and thus lacks the glycans that are part of the naturally occurring HA proteins) and was recovered in a denatured form, which needs to be refolded prior to use. The refolded protein failed to bind the broadly neutralizing antibody (bnAb) CR6261 which is binding to a conserved conformational stem epitope. No immunological or protection data from influenza challenge were shown.

In another paper Mallajosyula et al. (2014) also described an influenza HA stem polypeptide. In this design, based on HA from H1N1 A/Puerto Rico/8/1934, not only a large part of the HA1 sequence was deleted (residue 48 to 289, H3 numbering), but also large part of the N- and C-terminal sequences of HA2 (residues 323 to 369 and 443 to end, respectively). The polypeptide contained a foldon trimerization domain at the C-terminus and was also produced in *E. coli*, so is lacking the naturally occurring glycans on viral HA. The polypeptide was shown to bind the bnAbs CR6261, F10 and FI6v3, and protected mice from a leathal influenza virus challenge (1LD90 of H1N1 A/Puerto Rico/8/1934). Equivalent polypeptides derived from HA of H1N1 A/New Caledonia/20/1999 and H1N1 A/California/04/2009 could also partially protect. A polypeptide derived from H5N1 A/Viet Nam/1203/2004 only gave limited protection in this challenge model. Moreover, the challenge model used was mild with a relatively low dose administered (1-2 LD90).

Lastly, Yassine et al. (2015) also described the development of a stabilized HA stem polypeptide derived from HA of H1N1 A/New Caledonia/20/1999. In this design, a large part of the HA1 sequence (residue 43 to 313, H3 numbering) and HA2 sequence (residue 504 to end) have been deleted. In addition, the design contains two stabilizing mutations (K380M and E432L) in HA2 and is genetically fused to the ferritin subunit of *H. pylori* to create self-assembling nanoparticles displaying the stabilized HA-stem polypeptide. The stabilized HA-stem polypeptide seemed not soluble or functional without being fused to the ferritin subunit. The HA stem-ferritin polypeptide assembled to nanoparticles was tested in a heterosubtypic H5N1 2004 VN influenza virus challenge model ($25 \times LD_{50}$ and $1,000 \times TCID_{50}$ in mouse and ferrets, respectively) and could protect mice from death whereas only partial protection was observed in ferrets. It is unclear how much ferritin response would be induced in humans and which effect that would have for multiple administrations.

There thus still exists a need for a safe and effective "universal" vaccine that stimulates the production of a robust, broadly neutralizing antibody response and that offers protection against a broad set of current and future influenza virus strains (both seasonal and pandemic), in particular a vaccine that provides protection against one or more influenza A virus subtypes within phylogenetic group 1 and/or group 2, for the effective prevention and/or treatment of influenza.

SUMMARY

The present invention provides novel polypeptides derived from influenza hemagglutinin (HA), which polypeptides comprise the influenza HA stem domain and lack the globular head region, herein referred to as influenza hemagglutinin (HA) stem polypeptides. The polypeptides induce an immune response against HA when administered to a subject, in particular a human subject. The polypeptides of the invention present conserved epitopes of the membrane proximal stem of the HA molecule to the immune system in the absence of dominant epitopes that are present in the membrane distal head domain. Thus, part of the primary sequence of the HA0 protein, i.e. the part making up the head domain has been deleted, and the remaining amino acid sequence has been reconnected, either directly or, in some embodiments, by introducing a short flexible linking sequence ('linker') to restore the continuity of the amino acid chain. The resulting amino acid sequence is further modified by introducing specific modifications that stabilize the native 3-dimensional structure of the remaining part of the HA molecule.

In a first aspect, the present invention relates to group 1 influenza A hemagglutinin (HA) stem polypeptides comprising an HA1 and an HA2 domain, said polypeptides comprising an amino acid sequence which comprises, as compared to the amino acid sequence of a full-length HA polypeptide comprising an HA1 and an HA2 domain:

(i) a deletion of the head region in the HA1 domain;
(ii) a modification of the trimerization region in the HA2 domain, preferably a modification in the C-helix,
(iii) at least 2 cysteine residues (capable of) forming an intramonomeric disulphide bridge;
(iv) at least 2 cysteine residues (capable of) forming an intermonomeric disulphide bridge;

wherein the amino acid corresponding to the amino acid at position 392 is P, R or Y, preferably P or R, and the amino acid corresponding to the amino acid at position 434 is Q, and wherein the numbering of the amino acid positions is based on H3 numbering as used in Winter et al. (1981).

In certain embodiments, the present invention relates to group 1 influenza A hemagglutinin (HA) stem polypeptides comprising an HA1 and an HA2 domain, wherein said HA stem polypeptides comprise an amino acid sequence which comprises, as compared to the amino acid sequence of the full-length HA polypeptide (HA0) comprising an HA1 and an HA2 domain:

(i) a deletion of the head region in the HA1 domain, said deletion comprising at least the amino acid sequence from the amino acid corresponding to the amino acid at position 53 up to and including the amino acid corresponding to the amino acid at position 302;
(ii) a modification of the trimerization region in the HA2 domain, preferably a modification of the trimerization region in the C-helix, said trimerization region comprising the amino acid sequence from the amino acid corresponding to the amino acid at position 405 up to and including the amino acid corresponding to the amino acid at position 419;
(iii) a cysteine at the amino acid position corresponding to position 310 and a cysteine at the position corresponding to position 422 (capable of) forming an intramonomeric disulphide bridge;
(iv) a cysteine at the position corresponding to position 397 in combination with a cysteine at the position corresponding to position 405; or a cysteine at the position corresponding to position 396 in combination with a cysteine at the position corresponding to position 408; or a cysteine at the position corresponding to position 399 in combination with a cysteine at position 405;
wherein the amino acid at the position corresponding to position 392 is P, R or Y, preferably P or R, and wherein the amino acid at the position corresponding to position 434 is Q; and wherein the numbering of the amino acid positions is based on H3 numbering as used in Winter et al. (1981).

According to the present invention it has surprisingly been shown that the novel influenza HA stem polypeptides of the invention can be expressed in high levels, are overwhelmingly trimeric in cell culture supernatant, have an increased melting temperature which leads to greater stability. In addition, the HA stem polypeptides of the invention mimick the stem of the full-length HA by stably presenting the epitope of HA stem binding bnAbs, such as CR9114 and/or CR6261.

In a further aspect, the present invention provides nucleic acid molecules encoding the influenza HA stem polypeptides.

In yet another aspect, the invention provides vectors, in particular recombinant adenoviral vectors, comprising the nucleic acids encoding the influenza HA stem polypeptides.

In a further aspect, the invention provides methods for inducing an immune response against influenza HA in a subject in need thereof, the method comprising administering to the subject an influenza HA stem polypeptide, a nucleic acid molecule, and/or a vector according to the invention.

In another aspect, the invention provides pharmaceutical compositions comprising an influenza HA stem polypeptide, a nucleic acid molecule and/or a vector according to the invention, and a pharmaceutically acceptable carrier.

In a further aspect, the invention provides influenza HA stem polypeptides, nucleic acid molecules encoding said influenza HA stem polypeptides, and/or vectors comprising said nucleic acid molecules for use as a medicament, in particular for use as a vaccine for the prevention and/or treatment of a disease or condition caused by an influenza virus A strain from phylogenetic group 1 and/or 2 and/or an influenza B virus strain.

BRIEF DESCRIPTION OF THE FIGURES

FIG. 8. Schematic representation of the HA head domain (HA1) removal. In the parental design, the head domain is removed and the two HA1 ends are connected by an artificial "GGGG-linker" (left panel). In the polypeptides of the invention the ends are directly connected (alternative cutting position) or by means of a homologous linker sequence originating from the head domain.

FIG. 14: Numbering of amino acid positions in H1 A/California/07/09 and in UFV160664, according to H3 numbering of Winter et al. (1981).

FIG. 28: In vitro characterization of culture supernatants of EXPI-CHO expressed trimeric stem polypeptides derived from different Group 1 influenza strains wherein the mutations of the UFV160664 construct were transferred. A. Protein expression levels as determined by OCTET (anti-His2); B. SEC profiles, trimer and monomer peak indicated with respectively 'T' and 'M'; C. Binding curves of the polypeptides to mAb CR9114 and MD3606 as determined by AlphaLISA. The mutations of the trimeric stem polypeptide of the invention in strain A/California/07/09) are transferrable to other Group 1 backbones; trimeric mini-HA is expressed and binding of stem specific antibody CR9114 and multidomain MD3606 is observed.

DEFINITIONS

Figure 1:
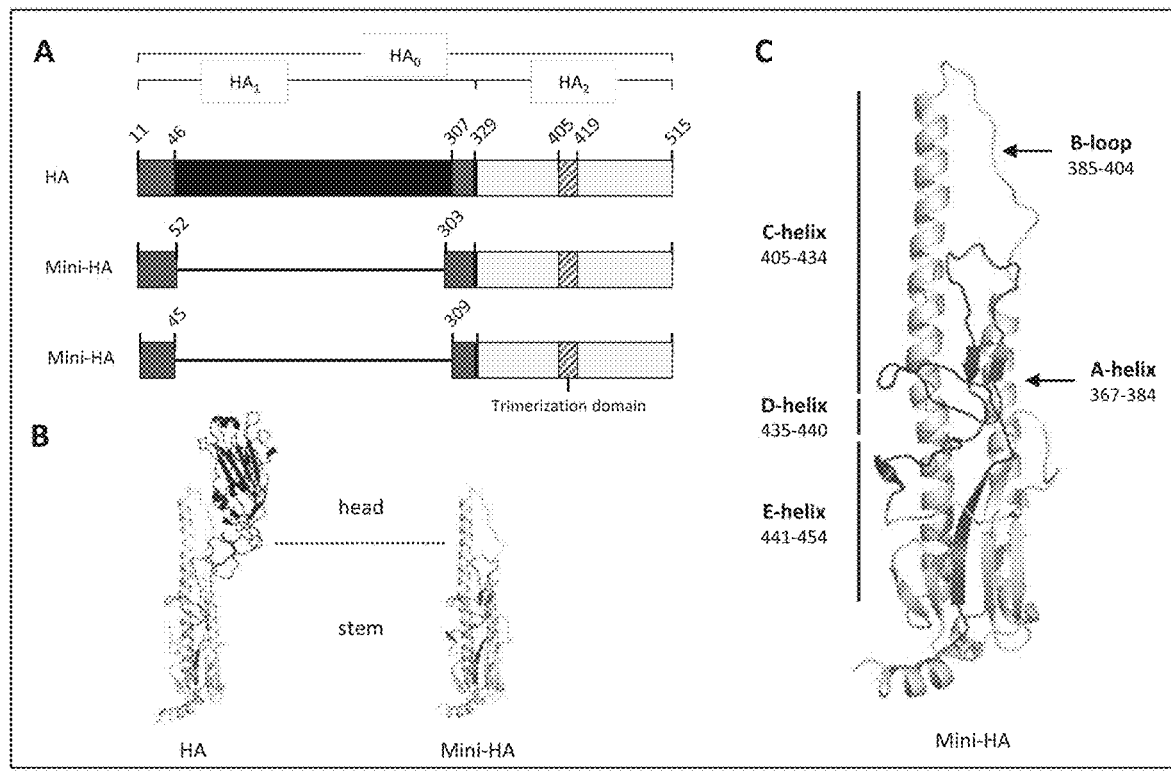
FIG. 1. A. Schematic overview of the polypeptides of the invention; B. Removal of the head region of HA results in the stem polypeptides of the invention (mini-HA); C. Three-dimensional representation of a stem-based polypeptide of the invention.

Definitions of terms as used in the present invention are given below.

An amino acid according to the invention can be any of the twenty naturally occurring (or 'standard' amino acids) or variants thereof, such as e.g. D-proline (the D-enantiomer of proline), or any variants that are not naturally found in proteins, such as e.g. norleucine. The standard amino acids can be divided into several groups based on their properties. Important factors are charge, hydrophilicity or hydrophobicity, size and functional groups. These properties are important for protein structure and protein-protein interactions. Some amino acids have special properties such as cysteine, that can form covalent disulfide bonds (or disulfide bridges) to other cysteine residues, proline that forms a cycle to the polypeptide backbone, and glycine that is more flexible than other amino acids. Table 12 shows the abbreviations and properties of the standard amino acids.

The term "included" or "including" as used herein is deemed to be followed by the words "without limitation".

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In certain embodiments, an infection refers to the pathological state resulting from the presence of the virus in a cell or a subject, or by the invasion of a cell or subject by the virus.

Influenza viruses are typically classified into influenza virus types: genus A, B and C. The term "influenza virus subtype" as used herein refers to influenza A virus variants that are characterized by combinations of the hemagglutinin (H) and neuramidase (N) viral surface proteins. According to the present invention influenza virus subtypes may be referred to by their H number, such as for example "influenza virus comprising HA of the H3 subtype", "influenza virus of the H3 subtype" or "H3 influenza", or by a combination of a H number and an N number, such as for example "influenza virus subtype H3N2" or "H3N2". The term "subtype" specifically includes all individual "strains", within each subtype, which usually result from mutations and show different pathogenic profiles, including natural isolates as well as man-made mutants or reassortants and the like. Such strains may also be referred to as various "isolates" of a viral subtype. Accordingly, as used herein, the terms "strains" and "isolates" may be used interchangeably. The current nomenclature for human influenza virus strains or isolates includes the type (genus) of virus, i.e. A, B or C, the geographical location of the first isolation, strain number and year of isolation, usually with the antigenic description of HA and NA given in brackets, e.g. A/Moscow/10/00 (H3N2). Non-human strains also include the host of origin in the nomenclature.

The influenza A virus subtypes can further be classified by reference to their phylogenetic group. Phylogenetic analysis has demonstrated a subdivision of hemagglutinins into two main groups: inter alia the H1, H2, H5 and H9 subtypes in phylogenetic group 1 ("group 1" influenza viruses) and inter alia the H3, H4, H7 and H10 subtypes in phylogenetic group 2 ("group 2" influenza viruses).

As used herein, the term "influenza virus disease" or "influenza" refers to the pathological condition resulting from the presence of an influenza virus, e.g. an influenza A or B virus, in a subject. As used herein, the terms "disease" and "disorder" are used interchangeably. In specific embodiments, the term refers to a respiratory illness caused by the infection of the subject by the influenza virus.

As used herein, the term "nucleic acid" or "nucleic acid molecule" is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for anti-sense therapy, hybridization probes and PCR primers.

Figure 2:
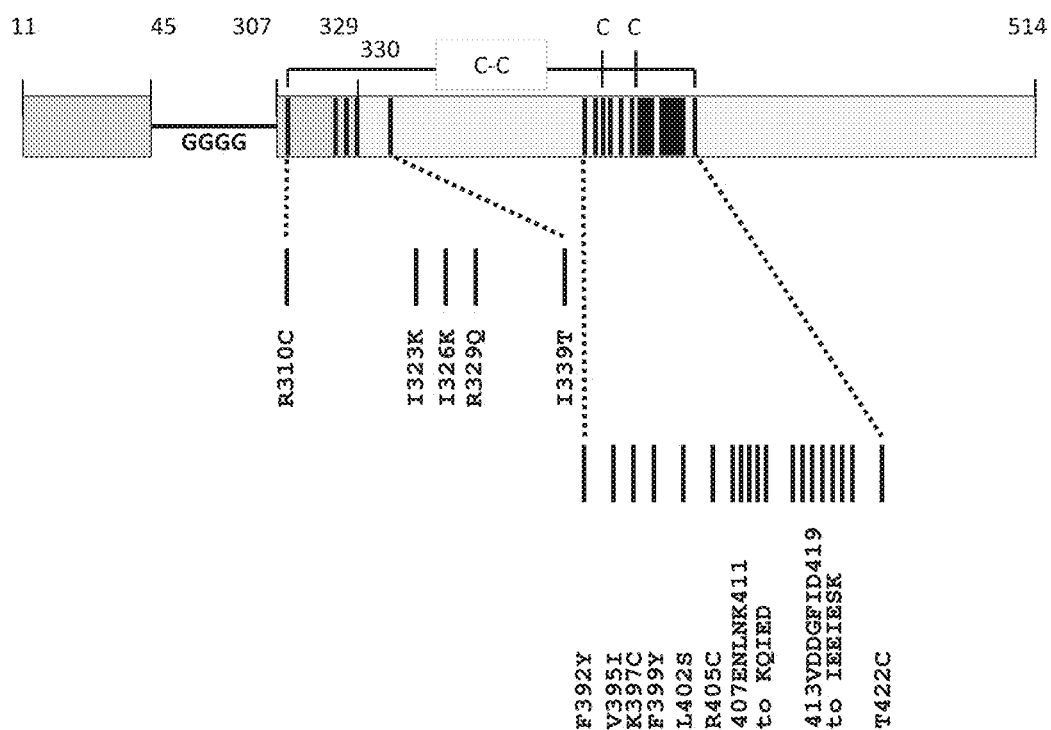
FIG. 2. Schematic drawing of the A/Brisbane based parental construct 5367.
Figure 14:
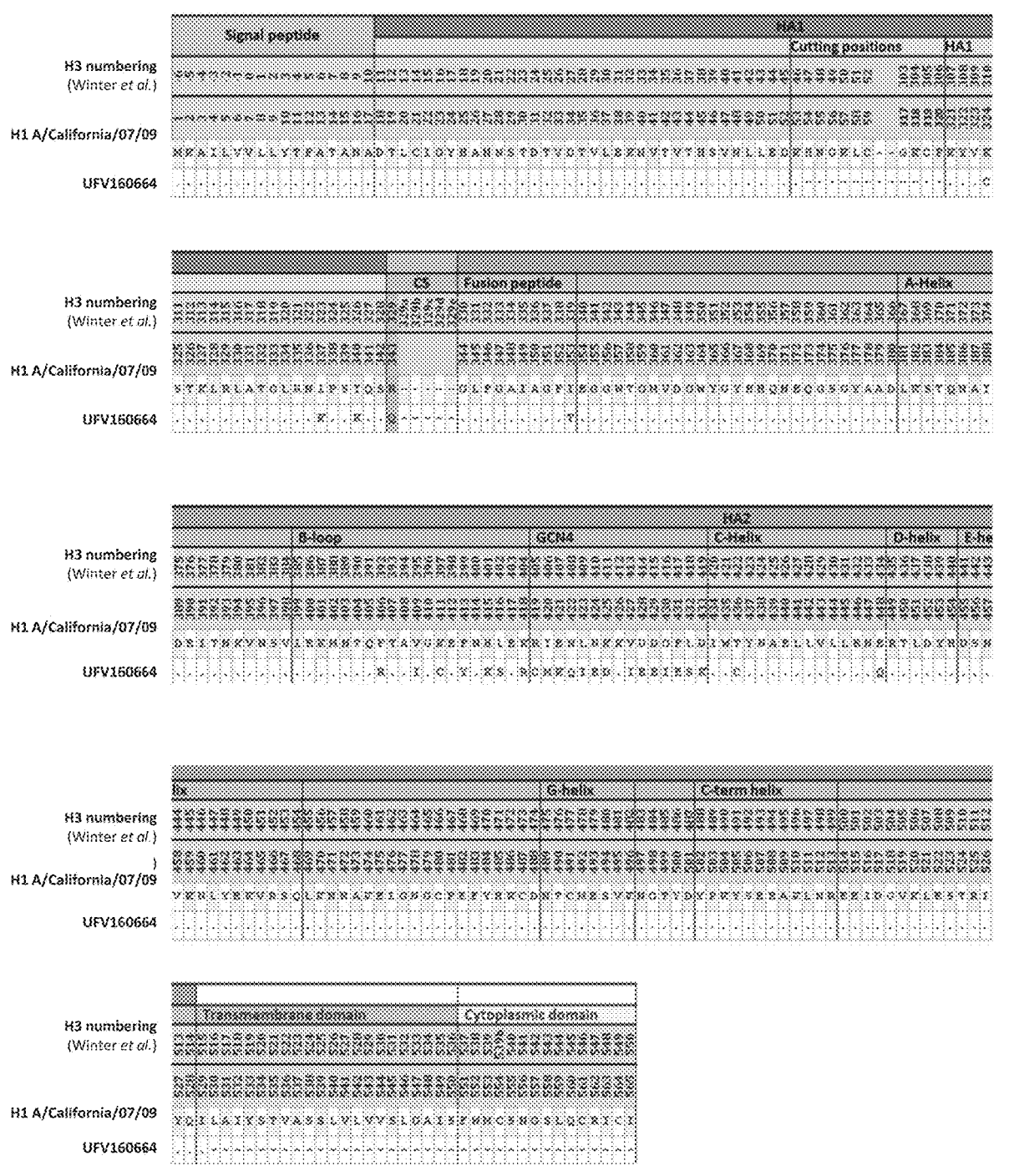

As used herein, the numbering of the amino acids in HA is based on H3 numbering, as described by Winter et al. (1981). The numbering of the amino acid residues or amino acid positions thus refers to the numbering in the full length H3 HA (in particular, the numbering of amino acid positions in A/Aichi/2/68), as described by and shown in FIG. 2 in Winter et al. (1981). The numbering in particular refers to the numbering of the amino acid positions in SEQ ID NO: 15. For example, the wording 'the amino acid at position 392" or "the amino acid corresponding to the amino acid at position 392" (which are used interchangeably throughout this application) refers to the amino acid residue that is at position 392 according to the H3 numbering of Winter et al. (1981). It is noted that, because in the polypeptides of the invention part of the HA1 domain (the head domain) has been deleted, the numbering, as used herein, does not necessarily refer to the actual positions of the amino acids in the HA stem polypeptides of the invention. It will furthermore be understood by the skilled person that equivalent amino acids in other influenza virus strains and/or subtypes, such as in H1 HA, and in the stem polypeptides of the invention, can be determined by sequence alignment (as shown e.g in FIG. 14).

"Polypeptide" refers to a polymer of amino acids linked by amide bonds as is known to those of skill in the art. As used herein, the term can refer to a single polypeptide chain linked by covalent amide bonds. The term can also refer to multiple polypeptide chains associated by non-covalent interactions such as ionic contacts, hydrogen bonds, Van der Waals contacts and hydrophobic contacts. Those of skill in the art will recognize that the term includes polypeptides that have been modified, for example by post-translational processing such as signal peptide cleavage, disulfide bond formation, glycosylation (e.g., N-linked and O-linked glycosylation), protease cleavage and lipid modification (e.g. S-palmitoylation).

"HA stem polypeptide" refers to a HA derived polypeptide which does not comprise the head domain of a naturally-occurring (or wild-type) hemagglutinin (HA). As used herein, the term "wild-type" refers to HA from influenza viruses that are circulating naturally.

DETAILED DESCRIPTION

Influenza viruses have a significant impact on global public health, causing millions of cases of severe illness each year, thousands of deaths, and considerable economic losses. Current trivalent or quidrivalent influenza vaccines elicit a potent neutralizing antibody response to the vaccine strains and closely related isolates, but rarely extend to more diverged strains within a subtype or to other subtypes. In addition, selection of the appropriate vaccine strains presents many challenges and frequently results in sub-optimal protection. Furthermore, predicting the subtype of the next pandemic virus, including when and where it will arise, is currently still impossible.

Hemagglutinin (HA) is the major envelope glycoprotein from influenza viruses which is the major target of neutralizing antibodies. Hemagglutinin has two main functions during the entry process. First, hemagglutinin mediates attachment of the virus to the surface of target cells through interactions with sialic acid receptors. Second, after endocytosis of the virus, hemagglutinin subsequently triggers the fusion of the viral and endosomal membranes to release its genome into the cytoplasm of the target cell. HA comprises a large ectodomain of ~500 amino acids that is cleaved by host-derived enzymes to generate 2 polypeptides (HA1 and HA2) that remain linked by a disulfide bond. The majority of the N-terminal fragment (the HA1 domain, 320-330 amino acids) forms a membrane-distal globular "head domain" that contains the receptor-binding site and most determinants recognized by virus-neutralizing antibodies. The smaller C-terminal portion (HA2 domain, ~180 amino acids) forms a stem-like structure that anchors the globular domain to the cellular or viral membrane. The degree of sequence identity between subtypes is smaller in the HA1 polypeptides (34%-59% identity between subtypes) than in the HA2 polypeptide (51%-80% identity). The most conserved region is the sequence around the protease cleavage site, particularly the HA2 N-terminal 23 amino acids, which is conserved among all influenza A virus subtypes (Lorieau et al., 2010). Part of this region is exposed as a surface loop in the HA precursor molecule (HA0), but becomes inaccessible when HA0 is cleaved into HA1 and HA2.

Most neutralizing antibodies bind to the loops that surround the receptor binding site and thereby interfere with receptor binding and attachment. Since these loops are highly variable, most antibodies targeting these regions are strain-specific, explaining why current vaccines elicit such limited, strain-specific immunity. Recently, however, fully human monoclonal antibodies against influenza virus hemagglutinin with broad cross-neutralizing potency were generated, such as e.g. CR6261. Functional and structural analysis have revealed that these antibodies interfere with the membrane fusion process and are directed against highly conserved epitopes in the stem domain of group 1 influenza HA protein (Throsby et al., 2008; Ekiert et al. 2009, WO 2008/028946). With the identification of CR9114 (as described in WO2013/007770) which cross-reacts with many group 1 and 2 HA molecules, it has become clear that it is possible for the human immune system to elicit very broad neutralizing antibodies against influenza viruses. However, given the need for a yearly vaccination scheme these antibodies are apparently not elicited, or only to a very low extent, following infection or vaccination with (seasonal) influenza viruses of subtypes H1 and/or H3.

According to the present invention novel HA stem polypeptides are provided that mimic the specific epitopes of the antibody CR6261 (comprising a heavy chain variable region of SEQ ID NO: 11 and a light chain variable region of SEQ ID NO: 12) and/or the antibody CR9114 (comprising a heavy chain variable region of SEQ ID NO: 9 and a light chain variable region of SEQ ID NO: 10). The polypeptides of the invention can be used to elicit influenza virus neutralizing antibodies, preferably cross-neutralizing antibodies when administered in vivo, either alone, or in combination with other prophylactic and/or therapeutic treatments. With "cross-neutralizing antibodies", antibodies are meant that are capable of neutralizing at least two, preferably at least three, four, or five different subtypes of influenza A viruses from phylogenetic group 1, or at least two, preferably at least three, four, or five different subtypes of influenza A viruses from phylogenetic group 2, or at least two different subtypes of influenza B viruses, or antibodies that are capable of neutralizing at least one group 1 influenza virus, and at least one group 2 influenza virus and/or at least on influenza B virus.

Influenza HA stem polypeptides stably presenting the epitopes of these antibodies have previously been described in WO2013/079473. At least some of these HA stem polypeptides were capable of stably presenting the epitope of CR6261 and/or CR9114 and were shown to be immunogenic in mice. Additional HA stem domain polypeptides, capable of stably presenting the epitope of CR6261 and/or CR9114 were described in WO2014/191435, WO2016/005480 and WO2016/005482.

The HA stem polypeptides of the present invention, comprising novel modifications, show an increased level of expression in mammalian cells, an increased propensity to trimerize (e.g. as measured by AlphaLISA) and/or an increased level of thermo-stability (e.g. as measured by, Dynamic Scanning Fluorimetry/Calorimetry (DSF/DSC)), as compared to the previously described HA stem polypeptides. In addition, the affinity of all tested bnAb to the polypeptide of the invention is less than 1 nM (measured by Octet and ELISA), which is similar to the affinity of the antibodies to full-length HA. This clearly shows that the polypeptides mimick the stem of native, full length HA. The novel HA stem polypeptides furthermore do not require any artificial linkers, tags, nor N- or C-terminal trimerization domains.

The present invention thus provides group 1 influenza A hemagglutinin (HA) stem polypeptides comprising an HA1 and an HA2 domain, said polypeptides comprising an amino acid sequence which comprises, as compared to the amino acid sequence of a full-length HA polypeptide (HA0) comprising an HA1 and an HA2 domain:
  (i) a deletion of the head region in the HA1 domain;
  (ii) a modification of the trimerization region in the HA2 domain, preferably a modification in the C-helix,
  (iii) at least 2 cysteine residues forming an intramonomeric disulphide bridge;

(iv) at least 2 cysteine residues forming an intermonomeric disulphide bridge;
wherein the amino acid corresponding to the amino acid at position 392 is P, R or Y, preferably P or R, and the amino acid corresponding to the amino acid at position 434 is Q, and wherein the numbering of the amino acid positions is based on H3 numbering according to Winter et al. (1981).

The present invention thus provides HA stem polypeptides (i.e. headless HA polypeptides), comprising:
a modification of the trimerization region in the HA2 domain, preferably a modification in the C-helix,
at least 2 cysteine residues forming an intramonomeric disulphide bridge;
at least 2 cysteine residues forming an intermonomeric disulphide bridge;
wherein the amino acid corresponding to the amino acid at position 392 is P, R or Y, preferably P or R, and the amino acid corresponding to the amino acid at position 434 is Q, and wherein the numbering of the amino acid positions is based on H3 numbering as used in Winter et al. (1981).

In certain embodiments, the present invention provides group 1 influenza A hemagglutinin (HA) stem polypeptides comprising an HA1 and an HA2 domain, wherein said HA stem polypeptides comprise an amino acid sequence which comprises, as compared to the amino acid sequence of a full-length HA polypeptide (HA0) comprising an HA1 and an HA2 domain comprising an HA1 and an HA2 domain:
(i) a deletion of the head region in the HA1 domain, said deletion comprising at least the amino acid sequence from the amino acid at position 53 up to and including the amino acid at position 302;
(ii) a modification of the trimerization region in the HA2 domain, preferably a modification in the trimerization region in the C-helix, said region comprising the amino acid sequence from the amino acid corresponding to the amino acid at position at position 405 up to and including the amino acid corresponding to the amino acid at position at position 419;
(iii) a cysteine at position 310 and a cysteine at position 422;
(iv) a cysteine at position 397 in combination with a cysteine at position 405; or a cysteine at position 396 in combination with a cysteine at position 408; or a cysteine at position 399 in combination with a cysteine at position 405;
wherein the amino acid corresponding to the amino acid at position 392 is P, R or Y, preferably P or R, and wherein the amino acid corresponding to the amino acid at position 434 is Q; wherein the numbering of the amino acid positions is based on H3 numbering according to Winter et al. (1981).

In certain embodiments, the present invention provides group 1 influenza A hemagglutinin (HA) stem polypeptides comprising:
(i) a deletion of the head region in the HA1 domain, said deletion comprising at least the amino acid sequence from the amino acid at position 53 up to and including the amino acid at position 302;
(ii) a modification of the trimerization region in the HA2 domain, preferably a modification in the trimerization region in the C-helix, said region comprising the amino acid sequence from the amino acid at position 405 up to and including the amino acid at position 419;
(iii) a mutation of the amino acids at positions 310 and 422 into C;
(iv) a mutation of the amino acid at position 397 into C and a mutation of the amino acid at position 405 into C; or a mutation of the amino acid at position 396 into C and a mutation of the amino acid at position 408 into C;
or a mutation of the amino acid at position 399 into C and a mutation of the amino acid at position 405 into C;
wherein the polypeptides further comprise at least one mutation in the B-loop, said B-loop comprising the amino acid sequence from the amino acid at position 385 up to and including the amino acid at position 404, wherein said at least one mutation in the B-loop is a mutation of the amino acid at position 392 into P, R or Y, preferably into P or R; and wherein the polypeptides comprise a mutation of the amino acid at position 434 into Q;
wherein the numbering of the amino acid positions is based on H3 numbering as used in Winter et al. (1981).

According to the present invention, it has surprisingly been found that HA stem polypeptides having the amino acid residue Y, P or R, preferably P or R, at position 392, e.g. by introducing a mutation of the amino acid at position 392 in the B-loop into Y, P or R, preferably into P or R; in combination with the amino acid position Q at position 434, e.g. by introducing a mutation of the amino acid at position 434 into Q, showed increased expression levels, an increased propensity to trimerize and/or an increased stability, compared to the previously described HA stem polypeptides. In addition, the HA stem polypeptides of the invention are capable of inducing an immune response against influenza virus.

As is known to those of skill in the art, a full-length influenza hemagglutinin (HA0) typically comprises an HA1 domain and an HA2 domain. The stem domain is formed by two segments of the HA1 domain and most or all of the HA2 domain. The two segments of the HA1 domain are separated, in the primary sequence, by the globular head domain. As described herein, the HA stem polypeptides of the invention comprise an amino acid sequence which comprises several modifications in the HA1 and/or HA2 domain, as compared to the amino acid sequence of the wild-type, full-length HA polypeptide (HA0), in particular the amino acid sequence of a group 1 HA.

Thus, at least part of the highly variable and immunodominant head in the HA1 domain of the influenza HA polypeptide, said part comprising at least the amino acid sequence starting with the amino acid at position 53 up to and including the amino acid at position 302, has been deleted from the full-length HA (HA0) protein to create a stem polypeptide, also called "mini-HA" (FIG. 1A, second design). The remaining parts of the HA1 domain are linked, either directly or through a linker of 1 to 10 amino acids. Thus, for example, when the amino acid sequence from the amino acid at position 53 up to and including the amino acid at position 302 is deleted, the amino acid at position 52 is linked to the amino acid at position 303, either directly, or through replacement of the deleted head region with a linker of 1 to 10 amino acids. The deletion of the amino acid sequence from the amino acid at position 53 up to and including the amino acid at position 302 is the minimal deletion in the HA1 domain (FIG. 1A, second design). According to the invention, also a larger part of the HA1 domain may be deleted, e.g. the amino acid sequence starting with the amino acid at position 46 up to and including the amino acid at position 308, as shown in FIG. 1A, third design.

In certain embodiments, the deletion in the HA1 domain comprises the amino acid sequence from the amino acid at position 46 up to and including the amino acid at position 306.

In certain embodiments, the deletion in the HA1 domain comprises the amino acid sequence from the amino acid at position 47 up to and including the amino acid at position 306.

In certain embodiments, the deletion in the HA1 domain comprises the amino acid sequence from the amino acid at position 48 up to and including the amino acid at position 306.

In certain embodiments, the deletion in the HA1 domain comprises the amino acid sequence from the amino acid at position 49 up to and including the amino acid at position 306.

In certain embodiments, the deletion in the HA1 domain comprises the amino acid sequence from the amino acid at position 50 up to and including the amino acid at position 306.

In certain embodiments, the deletion in the HA1 domain comprises the amino acid sequence from the amino acid at position 51 up to and including the amino acid at position 306.

In certain embodiments, the deletion in the HA1 domain comprises the amino acid sequence from the amino acid at position 52 up to and including the amino acid at position 306.

In certain embodiments, the deletion in the HA1 domain comprises the amino acid sequence from the amino acid at position 53 up to and including the amino acid at position 306.

In certain embodiments, the deletion in the HA1 domain comprises the amino acid sequence from the amino acid at position 53 up to and including the amino acid at position 305.

In certain embodiments, the deletion in the HA1 domain comprises the amino acid sequence from the amino acid at position 48 up to and including the amino acid at position 304.

In certain embodiments, the deletion in the HA1 domain comprises the amino acid sequence from the amino acid at position 48 up to and including the amino acid at position 305.

In certain embodiments, the deletion in the HA1 domain comprises the amino acid sequence from the amino acid at position 46 up to and including the amino acid at position 302.

In certain embodiments, the deletion in the HA1 domain comprises the amino acid sequence from the amino acid at position 46 up to and including the amino acid at position 308.

In certain embodiments, the deletion in the HA1 domain comprises the amino acid sequence from the amino acid at position 47 up to and including the amino acid at position 308.

In certain embodiments, the deletion in the HA1 domain comprises the amino acid sequence from the amino acid at position 48 up to and including the amino acid at position 308.

In certain embodiments, the deletion in the HA1 domain comprises the amino acid sequence from the amino acid at position 49 up to and including the amino acid at position 308.

In certain embodiments, the deletion in the HA1 domain comprises the amino acid sequence from the amino acid at position 50 up to and including the amino acid at position 308.

In certain embodiments, the deletion in the HA1 domain comprises the amino acid sequence from the amino acid at position 51 up to and including the amino acid at position 308.

In certain embodiments, the deletion in the HA1 domain comprises the amino acid sequence from the amino acid at position 52 up to and including the amino acid at position 308.

In certain embodiments, the deletion in the HA1 domain comprises the amino acid sequence from the amino acid at position 53 up to and including the amino acid at position 308.

In a preferred embodiment, the deletion in the HA1 domain comprises at least the amino acid sequence from the amino acid at position 47 up to and including the amino acid at position 306.

In a preferred embodiment, the deletion in the HA1 domain consists of the amino acid sequence from the amino acid at position 47 up to and including the amino acid at position 306.

In some embodiments, the deletion in the HA1 domain has been replaced by a linking sequence of 1 to 10 amino acids.

In addition, the HA stem polypeptides of the invention comprise a modification of the trimerization region in the HA2 domain, preferably a modification in the C-helix, in order to improve trimerization of the HA stem polypeptides after deletion of the head region. According to the invention, said modification in the HA2 domain is a modification that enhances trimerization of the HA stem polypeptide.

In certain embodiments, said modification comprises the introduction of a heterologous trimerization domain in the C-helix. It is generally understood that the C-helix comprises the amino acid sequence from the amino acid at position 405 up to and including the amino acid at position 434 (H3 numbering). In a preferred embodiment, said heterologous trimerization domain has been introduced at a position corresponding to the amino acid sequence from the amino acid at position 405 up to and including the amino acid at position 419 (FIG. 1A). Thus, in certain embodiments, the original (wt) amino acid sequence in the HA2 domain from position 405 up to position 419 has been replaced by a heterologous trimerization sequence of the same length, i.e. with an identical number of amino acids.

In certain embodiments, the heterologous trimerization domain is a GCN4 sequence.

In certain preferred embodiments, the heterologous trimerization sequence comprises an amino acid sequence selected from the group consisting of:

```
                                   (SEQ ID NO: 18)
            RMKQIEDKIEEIESK;

(SEQ ID NO: 19)
            RIKQIEDKIEEIESK;

(SEQ ID NO: 20)
            RMEALEKKVDDIEKK;

(SEQ ID NO: 21)
            RIEALEKKVDDIEKK;

(SEQ ID NO: 22)
            RMENLEKKVDDIEEK;
            and (SEQ ID NO: 23)
            RIENLEKKVDDIEEK.
```

In some embodiments, at least one of the amino acids of the heterologous trimerization sequence has been mutated into C, enabling the formation of an intermonomeric cysteine bridge.

In certain preferred embodiments, the heterologous trimerization sequence thus comprises an amino acid sequence selected from the group consisting of:

CMKQIEDKIEEIESK; (SEQ ID NO: 24)

CIKQIEDKIEEIESK; (SEQ ID NO: 25)

CMEALEKKVDDIEKK; (SEQ ID NO: 26)

CIEALEKKVDDIEKK; (SEQ ID NO: 27)

RMECLEKKVDDIEKK; (SEQ ID NO: 28) and

RIECLEKKVDDIEKK. (SEQ ID NO: 29)

In a preferred embodiment, the heterologous trimerization sequence comprises the amino acid sequence CMKQIEDKIEEIESK (SEQ ID NO: 24).

In certain embodiments, the modification comprises an optimization of the heptad repeat sequence in the C-helix, preferably in the trimerization region comprising the amino acid sequence from the amino acid at position 405 up to and including the amino acid at position 419. A heptad repeat, denoted [abcdefg]$_n$, typically has hydrophobic residues at a and d, and polar/charged residues at e and g. These motifs are the basis for most coiled coil structures, which are a structural motif in proteins in which alpha-helices are coiled together like the strands of a rope (dimers and trimers are the most common types) (Ciani et al., 2010).

As a further modification, the HA stem polypeptides according to the invention comprise at least two cysteine residues (capable of) forming an intramoneric cysteine (or disulphide) bridge. An engineered cysteine bridge can be introduced by mutating at least one (if the other is already a cysteine), but usually by mutating two residues that are spatially close into cysteine, which will spontaneously or by active oxidation form a covalent bond between the sulfur atoms of these residues. In a preferred embodiment, the polypeptides comprise a cysteine at position 310 and a cysteine at position 422, enabling the formation of an intramonomeric cysteine bridge. In certain embodiments, the polypeptides comprise a mutation of the amino acid at positions 310 and 422 into C, creating said intramonomeric cysteine bridge. These cysteine residues thus form an intramonomeric cysteine (or disulphide) bridge which stabilizes the protein (see FIG. 4).

Furthermore, in order to obtain stable trimeric HA stem polypeptides, the polypeptides of the invention comprise at least two cysteine residues forming an intermonomeric (interprotomeric) cysteine bridge. Thus, in certain embodiments, the polypeptides comprise a cysteine at position 397 in combination with a cysteine at position 405; or a cysteine at position 396 in combination with a cysteine at position 408; or a cysteine at position 399 in combination with a cysteine at position 405.

In certain embodiments, the polypeptides comprise a mutation of the amino acid at position 397 into C and a mutation of the amino acid at position 405 into C; or a mutation of the amino acid at position 396 into C and a mutation of the amino acid at position 408 into C; or a mutation of the amino acid at position 399 into C and a mutation of the amino acid at position 405 into C, creating an intermonomeric cysteine bridge between the cysteine at position 397 of a first monomer and the cysteine at position 405 of a second monomer; or between the cysteine at position 396 of a first monomer and the cysteine at position 408 of a second monomer; or between the cysteine at position 399 of a first monomer and the cysteine at position 405 of a second monomer. It is noted that, in some embodiments, the amino acids at position 405 and 408 are within the heterologous trimerization sequence.

In a preferred embodiment, the polypeptides comprise a cysteine at position 397 and a cysteine at position 405, creating an intermonomeric cysteine bridge between the cysteine at position 397 of a first monomer and the amino acid at position 405 of a second monomer.

In certain preferred embodiments, the polypeptides comprise a mutation of the amino acid at position 397 into cysteine and a mutation of the amino acid at position 405 into cysteine, creating an intermonomeric cysteine bridge between the cysteine at position 397 of a first monomer and the amino acid at position 405 of a second monomer.

Furthermore, in certain embodiments, at least one mutation has been introduced in the so-called B-loop, which B-loop comprises the amino acid sequence starting from the amino acid at position 385 up to and including the amino acid at position 404 (see FIG. 1C). According to the invention, the at least one mutation is a mutation of the amino acid at position 392 into P, R or Y, preferably into R or P. The mutation into R (a charged amino acid) eliminates the original exposed hydrophobic amino acid (F in most influenza HAs) after the head domain removal, and increases solubility and expression of the expressed stem polypeptides. The mutation into a P amino acid reduces the helix propensity of the B-loop. In certain embodiments, the at least one mutation in the B-loop is a mutation of the amino acid at position 392 into R. In certain embodiments, the at least one mutation in the B-loop is a mutation of the amino acid at position 392 into P.

Furthermore, in certain embodiments of the polypeptides of the invention, the amino acid corresponding to the amino acid at position 395 is I, the amino acid corresponding to the amino acid at position 399 is Y or C, preferably Y, the amino acid corresponding to the amino acid at position 400 is P, the amino acid corresponding to the amino acid at position 401 is K, the amino acid corresponding to the amino acid at position 402 is S, and/or the amino acid corresponding to the amino acid at position 404 is R or Q (again numbering according to H3 numbering). In certain embodiments, the amino acid at position 392 is P or R, the amino acid at position 395 is I; the amino acid at position 399 is Y; the amino acid at position 402 is S; and the amino acid at position 404 is R or Q.

In preferred embodiments, the polypeptides, as compared to a wild-type HA polypeptide, thus comprise at least one additional mutation in the B-loop selected from the group consisting of:

a mutation of the amino acid corresponding to the amino acid at position 395 into I;

a mutation of the amino acid corresponding to the amino acid at position 399 into Y or C, preferably Y;

a mutation of the amino acid corresponding to the amino acid at position 400 into P;

a mutation of the amino acid corresponding to the amino acid at position 401 into K;

a mutation of the amino acid corresponding to the amino acid at position 402 into S; and a mutation of the amino acid corresponding to the amino acid at position 404 into Q or R.

In certain embodiment, the polypeptides, as compared to a wild-type HA polypeptide, comprise a mutation of the amino acid at position 392 into P or R, a mutation of the amino acid at position 395 into I; a mutation of the amino acid at position 399 into Y; a mutation of the amino acid at position 402 into S; and optionally a mutation of the amino acid at position 404 into Q or R.

In certain embodiments, the amino acid at position 392 is P or R, the amino acid at position 395 is I; the amino acid at position 399 is Y; the amino acid at position 401 is K; the amino acid at position 402 is S; and optionally the amino acid at position 404 is R or Q.

In another preferred embodiment, the polypeptides, as compared to a wild-type HA polypeptide, comprise a mutation of the amino acid at position 392 into P or R, a mutation of the amino acid at position 395 into I; a mutation of the amino acid at position 399 into Y; a mutation of the amino acid at position 401 into K; a mutation of the amino acid at position 402 into S; and optionally a mutation of the amino acid at position 404 into R or Q.

In certain embodiments, the polypeptides of the invention comprise a B-loop comprising an amino acid sequence selected from the group consisting of:

IEKMNTQYTAIGKEYNKSER; (SEQ ID NO: 126)

IEKMNTQYTAIGCEYNKSER; (SEQ ID NO: 127)

IEKMNTQPTAIGCEYNKSEQ; (SEQ ID NO: 128)

IEKMNTQRTAIGCEFNKSEQ; (SEQ ID NO: 129)

IEKMNTQPTAIGCEYNKSER; (SEQ ID NO: 130)

IEKMNTQPTAIGCEFNKSEQ; (SEQ ID NO: 131)

IEKMNTQRTAIGCEYNKSER; (SEQ ID NO: 132)

IEKMNTQRTAICKEYPKSEQ; and (SEQ ID NO: 133)

IEKMNTQRTAIGKECNKSER. (SEQ ID NO: 134)

Furthermore, according to the invention, the amino acid at position 434 is Q. In certain embodiments, the HA stem polypeptides thus comprise a mutation of the amino acid at position 434 into Q which improves its hydrogen bond interactions. In certain embodiments, the amino acid at position 434 is Q and the amino acid at position 442 is A. In certain embodiments, the polypeptides comprise a mutation of the amino acid at position 434 into Q, and a mutation at position 442 into A. These mutations improve the trimer interface interactions in the D and E helices and the nearby fusion peptide and $B_2B_3$-loop.

It is again noted that as used herein the numbering of the amino acid positions is based on H3 numbering according to Winter et al. (1981). It is also again noted that the numbering of the amino acid positions as used herein is based on the numbering of the positions in a full length H3 HA polypeptide (HA0). Thus, as used herein, "an amino acid at position 434" refers to the amino acid at position 434 in H3 HA0. The numbering thus does not refer to the actual positions of the amino acids in the HA stem polypeptides of the invention, due to deletion of the head region (see FIG. 14).

Furthermore, in certain embodiments, the amino acid corresponding to the amino acid at position 323 is K and/or the amino acid corresponding to the amino acid at position 326 is K. In a preferred embodiment, the amino acid at position 323 is K and the amino acid at position 326 is K.

In certain embodiments, the amino acid corresponding to the amino acid at position 339 is T.

In certain embodiments, the amino acid corresponding to the amino acid at position 438 is E and/or the amino acid corresponding to the amino acid at position 442 is I.

In certain embodiments, the HA stem polypeptides thus further comprise one or more additional mutations in the HA1 and/or HA2 domain, as compared to a wild-type HA polypeptide.

In certain embodiments, the polypeptides comprise a mutation of the amino acid corresponding to the amino acid at position 323 into K and/or a mutation of the amino acid corresponding to the amino acid at position 326 into K. These mutations increase the solubility and expression of the molecule. In another embodiment, the stem polypeptides of the invention comprise a mutation of the amino acid at position 323 into K and mutation of the amino acid at position 326 into K.

In certain embodiments, the polypeptides comprise a mutation of the amino acid corresponding to the amino acid at position 339 into T. This mutation removes a solvent exposed hydrophobic amino acid in the fusion peptide loop (FP loop) and thereby increases the solubility of the molecule.

In certain preferred embodiments, the amino acid at position 323 is K, the amino acid at position 326 is K, the amino acid at position 339 is T, the amino acid at position 392 is Y, P or R, preferably P or R, the amino acid at position 395 is I, the amino acid at position 399 is Y, the amino acid at position 402 is S, the amino acid at position 404 is Q or R, the amino acid at position 434 is Q.

In certain preferred embodiments, the polypeptides comprise a mutation of the amino acid at position 323 into K, a mutation of the amino acid at position 326 into K, a mutation of the amino acid at position 339 into T, a mutation of the amino acid at position 392 into P or R, a mutation of the amino acid at position 395 into I, a mutation of the amino acid at position 399 into Y, a mutation of the amino acid at position 402 into S, a mutation of the amino acid at position 404 into Q or R, and a mutation of the amino acid at position 434 into Q.

In certain preferred embodiments, the amino acid at position 323 is K, the amino acid at position 326 is K, the amino acid at position 339 is T, the amino acid at position 392 is P or R, the amino acid at position 395 is I, the amino acid at position 399 is Y, the amino acid at position 402 is S, the amino acid at position 404 is Q or R, the amino acid at position 434 is Q, and the amino acid at position 442 is A.

In certain preferred embodiments, the polypeptides comprise a mutation of the amino acid at position 323 into K, a mutation of the amino acid at position 326 into K, a mutation of the amino acid at position 339 into T, a mutation of the amino acid at position 392 into P or R, a mutation of the amino acid at position 395 into I, a mutation of the amino acid at position 399 into Y, a mutation of the amino acid at position 402 into S, a mutation of the amino acid at position 404 into Q or R, and a mutation of the amino acid at position 434 into Q, and a mutation of the amino acid at position 442 into A.

In certain embodiments, the polypeptides comprise at least one further mutation selected from the group consisting of a mutation of the amino acid corresponding to the amino acid at position 438 into E as a possible alternative negatively charged amino acid and a mutation of the amino acid corresponding to the amino acid at position 442 into I to increase hydrophobicity in the trimer interface.

According to the invention, the HA stem polypeptide is a group 1 HA polypeptide. Thus, according to the invention, the modifications described herein have been introduced in HA of an influenza virus from phylogenetic group 1, such as an influenza virus comprising HA of the H1, H2 or H5 subtype, resulting in the HA stem polypeptides of the invention. In certain embodiments, the HA stem polypeptide is an H1 HA polypeptide. Thus, in certain embodiments, the HA stem polypeptide is derived from HA of an influenza A virus comprising HA of a H1 subtype, such as from the influenza virus A/Brisbane/59/2007 (H1N1), with the amino acid sequence SEQ ID NO:1, or A/California/07/09 (H1N1), with the amino acid sequence of SEQ ID NO: 2. It will be understood by the skilled person that the polypeptides of the invention may also be derived from HA of other influenza A virus strains from group 1, including but not limited to A/Texas/UR06-0526/2007 (H1N1) (SEQ ID NO: 3), A/NewYork/629/1995 (H1NT) (SEQ ID NO: 4), A/AA_Marton/1943 (H1N1) (SEQ ID NO: 5), A/Puerto Rico/8/1934 (H1), A/Michigan/45/2015 (H1), A/Adachi/2/57 (H2N2) (SEQ ID NO: 6), A/Singapore/1/57 (H2N2) (SEQ ID NO: 7), or influenza viruses comprising HA of the H5 subtype, including but not limited to A/Vietnam/1203/2004 (H5N1) (SEQ ID NO: 8) or A/Hong Kong/156/97 (H5).

As described above, the stem polypeptides may or may not comprise a linking sequence of 1-10 amino acid residues replacing the deleted HA1 sequence and thereby linking the two remaining HA1 parts. In certain embodiments, the linking sequence comprises from 1 to 5 amino acids. In certain embodiments, the linking sequence comprises 2, 3 or 4 amino acids. The linking sequence may be a heterologous linking sequence, i.e. an amino acid sequence that does not occur in naturally occurring, or wild-type, HA, such as, but not limited to G, GS, GGG, GSG, GSA, GSGS, GSAG, GGGG, GSAGS, GSGSG, GSAGSA, GSAGSAG, and GSGSGSG.

In preferred embodiments, the linking sequence is a homologous linking sequence, i.e. an amino acid sequence derived from the deleted corresponding head region such as, but not limited to AGSG, AGS, GSG, HAGA, DQEG, DTPV, FPKT, EPGD, EPG, TGNL. TPSS, TPS, ATGN, YPGD.

In preferred embodiments, the polypeptides do not comprise a linking sequence.

As described above, cleavage of the influenza HA0 protein (in HA1 and HA2) is required for its activity, facilitating the entry of the viral genome into the target cells by causing the fusion of the host endosomal membrane with the viral membrane.

In certain embodiments, the polypeptides of the invention comprise the natural protease cleavage site. Thus, it is known that the Arg (R)-Gly (G) sequence spanning HA1 and HA2 (i.e. amino acid positions 329 and 330) is a recognition site for trypsin and trypsin-like proteases and is typically cleaved for hemagglutinin activation (FIG. 1A).

In certain embodiments, the polypeptides do not comprise a protease cleavage site. Thus, in certain preferred embodiments, the protease cleavage site has been removed by mutation of the amino acid residue at position 329 into any amino acid other than arginine (R) or lysine (K). In certain embodiments, the amino acid residue at position 329 is not arginine (R). In a preferred embodiment, the polypeptides comprise a mutation of the amino acid at position 329 into glutamine (Q). Thus, in certain embodiments, the polypeptides of the invention comprise the cleavage site knock-out mutation R329Q to prevent putative cleavage of the molecule during production in vitro or in vivo after administration.

In other embodiments, the polypeptides comprise a polybasic cleavage site, e.g. a Furin cleavage site (as described in Example 6). Thus, the polypeptides can be cleaved by furin-like proteases within the cell to produce a cleaved mini-HA, similar to a natively folded and processed HA.

In certain embodiments, the polypeptides do not comprise a signal sequence. The signal sequence (sometimes referred to as signal peptide, targeting signal, localization signal, localization sequence, transit peptide, leader sequence or leader peptide) is a short peptide (usually 16-30 amino acids long) that is present at the N-terminus of the majority of newly synthesized proteins that are destined towards the secretory pathway. Signal sequences function to prompt a cell to translocate the protein, usually to the cellular membrane. In many instances the amino acids comprising the signal peptide are cleaved off the protein once its final destination has been reached. In influenza HA, the signal sequences typically comprise the first 16 amino acids of the amino acid sequence of the full-length HA0 (corresponding to the amino acids from position −6 to position 10 according to H3 numbering). In certain embodiments, the polypeptides comprise (part of) a signal sequence.

The polypeptides may comprise (part of) the wild-type signal sequence or may comprise (part of) alternative signal sequences, such as, but not limited to a signal sequence selected from the group of:

MGSTAILGLLLAVLQGVCA (SEQ ID NO: 136)

and

MGMTSALLALLALALKPGAWA. (SEQ ID NO: 137)

In certain embodiments, the polypeptides comprise an HA2 domain including the transmembrane and cytoplasmic domain (corresponding to the amino acid sequence starting with the amino acid corresponding to the amino acid at position 515 up to and including the amino acid corresponding to the amino acid at position 550 (H3 numbering)).

To produce secreted (soluble) stem polypeptides, in certain embodiments the polypeptides do not comprise the transmembrane and cytoplasmic domain. Thus, in certain embodiments, the polypeptides comprise a truncated HA2 domain, in particular an HA2 domain that is truncated at the C-terminal end. A truncated HA2 domain according to the invention thus is shorter than the full length HA2 sequence, by deletion of one or more amino acid residues at the C-terminal end of the HA2 domain.

In certain embodiments, the C-terminal part of the HA2 domain starting with the amino acid corresponding to the amino acid at position 516 has been deleted, thus removing substantially the full transmembrane and cytoplasmic domain.

Figure 12:
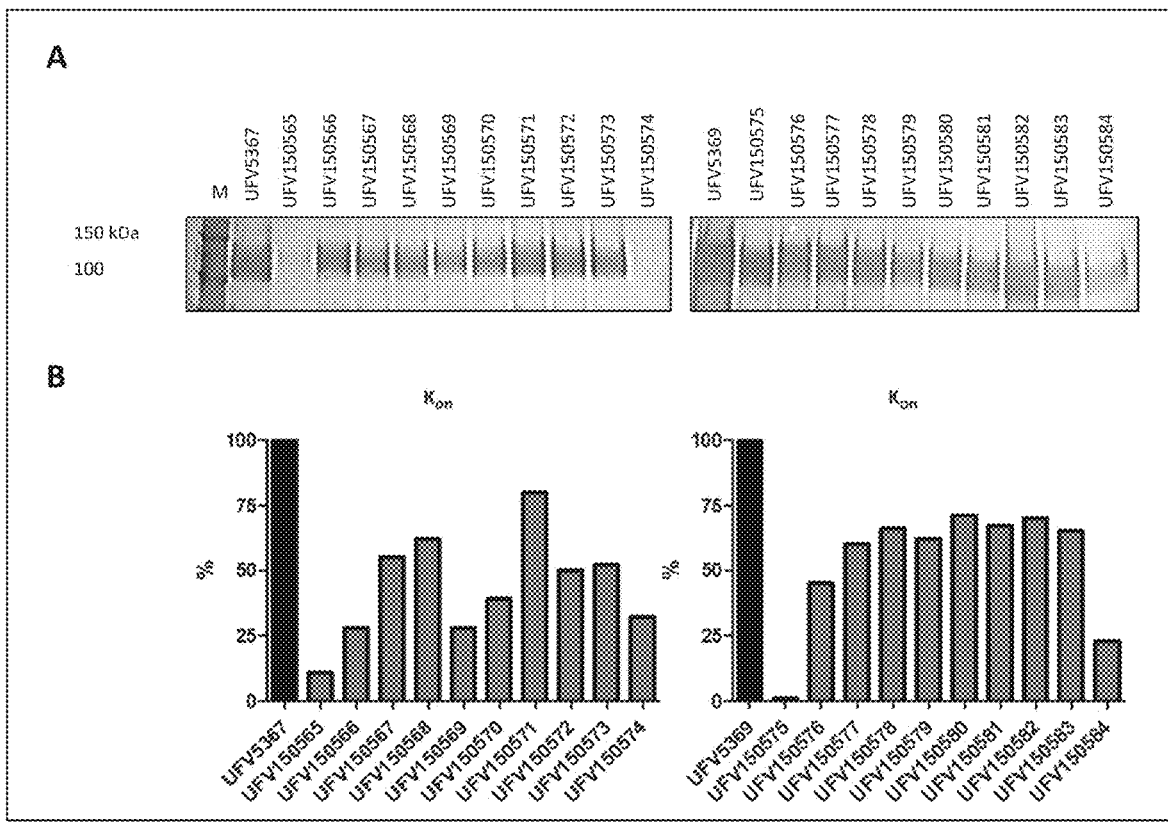
FIG. 12. Expression and antibody binding to polypeptide variants with alternative C-terminal truncations. A: Westernblot using an HA-specific single domain antibody. Almost all samples display a clear band on trimeric height that is similar to both reference polypeptides (UFV5367 and UFV5369). B: Binding of polypeptides to broadly neutralizing antibody CR9114 as determined by OCTET, shown are relative $K_{on}$ values of the polypeptides compared to reference design UFV5367 and UFV5369.

In certain embodiments, also a part of the C-terminal helix has been deleted. According to the present invention it has been found that even when a larger part of the HA2 domain is deleted, stable soluble HA stem polypeptides can be provided. Thus, in certain embodiments, the C-terminal part of the HA2 domain starting at he amino acid sequence at position 500, 501, 502, 503, 504, 505, 506, 507, 508, 509, 510, 511, 512, 513, 514 or 515 has been deleted (again numbering according to H3 numbering as described by Winter et al., supra) to produce a soluble polypeptide following expression in cells (FIG. 12).

In a preferred embodiment, the C-terminal part of the HA2 domain from the position corresponding to 516 has been deleted.

Optionally, a heterologous amino acid sequence (i.e. an amino acid sequence that does not naturally occur in influenza HA) has been linked to the (truncated) HA2 domain.

Thus, in certain embodiments, His-tag sequences, e.g. HHHHHH (SEQ ID NO: 113) or HHHHHHH (SEQ ID NO: 114.), or a FLAG tag (DYKDDDDK) (SEQ ID NO: 115) or a combination of these have been linked to the C-terminal amino acid of the (optionally truncated) HA2 domain for detection and/or purification purposes. In certain embodiments, the heterologous amino acid sequence, such as the His-tag sequence, may be connected to the (truncated) HA2 domain through a linker. In certain embodiments, the linker may contain (part of) a proteolytic cleavage site, e.g. the amino acid sequence IEGR (SEQ ID NO: 116) or LVPRGS (SEQ ID NO: 117) to enzymatically remove the His-tag sequence after purification.

In certain embodiments, the heterologous amino acid sequence that is linked to the C-terminal amino acid of the (truncated) HA2 domain comprises an amino acid sequence selected from the group consisting of:

GYIPEAPRDGQAYVRKDGEWVLLSTFL (foldon), (SEQ ID NO: 118),

SGRDYKDDDDKLVPRGSPGSGYIPEAPRDGQAYVRKDGEWVLLST

FLGHHHHHH (Flag-Foldon-His tag), (SEQ ID NO:

119),

SGRDYKDDDDKPGGGGSGGGGSGGGGSGGGGSGGGGSGGGGSGGG

GSHHHHHH (FLAG-GS linker-His tag), (SEQ ID

NO: 120),

EGRAAAGGSGGGGSMVFTLEDFVGDWRQTAGYNLDQVLEQGGVSS

LFQNLGVSVTPIQRIVLSGENGLKIDIHVIIPYEGLSGDQMGQIE

KIFKVVYPVDDHHFKVILHYGTLVIDGVTPNMIDYFGRPYEGIAV

FDGKKITVTGTLWNGNKIIDERLINPDGSLLFRVTINGVTGWRLC

ERILAAAAWSHPQFEKGAAWSHPQFEKGAAWSHPQFEK (Nanoluc-Strep tag), (SEQ ID NO: 121),

EGRAAAGGSGGGGSMVFTLEDFVGDWRQTAGYNLDQVLEQGGVSS

LFQNLGVSVTPIQRIVLSGENGLKIDIHVIIPYEGLSGDQMGQIE

KIFKVVYPVDDHHFKVILHYGTLVIDGVTPNMIDYFGRPYEGIAV

FDGKKITVTGTLWNGNKIIDERLINPDGSLLFRVTINGVTGWRLC

ERILAGAAEPEA (Nanoluc-C tag), (SEQ ID NO: 122),

EGRAAAWSHPQFEKGAAWSHPQFEKGAAWSHPQFEK (Strep tag, SEQ ID NO: 154),

EGRAAALPETGGGAAEPEA (Sortase-C tag), (SEQ ID

NO: 123),

SGRDYKDDDDKPGGGGSGGGGSGGGGSGGGGSGGGGSGGGGSGGG

GSWSHPQFEKGAAWSHPQFEKGAAWSHPQFEK (FLAG-GS linker-Strep tag), (SEQ ID NO: 124), and

EGRAAAEQKLISEEDLGGGGSGGGGSGGGGSGGGGSGGGGSGGGG

SGGGGSWSHPQFEKGAAWSHPQFEKGAAWSHPQFEK (Myc tag-

GS linker-Strep tag), (SEQ ID NO: 125).

In certain embodiments, a heterologous trimerization domain has been linked to the C-terminal amino acid of the (optionally truncated) HA2 domain, such as, but not limited to a "Foldon" trimerization domain (as described by Letarov et al. (1993); S-Guthe et al. (2004)), In certain embodiments, the HA stem polypeptides comprise an amino acid sequence comprising at least the amino acids 1-234 of SEQ ID NO: 30;
an amino acid sequence comprising at least the amino acids 1-234 of SEQ ID NO: 31;
an amino acid sequence comprising at least the amino acids 1-234 of SEQ ID NO: 52;
an amino acid sequence comprising at least the amino acids 1-234 of SEQ ID NO: 53;
an amino acid sequence comprising at least the amino acids 1-234 of SEQ ID NO: 54;
an amino acid sequence comprising at least the amino acids 1-234 of SEQ ID NO: 55;
an amino acid sequence comprising at least the amino acids 1-234 of SEQ ID NO: 56;
an amino acid sequence comprising at least the amino acids 1-234 of SEQ ID NO: 57;
an amino acid sequence comprising at least the amino acids 1-234 of SEQ ID NO: 58;
an amino acid sequence comprising at least the amino acids 1-237 of SEQ ID NO: 59;
an amino acid sequence comprising at least the amino acids 1-234 of SEQ ID NO: 60;
an amino acid sequence comprising at least the amino acids 1-234 of SEQ ID NO: 61;
an amino acid sequence comprising at least the amino acids 1-234 of SEQ ID NO: 62;
an amino acid sequence comprising at least the amino acids 1-234 of SEQ ID NO: 63;
an amino acid sequence comprising at least the amino acids 1-230 of SEQ ID NO: 64;
an amino acid sequence comprising at least the amino acids 1-231 of SEQ ID NO: 65;
an amino acid sequence comprising at least the amino acids 1-232 of SEQ ID NO: 66;
an amino acid sequence comprising at least the amino acids 1-233 of SEQ ID NO: 67;
an amino acid sequence comprising at least the amino acids 1-234 of SEQ ID NO: 68;
an amino acid sequence comprising at least the amino acids 1-235 of SEQ ID NO: 69;
an amino acid sequence comprising at least the amino acids 1-236 of SEQ ID NO: 70;

an amino acid sequence comprising at least the amino acids 1-237 of SEQ ID NO: 71;
an amino acid sequence comprising at least the amino acids 1-238 of SEQ ID NO: 72;
an amino acid sequence comprising at least the amino acids 1-234 of SEQ ID NO: 73;
an amino acid sequence comprising at least the amino acids 1-234 of SEQ ID NO: 74;
an amino acid sequence comprising at least the amino acids 1-228 of SEQ ID NO: 75;
an amino acid sequence comprising at least the amino acids 1-229 of SEQ ID NO: 76;
an amino acid sequence comprising at least the amino acids 1-230 of SEQ ID NO: 77;
an amino acid sequence comprising at least the amino acids 1-231 of SEQ ID NO: 78;
an amino acid sequence comprising at least the amino acids 1-232 of SEQ ID NO: 79;
an amino acid sequence comprising at least the amino acids 1-233 of SEQ ID NO: 80;
an amino acid sequence comprising at least the amino acids 1-234 of SEQ ID NO: 81;
an amino acid sequence comprising at least the amino acids 1-235 of SEQ ID NO: 82;
an amino acid sequence comprising at least the amino acids 1-234 of SEQ ID NO: 83;
an amino acid sequence comprising at least the amino acids 1-233 of SEQ ID NO: 84;
an amino acid sequence comprising at least the amino acids 1-235 of SEQ ID NO: 85;
an amino acid sequence comprising at least the amino acids 1-233 of SEQ ID NO: 86;
an amino acid sequence comprising at least the amino acids 1-234 of SEQ ID NO: 87;
an amino acid sequence comprising at least the amino acids 1-233 of SEQ ID NO: 88;
an amino acid sequence comprising at least the amino acids 1-234 of SEQ ID NO: 89;
an amino acid sequence comprising at least the amino acids 1-234 of SEQ ID NO: 90;
an amino acid sequence comprising at least the amino acids 1-234 of SEQ ID NO: 91;
an amino acid sequence comprising at least the amino acids 1-234 of SEQ ID NO: 92;
an amino acid sequence comprising at least the amino acids 1-234 of SEQ ID NO: 93;
an amino acid sequence comprising at least the amino acids 1-234 of SEQ ID NO: 94;
an amino acid sequence comprising at least the amino acids 1-234 of SEQ ID NO: 95;
an amino acid sequence comprising at least the amino acids 1-234 of SEQ ID NO: 96;
an amino acid sequence comprising at least the amino acids 1-233 of SEQ ID NO: 97;
an amino acid sequence comprising at least the amino acids 1-234 of SEQ ID NO: 98;
an amino acid sequence comprising at least the amino acids 1-234 of SEQ ID NO: 99;
an amino acid sequence comprising at least the amino acids 1-232 of SEQ ID NO: 100;
an amino acid sequence comprising at least the amino acids 1-237 of SEQ ID NO: 101;
an amino acid sequence comprising at least the amino acids 1-238 of SEQ ID NO: 102;
an amino acid sequence comprising at least the amino acids 1-231 of SEQ ID NO: 103;
an amino acid sequence comprising at least the amino acids 1-231 of SEQ ID NO: 104;
an amino acid sequence comprising at least the amino acids 1-237 of SEQ ID NO: 105;
an amino acid sequence comprising at least the amino acids 1-231 of SEQ ID NO: 106;
an amino acid sequence comprising at least the amino acids 1-237 of SEQ ID NO: 107;
an amino acid sequence comprising at least the amino acids 1-234 of SEQ ID NO: 108;
an amino acid sequence comprising at least the amino acids 1-231 of SEQ ID NO: 109;
an amino acid sequence comprising at least the amino acids 1-231 of SEQ ID NO: 110;
an amino acid sequence comprising at least the amino acids 1-237 of SEQ ID NO: 111;
an amino acid sequence comprising at least the amino acids 1-237 of SEQ ID NO: 112;
an amino acid sequence comprising at least the amino acids 1-234 of SEQ ID NO: 135;
an amino acid sequence comprising at least the amino acids 18-248 of SEQ ID NO: 147;
an amino acid sequence comprising at least the amino acids 18-248 of SEQ ID NO: 148;
an amino acid sequence comprising at least the amino acids 18-248 of SEQ ID NO: 149;
an amino acid sequence comprising at least the amino acids 17-247 of SEQ ID NO: 150;
an amino acid sequence comprising at least the amino acids 17-247 of SEQ ID NO: 151;
an amino acid sequence comprising at least the amino acids 16-246 of SEQ ID NO: 152; or
an amino acid sequence comprising at least the amino acids 18-248 of SEQ ID NO: 153.

In a preferred embodiment, the polypeptide comprises an amino acid sequence comprising at least the amino acids 1-231 of SEQ ID NO: 103, 104, 109 or 110.

In certain embodiments, the polypeptides comprise an amino acid sequence selected from the group consisting of SEQ ID NOs: 31, 31, 52-112 and 135.

In a preferred embodiment, the polypeptide comprises an amino acid sequence selected from the group consisting of SEQ ID NOs: 103, 104, 109 and 110.

In certain embodiments, the polypeptides are glycosylated when expressed in suitable cells (e.g. mammalian cells). The polypeptides may contain one or more native glycosylation motifs. In certain embodiments, the polypeptides comprise at least one additional/introduced glycosylation motif. In certain embodiments, the at least one glycosylation motif has been introduced by a mutation of the amino acid at position 402 into S. This mutation will introduce a n-linked glucosylation motif at position 400.

The polypeptides may also be administered in combination with or conjugated to nanoparticles, such as e.g. polymers, liposomes, virosomes, virus-like particles. The polypeptides may be combined with, encapsidated in or conjugated (e.g. covalently linked or adsorbed) to the nanoparticles The invention further provides nucleic acid molecules encoding the influenza HA stem polypeptides of the invention. It is understood by a skilled person that numerous different nucleic acid molecules can encode the same polypeptide as a result of the degeneracy of the genetic code. It is also understood that skilled persons may, using routine techniques, make nucleotide substitutions that do not affect the polypeptide sequence encoded by the polynucleotides described to reflect the codon usage of any particular host organism in which the polypeptides are to be expressed. Therefore, unless otherwise specified, a "nucleic acid molecule encoding an amino acid sequence" includes all nucleotide sequences that are degenerate versions of each other and that encode the same amino acid sequence.

In certain embodiments, the nucleic acid molecules encoding the influenza HA stem polypeptides are codon optimized for expression in mammalian cells, such as human cells. Methods of codon-optimization are known and have been described previously (e.g. WO 96/09378).

In certain embodiments, the nucleic acid molecules encoding the influenza HA stem polypeptide comprise a nucleic acid sequence selected from SEQ ID NO: 138-145.

The influenza hemagglutinin stem domain polypeptides can be prepared according to any technique deemed suitable to one of skill, including techniques described below. Thus, the polypeptides of the invention may be synthesized as DNA sequences by standard methods known in the art and cloned and subsequently expressed, in vitro or in vivo, using suitable restriction enzymes and methods known in the art.

The invention further relates to vectors comprising a nucleic acid molecule encoding a polypeptide of the invention. In certain embodiments, a nucleic acid molecule according to the invention thus is part of a vector, e.g. a plasmid. Such vectors can easily be manipulated by methods well known to the person skilled in the art, and are for instance designed to be capable of replication in prokaryotic and/or eukaryotic cells. The vector used can be any vector that is suitable for cloning DNA and can be used for transcription of the nucleic acid of interest. When host cells are used, it is preferred that the vector is an integrating vector. Alternatively, the vector may be an episomally replicating vector. The person skilled in the art is capable of choosing suitable expression vectors, and inserting the nucleic acid sequences of the invention in a functional manner. To obtain expression of nucleic acid sequences encoding polypeptides, it is well known to those skilled in the art that sequences capable of driving expression can be functionally linked to the nucleic acid sequences encoding the polypeptide, resulting in recombinant nucleic acid molecules encoding a protein or polypeptide in expressible format. Sequences driving expression may include promoters, enhancers and the like, and combinations thereof. These should be capable of functioning in the host cell, thereby driving expression of the nucleic acid sequences that are functionally linked to them. The person skilled in the art is aware that various promoters can be used to obtain expression of a gene in host cells. Promoters can be constitutive or regulated, and can be obtained from various sources, including viruses, prokaryotic, or eukaryotic sources, or artificially designed. Expression of nucleic acids of interest may be from the natural promoter or derivative thereof or from an entirely heterologous promoter (Kaufman, 2000). Some well-known and much used promoters for expression in eukaryotic cells comprise promoters derived from viruses, such as adenovirus, e.g. the E1A promoter, promoters derived from cytomegalovirus (CMV), such as the CMV immediate early (IE) promoter (referred to herein as the CMV promoter) (obtainable for instance from pcDNA, Invitrogen), promoters derived from Simian Virus 40 (SV40) (Das et al, 1985), and the like. Suitable promoters can also be derived from eukaryotic cells, such as methallothionein (MT) promoters, elongation factor 1α (EF-1α) promoter (Gill et al., 2001), ubiquitin C or UB6 promoter (Gill et al., 2001), actin promoter, an immunoglobulin promoter, heat shock promoters, and the like. Testing for promoter function and strength of a promoter is a matter of routine for a person skilled in the art, and in general may for instance encompass cloning a test gene such as lacZ, luciferase, GFP, etc. behind the promoter sequence, and test for expression of the test gene. Of course, promoters may be altered by deletion, addition, mutation of sequences therein, and tested for functionality, to find new, attenuated, or improved promoter sequences. According to the present invention, strong promoters that give high transcription levels in the eukaryotic cells of choice are preferred.

The constructs may be transfected into eukaryotic cells (e.g. plant, fungal, yeast or animal cells) or suitable prokaryotic expression systems like E. coli using methods that are well known to persons skilled in the art. In some cases, a suitable 'tag' sequence (such as for example, but not limited to, a his-, myc-, strep-, sortase, or flag-tag) or complete protein (such as for example, but not limited to, maltose binding protein or glutathione S transferase) may be added to the sequences of the invention, as described above, to allow for purification and/or identification of the polypeptides from the cells or supernatant. Optionally a sequence containing a specific proteolytic site can be included to afterwards remove the tag by proteolytic digestion.

In preferred embodiments, the polypeptides are produced in mammalian cells.

Purified polypeptides can be analyzed by spectroscopic methods known in the art (e.g. circular dichroism spectroscopy, Fourier Transform Infrared spectroscopy and NMR spectroscopy or X-ray crystallography) to investigate the presence of desired structures like helices and beta sheets. ELISA, AlphaLISA, biolayer interferometry (Octet) and FACS and the like can be used to investigate binding of the polypeptides of the invention to the broadly neutralizing antibodies, such as CR6261 and/or CR9114. Thus, polypeptides according to the invention having the correct conformation can be selected. Trimeric content can be analyzed for example by using SDS gel electrophoresis under non-reducing conditions, size exclusion chromatography in the presence of antibody Fab fragments of broadly neutralizing antibodies, such as CR6261 and/or CR9114, as well as AlphaLISA using differently labled antibodies. Stability of the polypeptides can be assessed as described above after temperature stress, freeze-thaw cycles, increased protein concentration, or agitation. The melting temperature of the polypeptide can further be assed by Differential Scanning Fluorimetry (DSF) and/or Differential Scanning calorimetry (DSC).

In certain embodiments, the vector is a human recombinant adenovirus. The present invention thus also provides recombinant adenoviral vectors comprising a nucleic acid molecule encoding a HA stem polypeptide according to the invention. In a preferred embodiment, the nucleic acid molecule encoding the stem polypeptide comprises a nucleic acid sequence selected from the group consisting of SEQ ID NO: 142, SEQ ID NO: 143, SEQ ID NO: 144 and SEQ ID NO: 145.

The preparation of recombinant adenoviral vectors is well known in the art. The term 'recombinant' for an adenovirus, as used herein implicates that it has been modified by the hand of man, e.g. it has altered terminal ends actively cloned therein and/or it comprises a heterologous gene, i.e. it is not a naturally occurring wild type adenovirus. In certain embodiments, an adenoviral vector according to the invention is deficient in at least one essential gene function of the E1 region, e.g. the E1a region and/or the E1b region, of the adenoviral genome that is required for viral replication. In certain embodiments, an adenoviral vector according to the invention is deficient in at least part of the non-essential E3 region. In certain embodiments, the vector is deficient in at least one essential gene function of the E1 region and at least part of the non-essential E3 region. The adenoviral vector can be "multiply deficient," meaning that the adenoviral vector is deficient in one or more essential gene functions in each of two or more regions of the adenoviral genome. For example, the aforementioned E1-deficient or E1-, E3-deficient adenoviral vectors can be further deficient in at least one essential gene of the E4 region and/or at least one essential gene of the E2 region (e.g., the E2A region and/or E2B region). Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913.

In certain embodiments, the adenovirus is a human adenovirus of the serotype 26 or 35.

The invention further provides pharmaceutical composition comprising a polypeptide, a nucleic acid, and/or a vector according to the invention, and pharmaceutically acceptable carrier. The invention in particular relates to pharmaceutical compositions comprising a therapeutically effective amount of the polypeptides, nucleic acids, and/or vectors of the invention. The pharmaceutical compositions further comprise a pharmaceutically acceptable carrier. In the present context, the term "pharmaceutically acceptable" means that the carrier, at the dosages and concentrations employed, will not cause unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The term "carrier" refers to a diluent, excipient, or vehicle with which the polypeptides, nucleic acids, and/or vectors are administered. Saline solutions and aqueous dextrose and glycerol solutions can e.g. be employed as liquid carriers, particularly for injectable solutions.

The invention further relates to polypeptides, nucleic acids, and/or vectors as described herein for use as a medicament.

The invention in particular relates to polypeptides, nucleic acids, and/or vectors as described herein for use in inducing an immune response against an influenza virus.

The invention also relates to methods for inducing an immune response against an influenza A virus in a subject in need thereof, the method comprising administering to said subject, a polypeptide, nucleic acid molecule and/or vector as described above. A subject according to the invention preferably is a mammal that is capable of being infected with an influenza virus, or otherwise can benefit from the induction of an immune response, such subject for instance being a rodent, e.g. a mouse, a ferret, or a domestic or farm animal, or a non-human-primate, or a human. Preferably, the subject is a human subject.

In certain embodiments, the invention provides methods for inducing an immune response against a group 1 influenza A virus. The immune response may comprise a humoral (i.e. the induction of influenza virus neutralizing antibodies) and/or a cellular immune response. In certain embodiments, the invention provides methods for inducing an immune response against at least two, three, four, five or six subtypes of influenza A viruses. In certain embodiments, the invention provides methods for inducing an immune response against an influenza virus comprising HA of the H1 subtype.

In certain embodiments, the immune response induced is effective to prevent and/or treat an influenza virus infection caused by a group 1 influenza A virus, such as an influenza A virus comprising HA of the H1 subtype, and/or an influenza A virus comprising HA of the H2 subtype, and/or an influenza A virus comprising HA of the H5 subtype. In certain embodiments, the immune response induced is effective to prevent and/or treat an influenza virus infection caused by an influenza A virus comprising HA of the H1 subtype.

The invention further relates to polypeptides, nucleic acids, and/or vectors as described herein for use as an influenza vaccine.

In certain embodiments, the polypeptides, nucleic acid molecules and/or vectors of the invention are administered in combination with an adjuvant. The adjuvant for may be administered before, concomitantly with, or after administration of the polypeptides, nucleic acid molecules and/or vectors of the invention. Examples of suitable adjuvants include aluminium salts such as aluminium hydroxide and/or aluminium phosphate; oil-emulsion compositions (or oil-in-water compositions), including squalene-water emulsions, such as MF59 (see e.g. WO 90/14837); saponin formulations, such as for example QS21 and Immunostimulating Complexes (ISCOMS) (see e.g. U.S. Pat. No. 5,057, 540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as E. coli heat labile enterotoxin LT, cholera toxin CT, pertussis toxin PT, or tetanus toxoid TT, Matrix M, or combinations thereof. In addition, known immunopotentiating technologies may be used, such as fusing the polypeptides of the invention to proteins known in the art to enhance immune response (e.g. tetanus toxoid, CRM197, rCTB, bacterial flagellins or others) or including the polypeptides in virosomes, or combinations thereof.

Administration of the polypeptides, nucleic acid molecules, and/or vectors according to the invention can be performed using standard routes of administration. Non-limiting examples include parenteral administration, such as intravenous, intradermal, transdermal, intramuscular, subcutaneous, etc, or mucosal administration, e.g. intranasal, oral, and the like. The skilled person will be capable to determine the various possibilities to administer the polypeptides, nucleic acid molecules, and/or vectors according to the invention, in order to induce an immune response.

In certain embodiments, the polypeptide, nucleic acid molecule, and/or vector is administered more than one time, i.e. in a so-called homologous prime-boost regimen. The administration of the second dose can be performed, for example, one week after the administration of the first dose, two weeks after the administration of the first dose, three weeks after the administration of the first dose, one month after the administration of the first dose, six weeks after the administration of the first dose, two months after the administration of the first dose, 3 months after the administration of the first dose, or 4 months or more after the administration of the first dose, etc, up to several years after the administration of the first dose of the polypeptide, nucleic acid molecule, and/or vector of the invention. It is also possible to administer the polypeptides, nucleic aid molecules and/or vectors more than twice, e.g. three times, four times, etc, so that the first priming administration is followed by more than one boosting administration.

The polypeptides, nucleic acid molecules, and/or vectors may also be administered, either as prime, or as boost, in a heterologous prime-boost regimen.

The invention further provides methods for preventing and/or treating, preferably preventing, an influenza virus disease in a subject in need thereof, comprising administering to said subject a polypeptide, a nucleic acid molecule and/or a vector as described herein. A therapeutically effective amount refers to an amount of the polypeptide, nucleic acid, and/or vector that is effective for preventing, ameliorating and/or treating a disease or condition resulting from infection by an influenza virus. Prevention encompasses inhibiting or reducing the spread of influenza virus or inhibiting or reducing the onset, development or progression of one or more of the symptoms associated with infection by an influenza virus. Amelioration as used in herein may refer to the reduction of visible or perceptible disease symptoms, viremia, or any other measurable manifestation of influenza infection.

A subject in need of treatment includes subjects that are already inflicted with a condition resulting from infection with an influenza virus, as well as those in which infection with influenza virus is to be prevented. The polypeptides, nucleic acids and/or vectors of the invention thus may be administered to a naive subject, i.e., a subject that does not have a disease caused by an influenza virus infection or has not been and is not currently infected with an influenza virus infection, or to subjects that already have been infected with an influenza virus.

In an embodiment, prevention and/or treatment may be targeted at patient groups that are susceptible to influenza virus infection. Such patient groups include, but are not limited to e.g., the elderly (e.g. ≥50 years old, ≥60 years old, and preferably ≥65 years old), the young (e.g. ≤5 years old, ≤1 year old), hospitalized patients, immunocompromised subjects, and patients who have been treated with an antiviral compound but have shown an inadequate antiviral response.

The polypeptides, nucleic acid molecules and/or vectors of the invention may be administered to a subject in combination with one or more other active agents, such as alternative influenza vaccines, monoclonal antibodies, antiviral agents, antibacterial agents, and/or immunomodulatory agents. The one or more other active agents may be beneficial in the treatment and/or prevention of an influenza virus disease or may ameliorate a symptom or condition associated with an influenza virus disease. In some embodiments, the one or more other active agents are pain relievers, anti-fever medications, or therapies that alleviate or assist with breathing.

The invention is further illustrated in the following examples and figures. The examples are not intended to limit the scope of the invention in any way.

EXAMPLES

Example 1: Preparation of Stem-Based Polypeptides of the Invention

In WO2013/079473, a first series of influenza hemagglutinin stem polypeptides, compositions and vaccines and methods of their use in the prevention and/or treatment of influenza, were described, including the polypeptides H1-mini2-cluster 1+5+6-GCN, both as membrane-bound form (with natural transmembrane domain, SEQ ID NO: 45 in WO2013/079473) and as soluble form thereof, s-H1-mini2-cluster1+5+6-GCN4 (without natural transmembrane domain, SEQ ID NO: 145 in WO2013/079473).

In WO2014/191435, additional stem polypeptides derived from the full-length HA of H1N1 A/Brisbane/59/2007 were described, which comprised additional mutations as compared to H1-mini2-cluster1+5+6-GCN4, and also stably presented the broadly neutralizing epitope of CR6261 and/or CR9114.

These stem polypeptides were all created by deleting he head domain from HAL in particular the region comprising the amino acids starting from position 46 up to and including the amino acid at position 306, and replacing the deleted region with a linker, as described in WO2013/079473. It is noted that in WO2013/079473, the numbering of the amino acid positions was based on the numbering of full length HA of influenza A/Brisbane/59/2007 (i.e. SEQ ID NO: 1 in WO2013/079473), whereas in the current invention the H3 numbering by Winter et al. is used.

The removal of the head domain leaves part of the molecule that was previously shielded from the aqueous solvent exposed, thereby destabilizing the structure of the polypeptides of the invention. For this reason, one or more amino acid residues in the B-loop, i.e. the region comprising the amino acids 385-404 (FIG. 1C) were mutated to stabilize the polypeptides. Similarly, in the area around the fusion peptide a number of hydrophobic residues are exposed to the solvent, caused by the fact that, unlike the native full-length HA, the polypeptides cannot be cleaved and undergo the associated conformational change that buries the hydrophobic fusion peptide in the interior of the protein. To address this issue some or all of the hydrophobic amino acid residues at position 323, 326, and 339 were mutated to hydrophilic residues as compared to the wild-type full-length HA from A/Brisale/59/2007.

Furthermore, the polypeptides were resistant to protease cleavage by a mutation of the natural cleavage site, e.g. by mutation of the amino acid at position 329 into Q.

In WO2016/005480 a further series of stem polypeptides was described, wherein the GCN4 derived sequence RMKQIEDKIEEIESK (SEQ ID NO: 18) was introduced at position 405 to 419, such as e.g. the polypeptides designated 127H1-t2, s127H1-t2, and s127H1-t2long, derived from A/Brisbane/59/2007. In addition, stem polypeptides with the same modifications were made using HA from different influenza strains, for example polypeptides based on HA deribed from the H1N1 A/California/07/09 strain, such as smH1Cali3964-127H1-t2, and mH1 Cali3964-127H1-t2.

In WO2016/005482 the introduction of an intermonomeric cysteine bridge was described, resulting in increased amounts of trimeric stem polypeptides, including the polypeptides designated 127H1-t2-cl18 (also referred to as 5367), and the soluble version 127H-t2-cl18long, which were based on HA of influenza A/Brisbane/59/2007. Similar polypeptides were designed based on e.g. HA of the influenza virus A/California/07/09, e.g. the polypeptides designated mH1 Cali3964-127H1-t2-cl18 (also referred to as 5369) and smH1 Cali3964-127H1t2-cl18long. These stem polypeptides comprised inter alia a deletion of the head region comprising the amino acids starting from position 46 up to and including the amino acid at position 306, wherein the resulting HA1 domains were linked through a 4-amino acid linker (GGGG); the GCN4 derived sequence RMKQIEDKIEEIESK (SEQ ID NO: 18) introduced in the HA2 domain at position 405-419; and a mutation of the amino acid at position 329 into Q to make the polypeptide resistant to protease cleavage. The polypeptides further comprised a mutation of the amino acid at position 397 into C and a mutation of the amino acid at position 405 into C (i.e. the first amino acid of the GCN4 sequence), thus forming an intermonomeric cysteine bridge between the cysteine at position 397 of a first monomer and the amino acid at position 405 of a second monomer.

Figure 3:
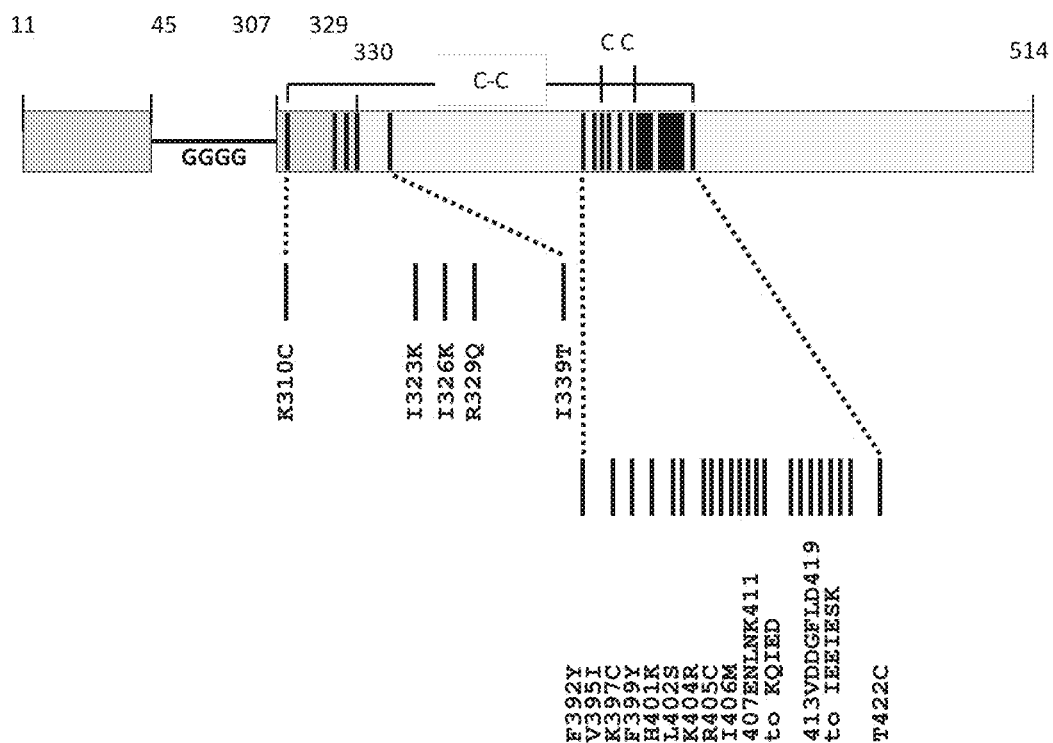
FIG. 3. Schematic drawing of the A/Brisbane based parental construct 5369.

In the research that led to the present invention, the previously described stem polypeptides have been optimized. The amino acid sequences of the wild-type HA derived from A/Brisbane/59/2007 and or A/California/07/09 are the sequences of SEQ ID NO: 1 and 2, respectively. The polypeptides UFV5367 (SEQ ID NO: 16) and UFV5369 (SEQ ID NO: 17) are herein referred to as the "parental strains/constructs" (schematically shown in FIGS. 2 and 3, respectively).

Novel HA stem polypeptides, including e.g. UFV150558 (SEQ ID NO: 30) and UFV150850 (SEQ ID NO: 53) thus were designed, which comprise additional modifications as compared to the previously described stem polypeptides UFV5367 (SEQ ID NO: 16) and UFV5369 (SEQ ID NO: 17). In particular, the polypeptides UFV150558 and UFV150850 comprise a mutation of the amino acid at position 392 in the B-loop into P or R, in combination with a mutation of the amino acid at position 434 into Q, or a mutation of the amino acid at position 392 in the B-loop into P or R, in combination with a mutation of the amino acid at position 434 into Q and a mutation at position 442 into A.

Figure 4:
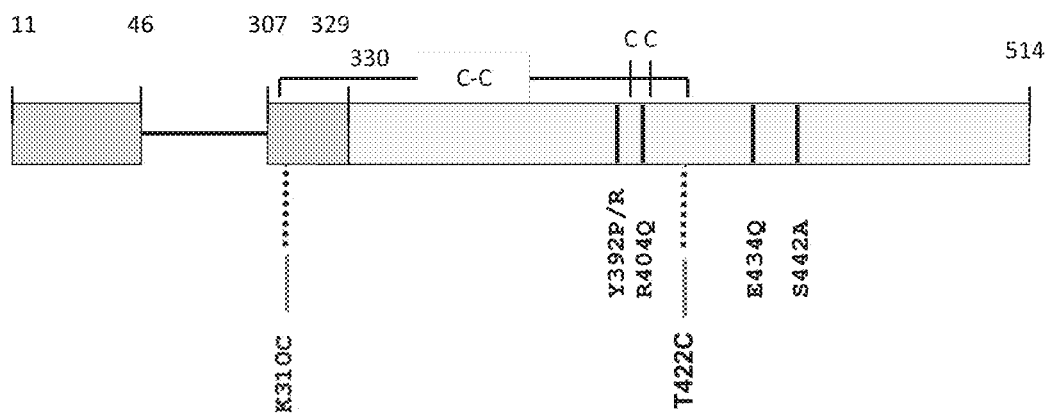
FIG. 4. Schematic drawing of an embodiment of a polypeptide of the invention, showing the new mutation of the amino acid at position 392 in the B-loop into P or R, a mutation of the amino acid at position 434 into Q and a mutation at position 442 into A, and further comprising a mutation of the amino acid at position 404 into Q.

In addition, further stem polypeptides were designed wherein no artificial linker was used to replace the deteled head region. The stem polypeptides UFV160655 (SEQ ID NO: 103), UFV160656 (SEQ ID NO: 104), UFV160664 (SEQ ID NO: 109) and UFV160665 (SEQ ID NO: 110) comprised a deletion of the head region from the amino acid at position 47 up to and including the amino acid at position 306, thus leaving a first part of the HA1 domain comprising the amino acids up to and including the amino acid 46, and a second part of the HA1 domain comprising the amino acids starting from the amino acid at position 307 up to the C-terminal amino acid of the HA1 domain (i.e. the amino acid at position 329). The first HA1 part was directly linked to the second HA1 part after deletion of the head, i.e. the remaining amino acid at position 46 (the C-terminal amino acid of the first part of the HA1 domain) was connected directly to the remaining amino acid at position 307 (the N-terminal amino acid of the second part of the HA1 domain). No artificial linker was introduced (see FIG. 1A, lower construct). The peptides also comprised the additional mutations of the amino acid at position 392 in the B-loop into P or R, in combination with a mutation of the amino acid at position 434 into Q, or in combination with a mutation of the amino acid at position 434 into Q and a mutation at position 442 into A (as schematically shown in FIG. 4).

Example 2: Expression of the Polypeptides According to the Invention

Protein Expression in Mammalian Cells

DNA fragments encoding the polypeptides of the invention UFV150558, UFV150850, UFV160655, UFV160656, UFV160664 and UFV160665) were synthesized (Genscript) and cloned in the pcDNA2004 plasmid (in-house modified pcDNA3 vector with an enhanced CMV promotor). The polypeptides were produced in HEK293F cells cultured in Freestyle™ medium by transient transfection using 293Fectin™ transfection reagent (Invitrogen) of the prepared expression plasmids. The polypeptides were produced in Expi-CHO cells cultures in ExpiCHO™Expression medium by transient transfection using the ExpiFectamine™ transfection reagent (Gibco, ThermoFisher Scientific). For the Expi-CHO cells culture the ExpiFectamine CHO enhancer and ExpiCHO feed (Gibco, ThermoFisher Scientific) were added 1 day post transfection. Culture supernatants containing the secreted polypeptides were harvested between day 7-11 (for ExpiCHO cells) by centrifugation, followed by filtration over a 0.2 µm bottle top filter (Corning).

Culture Supernatant Analysis

The level of expressed polypeptide in the harvested culture supernatant was assessed through Bio-Layer Interferometry using the OCTET platform. In short, biotinylated mAb CR9114 was immobilized on Streptavidin (SA) biosensors (Pall ForteBio) after which a standard curve was established by assessing the binding shift of a dilution series of a well-defined purified homologous polypeptide. Subsequently, the binding shift of pre-diluted harvested culture supernatants containing the polypeptides of the invention (5-15 µg/mL diluted in kinetics buffer) was measured and the concentration of the polypeptides was calculated using the established standard curve.

The trimer content of the polypeptides in the culture supernatants was assessed in AlphaLISA by simultaneous binding of 1.5 nM of CR9114 and 1.5 nM of a Streptactin tagged single domain antibody (SD15016) having the sequence of SEQ ID NO: 13. Chemiluminescent emission at 615 nm was measured following 2 hours incubation at room temperature of the polypeptides with the antibody and single domain antibody in the presence of anti-human-IgG Acceptor and Streptactin Donor beads (Perkin Elmer). Only trimeric molecules that displayed more than one correctly folded epitope were bound by both antibodies simultaneously and thus gave a signal in this assay (in contrast to monomers and potential aggregates). The polypeptides were titrated based on protein concentration, as assessed by OCTET.

Results and Conclusion

Figure 5:
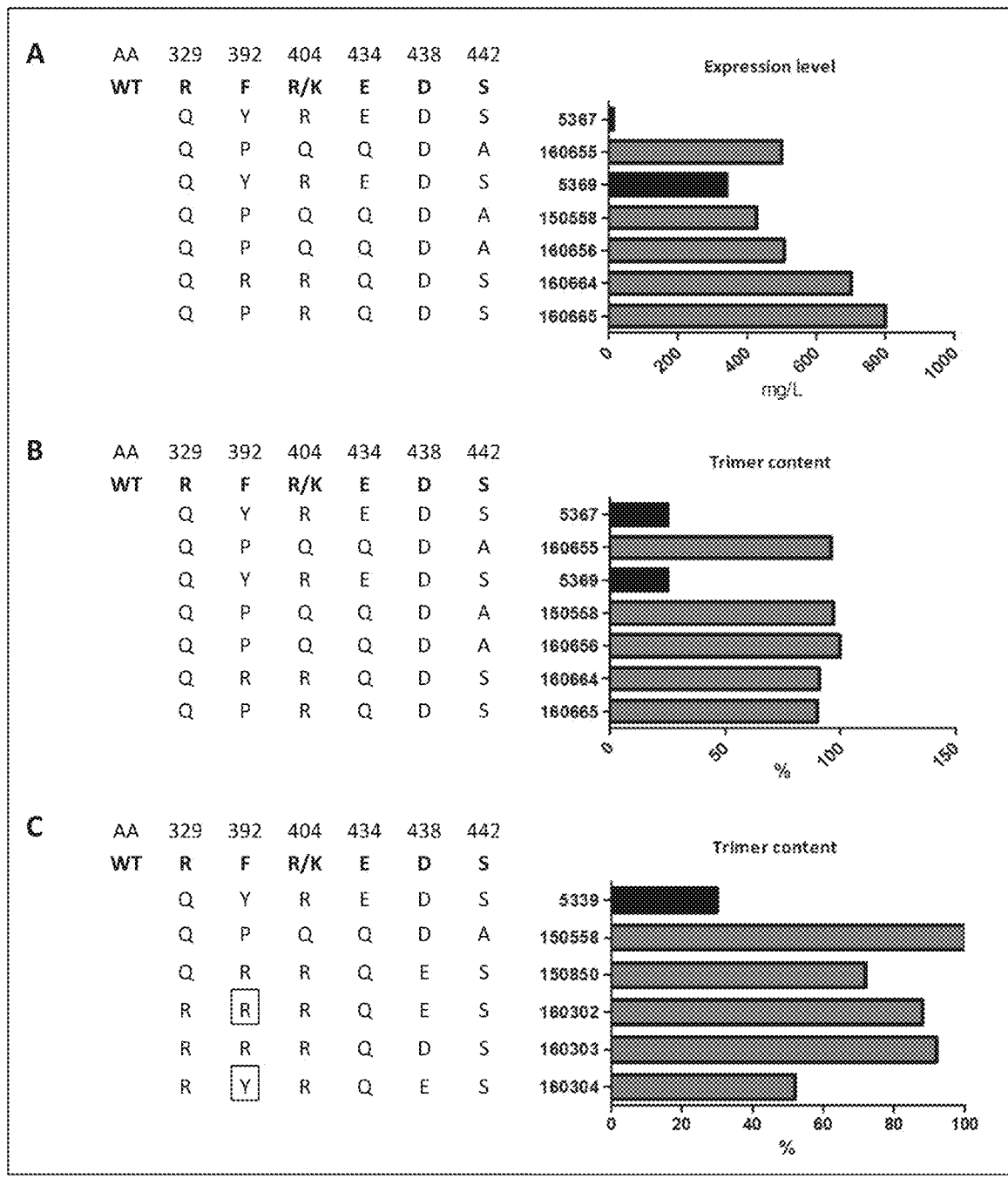
FIG. 5. Levels of expression and trimer content of several polypeptides of the invention (grey) and the parental designs (black). A: Protein expression levels as determined by OCTET (CR9114); B and C: Trimer content as determined by AlphaLISA (values are expressed in % relative to polypeptide UFV160656 that is set to 100%; value for polypeptide 5367 is an estimate based on Western blot). The experiment was performed multiple times and these data are representative for the values observed. The stabilizing mutations are shown in the left panels.
Figure 6:
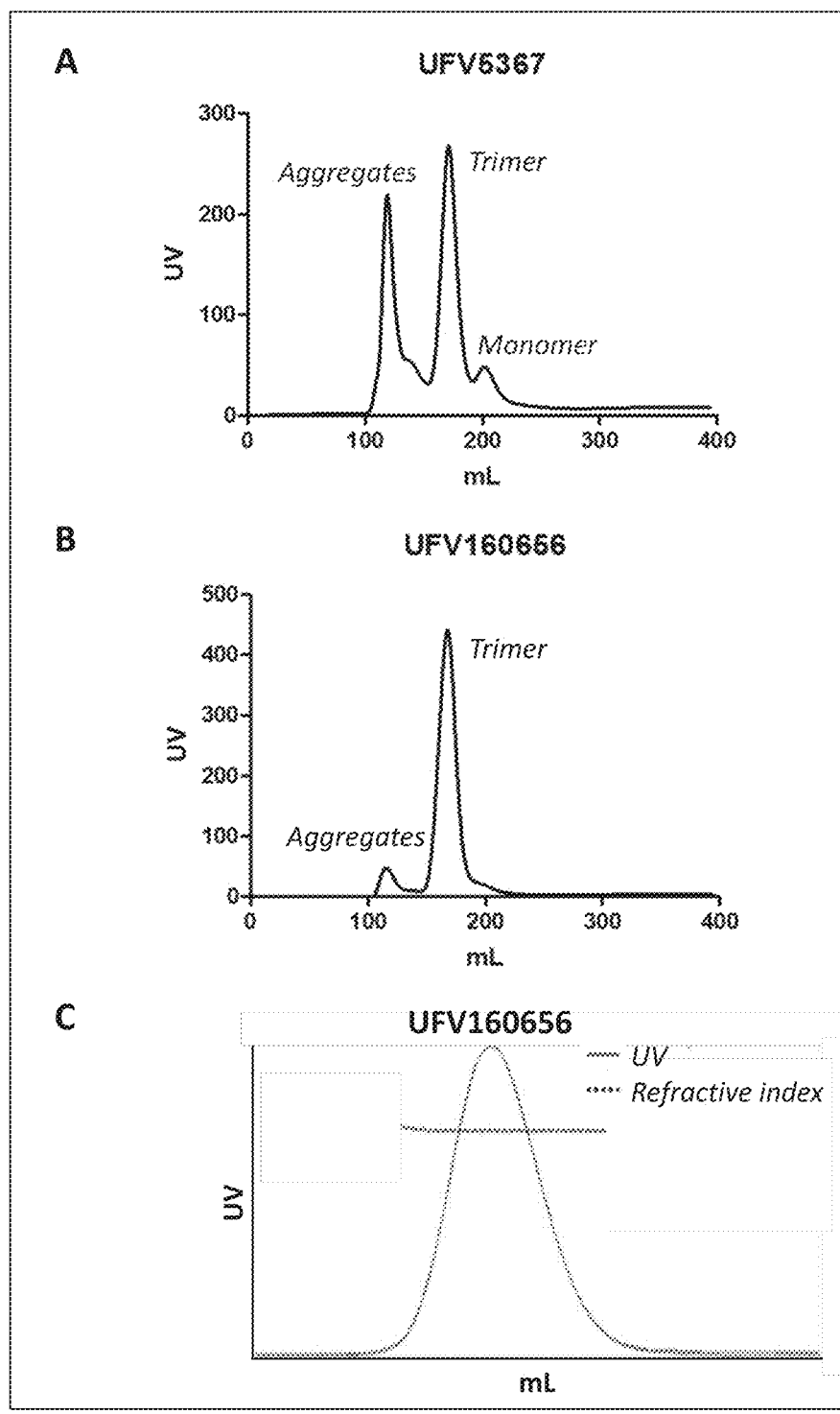
FIG. 6. The pooled Affinity Chromatography elution fractions separated by Size Exclusion Chromatography; aggregates, trimers and monomers are indicated (Panel A and B). SEC-MALS analysis of the pooled trimer fraction indicates that the polypeptide of the invention is very pure and homogeneous in molar mass (Panel C).

The polypeptide expression levels and trimer content were determined for three independent 70 mL ExpiCHO transfections at day 9 post transfection. The results are shown in FIG. 5. Compared to the previously described construct 5367 (SEQ ID NO: 16) (which comprises a deletion in the HA1 domain of amino acids starting from position 46 up to and including the amino acid at position 306, and comprises a 4G linker replacing the deleted portion in the HA1 domain), also referred to as the parental design/construct, the H1N1 A/Brisbane/07/59 based polypeptide UFV160655 (which comprises a deletion in the HA1 domain of amino acids starting from position 47 up to and including the amino acid at position 306, and does not comprise a 4G linker replacing the deleted portion in the HA1 domain, and includes the point mutations Y392P, R404Q, E434Q, and S442A) (SEQ ID NO: 103), clearly showed increased levels of expression (up to 40-fold), reaching ~500 mg/L culture supernatant (FIG. 5A).

The H1N1 A/California/07/09 derived parental polypeptide UFV5369 (SEQ ID NO: 17) was expressed at a level of ~350 mg/L culture supernatant. Polypeptide UFV150558, similar in design to polypeptide UFV5369, and further including the point mutations Y392P, R404Q, E434Q, and S442A (SEQ ID NO: 30) was expressed at a level of ~427 mg/L. The polypeptides UFV160656 (SEQ ID NO: 104) (comprising a deletion comprising the amino acids from position 47 up to and including the amino acid at position 306 and not comprising a 4G linker replacing the deleted portion in the HA1 domain, and comprising the point mutations Y392P, R404Q, E434Q, and S442A), UFV160664 (comprising the same deletion but only comprising the point mutations Y392R and E434Q) (SEQ ID NO: 109) and UFV160665 (comprising the same deletion and comprising the point mutations Y392P and E434Q) (SEQ ID NO: 110) were expressed at a higher level compared to 5369, up to ~800 mg/L culture supernatant (FIG. 5A).

With respect to the trimer content, all polypeptides comprising one or more of the additional new mutations, independent of both their strain backbone, the size of the deletion of the head and presence or absence of the 4G linker replacing the deleted portion of the HA1 domain, reached levels above 90% which were significantly higher than was obtained for the parental designs for which only ~25% of the expressed protein successfully formed trimers (FIG. 5B).

Additional polypeptides comprising a mutation of the amino acid at position 392 into Y, P or R in combination with a mutation of the amino acid at position 434 into Q were made, including UFV160302 (SEQ ID NO: 60) and UFV160303 (SEQ ID NO: 61). Polypeptide UFV160304 (SEQ ID NO: 62) that comprises a similar design as polypeptide UFV160302 but does not comprise the point mutation Y392R showed a lower trimer content (~1,7 fold) (FIG. 5C).

Taken together the polypeptides of the invention described in this Example, comprising a Y, P or R at position 392, in combination with a Q at position 434, displayed significantly increased levels of protein expression and trimer content (percentage of successfully formed trimers) compared to the parental designs. The presence of these amino acid at the positions 392 and 434 led to a significant improvement in expression, trimerization and stability.

Example 3: Purification of Trimeric Polypeptides of the Invention

Purification

The polypeptides were purified by means of a two-step protocol. First, the harvested and clarified culture supernatant was loaded on a HiScale 16/20 column (GE Healthcare) packed with an affinity resin (Capture Select) that consists of a HA specific single domain antibody, immobilized on Poros beads (obtained from ThermoFisher Scientific). This resin is highly specific for H1 strain derived hemagglutinin proteins. The column was intentionally overloaded by ~15% to improve isolation of the trimer. Following binding and equilibration in 50 mM Tris, 0.5 M NaCl, pH 7.4 the polypeptides were eluted by applying a step gradient to 0.1 M Tris, 2 M $MgCl_2$, 40% propylene glycol, pH 7.4. Based on the UV signal (A280) the elution fractions were pooled and filtrated through a Millex-GV 0.22 μm filter membrane (Merck Millipore). Subsequently, the collected elution peak was applied to a Superdex 200 pg 26/60 column (GE Healthcare) equilibrated in running buffer (20 mM Tris, 150 mM NaCl, pH 7.8) for polishing purpose, i.e. remove the minimal amount of multimeric and monomeric protein. The trimer fractions were pooled and purity was assessed by analytical SEC-MALS in a High Performance Liquid Chromatography (HPLC) Infinity 1260 series setup (Agilent). Of each purified polypeptide 40 μg was run (1 mL/min.) over a TSK gel G3000SW×1 column (Sigma-Aldrich) and the molar mass of the eluted material was measured by a miniDAWN Treos Multi Angle Light Scattering detector and Optilab T-rex differential refractometer (Wyatt Technology). The data were analyzed by the Astra 6 software package and molecular weight calculations were derived from the refractive index signal.

Results and Conclusion

The elution profile of the second purification step (Size Exclusion Chromatography) indicated that a large amount of non-trimeric (aggregates and monomer) polypeptide 5367 was present in the pooled elution fractions of the affinity column. In contrast, the chromatogram of UFV160656 showed only a small amount of aggregates whereas the major species present was the trimeric polypeptide (FIGS. 6A and B).

The yield of the parental constructs UFV5367 and UFV5369 was 5 and 70 mg/L, respectively, whereas the yields for the polypeptides of the invention varied from 120-240 mg/L. The recovery percentage, calculated by comparison of the amount of protein present in the culture supernatant and the trimeric end product, was roughly 40-60%. Analysis of the pooled trimer fractions by analytical SEC-MALS showed that the purified material is pure; no other peaks in the UV signal were observed (FIG. 6B). Furthermore, the calculated molecular weight, ~96-106 kDa, corresponded with the expected molecular weight of the glycosylated trimeric polypeptide (FIG. 6C).

The above data indicated that purification of the polypeptides was achieved by a straightforward 2 step protocol resulting in very pure trimeric protein with high efficiency and yields well above 100 mg/L culture supernatant.

Example 4: Characterization of Trimerization of Polypeptides of the Invention by Size Exclusion Chromatography in the Presence of Binding Fab Fragments Characterization The folding and temperature stability of the purified polypeptides was assessed by (i) SEC-MALS analysis in presence of Fab-fragments, (ii) by Enzyme-Linked Immuno Sorbent Assay (ELISA), and (iii) by Differential Scanning Fluorimetry (DSF).

In-solution binding of Fab fragments to the polypeptides of the invention (also referred to as "mini-HA proteins") was monitored by Size Exclusion Chromatography (SEC) and multi-angle light scattering (MALS) analysis using a high-performance liquid chromatography system (Agilent) and miniDAWN TREOS instrument coupled to a Optilab T-rEX Refractive Index detector (Wyatt Technology). In total, 40 μg of the polypeptide or Fab fragments of mAbs CR6261, CR9114 and a negative control antibody were applied to a TSK-Gel G3000SW×1 column (Sigma Aldrich) equilibrated in running buffer (150 mM NaPi, 50 mM NaCl, pH 7.0). Complex formation was verified by analysis of the polypeptides incubated in the presence of a 1.2-fold molar excess of Fab fragments. The data were analyzed by the Astra 6 software package and molecular weight calculations were derived from the refractive index signal.

The avidity of CR6261 and CR9114 binding to the polypeptides was assessed by biolayer interferometry measurements using an Octet RED384 (ForteBio). Biotinylated antibodies were immobilized on Streptavidin (SA) Dip and Read biosensors for kinetics (ForteBio). Real-time binding curves were measured by applying the sensor in a two-fold dilution series of the polypeptide in PBS diluted 10× concentrated kinetics buffer (ForteBio). The starting concentrations of the polypeptides were in the range of 0.15-10 nM. Dissociation constants (KD) were determined using steady state analysis, assuming a 1:1 binding model for bnAb to the polypeptides.

In addition, binding of antibodies and single domain antibodies (SDs) to the stem polypeptides of the invention was assessed by ELISA. First 50 μg per well of the protein was coated to the surface of OptiPlate-96 high bind plates (Perkin Elmer) in Phosphate Buffered Saline (PBS). Following overnight incubation at 4° C., washing (three times with PBS+0.05% Tween-20), blocking (1.5 hour at Room Temperature with PBS+0.05% Tween-20+1% Bovine Serum Albumin), and washing (three times with PBS+0.05% Tween-20), the plates were incubated for 1 hour at RT with the mAb and SDs in a three-fold dilution series with a starting concentration of 70 nM or 100 nM respectively. After another wash (three times with PBS+0.05% Tween-20) the Horse Radish Peroxidase conjugated to Mouse anti-human IgG (Jackson) was added in a 1:1000 dilution in block buffer (PBS+0.05% Tween-20+1% Bovine Serum Albumin). After another 1 hour incubation at RT and subsequent wash (three times with PBS+0.05% Tween-20), BM Chemiluminescence ELISA Substrate (Roche) was added and following a 15-minute incubation the luminescent signal was measured using a Synergy Neo plate reader (Perkin Elmer). The half maximum effective concentration ($EC_{50}$) values were calculated by the Spotfire suite (Tibco Software Inc.). The $EC_{50}$ is directly correlated to the binding strength of the respective antibody and thereby a measure for the quality of the antigen, i.e. its proper folding and stability.

The protein temperature stability was determined by DSF through monitoring the fluorescent emission of the polypeptide solution (6 μg) in the presence of 5× Sypro Orange Dye (ThermoFisher Scientific). Upon gradual increase of the temperature, from 25° C. to 95° C. (60° C. per hour), the polypeptides unfold and the fluorescent dye binds to the exposed hydrophobic residues. The melt curves were measured using a ViiA7 real time PCR machine (Applied BioSystems) and the $Tm_{50}$ values were calculated by the Spotfire suite (Tibco Software Inc.). The $Tm_{50}$ values represent the temperature at which 50% of the protein is unfolded and thus are a measure for the temperature stability of the polypeptides. Additionally, heat-induced denaturation was also determined by DSC in which the thermal transition midpoint (Tm) was determined by monitoring the difference in energy input between the sample and the reference cell using a MacriCal DSC system (Malvern). At a concentration of 1 mg/mL the samples were gradually heated, from 20° C. to 90° C. (100° C. per hour), and the runs were analyzed by the Origin software (Malvern). Based on the temperature (° C.) vs heat capacity (kcal/mol/° C.) plots the Tm values were calculated.

Results and Conclusion

The theoretical molecular weight of the trimeric polypeptides based on amino acids only is ~90 kDa, however, as each protein contains 5 N-linked glycosylation motifs (N×T/S) the molecular weight will be higher when produced in a mammalian expression system. The molecular weights as determined by SEC-MALS analysis were calculated to be in the range of 96-106 kDa indicating that the proteins are, as expected, significantly glycosylated (Table 1).

TABLE 1

Molecular weight of polypeptides of the invention (second column) and of the polypeptides in complex with the Fab fragments of bnAb CR6261 and CR9114 (third and fourth column) as determined by SEC-MALS using the signal for the refractive index. The molecular weight (MW) of Fab6261 and Fab9114 was determined at ~44 kDa.

| Polypeptide ID | MW polypeptide (kDa) | MW polypeptide + Fab6261 (kDa) | MW polypeptide + Fab9114 (kDa) |
|---|---|---|---|
| UFV5367 | 98 | 204 | 228 |
| UFV160655 | 96 | 204 | 225 |
| UFV5369 | 97 | 212 | 225 |
| UFV160656 | 103 | 217 | 235 |
| UFV160664 | 98 | 211 | 226 |
| UFV160665 | 106 | 235 | 254 |

Figure 7:
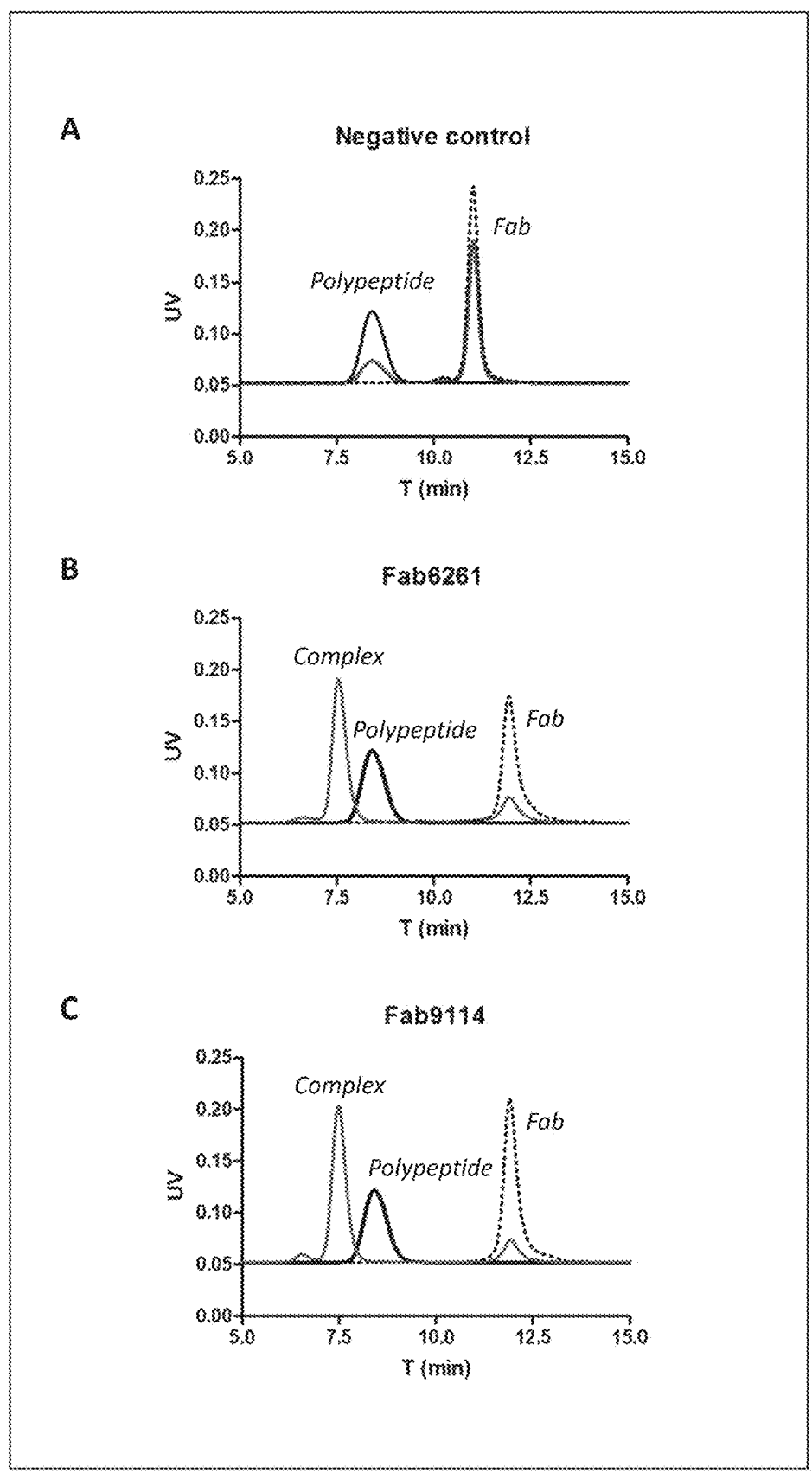
FIG. 7. SEC profiles of the trimeric stem polypeptide of the invention and Fab fragments. The overlay shows the chromatograms of the polypeptide (black), the Fab-fragment (dashed) and of the sample containing both (grey). The results for polypeptide 160656 are displayed. The overlapping peaks in panel A indicate that the Fab used as negative control does not bind to the polypeptide, whereas the polypeptides pre-incubated with Fab6261 (Panel B) and Fab9114 (Panel C) display a peak shift (reduced retention time) indicating complex formation (one trimer bound by three Fab fragments).

Antibody binding to the polypeptides indicates the correct folding of the polypeptides, and the presence of correctly folded epitopes of the broadly neutralizing antibodies (bnAbs). In solution binding of Fab-fragments CR9114, CR6261 and a non-binding Fab (negative control) was assessed by SEC-MALS analysis, as described above. Upon binding of the Fab-fragment to the polypeptide the molecular weight increase will result in a visible peak shift (shortened retention time) in the SEC. Furthermore, monitoring the MALS signal enables a molecular weight calculation of the complex formed. As anticipated, the Fab-fragment used as negative control did not bind; i.e. no peak shift of the polypeptide was observed upon addition of the Fab-fragment (FIG. 7A). In contrast, a clear peak shift to a shorter retention time was observed upon incubation with the other two Fab-fragments (FIGS. 7B and C). Furthermore, the molecular weight determination of the complex indicated that the polypeptide binds 3 Fab-fragments (Table 1), confirming that all three monomers within the trimeric polypeptide are properly folded and accessible for the antibodies.

To further assess the quality and folding of the polypeptides the dissociation constant ($K_D$) of the bnAbs CR6261 and CR9114 binding was determined by biolayer interferometry (Table 2). For all polypeptides, the binding avidity was below 1 nM indicating that the trimeric polypeptides represent the native HA stem surface.

TABLE 2

Binding of CR6261 and CR9114 to stem polypeptides of the invention. $K_D$ values of CR6261 and CR9114 binding as determined by biolayer interferometry and steady state analysis. Full length HA H1N1 A/Brisbane/59/07 was taken along for comparison.

| | $K_D$ (nM) | |
|---|---|---|
| Polypeptide ID | CR6261 | CR9114 |
| HA Brisbane | 1.1 | 0.71 |
| UFV5367 | 0.48 | 0.45 |
| UFV160655 | 0.55 | 0.49 |
| UFV5369 | 0.97 | 0.56 |
| UFV160656 | 0.60 | 0.54 |
| UFV160664 | 0.57 | 0.46 |
| UFV160665 | 0.56 | 0.39 |

Furthermore, the binding of antibodies was assessed by ELISA. Based on the S-curves $EC_{50}$ values were calculated that confirmed proper folding of the polypeptides. Both antibodies bound very strongly with $EC_{50}$ values below 1 nM (Table 3).

TABLE 3

Binding strength of antibodies to the purified polypeptides as determined by ELISA (Average EC50 values in nM of the S-curves of 3 independent assays).

| Polypeptide ID | CR6261 | CR9114 |
|---|---|---|
| UFV5367 | 0.417 | 0.410 |
| UFV160655 | 0.396 | 0.400 |
| UFV5369 | 0.391 | 0.389 |
| UFV160656 | 0.432 | 0.410 |
| UFV160664 | 0.395 | 0.379 |
| UFV160665 | 0.425 | 0.409 |

The thermal stability is a measure for the resilience of the polypeptides when exposed to stress, and thus for stability of the polypeptides. The polypeptides of the invention were gradually heated in the presence of a fluorescent dye that, over the course of the experiment, binds to the unfolding protein and the resulting change in fluorescence intensity was used to calculate the $Tm_{50}$ values (Table 4). Whereas the parental designs (UFV5367 and UFV5369) displayed a $Tm_{50}$ value of ~52 and ~57° C., respectively, strikingly, the polypeptides of the invention displayed values that are significantly higher (up to ~7° C.), indicating a significantly improved stability. A similar difference between the parental designs and the polypeptides of the invention was observed for the Tm values as determined by DSC. Overall the Tm-values (DSC) were ~2° C. higher than the $Tm_{50}$ values (DSF) which was due to the difference in the way these values are determined; for DSC, the temperature at the peak max was determined, whereas for DSF the temperature was determined at ½ peak heights.

TABLE 4

Overview of Tm50 values of the purified polypeptides as determined by DSF and DSC.

| Polypeptide ID | $Tm_{50}$ (° C.) DSF | $Tm_{50}$ (° C.) DSC |
|---|---|---|
| UFV5367 | 51.8 ± 0.09 | — |
| UFV160655 | 58.5 ± 0.21 | — |
| UFV5369 | 57.2 ± 0.08 | 59.1 ± 0.01 |
| UFV160656 | 64.1 ± 0.14 | 66.2 ± 0.07 |
| UFV160664 | 63.3 ± −0.12 | 65.3 ± 0.01 |
| UFV160665 | 62.5 ± 0.16 | 65.2 ± 0.16 |

The molecular weight of the polypeptides, the observed Fab-fragment binding in solution and the strong binding of Abs indicated that the parental designs and the polypeptides of the inventions are trimeric and well folded. Furthermore, as indicated by the calculated Tm50/Tm values, the polypeptides of the invention were considerably more resistant to thermal stress compared to the parental designs. Taken together the binding data and thermostability data indicate that the polypeptides of the invention are trimeric in solution, are properly folded (3 epitopes) and display significantly improved thermal stability compared to their parental designs.

Figure 8:
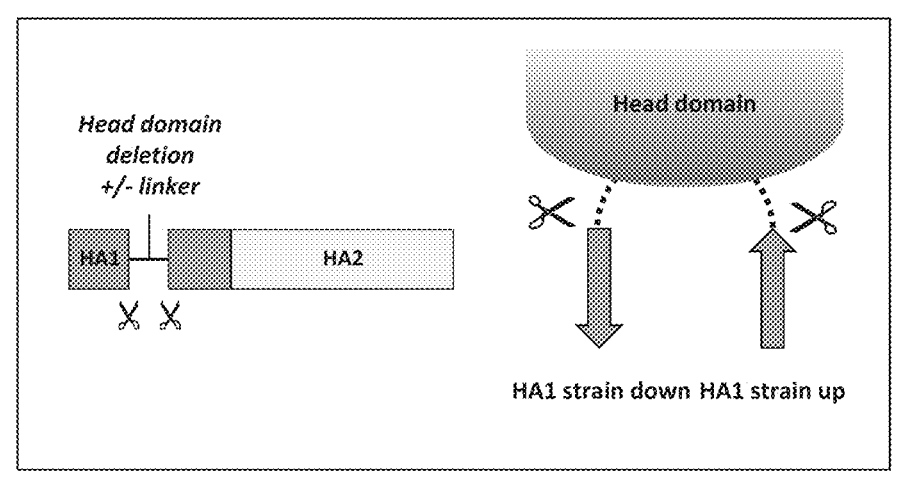

Example 5: Alternative Deletions, Linkers and Head Domain Sequences According to the Invention Designs The influenza hemagglutinin (HA) stem polypeptides of the invention described above were derived from full length HA by deleting a part of the HA1 domain comprising the amino acids from position 47 up to and including the amino acid at position 306. No linking sequence was introduced. In the parental designs the deletion comprised the amino acids 46-306 and the two HA1 ends after deletion were connected by an artificial "GGGG-linker" (FIG. 8).

In this Example, further alternative cutting positions of the head and alternative homologous linkers were explored. Table 5 shows alternative cutting positions for removal of the HA1 head domain. The HA1 ends in the parental design are indicated in grey. The construct UFV160360 (SEQ ID NO: 63) comprises a deletion from the amino acid at position 46 up to and including the amino acid at position 306 and a 4G linker replacing the deleted portion in the HA1 domain, and further comprises the point mutations Y392P, R404Q, E434Q, and S442A. New constructs were made wherein up to 7 additional amino acid residues of the HA1 domain (HA1 up), the first (N-terminal) HA1 domain, and up to 4 additional amino acid residues of the HA1 down strand (the second, or C-terminal HA1 domain) were included, or up to 2 amino acid residues deleted, thus varying the size of the head deletion. These constructs also all comprised the point mutations Y392P, R404Q, E434Q, and S442A.

TABLE 5

Alternative head domain deletions, see also FIG. 5).

| UVF# | HA1 up | | | | | | | | | | | | | Head domain deletions | | | | | | | HA1 down | | | | | | |
|---|---|---|---|---|---|---|---|---|---|---|---|---|---|---|---|---|---|---|---|---|---|---|---|---|---|---|---|
| A/Brisbane/59/07 | N | L | L | E | N | S | H | N | G | K | | | | | | | ... | I | G | K | C | P | K | Y | V | K |
| A/California/07/09 | N | L | L | E | D | K | H | N | G | K | L | C | K | | | | ... | I | G | E | C | P | K | Y | V | R |
| UFV160360 | N | L | L | E | D | G | G | G | G | | | | | | | | | | | | K | Y | V | C |

| | AA position # |
|---|---|
| | 41 42 43 44 45 46 47 48 50 51 52 53    302 303 304 305 306 307 308 |

| UFV160361 | N | L | L | E | D | | | | | | | | | | | | | | | | K | Y | V | C |
|---|---|---|---|---|---|---|---|---|---|---|---|---|---|---|---|---|---|---|---|---|---|---|---|---|
| UFV160362 | N | L | L | E | D | K | | | | | | | | | | | | | | | K | Y | V | C |

TABLE 5-continued

Alternative head domain deletions, see also FIG. 5).

| UVF# | HA1 up | Head domain deletions | HA1 down |
|---|---|---|---|
| UFV160363 | N L L E | D K H | K Y V C |
| UFV160364 | N L L E | D K H N | K Y V C |
| UFV160365 | N L L E | D K H N G | K Y V C |
| UFV160366 | N L L E | D K H N G K | K Y V C |
| UFV160367 | N L L E | D K H N G K L | K Y V C |
| UFV160368 | N L L E | D K H N G K L G* | K Y V C |
| UFV160369 | N L L E | D K H N G K L G* | P K Y V C |
| UFV160370 | N L L E | D K H | G* P K Y V C |
| UFV160371 | N L L E | D | G E G* P K Y V C |
| UFV160372 | N L L E | D | V C |
| UFV160373 | N L L E | D K | V C |
| UFV160374 | N L L E | D K H | V C |
| UFV160375 | N L L E | D K H N | V C |
| UFV160376 | N L L E | D K H N G | V C |
| UFV160377 | N L L E | D K H N G K | V C |
| UFV160378 | N L L E | D K H N G K L | V C |
| UFV160379 | N L L E | D K H N G K L G* | V C |

The * indicates the mutation of a free cysteine (C) to a G.
The numbers of the amino acid positions indicate amino acid position according to H3 numbering convention.

Table 6 below shows alternative homologous linkers. The HA1 ends in the parental design are indicated in dark grey. Up to 5 residue long homologous linkers, i.e. originating from the HA1 domain were introduced to connect the HA1 ends. Again, the other constructs also all comprised the point mutations Y392P, R404Q, E434Q, and S442A.

TABLE 6

Alternative linkers derived from the deleted homologous head domain.

| # | HA1 up | Introduced Linkers | HA1 down |
|---|---|---|---|
| A/Brisbane/59/07 | N L L E N S H N G K | ...I G K C | P K Y V K |
| A/California/07/09 | N L L E D K H N G K L C K | ...I G E C | P K Y V R |

| | AA position # | | |
|---|---|---|---|
| | 41 42 43 44 45 46 47 48 49 50 51 52 53 | | 305 306 307 308 309 310 |
| UFV160360 | N L L E D G G G | | K Y V C |
| UFV160380 | N L L E D A G S G | | K Y V C |
| UFV160381 | N L L E D A G S | | K Y V C |
| UFV160382 | N L L E D A G S G I | | K Y V C |
| UFV160383 | N L L E D A G S G I | | V C |
| UFV160384 | N L L E D G S G I | | K Y V C |
| UFV160385 | N L L E D G S G | | K Y V C |
| UFV160386 | N L L E D H A G A | | K Y V C |

TABLE 6-continued

Alternative linkers derived from the deleted homologous head domain.

| # | HA1 up | | | | | Introduced Linkers | | | | HA1 down | | | |
|---|---|---|---|---|---|---|---|---|---|---|---|---|---|
| UFV160387 | N | L | L | E | D | D | Q | E | G | K | Y | V | C |
| UFV160388 | N | L | L | E | D | D | T | P | V | K | Y | V | C |
| UFV160389 | N | L | L | E | D | F | P | K | T | K | Y | V | C |
| UFV160390 | N | L | L | E | D | E | P | G | D | K | Y | V | C |
| UFV160391 | N | L | L | E | D | E | P | G |   | K | Y | V | C |
| UFV160392 | N | L | L | E | D | T | G | N | L | K | Y | V | C |
| UFV160393 | N | L | L | E | D | T | P | S | S | K | Y | V | C |
| UFV160394 | N | L | L | E | D | T | P | S |   | K | Y | V | C |
| UFV160395 | N | L | L | E | D | A | T | G | N | K | Y | V | C |
| UFV160396 | N | L | L | E | D | Y | P | G | D | K | Y | V | C |
| UFV160397 | N | L | L | E | D | Y | P | G | D |   |   | V | C |

The amino acid positions indicate amino acid position according to H3 numbering convention.

Characterization

DNA fragments encoding the polypeptides listed in table 5 and 6 were synthesized (Genscript) and cloned in the pcDNA2004 plasmid (in-house modified pcDNA3 vector with an enhanced CMV promotor). The polypeptides, including a C-terminal FLAG-linker-His tag for screening purpose, were produced in eukaryotic cell line Expi293F cells at microscale (200 μL). In short, cells were seeded in a 96-well microplate format (Greiner) at a cell density of 2.5E+06 viable cells (vc)/mL in Opti-MEM (Gibco). Cells were transiently transfected using the ExpiFectamine 293 transfection kit (Gibco) and incubation for 3 days at 37° C., 250 rpm, 8% CO2 and 75% humidity. The culture supernatants were harvested by centrifugation (10 min. at 400×g) using a white 96-well Filter plates (0.22 μm PVDF membrane) to remove aggregates and cell debris.

The amount of polypeptides present in the culture supernatant, protein folding and trimer content were all assessed by Amplified Homogeneous Assay (AlphaLISA). Appropriate polypeptide dilutions in the linear range of the curve were used for analysis and all data was normalized to construct UFV160360 (SEQ ID NO: 63) that was set to 100%.

The relative polypeptide quantity in the harvested culture supernatant was determined by using Nickel donor beads (Perkin Elmer) and Anti-Flag Acceptor beads (Perkin Elmer). Appropriate dilutions of the culture supernatant in the linear range of the curve were used to avoid the hook-effect.

Similarly, the folding of the expressed polypeptides was verified by assessment of binding of antibodies CR9114 (2 nM) and single domain SD15004 (2 nM). For detection of the antibody binding Anti-human IgG Acceptor beads (Perkin Elmer) and Nickel Donor beads (Perkin Elmer) was used, for detecting binding of the Streptactin-tagged single domain Anti-His Acceptor beads (Perkin Elmer) and Streptactin Donor beads (Perkin Elmer) were used.

The multimer content was measured by simultaneous binding of CR9114 (2 nM) and Streptactin tagged SD15016 (2 nM) using a protocol similar to as described in example 2. The polypeptide was titrated based on protein concentration, as determined by OCTET. Only trimeric molecules offering both antibodies to bind give a signal in this assay (in contrast to monomers, dimers and potential aggregates).

Results and Conclusion

Figure 9:
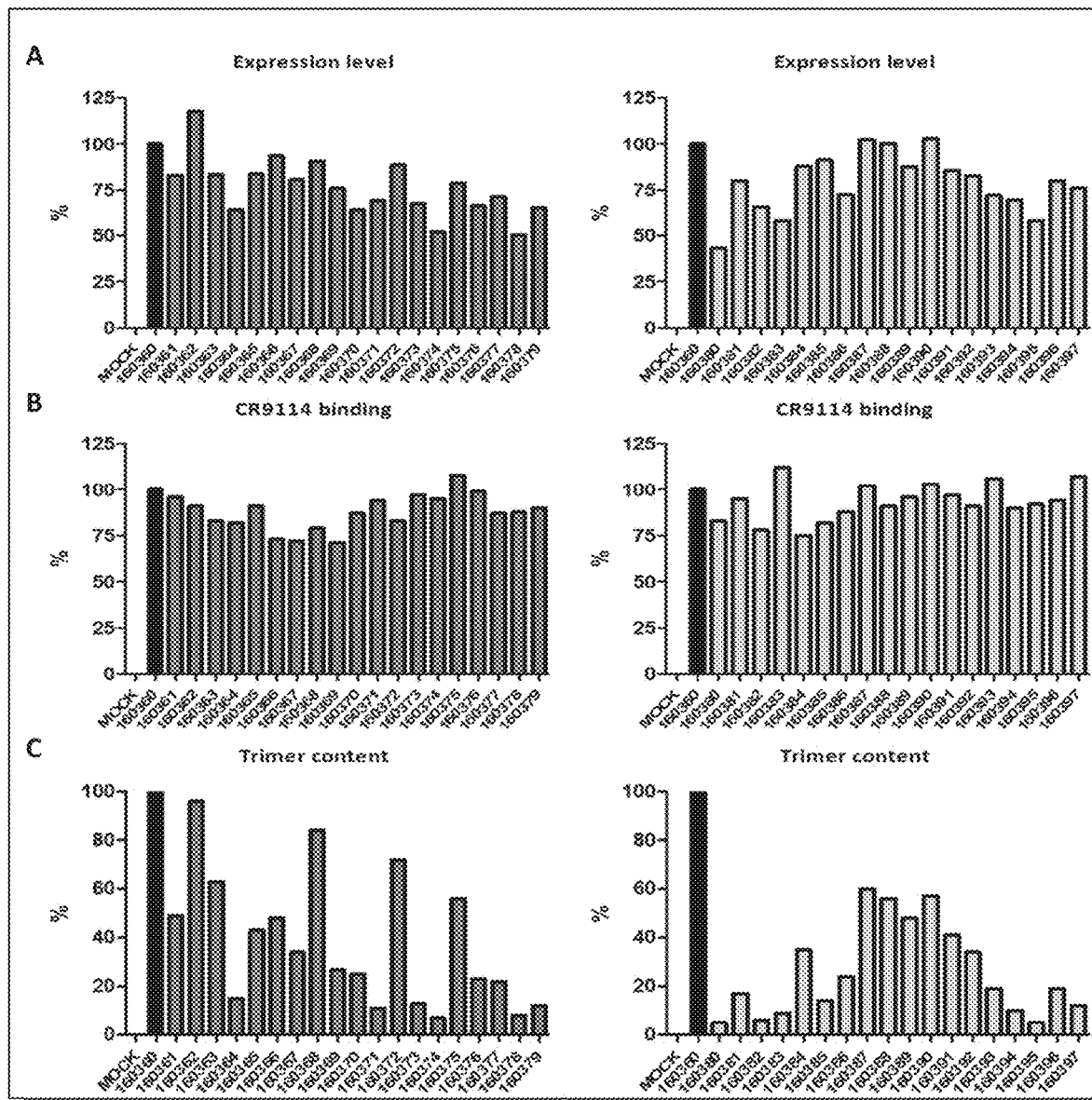
FIG. 9. Expression levels, antibody binding and trimer content of the polypeptides of the invention, as determined by AlphaLISA. A: expression levels, B: CR9114 binding and C: Trimer content. Designs including the alternative cuts are colored grey (left panel), designs including alternative linkers are colored light grey. All data are normalized to reference design UFV160360 (black).

Overall the polypeptides were expressed at a similar level to the reference protein (UFV160360) and no significant differences were observed between the designs with the alternative cutting positions (i.e. alternative head domain deletions) and the designs in which the HA1 ends were connected with a linker originating from the head domain (FIG. 9A). Similarly, no significant differences were observed for binding of bnAb CR9114 (FIG. 9B).

In contrast, some differences in relative trimer content were observed (FIG. 9C); the designs were less prone to forming trimeric mini-HA. On average, a ~2-fold decrease was observed for the designs in which an alternative cut was introduced whereas a ~3-fold decrease was observed across the designs in which the "GGGG-linker" is replaced by a sequence from the head domain.

These results show that although the trimeric content is somewhat decreased, well expressing and stable stem polypeptides were obtained which were correctly folded to present the epitope of the broadly neutralizing antibody CR9114.

Example 6: HA1/HA2 Cleavage Site Variations: Knock Out, Monobasic and Polybasic Cleavage Site Cleavage of the influenza HA0 protein (in HA1 and HA2) is required for its activity, facilitating the entry of the viral genome into the target cells by causing the fusion of host membrane with the viral membrane. The polypeptides of the invention described above were all expressed with the cleavage site knock-out mutation R329Q to prevent putative cleavage of the molecule during production in vitro and/or in vivo.

In this Example, several stem polypeptides were expressed with the natural monobasic cleavage site or including a polybasic cleavage site, e.g. a Furin cleavage site (Table 7). The polypeptides also comprised the mutations at position 392 and 434.

TABLE 7

Cleavage site variants.

| Polypeptide ID | Cleavage site | Sequence |
|---|---|---|
| UFV150850 | Knocked out | R329Q |
| UFV160302 | Monobasic | R329 (wildtype) |
| UFV160301 | Polybasic | RRRKK |
| UFV160503 | Polybasic | RKRR |

Culture Supernatant Analysis

DNA fragments encoding the polypeptides listed in table 7 were synthesized as described in Example 5.

The level of expressed polypeptide in the harvested culture supernatant was assessed through Bio-Layer Interferometry using the OCTET platform. In short biotinylated mAb CR9114 was immobilized on Streptavidin (SA) biosensors (Pall FortéBio) following which a standard curve was established by assessing the binding shift of a dilution series of a well-defined purified homologous polypeptide.

Subsequently the binding shift of pre-diluted harvested culture supernatant containing the polypeptide (5-15 µg/mL diluted in kinetics buffer) was measured and the concentration was calculated using the established reference curve.

Results and Conclusion

Figure 10:
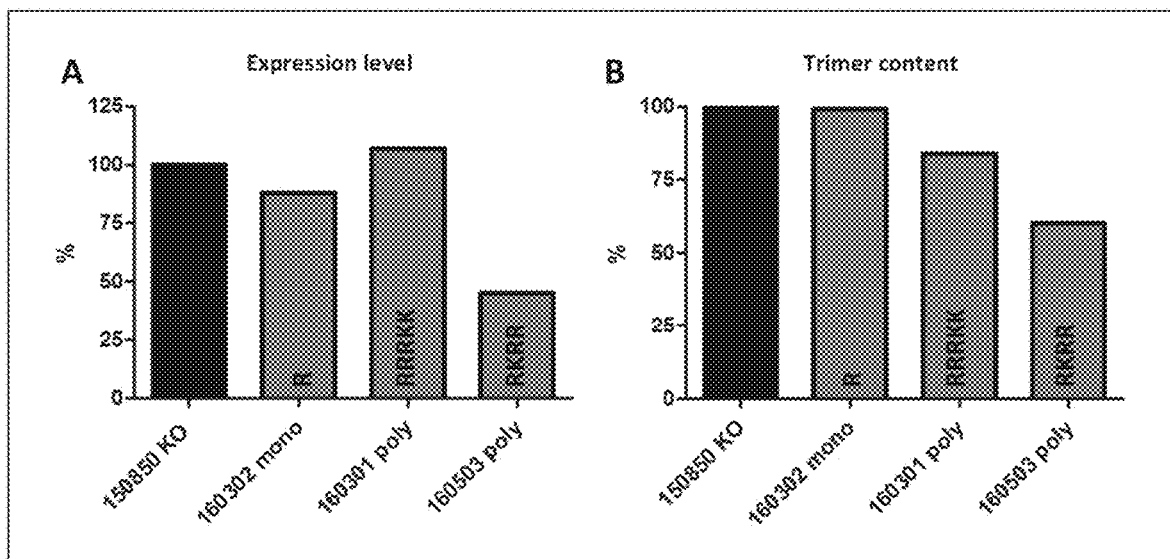
FIG. 10. Expression levels and trimerization of polypeptides of the invention. Expression levels were determined by OCTET (panel A) and trimer content by AlphaLISA (panel B). Data are normalized to reference polypeptide UFV150850.

No effect on the expression level was observed for the polypeptides in which a monobasic (R)- or polybasic cleavage site (RRRKK) was inserted, i.e. UFV160302 and UFV160301 respectively (FIG. 10). Both polypeptides were expressed at similar levels and showed similar levels of trimer content compared to the reference polypeptide UFV150850, which is resistant to protease cleavage through mutation of the amino acid at position 329 into Q.

For the second introduced polybasic cleavage site introduced (RKRR) a ~2-fold decrease in expression level and trimer content was observed (UFV160503).

Example 7: Example Sequences of GCN4 or Alternative Heptad Repeat Trimerization Domains Designs In the polypeptides of the invention as described above, the N-terminal end of the C-helix (top part of the molecule, see FIG. 1C), in particular the amino acid sequence starting from the amino acid at position 405 up to and including the amino acid at position 419 of the HA2 domain, was replaced by the GCN4 trimerization domain of SEQ ID NO: 113 in order to improve the trimerization tendency of the molecule. In this Example, optimizations of the coiled-coil interface were successfully explored by optimization of the heptad repeat sequence of the C-helix. Table 8 shows an alternative trimerization sequence in the polypeptide UFV160090 (SEQ ID NO: 56). The mutations in the N-terminal region of the C-helix are highlighted in light grey. The trimerization sequence of UFV160097 (SEQ ID NO: 58) is identical to the polypeptides as described in Example 1. The differences of the heptad repeat sequence in the N-terminal part of the C-helix with the Wild type HA are highlighted in grey.

TABLE 8

Sequences of GCN4 or alternative hepta repeat trimerization domains (for A/California/07/09 HA derived polypeptides).

| C-helix trimerization domain | UFV# | C-helix (amino acid position of N-terminal region) | | | | | | | | | | | | | | |
|---|---|---|---|---|---|---|---|---|---|---|---|---|---|---|---|
| | | 405 | 406 | 407 | 408 | 409 | 410 | 411 | 412 | 413 | 414 | 415 | 416 | 417 | 418 | 419 |
| wt A/California/07/09 | wt | R | I | E | N | L | N | K | K | V | D | D | G | F | L | D |
| GCN4 | 160097 | C | M | K | Q | I | E | D | K | I | E | E | I | E | S | K |
| alternative heptad repeat | 160090 | C | I | E | A | K | E | K | K | V | D | D | I | E | K | K |

Numbers at the top indicate amino acid position according to H3 numbering convention.

Culture Supernatant Analysis

DNA fragments encoding the polypeptides listed in Table 8 were synthesized as described above in Example 5.

All assessments on the harvested culture supernatants were performed by AlphaLISA similar as described for example 5. The CR9114 binding data was normalized on expression level.

Results and Conclusion

Figure 11:
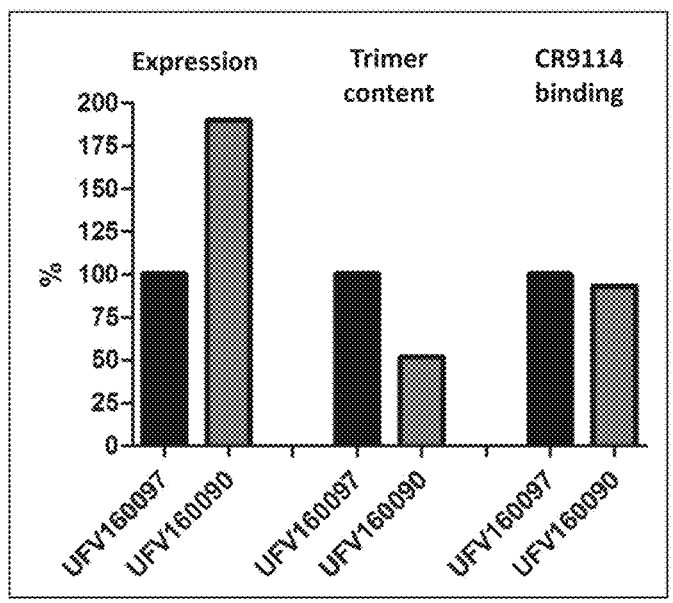
FIG. 11. Normalized expression levels, trimer content and CR9114 binding. Culture supernatants were analyzed by AlphaLISA. Reference construct UFV160097 contains the GCN4 like heptad repeat and is indicated in black whereas the polypeptide containing the alternative heptad repeat is colored grey. The CR9114 binding levels were normalized by the determined expression level.

AlphaLISA assessment of the harvested culture supernatants on polypeptide expression level, trimer content and CR9114 binding indicated that an alternative optimization of the C-helix trimer interface (i.e. other than the GCN4-like repeat, as present in the polypeptides described above) was tolerated. An improved protein expression level was observed (~2 fold), although a reduction in trimer content was observed (~2 fold). Binding of CR9114 was not affected (FIG. 11).

Example 8: Alternative Truncations at the C-Terminus of the Stem Polypeptides of the Invention Designs Hemagglutinin is a membrane protein that is located on the surface of the viral particle with the C-terminal part of the protein embedded in the viral membrane. For the soluble versions of the polypeptides of the invention the transmembrane domain was deleted by a truncation at the start of the transmembrane domain (TM). Additionally, alternative truncation positions were evaluated as well (Table 9 and 10).

TABLE 9

Alternative truncations of the C-terminus of the HA2 domain (for A/Brisbane/59/07 HA derived polypeptides).

| UVF# | 496 | 497 | 498 | 499 | 500 | 501 | 502 | 503 | 504 | 505 | 506 | 507 | 508 | 509 | 510 | 511 | 512 | 513 | 514 | 515 | 516 | 517 | 518 | 519 | TM domain |
|---|---|---|---|---|---|---|---|---|---|---|---|---|---|---|---|---|---|---|---|---|---|---|---|---|---|
| A/Brisbane/59/07 | K | L | N | R | E | K | I | D | G | V | K | L | E | S | M | G | V | Y | Q | I | L | A | I | Y | |
| UFV5367 | K | L | N | R | E | K | I | D | G | V | K | L | E | S | M | G | V | Y | Q | I | | | | | |
| UFV150565 | K | L | N | R | E | K | I | D | G | V | K | L | E | S | M | G | V | Y | Q | I | L | A | I | Y | |
| UFV150566 | K | L | N | R | E | K | I | D | G | V | K | L | E | S | M | G | V | Y | Q | I | L | A | | | |
| UFV150567 | K | L | N | R | E | K | I | D | G | V | K | L | E | S | M | G | V | Y | | | | | | | |
| UFV150568 | K | L | N | R | E | K | I | D | G | V | K | L | E | S | M | G | | | | | | | | | |
| UFV150569 | K | L | N | R | E | K | I | D | G | V | K | L | E | S | | | | | | | | | | | |
| UFV150570 | K | L | N | R | E | K | I | D | G | V | K | L | | | | | | | | | | | | | |
| UFV150571 | K | L | N | R | E | K | I | D | G | V | | | | | | | | | | | | | | | |
| UFV150572 | K | L | N | R | E | K | I | D | | | | | | | | | | | | | | | | | |
| UFV150573 | K | L | N | R | E | K | | | | | | | | | | | | | | | | | | | |
| UFV150574 | K | L | N | R | | | | | | | | | | | | | | | | | | | | | |

Numbers at the top indicate amino acid position according to H3 numbering convention.

TABLE 10

Truncation of the C-terminus of the HA2 domain (for A/Califrnia/07/09 HA derived polypeptides).

| UVF# | 496 | 497 | 498 | 499 | 500 | 501 | 502 | 503 | 504 | 505 | 506 | 507 | 508 | 509 | 510 | 511 | 512 | 513 | 514 | 515 | 516 | 517 | 518 | 519 | TM Domain |
|---|---|---|---|---|---|---|---|---|---|---|---|---|---|---|---|---|---|---|---|---|---|---|---|---|---|
| A/California/07/09 | K | L | N | R | E | E | I | D | G | V | K | L | E | S | T | R | I | Y | Q | I | L | A | I | Y | |
| UFV5369 | K | L | N | R | E | E | I | D | G | V | K | L | E | S | T | R | I | Y | Q | I | | | | | |
| UFV150575 | K | L | N | R | E | E | I | D | G | V | K | L | E | S | T | R | I | Y | Q | I | L | A | I | Y | |
| UFV150576 | K | L | N | R | E | E | I | D | G | V | K | L | E | S | T | R | I | Y | Q | I | L | A | | | |
| UFV150577 | K | L | N | R | E | E | I | D | G | V | K | L | E | S | T | R | I | Y | | | | | | | |
| UFV150578 | K | L | N | R | E | E | I | D | G | V | K | L | E | S | T | R | | | | | | | | | |
| UFV150579 | K | L | N | R | E | E | I | D | G | V | K | L | E | S | | | | | | | | | | | |
| UFV150580 | K | L | N | R | E | E | I | D | G | V | K | L | | | | | | | | | | | | | |
| UFV150581 | K | L | N | R | E | E | I | D | G | V | | | | | | | | | | | | | | | |
| UFV150582 | K | L | N | R | E | E | I | D | | | | | | | | | | | | | | | | | |
| UFV150583 | K | L | N | R | E | E | | | | | | | | | | | | | | | | | | | |
| UFV150584 | K | L | N | R | | | | | | | | | | | | | | | | | | | | | |

Numbers at the top indicate amino acid position according to H3 numbering convention.

Culture Supernatant Analysis

DNA fragments encoding the polypeptides listed in Table 9 and Table 10 were synthesized as described in Example 5.

The harvested culture supernatants were analyzed for the presence of expressed polypeptide by Western Blotting. Samples were run on an SDS-PAGE gel, 4-12% Bis-Tris (ThermoFisher Scientific) under non-reducing conditions and transferred to a PVDF membrane using the iBlot id 2.0 system (ThermoFisher Scientific). For visualization of the bands corresponding with the polypeptides the membrane was blocked with 0.2% blocking agent (Milk powder—BioRad) in TBST prior to incubation with the H1 strain specific derived Hemagglutinin proteins and biotinylated single domain antibody (Influenza 6) sufficiently dilution in block buffer. Following washing (TBST) the membrane was incubated with HRP-labelled Streptavidin (Becton Dickinson 1:250 dilution in block buffer). Subsequently, following another wash step (TBST) the protein bands were visualized by incubation with Trueblue peroxidase substrate (KPL).

Binding of broadly neutralizing monoclonal antibody CR9114 to the expressed polypeptides of the invention was assessed in the harvested culture supernatant through Bio-Layer Interferometry using the OCTET platform. In short, two-fold diluted supernatants in kinetics buffer (Pall ForteBio) were assessed by Streptavidin (SA) biosensors (Pall ForteBio) loaded with biotinylated CR9114. Curve fitting over the initial 20 seconds of the association step is performed to calculate $K_{on}$ values; the concentration of the polypeptides in the culture supernatants was set to 50 mM and the curves were fitted in a 1:1 model. A MOCK sample was included as negative control.

Results and Conclusion

Minimal effect of the alternative C-terminal truncations was observed on the expression level of the polypeptides. All variants, except UFV150565 and UFV150574, displayed a clear band at trimeric height in the Western blot analysis of harvested culture supernatants (FIG. 12A).

The Octet analysis indicated that almost all designs (except UFV150575) did bind to the immobilized CR9114 (FIG. 12B), although overall lower $K_{on}$ values were observed for the C-terminal variants compared to the reference designs 5367 and 5369. This likely was partially due to the basic curve fitting procedure assuming identical protein concentration for all designs; however, binding of the polypeptide to the antibody is evident.

The results clearly show that truncations up to position 502 are possible.

Example 9: Interprotomeric Disulfide Bridges; Alternative Positions

Designs

The polypeptides of the invention are purified from the culture supernatant as covalent trimeric proteins. In the polypeptides as described earlier the covalent link has been established by the introduction of two cysteine residues, in the B-loop (position 397) and C-helix (position 405), that form a disulfide bridge by pairing with the cysteine residue in the adjacent monomer (intermonomeric disulphide bridge). In this Example, two alternative positions for these interprotomeric disulfide bridges were explored (Table 11).

TABLE 11

Alternative positions for the cysteine residues that form inter-protomeric disulfide bridges. * Knocked out N-linked glycan motif (N x S) at position 400.

| Polypeptide ID | Cysteine introduction at amino acid postion | Parental Influenza Virus Strain |
| --- | --- | --- |
| UFV160090 | 397 + 405 | H1N1 A/California/07/09 |
| UFV160093 | 398 + 405 | H1N1 A/California/07/09 |
| UFV160088* | 396 + 408 | H1N1 A/Brisbane/59/07 |

Culture Supernatant Analysis

DNA fragments encoding the polypeptides were synthesized as described above.

All assessments on the harvested culture supernatants were performed by AlphaLISA as described in Example 7.

Results and Conclusion

Figure 13:
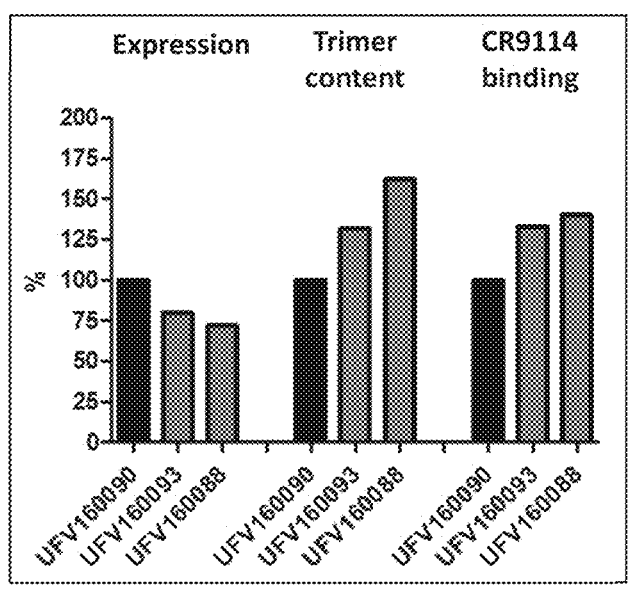
FIG. 13. Normalized expression level, trimer content and CR9114 binding. Culture supernatants were analyzed by AlphaLISA. Reference construct UFV160090 is indicated in black whereas the polypeptide containing introduced cysteines at alternative positions are colored grey. Trimer content and CR9114 binding levels were normalized based on the determined expression level.

AlphaLISA assessment of the harvested culture supernatants on polypeptide expression level, trimer content and CR9114 binding indicated that the alternative inter-protomeric disulfide bridges displayed similar or better than the reference polypeptide UFV160090 (FIG. 13). These data indicated introduction of cysteine residues at positions 398 and 405 (UFV160093) and 396 and 408 (UFV160088) provided an alternative to the inter-protomeric disulfide bridge formed by the introduced cysteines at the positions 397 and 405 (UFV160090).

Example 10: Protection Against Lethal Challenge with H1N1 A/Brisbane/59/07 after Immunization of Naïve Mice with Polypeptides of the Invention In this example, the protective efficacy (based on survival proportion at the end of the follow-up period) of a dose range of A10H3-adjuvanted UFV160664 in comparison to mock-immunized (PBS) animals and to a fixed dose of UFV4900 (exploratory) was evaluated.

Groups of 8-11 female BALB/c mice (age 6-8 weeks) were intramuscularly immunized 2 times at a 3-week interval with a dose range of soluble trimeric UFV160664 adjuvanted with 50 µg A10H3 (formulated as 2% Alyhydrogel). The dose range consisted of 4 10-fold dilutions starting at 30 µg up till 0.03 µg. As a positive control for the challenge model mice were immunized twice with 30 µg soluble trimeric UFV4900 (n=10), while 2 immunizations with PBS served as a negative control (n=11). Four weeks after the last immunization mice were bled to analyze the immune response (H1N1 A/Brisbane/59/07 full-length (FL) HA ELISA), and one day later the mice were challenged with 25×LD50 mouse-adapted H1N1 A/Brisbane/59/07 challenge virus and monitored (survival, weight, clinical scores) for 3 weeks. Survival proportion at end of follow-up was the primary outcome parameter.

Results

Figure 15:
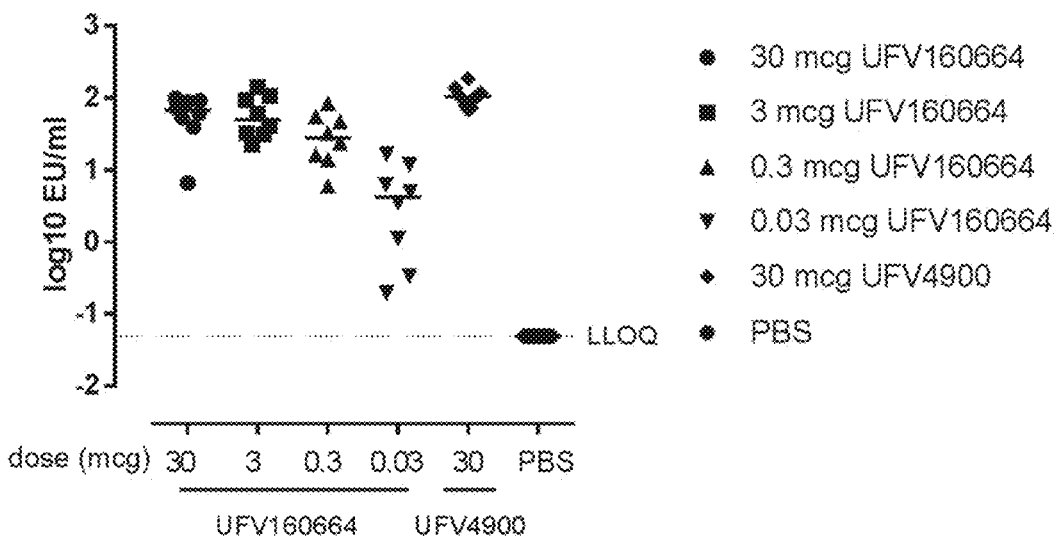
FIG. 15: H1 A/Brisbane/59/07 FL HA-specific antibody titers after immunization of mice with polypeptides of the invention. The dashed line indicates the LLOQ (Lower Limit of Quantification), the horizontal line per group denotes the group median.

It was shown that A10H3-adjuvanted UFV160664 was immunogenic as H1N1 A/Brisbane/59/07 FL HA ELISA titers were significantly increased (P<0.001; Mann-Whitney-U test with stepwise, starting at highest dose and Bonferroni adjustment for multiple comparisons) compared to the PBS group for all doses tested. Titers of the 30 µg UFV160664 dose immunized animals were comparable to the 30 µg UFV4900 group (FIG. 15).

Figure 16:
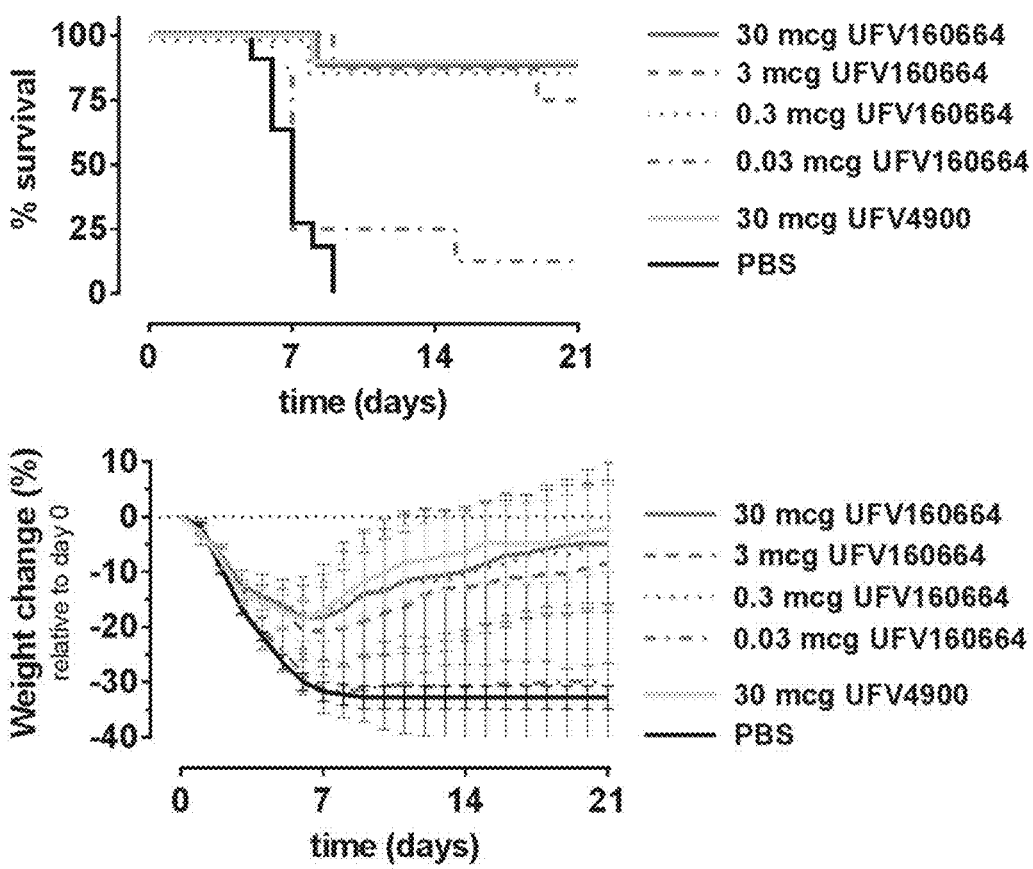
FIG. 16: Upper panel: Survival proportion during the follow-up period after H1N1 A/Brisbane/59/07 challenge of mice immunized with polypeptides of the invention. Bottom panel: Relative bodyweight during the follow-up period after H1N1 A/Brisbane/59/07 challenge of mice immunized with polypeptides of the invention. Relative bodyweight change was expressed relative to Day 0. Cumulative bodyweight loss during the follow-up period was determined by calculating the Area Under the Curve (AUC). Error bars denote 95% confidence interval.

In addition, AlOH$_3$-adjuvanted UFV160664 provided significant protection (P≤0.003; Fisher's exact test, Bonferroni correction over constructs, and step-wise testing, starting at highest dose) for all doses, except 0.03 µg, compared to the PBS group. Survival proportion of the 30 µg UFV160664 group (87.5%) was comparable to the 30 µg UFV4900 group (90%) (FIG. 16; upper panel). The bodyweight loss (defined by area under the curve) was significantly reduced (P≤0.012; ANOVA, 2-fold Bonferroni correction over constructs, and step-wise testing, starting at highest dose) for all doses, except 0.03 µg, compared to the PBS group. Bodyweight loss of the 30 µg UFV160664 group was comparable to the 30 µg UFV4900 group (FIG. 16; lower panel).

Conclusion

According to the present invention, it has been shown that AlOH$_3$-adjuvanted UFV160664 is immunogenic and provides protection in a lethal H1N1 A/Brisbane/59/07 mouse challenge model. The immunogenicity and protective efficacy is comparable to AlOH$_3$-adjuvanted UFV4900.

Example 11: Protection Against Lethal Challenge with H1N1 A/Puerto Rico/8/34 after Immunization of Naïve Mice with Polypeptides of the Invention In this example, the protective efficacy (based on survival proportion at the end of the follow-up period) of a dose range of 2% Adjuplex-adjuvanted UFV160664 in comparison to mock-immunized (PBS) animals and to a fixed dose of UFV4900 (exploratory) was evaluated.

Again, groups of 8-11 female BALB/c mice (age 6-8 weeks) were intramuscularly immunized 2 times at a 3-week interval with a dose range of soluble trimeric UFV160664 adjuvanted with 2% (v/v) Adjuplex. The dose range consisted of 4 10-fold dilutions starting at 30 mcg up till 0.03 µg. As a positive control for the challenge model mice were immunized twice with 30 µg soluble trimeric UFV4900 (n=10), while 2 immunizations with PBS served as a negative control (n=11). Four weeks after the last immunization mice were challenged with 12.5×LD50 mouse-adapted H1N1 A/Puerto Rico/8/34 challenge virus and monitored (survival, weight, clinical scores) for 3 weeks. Survival proportion at end of follow-up was the primary outcome parameter.

Results

Figure 17:
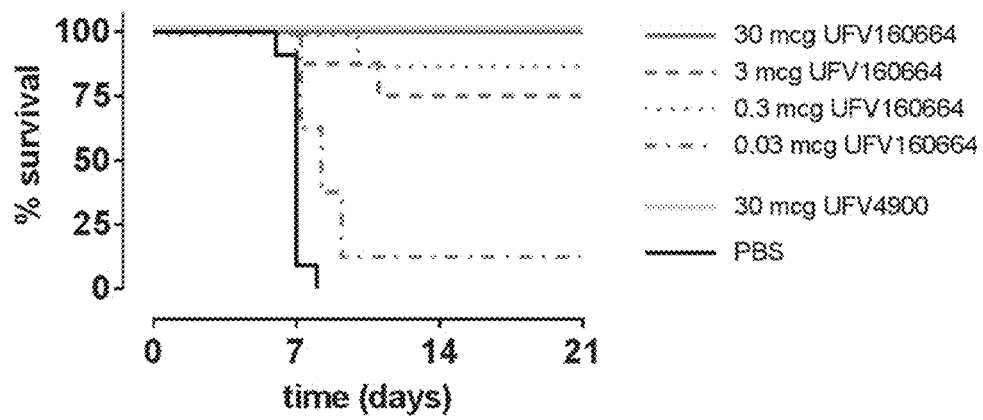
FIG. 17: Upper panel: Survival proportion during the follow-up period after H1N1 A/Puerto Rico/8/34 challenge of mice immunized with polypeptides of the invention. Bottom panel: Relative bodyweight during the follow-up period after H1N1 A/Puerto Rico/8/34 challenge of mice immunized with polypeptides of the invention. Relative bodyweight change was expressed relative to Day 0. Cumulative bodyweight loss during the follow-up period was determined by calculating the Area Under the Curve (AUC). Error bars denote 95% confidence interval.
Figure 17:
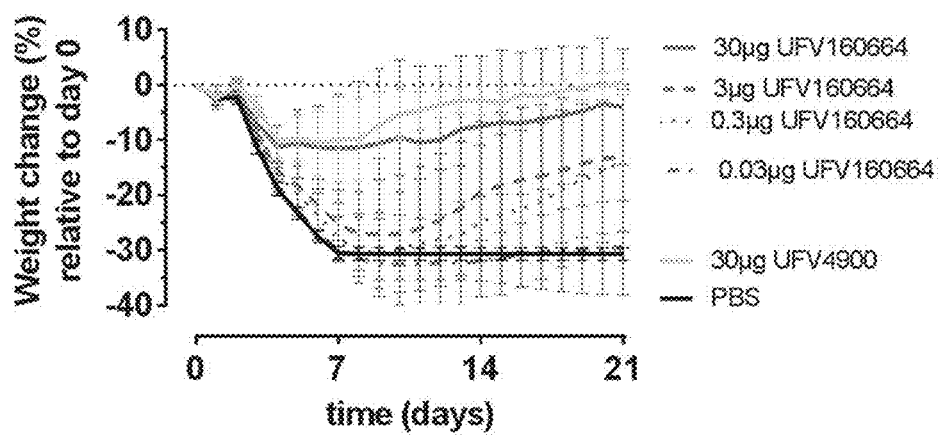

It was shown that 2% Adjuplex-adjuvanted UFV160664 provided significant protection (P<0.003; Fisher's exact test, Bonferroni correction over constructs, and step-wise testing, starting at highest dose) for all doses, except 0.03 µg, compared to the PBS group. Survival proportion of the 30 µg UFV160664 group (100%) was identical to the 30 µg UFV4900 group (100%) (FIG. 17; upper panel).

The bodyweight loss (defined by area under the curve) was significantly reduced (P≤0.026; ANOVA, 2-fold Bonferroni correction over constructs, and step-wise testing, starting at highest dose) for all doses, compared to the PBS group. Bodyweight loss of the 30 mcg UFV160664 group was comparable to the 30 mg UFV4900 group (FIG. 17, lower panel).

Conclusion

According to the present invention, it has been shown that 2% Adjuplex-adjuvanted UFV160664 provides protection in a lethal H1N1 A/Puerto Rico/8/34 mouse challenge model. Protective efficacy is comparable to 2% Adjuplex-adjuvanted UFV4900.

Example 12: Polypeptides of the Invention are Immunogenic and Shows Comparable Efficacy Relative to a Standard-of-Care Vaccine in a H1N1 A/Netherlands/602/09 Naïve Ferret Challenge Model In this example, the in vivo immunogenicity and protective efficacy (based on lung viral load at end of follow-up) of two doses of UFV160664 in comparison to adjuvant-only immunized animals and to a standard-of-care seasonal influenza vaccine in a H1N1 A/Netherlands/602/09 naïve ferret challenge model was evaluated.

Groups (n=6) of naïve female ferrets were immunized intramuscularly three times, 3 weeks apart, with 50 or 5 µg UFV160664 adjuvanted with 5% Adjuplex. A negative control group was immunized with adjuvant only. A reference group representing standard of care was immunized with a commercially available standard-of-care (SoC) seasonal influenza vaccine. Four weeks after the final immunization animals were challenged intratracheally with $10^6$ TCID50 H1N1 A/Netherlands/602/09 at day 0. During the 4-day follow-up period several virological and clinical parameters were recorded.

Results

Figure 18:
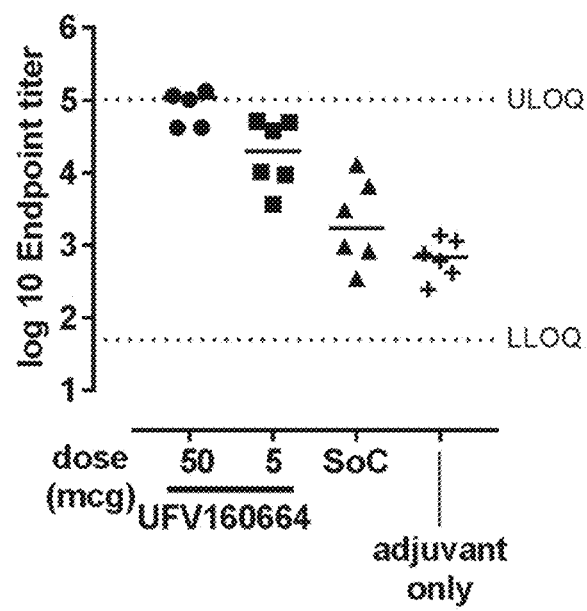
FIG. 18: H1 A/California/07/09 FL HA-specific antibody titers after immunization of ferrets with polypeptides of the invention. Statistical comparison of different dosages of polypeptide of the invention and SOC to the adjuvant only group using censored ANOVA with post-hoc t-test, starting at highest dose and Bonferroni adjustment for multiple comparisons. Dashed lines indicate ULLOQ (Upper Limit of Quantification) and LLOQ. Horizontal line per group denotes group median.

It was shown that both doses of 5% Adjuplex-adjuvanted UFV160664 induced significantly higher H1 A/California/07/09 HA-specific antibody titers compared to the adjuvant only group titers (P<0.001; censored ANOVA, with post-hoc t-test. Bonferroni correction for multiple comparisons and stepwise testing, starting at the highest dose), while SoC did not (FIG. 18). Both doses of 5% Adjuplex-adjuvanted UFV160664 induced significant higher H1 A/California/07/09 HA-specific antibody titers compared to the adjuvant only group titers (P<0.001; censored ANOVA, with post-hoc t-test, Bonferroni correction for multiple comparisons and stepwise testing, starting at the highest dose), while SoC did not (FIG. 18).

Figure 19:
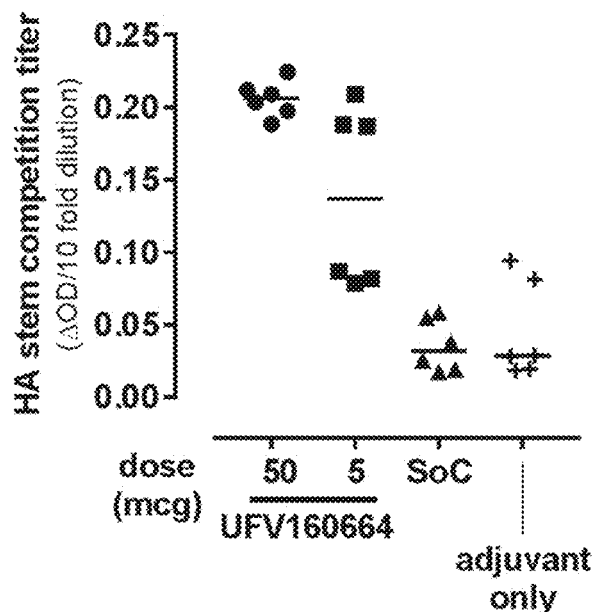
FIG. 19: H1 A/California/07/09 FL HA stem-specific antibody titers after immunization of ferrets with polypeptides of the invention. Statistical comparison of different dosages of polypeptide of the invention and SOC to the adjuvant only group using censored ANOVA with post-hoc t-test, starting at highest dose and Bonferroni adjustment for multiple comparisons. Horizontal line per group denotes group median.

In addition, both doses of 5% Adjuplex-adjuvanted UFV160664 induced significantly higher H1 A/California/07/09 HA stem-specific antibody titers (measured with a CR9114 competition assay) compared to the adjuvant only group titers (P<0.001; censored ANOVA, with post-hoc t-test, Bonferroni correction for multiple comparisons and stepwise testing, starting at the highest dose), while SoC did not (FIG. 19).

Figure 20:
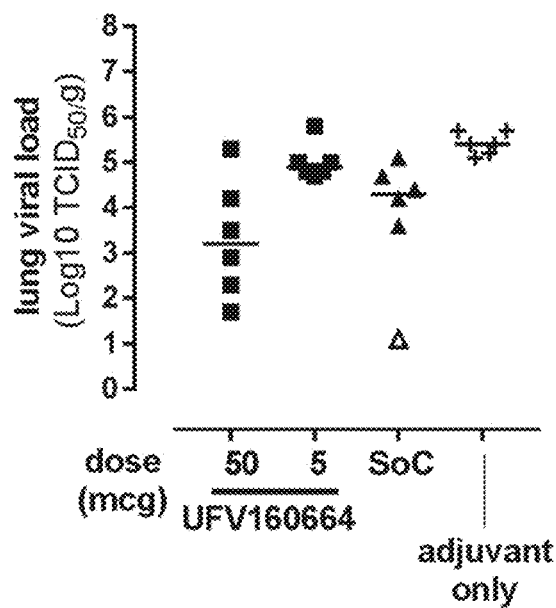
FIG. 20: Lung viral load titers at the end of the follow-up period (day 4 after challenge) after immunization of ferrets with polypeptides of the invention followed by challenge with H1N1 A/NL/602/09. Horizontal line per group denotes group median, open symbols denote samples at the Limit Of Detection (LOD).

The 50 µg 5% Adjuplex-adjuvanted UFV160664 dose and SoC significantly reduced lung viral load compared to the adjuvant only group titers (50 µg UFV160664: P<0.001, SoC: P<0.05; censored ANOVA, with post-hoc t-test, Bonferroni correction for multiple comparisons and stepwise testing, starting at the highest dose) (FIG. 20).

Conclusion

According to the present invention it has been shown that both doses of 5% Adjuplex-adjuvanted UFV160664 are immunogenic and that the 50 µg dose provides protection comparable to SoC vaccine reference group.

Example 13: Polypeptides of the Invention Shows Comparable Efficacy Relative to a Positive Control in a H5N1 A/Indonesia/05/05 Naïve Ferret Challenge Model In this example, the in vivo immunogenicity and protective efficacy (based on lung viral load at end of follow-up) of two doses of UFV160664 was evaluated in comparison to adjuvant-only immunized animals and to a positive control group, immunized with H5 FL HA homologous to the challenge strain (exploratory) in a heterosubtypic H5N1 A/Indonesia/05/05 naïve ferret challenge model.

Groups (n=6) of naïve female ferrets were immunized intramuscularly three times, 3 weeks apart, with 50 or 5 µg UFV160664 adjuvanted with 5% Adjuplex. A negative control group was immunized with adjuvant only. A positive control group was immunized 5% Adjuplex adjuvanted H5 A/Indonesia/05/05 HA, homologous to the challenge strain. Four weeks after the final immunization animals were challenged intratracheally with $10^5$ TCID50 H5N1 A/Indonesia/05/05 at day 0. During the 5 day follow-up period several virological and clinical parameters were recorded.

Results

Figure 21:
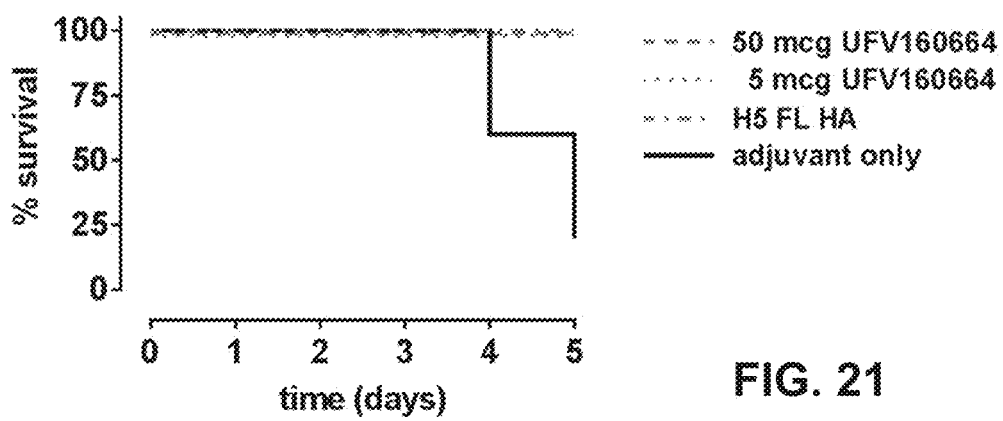
FIG. 21: Survival during the 5 day follow-up period of ferrets immunized with polypeptides of the inventions, H5 FL HA (positive challenge control) and adjuvant only (negative challenge control), followed by challenge with H5N1 A/Indonesia/05/05.
Figure 22:
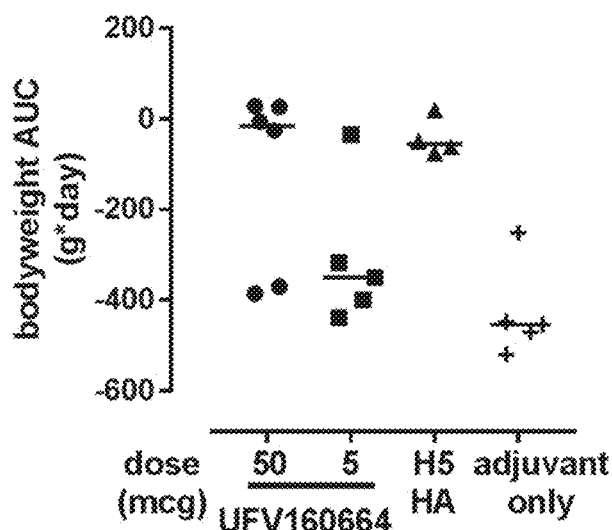
FIG. 22: Cumulative (AUC) bodyweight loss of individual animals, obtained from consecutive daily bodyweight measurements during the follow-up period (day 0 to 5), relative to the bodyweight ay day 0 after immunization of ferrets with polypeptides of the invention followed by challenge with H5N1 A/Indonesia/05/05. Horizontal line per group denotes group median.

It was shown that animals immunized with both doses of 5% Adjuplex-adjuvanted UFV160664 and the positive control group survived the follow-up period, while the survival proportion of the adjuvant-only group was 25% (FIG. 21). The cumulative bodyweight loss during follow up was reduced for four out of 6 animals immunized with 5% Adjuplex-adjuvanted 50 µg UFV160664 compared to the adjuvant only group. The positive control group had comparable reduction in body weight loss to the four animals of the 50 μg UFV160664 group, and reduction in bodyweight loss was significantly less compared to the adjuvant only group (P<0.001; ANOVA, with post-hoc t-test, Bonferroni correction for multiple comparisons and stepwise testing, starting at the highest dose) (FIG. 22).

Figure 23:
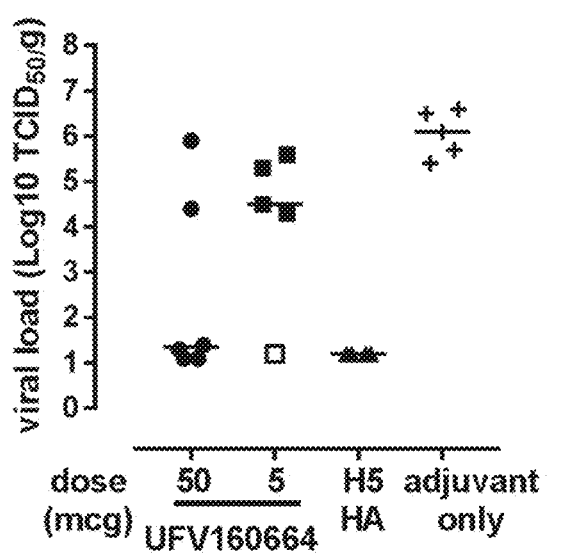
FIG. 23: Lung viral load titers at day of death or the end of the follow-up period (day 5 after challenge) after immunization of ferrets with polypeptides of the invention followed by challenge with H5N1 A/Indonesia/05/05. Horizontal line per group denotes group median, open symbols denote samples at the Limit Of Detection (LOD).

Both the 5% Adjuplex-adjuvanted 50 mcg UFV160664 and the positive control group significantly reduced lung viral load compared to the adjuvant only group (50 μg UFV160664: P<0.01, positive control: P<0.05; censored ANOVA, with post-hoc t-test, Bonferroni correction for multiple comparisons and stepwise testing, starting at the highest dose) (FIG. 23).

Figure 24:
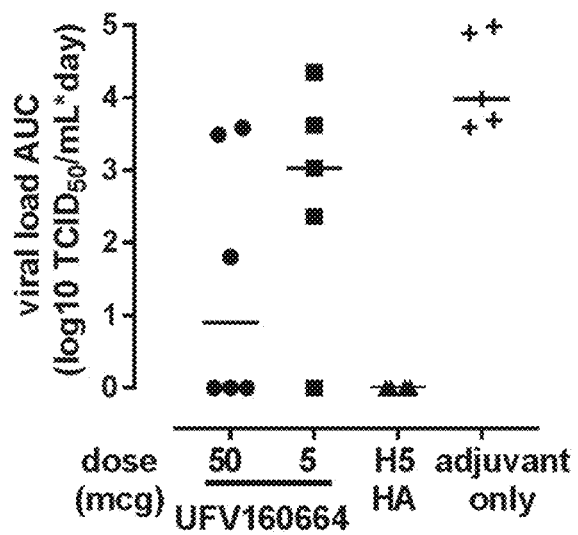
FIG. 24: Cumulative (AUC) throat viral load, obtained from consecutive daily throat swabs during the follow-up period (day 0 to 5), relative to the bodyweight ay day 0 after immunization of ferrets with polypeptides of the invention followed by challenge with H5N1 A/Indonesia/05/05. Horizontal line per group denotes group median.

Both the 5% Adjuplex-adjuvanted 50 μg UFV160664 and the positive control group significantly reduced cumulative (daily swabs) throat viral load compared to the adjuvant only group (50 mcg UFV160664: P<0.05, positive control: P<0.001; ANOVA, with post-hoc t-test, Bonferroni correction for multiple comparisons and stepwise testing, starting at the highest dose) (FIG. 24).

Conclusion

According to the present invention, it was show that both the 5 μg and 50 μg UFV160664 doses prevented mortality. In addition, the 50 μg UFV160664 dose reduced bodyweight loss and significantly reduced lung and throat viral load, comparable to the positive control group.

Example 14: Humoral and Cellular Immunogenicity after Immunization of Naïve Mice with Adenoviral Vector Expressing Polypeptide of the Invention In this example, the humoral and cellular immunogenicity of a dose range of an adenovector 26 (Ad26) containing nucleic acid expressing a polypeptide of the invention (in particular polypeptide UFV 171590), was evaluated. For comparison, control mice were immunized with the empty adenovector, a fixed dose of 2% Adjuplex adjuvanted UFV160664 protein, or a heterologous immunization regimen of UFV171590 prime, adjuvanted UFV160664 boost, was evaluated. Groups of female BALB/c mice received two intramuscular immunizations, four weeks apart. Three groups of eight mice were immunized with either $10^8$, $10^9$ or $10^{10}$ virus particles (vp) of UFV171590. As negative control, four mice received two immunizations with $10^{10}$ vp of the empty adenovector (Ad26_empty). A group of five mice received two protein immunizations with 30 μg of soluble trimeric UFV160664 adjuvanted with 2% Adjuplex. A group of five mice received a prime immunization with $10^{10}$ vp UFV171590, followed by a boost immunization with 30 μg UFV160664 adjuvanted with 2% Adjuplex. Three weeks after the boost immunization mice were sacrificed and blood and spleen samples were isolated to analyze the humoral immune response to H1 A/California/07/09 (full-length (FL) ELISA and stem-competition ELISA) and the cellular immune response to UFV160664 peptides (T-cell ELISpot), respectively.

Results

Figure 25:
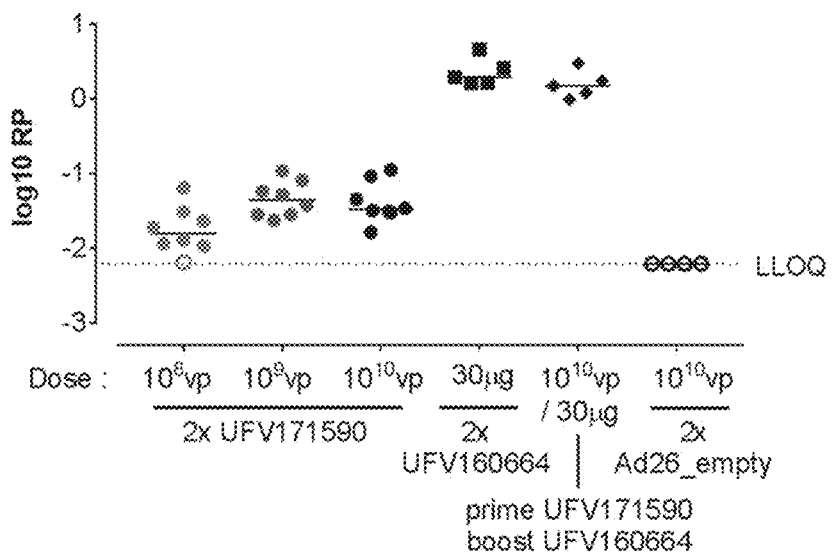
FIG. 25: H1 A/California/07/09 FL HA-specific antibody titers after immunization of mice with polypeptides of the invention. The dashed line indicates the LLOQ (Lower Limit of Quantification), open symbols represent samples on LLOQ, the horizontal line per group denotes the group median.
Figure 26:
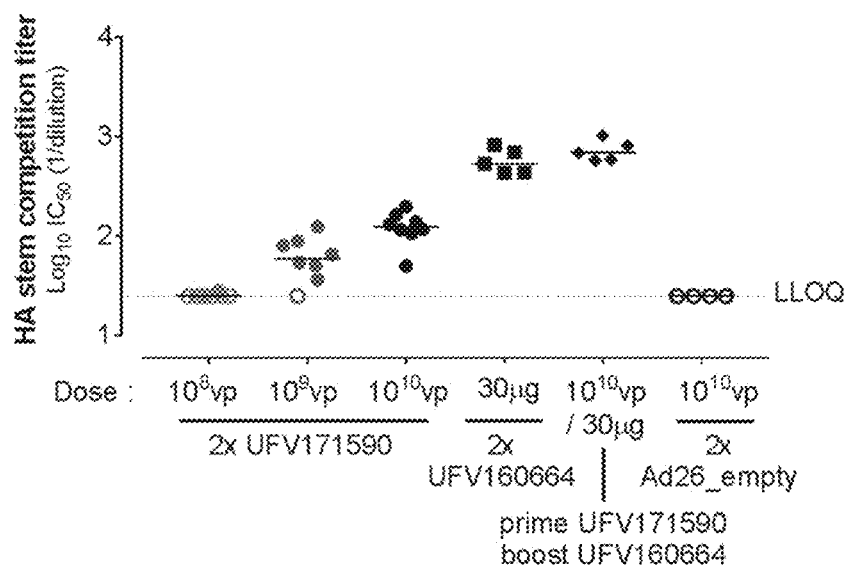
FIG. 26: H1 A/California/07/09 FL HA stem-specific antibody titers after immunization of mice with polypeptides of the invention. The dashed line indicates the LLOQ (Lower Limit of Quantification), open symbols represent samples on LLOQ, the horizontal line per group denotes the group median.

It was shown that all doses of the adenovector containing nucleic acid expressing the polypeptide of this invention induced significant H1 A/California FL HA ELISA binding titers compared to immunization with the empty vector ($10^8$ vp, $10^9$ vp and $10^{10}$ vp: p<0.001, likelihood ratio test-based Tobit regression model). (FIG. 25). In addition, significant HA stem-specific antibody titers (measured with a CR9114 competition assay) were induced by $10^9$ and $10^{10}$ vp of UFV171590 compared to the empty vector (p<0.001; likelihood ratio test-based Tobit regression model) (FIG. 26). Both prime-boost with adjuvanted UFV160664 as well as UFV171590 prime, adjuvanted UFV160664 boost, induced significant H1 A/California/07/09 FL HA binding titers (FIG. 25) and HA stem-specific antibody titers (p<0.001 likelihood ratio test-based Tobit regression model) (FIG. 26).

Figure 27:
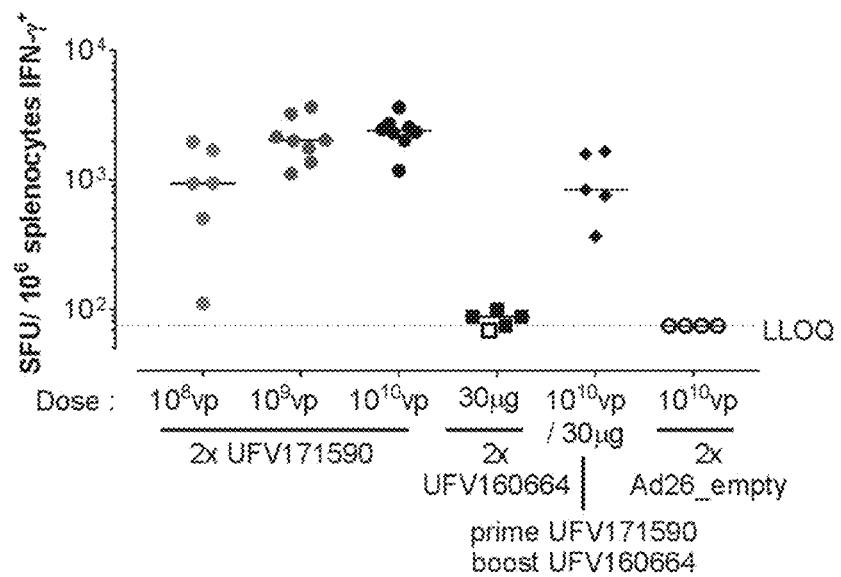
FIG. 27: IFN-γ producing T-cells per million splenocytes of immunized mice, after in vitro stimulation with UFV160664 peptides. The dashed line indicates the LLOQ (Lower Limit of Quantification), open symbols represent samples on LLOQ, the horizontal line per group denotes the group median.

In addition to a significant humoral response, UFV171590 induced a significant IFN-γ T-cell response compared to the empty vector as measured after stimulation by UFV160664 peptides by T-cell ELISpot (FIG. 27). All doses of UFV171590 induced significant T-cell responses (p<0.001; likelihood ratio test-based Tobit regression model), as well as the group of mice which received UFV171590-prime followed by UFV160664-boost immunization (p<0.001). Two immunizations with adjuvanted UFV160664 did not induce a detectable IFN-γ T-cell response (FIG. 27).

Conclusion

It has been shown that an adenovector 26 expressing a polypeptide of the invention (UFV171590) induces significant humoral and cellular responses to H1 A/California/07/09 FL HA in a mouse model, either in a homologous immunization regimen or in combination with adjuvanted UFV160664 boost. Adjuvanted UFV160664 also induced a significant humoral immune response but did not induce a detectable T-cell response in absence of a prime with UFV171590.

Example 15: Transfer of Mutations from Polypeptide 160664 to Different Group 1 Backbones Protein Expression in Mammalian Cells DNA fragments encoding additional polypeptides of the invention (i.e. based on different HA backbones, see FIG. 28A) were synthesized (Genscript) and cloned in the pcDNA2004 plasmid (in-house modified pcDNA3 vector with an enhanced CMV promotor). The polypeptides were produced in Expi-CHO cell cultures in ExpiCHO™ Expression medium by transient transfection using the ExpiFectamine™ (Gibco, ThermoFisher Scientific). To the Expi-CHO cells cultures, ExpiFectamine CHO enhancer and ExpiCHO feed (Gibco, ThermoFisher Scientific) was added one day post transfection. Culture supernatants containing secreted polypeptides were harvested at day 7 by centrifugation followed by 0.2 μm filtration.

Culture Supernatant Analysis

The level of expressed polypeptide in the harvested culture supernatant was assessed through Bio-Layer Interferometry using the OCTET platform. In short, biotinylated mAb CR9114 was immobilized on Streptavidin (SA) biosensors (Pall FortéBio) following which a standard curve was established by assessing the binding shift of a dilution series of a well-defined purified homologous polypeptide. Subsequently the binding shift of pre-diluted harvested culture supernatant containing the polypeptide (~5-15 μg/mL diluted in kinetics buffer) was measured and the concentration was calculated using the established calibration curve.

Secondly, the content of polypeptides of the invention in the Expi-CHO culture harvests was assessed by analytical SEC in a High-Performance Liquid Chromatography (HPLC) Infinity 1260 series setup (Agilent). Culture supernatant containing the polypeptide ~3 μg protein injection, except for UFV180500 (0.8 μg), was run (1 mL/min.) over a TSK gel G3000SWx1 column (Sigma-Aldrich) and the eluate was monitored by UV detection (OD280, mAU). The SEC profiles were analyzed by the Astra 6 software package (Wyatt Technology). Folding of the polypeptide was assessed by Amplified Homogeneous Assay (AlphaLISA). This in-solution and in-binding equilibrium assay is based on successful binding of both a donor and acceptor bead to the polypeptide. When in close proximity, laser irradiation of the donor bead at 680 nm generates a flow of singlet oxygen, triggering chemical events in nearby acceptor bead, resulting in a chemiluminescent emission at 615 nm. AlphaLISA assay was performed by simultaneous addition of Nickel donor beads (10 µg/mL) and anti-human IgG acceptor beads (10 µg/mL, both PerkinElmer) to culture supernatant in presence of either CR9114 (2 nM) or MD3606 (2 nM). The polypeptide-containing culture supernatants were titrated in a 3-fold dilution range starting at 1667 ng/mL. Read out was performed after 2 hours of incubation (room temperature) using the EnSight™ multimode plate reader (PerkinElmer).

Results and Conclusion

Analysis of the 35 mL ExpiCHO transfections shows the His-tagged polypeptides are expressed (FIG. 28A). The expression levels varied from 42 mg/L (backbone H5 A/Vietnam/1203/04) up to 375 mg/L (backbone H1 A/California/07/09) and indicate that all polypeptides express well. Furthermore, the SEC profiles (FIG. 28B) show that for each expressed polypeptide a significant trimeric (T) and a monomeric (M) fraction is detectable. Differences in relative trimer and monomer content were observed depending on the utilized backbone strain. To further assess the correct folding of the polypeptide, binding of a relevant antibody (CR9114) and multidomain (MD3606) was assessed by AlphaLISA. For all polypeptide a specific binding signal for both CR9114 and MD3606 was observed (FIG. 28C). The expression, SEC profiles and binding data indicate that the mutations according to the present invention (e.g. the mutations of UFV160664, which is based on strain A/California/07/09) are transferrable to other Group 1 backbones. Thus, the polypeptides UFV180496, UFV180497, UFV190498, UFV180499, UFV180500 and UFV180501, were all correctly folded and trimeric and secreted into the culture supernatant.

TABLE 12

Standard amino acids, abbreviations and properties

| Amino Acid | 3-Letter | 1-Letter | Side chain polarity | Side chain charge (pH 7.4) |
|---|---|---|---|---|
| alanine | Ala | A | nonpolar | Neutral |
| arginine | Arg | R | polar | Positive |
| asparagine | Asn | N | polar | Neutral |
| aspartic acid | Asp | D | polar | Negative |
| cysteine | Cys | C | nonpolar | Neutral |
| glutamic acid | Glu | E | polar | Negative |
| glutamine | Gln | Q | polar | Neutral |
| glycine | Gly | G | nonpolar | Neutral |
| histidine | His | H | polar | positive (10%) neutral (90%) |
| isoleucine | Ile | I | nonpolar | Neutral |
| leucine | Leu | L | nonpolar | Neutral |
| lysine | Lys | K | polar | Positive |
| methionine | Met | M | nonpolar | Neutral |
| phenylalanine | Phe | F | nonpolar | Neutral |
| proline | Pro | P | nonpolar | Neutral |
| serine | Ser | S | polar | Neutral |
| threonine | Thr | T | polar | Neutral |
| tryptophan | Trp | W | nonpolar | Neutral |
| tyrosine | Tyr | Y | polar | Neutral |
| valine | Val | V | nonpolar | Neutral |

REFERENCES

Bommakanti et al. (2010), Proc. Natl. Acad. Sci. USA 107(31): 13701-13706.
Bommakanti et al. (2012), J Virol 86: 13434.
Ciani et al. (2010), Proc. Natl. Acad. Sci. USA 107(46): 19850-19855.
Ekiert et al. (2009), Science 324:246.
Ekiert et al. (2011), Science 333: 844.
Das et al. (1985), Prog Nucleic Acid Res Mol Biol 32: 217-236.
Gill et al. (2001), Gene Therapy 8: 1539-1546.
Kaufmann (2000), Mol Biotechnol 16: 151-160.
Letarov et al. (1993), Biochemistry Moscow 64: 817-823.
Lorieau et al. (2010), Proc. Natl. Acad. Sci. USA, 107: 11341.
Lu et al. (2014), Proc. Natl. Acad. Sci. USA, 111: 125-130.
Mallajosyula et al. (2014), PNAS, published online Jun. 9, 2014: E2514-E2523.
S-Guthe et al. (2004), J. Mol. Biol. 337: 905-915.
Steel et al. (2010), mBio 1(1): 1-9.
Throsby et al. (2008), Plos One 12(3): 1-15.
Winter et al. (1981) Nature 292: 72-75.

```
SEQUENCES
SEQ ID NO 1: H1 Full length (A/Brisbane/59/2007)
MKVKLLVLLC TFTATYADTI CIGYHANNST DTVDTVLEKN VTVTHSVNLL    50

ENSHNGKLCL LKGIAPLQLG NCSVAGWILG NPECELLISK ESWSYIVEKP   100

NPENGTCYPG HFADYEELRE QLSSVSSFER FEIFPKESSW PNHTVTGVSA   150

SCSHNGESSF YRNLLWLTGK NGLYPNLSKS YANNKEKEVL VLWGVHHPPN   200

IGDQKALYHT ENAYVSVVSS HYSRKFTPEI AKRPKVRDQE GRINYYWTLL   250

EPGDTIIFEA NGNLIAPRYA FALSRGFGSG IINSNAPMDK CDAKCQTPQG   300

AINSSLPFQN VHPVTIGECP KYVRSAKLRM VTGLRNIPSI QSRGLFGAIA   350

GFIEGGWTGM VDGWYGYHHQ NEQGSGYAAD QKSTQNAING ITNKVNSVIE   400

KMNTQFTAVG KEFNKLERRM ENLNKKVDDG FIDIWTYNAE LLVLLENERT   450

LDFHDSNVKN LYEKVKSQLK NNAKEIGNGC FEFYHKCNDE CMESVKNGTY   500
```

```
DYPKYSEESK LNREKIDGVK LESMGVYQIL AIYSTVASSL VLLVSLGAIS    550

FWMCSNGSLQ CRICI                                         565

SEQ ID NO 2: H1 Full length (A/California/07/2009)
MKAILVVLLYTFATANADTLCIGYHANNSTDTVDTVLEKNVTVTHSVNLLEDKHNGK

LCKLRGVAPLHLGKCNIAGWILGNPECESLSTASSWSYIVETPSSDNGTCYPGDFID

YEELREQLSSVSSFERFEIFPKTSSWPNHDSNKGVTAACPHAGAKSFYKNLIWLVKK

GNSYPKLSKSYINDKGKEVLVLWGIHHPSTSADQQSLYQNADAYVFVGSSRYSKKFK

PEIAIRPKVRDQEGRMNYYWTLVEPGDKITFEATGNLVVPRYAFAMERNAGSGIIIS

DTPVHDCNTTCQTPKGAINTSLPFQNIHPITIGKCPKYVKSTKLRLATGLRNIPSIQ

SRGLFGAIAGFIEGGWTGMVDGWYGYHHQNEQGSGYAADLKSTQNAIDEITNKVNSV

IEKMNTQFTAVGKEFNHLEKRIENLNKKVDDGFLDIWTYNAELLVLLENERTLDYHD

SNVKNLYEKVRSQLKNNAKEIGNGCFEFYHKCDNTCMESVKNGTYDYPKYSEEAKLN

REEIDGVKLESTRIYQILAIYSTVASSLVLVVSLGAISFWMCSNGSLQCRICI

SEQ ID NO 3: A/Texas/UR06-0526/2007 (H1N1)
MKVKLLVLLCTFTATYADTICIGYHANNSTDTVDTVLEKNVTVTHSVNLLEDSHNGK

LCLLKGTAPLQLGNCSVAGWILGNPECELLISKESWSYIVETPNPENGTCYPGYFAD

YEELREQLSSVSSFERFEIFPKESSWPNHTVTGVSASCSHNGKSSFYRNLLWLTGKN

GLYPNLSKSYANNKEKEVLVLWGVHHPPNIGDQRALYHTENAYVSVVSSHYSRRFTP

EIAKRPKVRDQEGRINYYWTLLEPGDTIIFEANGNLIAPRFAFALSRGFGSGIITSN

APMGECDAKCQTPQGAINSSLPFQNVHPVTIGECPKYVRSAKLRMVTGLRNIPSIQS

RGLFGAIAGFIEGGWTGMVDGWYGYHHQNEQGSGYAADQKSTQNAINGITNKVNSVI

EKMNTQFTAVGKEFNKLERRMENLNKKVDDGFLDIWTYNAELLVLLENERTLDFHDS

NVKNLYEKVKNQLKNNAKEIGNGCFEFYHKCNDECMESVKNGTYDYPKYSEESKLNR

EKIDGVKLESMGVYQILAIYSTVASSLVLLISLGAISFWMCSNGSLQCRICI

SEQ ID NO 4: A/NewYork/629/1995 (H1N1)
MKVKLLVLLCAFTATYADTICIGYHANNSTDTVDTVLEKNVTVTHSVNLLEDSHNGK

LCRLKGTAPLQLGNCSVAGWILGNPECESLFSKESWSYIAETPNPENGTCYPGYFAD

YEELREQLSSVSSFERFEIFPKESSWPNHTVTKGVTASCSHNGKSSFYKNLLWLTEK

NGLYPNLSKSYVNNKEKEVLVLWGVHHPSNIGDQRAIYHTENAYVSVVSSHYSRRFT

PEIAKRPKVRDQEGRINYYWTLLEPGDTIIFEANGNLIAPWYAFALSRGFGSGIITS

NASMSECDAKCQTPQGAINSSLPFQNVHPVTIGECPKYVRSTKLRMVTGLRNIPSIQ

SRGLFGAIAGFIEGGWTGMIDGWYGYHHQNEQGSGYAADQKSTQNAIDGITNKVNSV

IEKMNTQFTAVGKEFNKLERRMENLNKKVDDGFLDIWTYNAELLVLLENERTLDFHD

SNVKNLYEKVKNQLKNNAKEIGNGCFEFYHKCNNECMESVKNGTYDYPKYSEESKLN

REKIDGVKLESMGVYQILAIYSTVASSLVLLVSLGAISFWMCSNGSLQCRICI

SEQ ID NO 5: A/AA_Marton/1943 (H1N1)
MKARLLVLLCALAATDADTICIGYHANNSTDTVDTVLEKNVTVTHSVNLLEDSHNGK

LCRLKGIAPLQLGKCNIAGWILGNPECESLLSERSWSYIVETPNSENGTCYPGDFID

YEELREQLSSVSSFERFEIFSKESSWPKHNTTRGVTAACSHAGKSSFYRNLLWLTEK

DGSYPNLNNSYVNKKGKEVLVLWGVHHPSNIKDQQTLYQKENAYVSVVSSNYNRRFT

PEIAERPKVRGQAGRMNYYWTLLKPGDTIMFEANGNLIAPWYAFALSRGFGSGIITS

NASMHECDTKCQTPQGAINSSLPFQNIHPVTIGECPKYVRSTKLRMVTGLRNIPSIQ
```

-continued

SRGLFGAIAGFIEGGWTGMIDGWYGYHHQNEQGSYAADQKSTQNAINGITNKVNSV

IEKMNTQFTAVGKEFNNLEKRMENLNKKVDDGFLDIWTYNAELLVLLENERTLDFHD

SNVKNLYEKVKNQLRNNAKEIGNGCFEFYHKCNNECMESVKNGTYDYPKYSEESKLN

REKIDGVKLESMGVYQILAIYSTVASSLVLLVSLGAISFWMCSNGSLQCRICI

SEQ ID NO 6: A/Adachi/2/57 (H2N2)
MAIIYLILLFTAVRGDQICIGYHANNSTEKVDTILERNVTVTHAKDILEKTHNGKLC

KLNGIPPLELGDCSIAGWLLGNPECDRLLSVPEWSYIMEKENPRNGLCYPGSFNDYE

ELKHLLSSVKHFEKVKILPKDRWTQHTTTGGSQACAVSGNPSFFRNMVWLTKKGSDY

PVAKGSYNNTSGEQMLIIWGVHHPIDETEQRTLYQNVGTYVSVGTSTLNKRSTPEIA

TRPKVNGLGSRMEFSWTLLDMWDTINFESTGNLIAPEYGFKISKRGSSGIMKTEGTL

ENCETKCQTPLGAINTTLPFHNVHPLTIGECPKYVKSEKLVLATGLRNVPQIESRGL

FGAIAGFIEGGWQGMVDGWYGYHHSNDQGSGYAADKESTQKAFDGITNKVNSVIEKM

NTQFEAVGKEFGNLERRLENLNKKMEDGFLDVWTYNAELLVLMENERTLDFHDSNVK

NLYDKVRMQLRDNVKELGNGCFEFYHKCDDECMNSVKNGTYDYPKYEEESKLNRNEI

KGVKLSSMGVYQILAIYATVAGSLSLAIMMAGISFWMCSNGSLQCRICI

SEQ ID NO 7: A/Singapore/1/57 (H2N2)
MAIIYLILLFTAVRGDQICIGYHANNSTEKVDTILERNVTVTHAKDILEKTHNGKLC

KLNGIPPLELGDCSIAGWLLGNPECDRLLSVPEWSYIMEKENPRDGLCYPGSFNDYE

ELKHLLSSVKHFEKVKILPKDRWTQHTTTGGSRACAVSGNPSFFRNMVWLTEKGSNY

PVAKGSYNNTSGEQMLIIWGVHHPNDEKEQRTLYQNVGTYVSVGTSTLNKRSTPDIA

TRPKVNGLGSRMEFSWTLLDMWDTINFESTGNLIAPEYGFKISKRGSSGIMKTEGTL

ENCETKCQTPLGAINTTLPFHNVHPLTIGECPKYVKSEKLVLATGLRNVPQIESRGL

FGAIAGFIEGGWQGMIDGWYGYHHSNDQGSGYAADKESTQKAFDGITNKVNSVIEKM

NTQFEAVGKEFSNLERRLENLNKKMEDGFLDVWTYNAELLVLMENERTLDFHDSNVK

NLYDKVRMQLRDNVKELGNGCFEFYHKCDDECMNSVKNGTYDYPKYEEESKLNRNEI

KGVKLSSMGVYQILAIYATVAGSLSLAIMMAGISFWMCSNGSLQCRICI

SEQ ID NO 8: A/Viet Nam/1203/2004 H5N1)
MEKIVLLFAIVSLVKSDQICIGYHANNSTEQVDTIMEKNVTVTHAQDILEKKHNGKL

CDLDGVKPLILRDCSVAGWLLGNPMCDEFINVPEWSYIVEKANPVNDLCYPGDFNDY

EELKHLLSRINHFEKIQIIPKSSWSSHEASLGVSSACPYQGKSSFFRNVVWLIKKNS

TYPTIKRSYNNTNQEDLLVLWGIHHPNDAAEQTKLYQNPTTYISVGTSTLNQRLVPR

IATRSKVNGQSGRMEFFWTILKPNDAINFESNGNFIAPEYAYKIVKKGDSTIMKSEL

EYGNCNTKCQTPMGAINSSMPFHNIHPLTIGECPKYVKSNRLVLATGLRNSPQRERR

RKKRGLFGAIAGFIEGGWQGMVDGWYGYHHSNEQGSGYAADKESTQKAIDGVTNKVN

SIIDKMNTQFEAVGREFNNLERRIENLNKKMEDGFLDVWTYNAELLVLMENERTLDF

HDSNVKNLYDKVRLQLRDNAKELGNGCFEFYHKCDNECMESVRNGTYDYPQYSEEAR

LKREEISGVKLESIGIYQILSIYSTVASSLALAIMVAGLSLWMCSNGSLQCRICI

>CR9114 VH PROTEIN (SEQ ID NO: 9)
QVQLVQSGAEVKKPGSSVKVSCKSSGGTSNNYAISWVRQAPGQGLDWMGGISPIFGS

TAYAQKFQGRVTISADIFSNTAYMELNSLTSEDTAVYFCARHGNYYYYSGMDVWGQG

TTVTVSS

-continued

>CR9114 VL PROTEIN (SEQ ID NO: 10)
SYVLTQPPAVSGTPGQRVTISCSGSDSNIGRRSVNWYQQFPGTAPKLLIYSNDQRPS

VVPDRFSGSKSGTSASLAISGLQSEDEAEYYCAAWDDSLKGAVFGGGTQLTVL

>CR6261 VH PROTEIN (SEQ ID NO: 11)
E V Q L V E S G A E V K K P G S S V K V S C K A S G G P F

R S Y A I S W V R Q A P G Q G P E W M G G I I P I F G T T

K Y A P K F Q G R V T I T A D D F A G T V Y M E L S S L R

S E D T A M Y Y C A K H M G Y Q V R E T M D V W G K G T T

V T V S S

>CR6261 VL PROTEIN (SEQ ID NO: 12)
Q S V L T Q P P S V S A A P G Q K V T I S C S G S S S N I

G N D Y V S W Y Q Q L P G T A P K L L I Y D N N K R P S G

I P D R F S G S K S G T S A T L G I T G L Q T G D E A N Y

Y C A T W D R R P T A Y V V F G G G T K L T V L G

SEQ ID NO 13: SD15016
EVQLVESGGGLVQAGGSLRLSCVASGMFFGIAAMGWYRQAPGKQRELVANITSDFST

NYADSVKDRFTISRDNAENTVYLQMNSLKPEDTAVYYCAADSLGTGWRHYYYWGQGT

QVTVSSAAAWSHPQFEKGAAWSHPQFEKGAAWSHPQFEK

SEQ ID NO: 14: SD15004
EVQLVESGGGLVQPGGSLRLSCAVSISIFDIYAMDWYRQAPGKQRDLVATSFRDGST

NYADSVKGRFTISRDNAKNTLYLQMNSLKPEDTAVYLCHVSLYRDPLGVAGGMGVYW

GKGALVTVSSAAAWSHPQFEKGAAWSHPQFEKGAAWSHPQFEK

SEQ ID NO: 15 CAA24269.1 haemagglutinin (Influenza A
virus (A/Aichi/2/1968 (H3N2) (excluding signal sequence)
QDLPGNDNST ATLCLGHHAV PNGTLVKTIT DDQIEVTNAT ELVQSSSTGK      50

ICNNPHRILD GIDCTLIDAL LGDPHCDVFQ NETWDLEVER SKAFSNCYPY     100

DVPDYASLRS LVASSGTLEF ITEGFTWTGV TQNGGSNACK RGPGSGFFSR     150

LNWLTKSGST YPVLNVTMPN NDNFDKLYIW GIHHPSTNQE QTSLYVQASG     200

RVTVSTRRSQ QTIIPNIGSR PWVRGLSSRI SIYWTIVKPG DVLVINSNGN     250

LIAPRGYFKM RTGKSSIMRS DAPIDTCISE CITPNGSIPN DKPFQNVNKI     300

TYGACPKYVK QNTLKLATGM RNVPEKQTRG LFGAIAGFIE NGWEGMIDGW     350

YGFRHQNSEG TGQAADLKST QAAIDQINGK LNRVIEKTNE KFHQIEKEFS     400

EVEGRIQDLE KYVEDTKIDL WSYNAELLVA LENQHTIDLT DSEMNKLFEK     450

TRRQLRENAE EMGNGCFKIY HKCDNACIES IRNGTYDHDV YRDEALNNRF     500

QIKGVELKSG YKDWILWISF AISCFLLCVV LLGFIMWACQ RGNIRCNICI     550

SEQ ID NO 16: UFV5367
DTICIGYHANNSTDTVDTVLEKNVTVTHSVNLLENGGGGKYVCSAKLRMVTGLRNKP

SKQSQGLFGAIAGFTEGGWTGMVDGWYGYHHQNEQGSGYAADQKSTQNAINGITNKV

NSVIEKMNTQYTAIGCEYNKSERCMKQIEDKIEEIESKIWCYNAELLVLLENERTLD

FHDSNVKNLYEKVKSQLKNNAKEIGNGCFEFYHKCNDECMESVKNGTYDYPKYSEES

KLNREKIDGVKLESMGVYQI

SEQ ID NO: 17: UFV5369
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQYTAIGCEYNKSERCMKQIEDKIEEIESKIWCYNAELLVLLENERTLD

YHDSNVKNLYEKVRSQLKNNAKEIGNGCFEFYHKCDNTCMESVKNGTYDYPKYSEEA

KLNREEIDGVKLESTRIYQI

SEQ ID NO 135: UFV150553
DTICIGYHANNSTDTVDTVLEKNVTVTHSVNLLENGGGGKYVCSAKLRMVTGLRNKP

SKQSQGLFGAIAGFTEGGWTGMVDGWYGYHHQNEQGSGYAADQKSTQNAINGITNKV

NSVIEKMNTQRTAIGCEFNKSEQCMKQIEDKIEEIESKIWCYNAELLVLLENQRTLD

FHDSNVKNLYEKVKSQLKNNAKEIGNGCFEFYHKCNDECMESVKNGTYDYPKYSEES

KLNREKIDGVKLESMGVYQI

SEQ ID NO 30: UFV150558
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQPTAIGCEYNKSEQCMKQIEDKIEEIESKIWCYNAELLVLLENQRTLD

YHDANVKNLYEKVRSQLKNNAKEIGNGCFEFYHKCDNTCMESVKNGTYDYPKYSEEA

KLNREEIDGVKLESTRIYQI

SEQ ID NO 31: UFV150559
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQRTAIGCEFNKSEQCMKQIEDKIEEIESKIWCYNAELLVLLENQRTLD

YHDSNVKNLYEKVRSQLKNNAKEIGNGCFEFYHKCDNTCMESVKNGTYDYPKYSEEA

KLNREEIDGVKLESTRIYQI

SEQ ID NO 32: UFV150565
DTICIGYHANNSTDTVDTVLEKNVTVTHSVNLLENGGGGKYVCSAKLRMVTGLRNKP

SKQSQGLFGAIAGFTEGGWTGMVDGWYGYHHQNEQGSGYAADQKSTQNAINGITNKV

NSVIEKMNTQYTAIGCEYNKSERCMKQIEDKIEEIESKIWCYNAELLVLLENERTLD

FHDSNVKNLYEKVKSQLKNNAKEIGNGCFEFYHKCNDECMESVKNGTYDYPKYSEES

KLNREKIDGVKLESMGVYQILAIY

SEQ ID NO 33: UFV150566
DTICIGYHANNSTDTVDTVLEKNVTVTHSVNLLENGGGGKYVCSAKLRMVTGLRNKP

SKQSQGLFGAIAGFTEGGWTGMVDGWYGYHHQNEQGSGYAADQKSTQNAINGITNKV

NSVIEKMNTQYTAIGCEYNKSERCMKQIEDKIEEIESKIWCYNAELLVLLENERTLD

FHDSNVKNLYEKVKSQLKNNAKEIGNGCFEFYHKCNDECMESVKNGTYDYPKYSEES

KLNREKIDGVKLESMGVYQILA

SEQ ID NO 34: UFV150567
DTICIGYHANNSTDTVDTVLEKNVTVTHSVNLLENGGGGKYVCSAKLRMVTGLRNKP

SKQSQGLFGAIAGFTEGGWTGMVDGWYGYHHQNEQGSGYAADQKSTQNAINGITNKV

NSVIEKMNTQYTAIGCEYNKSERCMKQIEDKIEEIESKIWCYNAELLVLLENERTLD

FHDSNVKNLYEKVKSQLKNNAKEIGNGCFEFYHKCNDECMESVKNGTYDYPKYSEES

KLNREKIDGVKLESMGVY

SEQ ID NO 35: UFV150568
DTICIGYHANNSTDTVDTVLEKNVTVTHSVNLLENGGGGKYVCSAKLRMVTGLRNKP

SKQSQGLFGAIAGFTEGGWTGMVDGWYGYHHQNEQGSGYAADQKSTQNAINGITNKV

NSVIEKMNTQYTAIGCEYNKSERCMKQIEDKIEEIESKIWCYNAELLVLLENERTLD

FHDSNVKNLYEKVKSQLKNNAKEIGNGCFEFYHKCNDECMESVKNGTYDYPKYSEES

KLNREKIDGVKLESMG

SEQ ID NO 36: UFV150569
DTICIGYHANNSTDTVDTVLEKNVTVTHSVNLLENGGGGKYVCSAKLRMVTGLRNKP

SKQSQGLFGAIAGFTEGGWTGMVDGWYGYHHQNEQGSGYAADQKSTQNAINGITNKV

NSVIEKMNTQYTAIGCEYNKSERCMKQIEDKIEEIESKIWCYNAELLVLLENERTLD

FHDSNVKNLYEKVKSQLKNNAKEIGNGCFEFYHKCNDECMESVKNGTYDYPKYSEES

KLNREKIDGVKLES

SEQ ID NO 37: UFV150570
DTICIGYHANNSTDTVDTVLEKNVTVTHSVNLLENGGGGKYVCSAKLRMVTGLRNKP

SKQSQGLFGAIAGFTEGGWTGMVDGWYGYHHQNEQGSGYAADQKSTQNAINGITNKV

NSVIEKMNTQYTAIGCEYNKSERCMKQIEDKIEEIESKIWCYNAELLVLLENERTLD

FHDSNVKNLYEKVKSQLKNNAKEIGNGCFEFYHKCNDECMESVKNGTYDYPKYSEES

KLNREKIDGVKL

SEQ ID NO 38: UFV150571
DTICIGYHANNSTDTVDTVLEKNVTVTHSVNLLENGGGGKYVCSAKLRMVTGLRNKP

SKQSQGLFGAIAGFTEGGWTGMVDGWYGYHHQNEQGSGYAADQKSTQNAINGITNKV

NSVIEKMNTQYTAIGCEYNKSERCMKQIEDKIEEIESKIWCYNAELLVLLENERTLD

FHDSNVKNLYEKVKSQLKNNAKEIGNGCFEFYHKCNDECMESVKNGTYDYPKYSEES

KLNREKIDGV

SEQ ID NO 39: UFV150572
DTICIGYHANNSTDTVDTVLEKNVTVTHSVNLLENGGGGKYVCSAKLRMVTGLRNKP

SKQSQGLFGAIAGFTEGGWTGMVDGWYGYHHQNEQGSGYAADQKSTQNAINGITNKV

NSVIEKMNTQYTAIGCEYNKSERCMKQIEDKIEEIESKIWCYNAELLVLLENERTLD

FHDSNVKNLYEKVKSQLKNNAKEIGNGCFEFYHKCNDECMESVKNGTYDYPKYSEES

KLNREKID

SEQ ID NO 40: UFV150573
DTICIGYHANNSTDTVDTVLEKNVTVTHSVNLLENGGGGKYVCSAKLRMVTGLRNKP

SKQSQGLFGAIAGFTEGGWTGMVDGWYGYHHQNEQGSGYAADQKSTQNAINGITNKV

NSVIEKMNTQYTAIGCEYNKSERCMKQIEDKIEEIESKIWCYNAELLVLLENERTLD

FHDSNVKNLYEKVKSQLKNNAKEIGNGCFEFYHKCNDECMESVKNGTYDYPKYSEES

KLNREK

SEQ ID NO 41: UFV150574
DTICIGYHANNSTDTVDTVLEKNVTVTHSVNLLENGGGGKYVCSAKLRMVTGLRNKP

SKQSQGLFGAIAGFTEGGWTGMVDGWYGYHHQNEQGSGYAADQKSTQNAINGITNKV

NSVIEKMNTQYTAIGCEYNKSERCMKQIEDKIEEIESKIWCYNAELLVLLENERTLD

FHDSNVKNLYEKVKSQLKNNAKEIGNGCFEFYHKCNDECMESVKNGTYDYPKYSEES

KLNR

SEQ ID NO 42: UFV150575
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQYTAIGCEYNKSERCMKQIEDKIEEIESKIWCYNAELLVLLENERTLD

YHDSNVKNLYEKVRSQLKNNAKEIGNGCFEFYHKCDNTCMESVKNGTYDYPKYSEEA

KLNREEIDGVKLESTRIYQILAIY

-continued

SEQ ID NO 43: UFV150576
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQYTAIGCEYNKSERCMKQIEDKIEEIESKIWCYNAELLVLLENERTLD

YHDSNVKNLYEKVRSQLKNNAKEIGNGCFEFYHKCDNTCMESVKNGTYDYPKYSEEA

KLNREEIDGVKLESTRIYQILA

SEQ ID NO 44: UFV150577
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQYTAIGCEYNKSERCMKQIEDKIEEIESKIWCYNAELLVLLENERTLD

YHDSNVKNLYEKVRSQLKNNAKEIGNGCFEFYHKCDNTCMESVKNGTYDYPKYSEEA

KLNREEIDGVKLESTRIY

SEQ ID NO 45: UFV150578
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQYTAIGCEYNKSERCMKQIEDKIEEIESKIWCYNAELLVLLENERTLD

YHDSNVKNLYEKVRSQLKNNAKEIGNGCFEFYHKCDNTCMESVKNGTYDYPKYSEEA

KLNREEIDGVKLESTR

SEQ ID NO 46: UFV150579
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQYTAIGCEYNKSERCMKQIEDKIEEIESKIWCYNAELLVLLENERTLD

YHDSNVKNLYEKVRSQLKNNAKEIGNGCFEFYHKCDNTCMESVKNGTYDYPKYSEEA

KLNREEIDGVKLES

SEQ ID NO 47: UFV150580
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQYTAIGCEYNKSERCMKQIEDKIEEIESKIWCYNAELLVLLENERTLD

YHDSNVKNLYEKVRSQLKNNAKEIGNGCFEFYHKCDNTCMESVKNGTYDYPKYSEEA

KLNREEIDGVKL

SEQ ID NO 48: UFV150581
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQYTAIGCEYNKSERCMKQIEDKIEEIESKIWCYNAELLVLLENERTLD

YHDSNVKNLYEKVRSQLKNNAKEIGNGCFEFYHKCDNTCMESVKNGTYDYPKYSEEA

KLNREEIDGV

SEQ ID NO 49: UFV150582
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQYTAIGCEYNKSERCMKQIEDKIEEIESKIWCYNAELLVLLENERTLD

YHDSNVKNLYEKVRSQLKNNAKEIGNGCFEFYHKCDNTCMESVKNGTYDYPKYSEEA

KLNREEID

SEQ ID NO 50: UFV150583
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQYTAIGCEYNKSERCMKQIEDKIEEIESKIWCYNAELLVLLENERTLD

YHDSNVKNLYEKVRSQLKNNAKEIGNGCFEFYHKCDNTCMESVKNGTYDYPKYSEEA

KLNREE

SEQ ID NO 51: UFV150584
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQYTAIGCEYNKSERCMKQIEDKIEEIESKIWCYNAELLVLLENERTLD

YHDSNVKNLYEKVRSQLKNNAKEIGNGCFEFYHKCDNTCMESVKNGTYDYPKYSEEA

KLNR

SEQ ID NO 52: UFV150849
DTICIGYHANNSTDTVDTVLEKNVTVTHSVNLLENGGGGKYVCSAKLRMVTGLRNKP

SKQSQGLFGAIAGFTEGGWTGMVDGWYGYHHQNEQGSGYAADQKSTQNAINGITNKV

NSVIEKMNTQRTAIGCEYNKSERCMKQIEDKIEEIESKIWCYNAELLVLLENQRTLE

FHDSNVKNLYEKVKSQLKNNAKEIGNGCFEFYHKCNDECMESVKNGTYDYPKYSEES

KLNREKIDGVKLESMGVYQI

SEQ ID NO 53: UFV150850
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQRTAIGCEYNKSERCMKQIEDKIEEIESKIWCYNAELLVLLENQRTLE

YHDSNVKNLYEKVRSQLKNNAKEIGNGCFEFYHKCDNTCMESVKNGTYDYPKYSEEA

KLNREEIDGVKLESTRIYQI

SEQ ID NO 54: UFV150552
DTICIGYHANNSTDTVDTVLEKNVTVTHSVNLLENGGGGKYVCSAKLRMVTGLRNKP

SKQSQGLFGAIAGFTEGGWTGMVDGWYGYHHQNEQGSGYAADQKSTQNAINGITNKV

NSVIEKMNTQPTAIGCEYNKSEQCMKQIEDKIEEIESKIWCYNAELLVLLENQRTLD

FHDANVKNLYEKVKSQLKNNAKEIGNGCFEFYHKCNDECMESVKNGTYDYPKYSEES

KLNREKIDGVKLESMGVYQI

SEQ ID NO 55: UFV160088
DTICIGYHANNSTDTVDTVLEKNVTVTHSVNLLENGGGGKYVCSAKLRMVTGLRNKP

SKQSRGLFGAIAGFIEGGWTGMVDGWYGYHHQNEQGSGYAADQKSTQNAINGITNKV

NSVIEKMNTQRTAICKEYPKSEQRMECLEKKVDDIEKKIWCYNAELLVLLENQRTLE

FHDINVKNLYEKVKSQLKNNAKEIGNGCFEFYHKCNDECMESVKNGTYDYPKYSEES

KLNREKIDGVKLESMGVYQI

SEQ ID NO 56: UFV160090
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQRTAIGCEYNKSERCIEALEKKVDDIEKKIWCYNAELLVLLENQRTLE

YHDSNVKNLYEKVRSQLKNNAKEIGNGCFEFYHKCDNTCMESVKNGTYDYPKYSEEA

KLNREEIDGVKLESTRIYQI

SEQ ID NO 57: UFV160093
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQRTAIGKECNKSERCIEALEKKVDDIEKKIWCYNAELLVLLENQRTLE

YHDSNVKNLYEKVRSQLKNNAKEIGNGCFEFYHKCDNTCMESVKNGTYDYPKYSEEA

KLNREEIDGVKLESTRIYQI

SEQ ID NO 58: UFV160097
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQRTAIGCEYNKSERCMKQIEDKIEEIESKIWCYNAELLVLLENQRTLE

YHDSNVKNLYEKVRSQLKNNAKEIGNGCFEFYHKCDNTCMESVKNGTYDYPKYSEEA

KLNREEIDGVKLESTRIYQI

SEQ ID NO 59: UFV160301
DTLCIGYHANNSTDTVDTVLEKNVTVTHSVNLLEDGGGGKYVCSTKLRLATGLRNKP

SKQRRRKKGLFGAIAGFTEGGWTGMVDGWYGYHHQNEQGSGYAADLKSTQNAIDEIT

NKVNSVIEKMNTQRTAIGCEYNKSERCMKQIEDKIEEIESKIWCYNAELLVLLENQR

TLEYHDSNVKNLYEKVRSQLKNNAKEIGNGCFEFYHKCDNTCMESVKNGTYDYPKYS

EEAKLNREEIDGVKLESTRIYQI

SEQ ID NO 60: UFV160302
DTLCIGYHANNSTDTVDTVLEKNVTVTHSVNLLEDGGGGKYVCSTKLRLATGLRNKP

SKQSRGLFGAIAGFTEGGWTGMVDGWYGYHHQNEQGSGYAADLKSTQNAIDEITNKV

NSVIEKMNTQRTAIGCEYNKSERCMKQIEDKIEEIESKIWCYNAELLVLLENQRTLE

YHDSNVKNLYEKVRSQLKNNAKEIGNGCFEFYHKCDNTCMESVKNGTYDYPKYSEEA

KLNREEIDGVKLESTRIYQI

SEQ ID NO 61: UFV160303
DTLCIGYHANNSTDTVDTVLEKNVTVTHSVNLLEDGGGGKYVCSTKLRLATGLRNKP

SKQSRGLFGAIAGFTEGGWTGMVDGWYGYHHQNEQGSGYAADLKSTQNAIDEITNKV

NSVIEKMNTQRTAIGCEYNKSERCMKQIEDKIEEIESKIWCYNAELLVLLENQRTLD

YHDSNVKNLYEKVRSQLKNNAKEIGNGCFEFYHKCDNTCMESVKNGTYDYPKYSEEA

KLNREEIDGVKLESTRIYQI

SEQ ID NO 62: UFV160304
DTLCIGYHANNSTDTVDTVLEKNVTVTHSVNLLEDGGGGKYVCSTKLRLATGLRNKP

SKQSRGLFGAIAGFTEGGWTGMVDGWYGYHHQNEQGSGYAADLKSTQNAIDEITNKV

NSVIEKMNTQYTAIGCEYNKSERCMKQIEDKIEEIESKIWCYNAELLVLLENQRTLE

YHDSNVKNLYEKVRSQLKNNAKEIGNGCFEFYHKCDNTCMESVKNGTYDYPKYSEEA

KLNREEIDGVKLESTRIYQI

SEQ ID NO: 63: UFV160360
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQPTAIGCEYNKSEQCMKQIEDKIEEIESKIWCYNAELLVLLENQRTLD

YHDANVKNLYEKVRSQLKNNAKEIGNGCFEFYHKCDNTCMESVKNGTYDYPKYSEEA

KLNREEIDGVKLESTRIYQI

SEQ ID NO 64: UFV160361
DTLCIGYHANNSTDTVDTVLEKNVTVTHSVNLLEDKYVCSTKLRLATGLRNKPSKQS

QGLFGAIAGFTEGGWTGMVDGWYGYHHQNEQGSGYAADLKSTQNAIDEITNKVNSVI

EKMNTQPTAIGCEYNKSEQCMKQIEDKIEEIESKIWCYNAELLVLLENQRTLDYHDA

NVKNLYEKVRSQLKNNAKEIGNGCFEFYHKCDNTCMESVKNGTYDYPKYSEEAKLNR

EEIDGVKLESTRIYQI

SEQ ID NO 65: UFV160362
DTLCIGYHANNSTDTVDTVLEKNVTVTHSVNLLEDKKYVCSTKLRLATGLRNKPSKQ

SQGLFGAIAGFTEGGWTGMVDGWYGYHHQNEQGSGYAADLKSTQNAIDEITNKVNSV

IEKMNTQPTAIGCEYNKSEQCMKQIEDKIEEIESKIWCYNAELLVLLENQRTLDYHD

ANVKNLYEKVRSQLKNNAKEIGNGCFEFYHKCDNTCMESVKNGTYDYPKYSEEAKLN

REEIDGVKLESTRIYQI

SEQ ID NO 66: UFV160363
DTLCIGYHANNSTDTVDTVLEKNVTVTHSVNLLEDKHKYVCSTKLRLATGLRNKPSK

QSQGLFGAIAGFTEGGWTGMVDGWYGYHHQNEQGSGYAADLKSTQNAIDEITNKVNS

VIEKMNTQPTAIGCEYNKSEQCMKQIEDKIEEIESKIWCYNAELLVLLENQRTLDYH

DANVKNLYEKVRSQLKNNAKEIGNGCFEFYHKCDNTCMESVKNGTYDYPKYSEEAKL

NREEIDGVKLESTRIYQI

SEQ ID NO 67: UFV160364
DTLCIGYHANNSTDTVDTVLEKNVTVTHSVNLLEDKHNKYVCSTKLRLATGLRNKPS

KQSQGLFGAIAGFTEGGWTGMVDGWYGYHHQNEQGSGYAADLKSTQNAIDEITNKVN

SVIEKMNTQPTAIGCEYNKSEQCMKQIEDKIEEIESKIWCYNAELLVLLENQRTLDY

HDANVKNLYEKVRSQLKNNAKEIGNGCFEFYHKCDNTCMESVKNGTYDYPKYSEEAK

LNREEIDGVKLESTRIYQI

SEQ ID NO 68: UFV160365
DTLCIGYHANNSTDTVDTVLEKNVTVTHSVNLLEDKHNGKYVCSTKLRLATGLRNKP

SKQSQGLFGAIAGFTEGGWTGMVDGWYGYHHQNEQGSGYAADLKSTQNAIDEITNKV

NSVIEKMNTQPTAIGCEYNKSEQCMKQIEDKIEEIESKIWCYNAELLVLLENQRTLD

YHDANVKNLYEKVRSQLKNNAKEIGNGCFEFYHKCDNTCMESVKNGTYDYPKYSEEA

KLNREEIDGVKLESTRIYQI

SEQ ID NO 69: UFV160366
DTLCIGYHANNSTDTVDTVLEKNVTVTHSVNLLEDKHNGKKYVCSTKLRLATGLRNK

PSKQSQGLFGAIAGFTEGGWTGMVDGWYGYHHQNEQGSGYAADLKSTQNAIDEITNK

VNSVIEKMNTQPTAIGCEYNKSEQCMKQIEDKIEEIESKIWCYNAELLVLLENQRTL

DYHDANVKNLYEKVRSQLKNNAKEIGNGCFEFYHKCDNTCMESVKNGTYDYPKYSEE

AKLNREEIDGVKLESTRIYQI

SEQ ID NO 70: UFV160367
DTLCIGYHANNSTDTVDTVLEKNVTVTHSVNLLEDKHNGKLKYVCSTKLRLATGLRN

KPSKQSQGLFGAIAGFTEGGWTGMVDGWYGYHHQNEQGSGYAADLKSTQNAIDEITN

KVNSVIEKMNTQPTAIGCEYNKSEQCMKQIEDKIEEIESKIWCYNAELLVLLENQRT

LDYHDANVKNLYEKVRSQLKNNAKEIGNGCFEFYHKCDNTCMESVKNGTYDYPKYSE

EAKLNREEIDGVKLESTRIYQI

-continued

SEQ ID NO 71: UFV160368
DTLCIGYHANNSTDTVDTVLEKNVTVTHSVNLLEDKHNGKLGKYVCSTKLRLATGLR
NKPSKQSQGLFGAIAGFTEGGWTGMVDGWYGYHHQNEQGSGYAADLKSTQNAIDEIT
NKVNSVIEKMNTQPTAIGCEYNKSEQCMKQIEDKIEEIESKIWCYNAELLVLLENQR
TLDYHDANVKNLYEKVRSQLKNNAKEIGNGCFEFYHKCDNTCMESVKNGTYDYPKYS
EEAKLNREEIDGVKLESTRIYQI

SEQ ID NO 72: UFV160369
DTLCIGYHANNSTDTVDTVLEKNVTVTHSVNLLEDKHNGKLGPKYVCSTKLRLATGL
RNKPSKQSQGLFGAIAGFTEGGWTGMVDGWYGYHHQNEQGSGYAADLKSTQNAIDEI
TNKVNSVIEKMNTQPTAIGCEYNKSEQCMKQIEDKIEEIESKIWCYNAELLVLLENQ
RTLDYHDANVKNLYEKVRSQLKNNAKEIGNGCFEFYHKCDNTCMESVKNGTYDYPKY
SEEAKLNREEIDGVKLESTRIYQI

SEQ ID NO: 73: UFV160370
DTLCIGYHANNSTDTVDTVLEKNVTVTHSVNLLEDKHGPKYVCSTKLRLATGLRNKP
SKQSQGLFGAIAGFTEGGWTGMVDGWYGYHHQNEQGSGYAADLKSTQNAIDEITNKV
NSVIEKMNTQPTAIGCEYNKSEQCMKQIEDKIEEIESKIWCYNAELLVLLENQRTLD
YHDANVKNLYEKVRSQLKNNAKEIGNGCFEFYHKCDNTCMESVKNGTYDYPKYSEEA
KLNREEIDGVKLESTRIYQI

SEQ ID NO 74: UFV160371
DTLCIGYHANNSTDTVDTVLEKNVTVTHSVNLLEDGEGPKYVCSTKLRLATGLRNKP
SKQSQGLFGAIAGFTEGGWTGMVDGWYGYHHQNEQGSGYAADLKSTQNAIDEITNKV
NSVIEKMNTQPTAIGCEYNKSEQCMKQIEDKIEEIESKIWCYNAELLVLLENQRTLD
YHDANVKNLYEKVRSQLKNNAKEIGNGCFEFYHKCDNTCMESVKNGTYDYPKYSEEA
KLNREEIDGVKLESTRIYQI

SEQ ID NO 75: UFV160372
DTLCIGYHANNSTDTVDTVLEKNVTVTHSVNLLEDVCSTKLRLATGLRNKPSKQSQG
LFGAIAGFTEGGWTGMVDGWYGYHHQNEQGSGYAADLKSTQNAIDEITNKVNSVIEK
MNTQPTAIGCEYNKSEQCMKQIEDKIEEIESKIWCYNAELLVLLENQRTLDYHDANV
KNLYEKVRSQLKNNAKEIGNGCFEFYHKCDNTCMESVKNGTYDYPKYSEEAKLNREE
IDGVKLESTRIYQI

SEQ ID NO 76: UFV160373
DTLCIGYHANNSTDTVDTVLEKNVTVTHSVNLLEDKVCSTKLRLATGLRNKPSKQSQ
GLFGAIAGFTEGGWTGMVDGWYGYHHQNEQGSGYAADLKSTQNAIDEITNKVNSVIE
KMNTQPTAIGCEYNKSEQCMKQIEDKIEEIESKIWCYNAELLVLLENQRTLDYHDAN
VKNLYEKVRSQLKNNAKEIGNGCFEFYHKCDNTCMESVKNGTYDYPKYSEEAKLNRE
EIDGVKLESTRIYQI

SEQ ID NO 77: UFV160374
DTLCIGYHANNSTDTVDTVLEKNVTVTHSVNLLEDKHVCSTKLRLATGLRNKPSKQS
QGLFGAIAGFTEGGWTGMVDGWYGYHHQNEQGSGYAADLKSTQNAIDEITNKVNSVI
EKMNTQPTAIGCEYNKSEQCMKQIEDKIEEIESKIWCYNAELLVLLENQRTLDYHDA
NVKNLYEKVRSQLKNNAKEIGNGCFEFYHKCDNTCMESVKNGTYDYPKYSEEAKLNR
EEIDGVKLESTRIYQI

SEQ ID NO 78: UFV160375
DTLCIGYHANNSTDTVDTVLEKNVTVTHSVNLLEDKHNVCSTKLRLATGLRNKPSKQ

SQGLFGAIAGFTEGGWTGMVDGWYGYHHQNEQGSGYAADLKSTQNAIDEITNKVNSV

IEKMNTQPTAIGCEYNKSEQCMKQIEDKIEEIESKIWCYNAELLVLLENQRTLDYHD

ANVKNLYEKVRSQLKNNAKEIGNGCFEFYHKCDNTCMESVKNGTYDYPKYSEEAKLN

REEIDGVKLESTRIYQI

SEQ ID NO 79: UFV160376
DTLCIGYHANNSTDTVDTVLEKNVTVTHSVNLLEDKHNGVCSTKLRLATGLRNKPSK

QSQGLFGAIAGFTEGGWTGMVDGWYGYHHQNEQGSGYAADLKSTQNAIDEITNKVNS

VIEKMNTQPTAIGCEYNKSEQCMKQIEDKIEEIESKIWCYNAELLVLLENQRTLDYH

DANVKNLYEKVRSQLKNNAKEIGNGCFEFYHKCDNTCMESVKNGTYDYPKYSEEAKL

NREEIDGVKLESTRIYQI

SEQ ID NO 80: UFV160377
DTLCIGYHANNSTDTVDTVLEKNVTVTHSVNLLEDKHNGKVCSTKLRLATGLRNKPS

KQSQGLFGAIAGFTEGGWTGMVDGWYGYHHQNEQGSGYAADLKSTQNAIDEITNKVN

SVIEKMNTQPTAIGCEYNKSEQCMKQIEDKIEEIESKIWCYNAELLVLLENQRTLDY

HDANVKNLYEKVRSQLKNNAKEIGNGCFEFYHKCDNTCMESVKNGTYDYPKYSEEAK

LNREEIDGVKLESTRIYQI

SEQ ID NO 81: UFV160378
DTLCIGYHANNSTDTVDTVLEKNVTVTHSVNLLEDKHNGKLVCSTKLRLATGLRNKP

SKQSQGLFGAIAGFTEGGWTGMVDGWYGYHHQNEQGSGYAADLKSTQNAIDEITNKV

NSVIEKMNTQPTAIGCEYNKSEQCMKQIEDKIEEIESKIWCYNAELLVLLENQRTLD

YHDANVKNLYEKVRSQLKNNAKEIGNGCFEFYHKCDNTCMESVKNGTYDYPKYSEEA

KLNREEIDGVKLESTRIYQI

SEQ ID NO 82: UFV160379
DTLCIGYHANNSTDTVDTVLEKNVTVTHSVNLLEDKHNGKLGVCSTKLRLATGLRNK

PSKQSQGLFGAIAGFTEGGWTGMVDGWYGYHHQNEQGSGYAADLKSTQNAIDEITNK

VNSVIEKMNTQPTAIGCEYNKSEQCMKQIEDKIEEIESKIWCYNAELLVLLENQRTL

DYHDANVKNLYEKVRSQLKNNAKEIGNGCFEFYHKCDNTCMESVKNGTYDYPKYSEE

AKLNREEIDGVKLESTRIYQI

SEQ ID NO 83: UFV160380
DTLCIGYHANNSTDTVDTVLEKNVTVTHSVNLLEDAGSGKYVCSTKLRLATGLRNKP

SKQSQGLFGAIAGFTEGGWTGMVDGWYGYHHQNEQGSGYAADLKSTQNAIDEITNKV

NSVIEKMNTQPTAIGCEYNKSEQCMKQIEDKIEEIESKIWCYNAELLVLLENQRTLD

YHDANVKNLYEKVRSQLKNNAKEIGNGCFEFYHKCDNTCMESVKNGTYDYPKYSEEA

KLNREEIDGVKLESTRIYQI

SEQ ID NO 84: UFV160381
DTLCIGYHANNSTDTVDTVLEKNVTVTHSVNLLEDAGSKYVCSTKLRLATGLRNKPS

KQSQGLFGAIAGFTEGGWTGMVDGWYGYHHQNEQGSGYAADLKSTQNAIDEITNKVN

SVIEKMNTQPTAIGCEYNKSEQCMKQIEDKIEEIESKIWCYNAELLVLLENQRTLDY

HDANVKNLYEKVRSQLKNNAKEIGNGCFEFYHKCDNTCMESVKNGTYDYPKYSEEAK

LNREEIDGVKLESTRIYQI

SEQ ID NO 85: UFV160382
DTLCIGYHANNSTDTVDTVLEKNVTVTHSVNLLEDAGSGIKYVCSTKLRLATGLRNK

PSKQSQGLFGAIAGFTEGGWTGMVDGWYGYHHQNEQGSGYAADLKSTQNAIDEITNK

VNSVIEKMNTQPTAIGCEYNKSEQCMKQIEDKIEEIESKIWCYNAELLVLLENQRTL

DYHDANVKNLYEKVRSQLKNNAKEIGNGCFEFYHKCDNTCMESVKNGTYDYPKYSEE

AKLNREEIDGVKLESTRIYQI

SEQ ID NO 86: UFV160383
DTLCIGYHANNSTDTVDTVLEKNVTVTHSVNLLEDAGSGIVCSTKLRLATGLRNKPS

KQSQGLFGAIAGFTEGGWTGMVDGWYGYHHQNEQGSGYAADLKSTQNAIDEITNKVN

SVIEKMNTQPTAIGCEYNKSEQCMKQIEDKIEEIESKIWCYNAELLVLLENQRTLDY

HDANVKNLYEKVRSQLKNNAKEIGNGCFEFYHKCDNTCMESVKNGTYDYPKYSEEAK

LNREEIDGVKLESTRIYQI

SEQ ID NO 87: UFV160384
DTLCIGYHANNSTDTVDTVLEKNVTVTHSVNLLEDGSGIKYVCSTKLRLATGLRNKP

SKQSQGLFGAIAGFTEGGWTGMVDGWYGYHHQNEQGSGYAADLKSTQNAIDEITNKV

NSVIEKMNTQPTAIGCEYNKSEQCMKQIEDKIEEIESKIWCYNAELLVLLENQRTLD

YHDANVKNLYEKVRSQLKNNAKEIGNGCFEFYHKCDNTCMESVKNGTYDYPKYSEEA

KLNREEIDGVKLESTRIYQI

SEQ ID NO 88: UFV160385
DTLCIGYHANNSTDTVDTVLEKNVTVTHSVNLLEDGSGKYVCSTKLRLATGLRNKPS

KQSQGLFGAIAGFTEGGWTGMVDGWYGYHHQNEQGSGYAADLKSTQNAIDEITNKVN

SVIEKMNTQPTAIGCEYNKSEQCMKQIEDKIEEIESKIWCYNAELLVLLENQRTLDY

HDANVKNLYEKVRSQLKNNAKEIGNGCFEFYHKCDNTCMESVKNGTYDYPKYSEEAK

LNREEIDGVKLESTRIYQI

SEQ ID NO 89: UFV160386
DTLCIGYHANNSTDTVDTVLEKNVTVTHSVNLLEDHAGAKYVCSTKLRLATGLRNKP

SKQSQGLFGAIAGFTEGGWTGMVDGWYGYHHQNEQGSGYAADLKSTQNAIDEITNKV

NSVIEKMNTQPTAIGCEYNKSEQCMKQIEDKIEEIESKIWCYNAELLVLLENQRTLD

YHDANVKNLYEKVRSQLKNNAKEIGNGCFEFYHKCDNTCMESVKNGTYDYPKYSEEA

KLNREEIDGVKLESTRIYQI

SEQ ID NO 90: UFV160387
DTLCIGYHANNSTDTVDTVLEKNVTVTHSVNLLEDDQEGKYVCSTKLRLATGLRNKP

SKQSQGLFGAIAGFTEGGWTGMVDGWYGYHHQNEQGSGYAADLKSTQNAIDEITNKV

NSVIEKMNTQPTAIGCEYNKSEQCMKQIEDKIEEIESKIWCYNAELLVLLENQRTLD

YHDANVKNLYEKVRSQLKNNAKEIGNGCFEFYHKCDNTCMESVKNGTYDYPKYSEEA

KLNREEIDGVKLESTRIYQI

SEQ ID NO 91: UFV160388
DTLCIGYHANNSTDTVDTVLEKNVTVTHSVNLLEDDTPVKYVCSTKLRLATGLRNKP

SKQSQGLFGAIAGFTEGGWTGMVDGWYGYHHQNEQGSGYAADLKSTQNAIDEITNKV

NSVIEKMNTQPTAIGCEYNKSEQCMKQIEDKIEEIESKIWCYNAELLVLLENQRTLD

YHDANVKNLYEKVRSQLKNNAKEIGNGCFEFYHKCDNTCMESVKNGTYDYPKYSEEA

KLNREEIDGVKLESTRIYQI

SEQ ID NO 92: UFV160389
DTLCIGYHANNSTDTVDTVLEKNVTVTHSVNLLEDFPKTKYVCSTKLRLATGLRNKP

SKQSQGLFGAIAGFTEGGWTGMVDGWYGYHHQNEQGSGYAADLKSTQNAIDEITNKV

NSVIEKMNTQPTAIGCEYNKSEQCMKQIEDKIEEIESKIWCYNAELLVLLENQRTLD

YHDANVKNLYEKVRSQLKNNAKEIGNGCFEFYHKCDNTCMESVKNGTYDYPKYSEEA

KLNREEIDGVKLESTRIYQI

SEQ ID NO 93: UFV160390
DTLCIGYHANNSTDTVDTVLEKNVTVTHSVNLLEDEPGDKYVCSTKLRLATGLRNKP

SKQSQGLFGAIAGFTEGGWTGMVDGWYGYHHQNEQGSGYAADLKSTQNAIDEITNKV

NSVIEKMNTQPTAIGCEYNKSEQCMKQIEDKIEEIESKIWCYNAELLVLLENQRTLD

YHDANVKNLYEKVRSQLKNNAKEIGNGCFEFYHKCDNTCMESVKNGTYDYPKYSEEA

KLNREEIDGVKLESTRIYQI

SEQ ID NO 94: UFV160391
DTLCIGYHANNSTDTVDTVLEKNVTVTHSVNLLEDEPGKYVCSTKLRLATGLRNKPS

KQSQGLFGAIAGFTEGGWTGMVDGWYGYHHQNEQGSGYAADLKSTQNAIDEITNKVN

SVIEKMNTQPTAIGCEYNKSEQCMKQIEDKIEEIESKIWCYNAELLVLLENQRTLDY

HDANVKNLYEKVRSQLKNNAKEIGNGCFEFYHKCDNTCMESVKNGTYDYPKYSEEAK

LNREEIDGVKLESTRIYQI

SEQ ID NO 95: UFV160392
DTLCIGYHANNSTDTVDTVLEKNVTVTHSVNLLEDTGNLKYVCSTKLRLATGLRNKP

SKQSQGLFGAIAGFTEGGWTGMVDGWYGYHHQNEQGSGYAADLKSTQNAIDEITNKV

NSVIEKMNTQPTAIGCEYNKSEQCMKQIEDKIEEIESKIWCYNAELLVLLENQRTLD

YHDANVKNLYEKVRSQLKNNAKEIGNGCFEFYHKCDNTCMESVKNGTYDYPKYSEEA

KLNREEIDGVKLESTRIYQI

SEQ ID NO: 96: UFV160393
DTLCIGYHANNSTDTVDTVLEKNVTVTHSVNLLEDTPSSKYVCSTKLRLATGLRNKP

SKQSQGLFGAIAGFTEGGWTGMVDGWYGYHHQNEQGSGYAADLKSTQNAIDEITNKV

NSVIEKMNTQPTAIGCEYNKSEQCMKQIEDKIEEIESKIWCYNAELLVLLENQRTLD

YHDANVKNLYEKVRSQLKNNAKEIGNGCFEFYHKCDNTCMESVKNGTYDYPKYSEEA

KLNREEIDGVKLESTRIYQI

SEQ ID NO 97: UFV160394
DTLCIGYHANNSTDTVDTVLEKNVTVTHSVNLLEDTPSKYVCSTKLRLATGLRNKPS

KQSQGLFGAIAGFTEGGWTGMVDGWYGYHHQNEQGSGYAADLKSTQNAIDEITNKVN

SVIEKMNTQPTAIGCEYNKSEQCMKQIEDKIEEIESKIWCYNAELLVLLENQRTLDY

HDANVKNLYEKVRSQLKNNAKEIGNGCFEFYHKCDNTCMESVKNGTYDYPKYSEEAK

LNREEIDGVKLESTRIYQI

SEQ ID NO 98: UFV160395
DTLCIGYHANNSTDTVDTVLEKNVTVTHSVNLLEDATGNKYVCSTKLRLATGLRNKP

SKQSQGLFGAIAGFTEGGWTGMVDGWYGYHHQNEQGSGYAADLKSTQNAIDEITNKV

NSVIEKMNTQPTAIGCEYNKSEQCMKQIEDKIEEIESKIWCYNAELLVLLENQRTLD

YHDANVKNLYEKVRSQLKNNAKEIGNGCFEFYHKCDNTCMESVKNGTYDYPKYSEEA

KLNREEIDGVKLESTRIYQI

SEQ ID NO 99: UFV160396
DTLCIGYHANNSTDTVDTVLEKNVTVTHSVNLLEDYPGDKYVCSTKLRLATGLRNKP

SKQSQGLFGAIAGFTEGGWTGMVDGWYGYHHQNEQGSGYAADLKSTQNAIDEITNKV

NSVIEKMNTQPTAIGCEYNKSEQCMKQIEDKIEEIESKIWCYNAELLVLLENQRTLD

YHDANVKNLYEKVRSQLKNNAKEIGNGCFEFYHKCDNTCMESVKNGTYDYPKYSEEA

KLNREEIDGVKLESTRIYQI

SEQ ID NO 100: UFV160397
DTLCIGYHANNSTDTVDTVLEKNVTVTHSVNLLEDYPGDVCSTKLRLATGLRNKPSK

QSQGLFGAIAGFTEGGWTGMVDGWYGYHHQNEQGSGYAADLKSTQNAIDEITNKVNS

VIEKMNTQPTAIGCEYNKSEQCMKQIEDKIEEIESKIWCYNAELLVLLENQRTLDYH

DANVKNLYEKVRSQLKNNAKEIGNGCFEFYHKCDNTCMESVKNGTYDYPKYSEEAKL

NREEIDGVKLESTRIYQI

SEQ ID NO 101: UFV160503
DTLCIGYHANNSTDTVDTVLEKNVTVTHSVNLLEDGGGGKYVCSTKLRLATGLRNKP

SKQSRKRRGLFGAIAGFTEGGWTGMVDGWYGYHHQNEQGSGYAADLKSTQNAIDEIT

NKVNSVIEKMNTQRTAIGCEYNKSERCMKQIEDKIEEIESKIWCYNAELLVLLENQR

TLEYHDSNVKNLYEKVRSQLKNNAKEIGNGCFEFYHKCDNTCMESVKNGTYDYPKYS

EEAKLNREEIDGVKLESTRIYQI

SEQ ID NO 102: UFV160504
DTLCIGYHANNSTDTVDTVLEKNVTVTHSVNLLEDGGGGKYVCSTKLRLATGLRNKP

QRERRRKKRGLFGAIAGFTEGGWTGMVDGWYGYHHQNEQGSGYAADLKSTQNAIDEI

TNKVNSVIEKMNTQRTAIGCEYNKSERCMKQIEDKIEEIESKIWCYNAELLVLLENQ

RTLEYHDSNVKNLYEKVRSQLKNNAKEIGNGCFEFYHKCDNTCMESVKNGTYDYPKY

SEEAKLNREEIDGVKLESTRIYQI

SEQ ID NO 103: UFV160655
DTICIGYHANNSTDTVDTVLEKNVTVTHSVNLLENSKYVCSAKLRMVTGLRNKPSKQ

SQGLFGAIAGFTEGGWTGMVDGWYGYHHQNEQGSGYAADQKSTQNAINGITNKVNSV

IEKMNTQPTAIGCEYNKSEQCMKQIEDKIEEIESKIWCYNAELLVLLENQRTLDFHD

ANVKNLYEKVKSQLKNNAKEIGNGCFEFYHKCNDECMESVKNGTYDYPKYSEESKLN

REKIDGVKLESMGVYQI

SEQ ID NO 104: UFV160656
DTLCIGYHANNSTDTVDTVLEKNVTVTHSVNLLEDKKYVCSTKLRLATGLRNKPSKQ

SQGLFGAIAGFTEGGWTGMVDGWYGYHHQNEQGSGYAADLKSTQNAIDEITNKVNSV

IEKMNTQPTAIGCEYNKSEQCMKQIEDKIEEIESKIWCYNAELLVLLENQRTLDYHD

ANVKNLYEKVRSQLKNNAKEIGNGCFEFYHKCDNTCMESVKNGTYDYPKYSEEAKLN

REEIDGVKLESTRIYQI

SEQ ID NO 105: UFV160657
DTLCIGYHANNSTDTVDTVLEKNVTVTHSVNLLEDKHNGKLGKYVCSTKLRLATGLR

NKPSKQSQGLFGAIAGFTEGGWTGMVDGWYGYHHQNEQGSGYAADLKSTQNAIDEIT

NKVNSVIEKMNTQPTAIGCEYNKSEQCMKQIEDKIEEIESKIWCYNAELLVLLENQR

TLDYHDANVKNLYEKVRSQLKNNAKEIGNGCFEFYHKCDNTCMESVKNGTYDYPKYS

EEAKLNREEIDGVKLESTRIYQI

SEQ ID NO 106: UFV160658
DTLCIGYHANNSTDTVDTVLEKNVTVTHSVNLLEDKKYVCSTKLRLATGLRNKPSKQ

SQGLFGAIAGFTEGGWTGMVDGWYGYHHQNEQGSGYAADLKSTQNAIDEITNKVNSV

IEKMNTQRTAIGCEYNKSERCMKQIEDKIEEIESKIWCYNAELLVLLENQRTLEYHD

SNVKNLYEKVRSQLKNNAKEIGNGCFEFYHKCDNTCMESVKNGTYDYPKYSEEAKLN

REEIDGVKLESTRIYQI

SEQ ID NO 107: UFV160659
DTLCIGYHANNSTDTVDTVLEKNVTVTHSVNLLEDKHNGKLGKYVCSTKLRLATGLR

NKPSKQSQGLFGAIAGFTEGGWTGMVDGWYGYHHQNEQGSGYAADLKSTQNAIDEIT

NKVNSVIEKMNTQRTAIGCEYNKSERCMKQIEDKIEEIESKIWCYNAELLVLLENQR

TLEYHDSNVKNLYEKVRSQLKNNAKEIGNGCFEFYHKCDNTCMESVKNGTYDYPKYS

EEAKLNREEIDGVKLESTRIYQI

SEQ ID NO: 108: UFV160663
DTLCIGYHANNSTDTVDTVLEKNVTVTHSVNLLEDGGGGKYVCSTKLRLATGLRNKP

SKQSQGLFGAIAGFTEGGWTGMVDGWYGYHHQNEQGSGYAADLKSTQNAIDEITNKV

NSVIEKMNTQRTAIGCEYNKSERCMKQIEDKIEEIESKIWCYNAELLVLLENQRTLD

YHDSNVKNLYEKVRSQLKNNAKEIGNGCFEFYHKCDNTCMESVKNGTYDYPKYSEEA

KLNREEIDGVKLESTRIYQI

SEQ ID NO 109: UFV160664
DTLCIGYHANNSTDTVDTVLEKNVTVTHSVNLLEDKKYVCSTKLRLATGLRNKPSKQ

SQGLFGAIAGFTEGGWTGMVDGWYGYHHQNEQGSGYAADLKSTQNAIDEITNKVNSV

IEKMNTQRTAIGCEYNKSERCMKQIEDKIEEIESKIWCYNAELLVLLENQRTLDYHD

SNVKNLYEKVRSQLKNNAKEIGNGCFEFYHKCDNTCMESVKNGTYDYPKYSEEAKLN

REEIDGVKLESTRIYQI

SEQ ID NO 110: UFV160665
DTLCIGYHANNSTDTVDTVLEKNVTVTHSVNLLEDKKYVCSTKLRLATGLRNKPSKQ

SQGLFGAIAGFTEGGWTGMVDGWYGYHHQNEQGSGYAADLKSTQNAIDEITNKVNSV

IEKMNTQPTAIGCEYNKSERCMKQIEDKIEEIESKIWCYNAELLVLLENQRTLDYHD

SNVKNLYEKVRSQLKNNAKEIGNGCFEFYHKCDNTCMESVKNGTYDYPKYSEEAKLN

REEIDGVKLESTRIYQI

SEQ ID NO 111: UFV160666
DTLCIGYHANNSTDTVDTVLEKNVTVTHSVNLLEDKHNGKLGKYVCSTKLRLATGLR

NKPSKQSQGLFGAIAGFTEGGWTGMVDGWYGYHHQNEQGSGYAADLKSTQNAIDEIT

NKVNSVIEKMNTQRTAIGCEYNKSERCMKQIEDKIEEIESKIWCYNAELLVLLENQR

TLDYHDSNVKNLYEKVRSQLKNNAKEIGNGCFEFYHKCDNTCMESVKNGTYDYPKYS

EEAKLNREEIDGVKLESTRIYQI

SEQ ID NO 112: UFV160667
DTLCIGYHANNSTDTVDTVLEKNVTVTHSVNLLEDKHNGKLGKYVCSTKLRLATGLR

NKPSKQSQGLFGAIAGFTEGGWTGMVDGWYGYHHQNEQGSGYAADLKSTQNAIDEIT

NKVNSVIEKMNTQPTAIGCEYNKSERCMKQIEDKIEEIESKIWCYNAELLVLLENQR

TLDYHDSNVKNLYEKVRSQLKNNAKEIGNGCFEFYHKCDNTCMESVKNGTYDYPKYS

EEAKLNREEIDGVKLESTRIYQI

SEQ ID NO 138: UFV160655
ATGAAAGTCAAACTGCTGGTCCTGCTGTGCACCTTCACCGCCACTTACGCCGACACC

ATCTGTATTGGGTACCACGCTAACAACTCCACCGACACAGTGGATACCGTGCTGGAG

AAGAACGTGACCGTGACACACTCTGTGAACCTGCTGGAGAATTCCAAGTACGTCTGC

AGCGCCAAGCTGAGGATGGTGACAGGCCTGAGAAATAAGCCCAGCAAGCAGTCCCAG

GGCCTGTTCGGAGCAATCGCAGGCTTTACCGAGGGAGGATGGACAGGAATGGTGGAC

GGATGGTACGGCTATCACCACCAGAACGAGCAGGGCTCCGGCTATGCCGCCGATCAG

AAGTCTACCCAGAACGCCATCAATGGCATCACAAACAAGGTCAATAGCGTGATCGAG

AAGATGAACACCCAGCCTACAGCCATCGGCTGCGAGTACAATAAGTCCGAGCAGTGC

ATGAAGCAGATCGAGGACAAGATCGAGGAGATCGAGTCTAAGATCTGGTGCTATAAC

GCCGAGCTGCTGGTGCTGCTCGAGAATCAGAGGACCCTGGACTTCCACGATGCCAAC

GTGAAGAATCTGTACGAGAAGGTGAAGTCCCAGCTGAAGAACAATGCCAAGGAGATC

GGCAACGGCTGTTTCGAGTTTTACCACAAGTGCAACGACGAGTGTATGGAGTCCGTG

AAGAATGGCACATACGATTATCCTAAGTATTCTGAGGAGAGCAAACTGAATCGGGAA

AAAATCGATGGCGTGAAACTGGAATCAATGGGGGTGTATCAGATCTAATAA

SEQ ID NO 139: UFV160656
ATGAAGGCCATCCTGGTGGTGCTGCTGTACACCTTCGCCACAGCCAACGCCGACACC

CTGTGCATCGGGTACCACGCCAACAATTCCACCGACACAGTGGATACAGTGCTGGAG

AAGAATGTGACCGTGACACACTCCGTGAACCTGCTGGAGGATAAGAAGTACGTCTGC

AGCACCAAGCTGAGGCTGGCCACAGGCCTGAGAAACAAGCCAAGCAAGCAGTCCCAG

GGCCTGTTCGGAGCCATCGCCGGCTTTACCGAGGGAGGATGGACAGGAATGGTGGAC

GGATGGTACGGCTATCACCACCAGAACGAGCAGGGCAGCGGATACGCCGCCGACCTG

AAGTCCACCCAGAATGCCATCGACGAGATTACCAACAAGGTCAATAGCGTGATTGAG

AAGATGAACACCCAGCCCACAGCCATCGGCTGCGAGTACAATAAGAGCGAGCAGTGT

ATGAAGCAGATTGAGGATAAGATTGAGGAGATTGAGTCCAAGATTTGGTGCTATAAC

GCCGAGCTGCTGGTGCTGCTCGAGAATCAGAGGACCCTGGACTACCACGATGCCAAC

GTGAAGAATCTGTATGAGAAGGTGAGGAGCCAGCTGAAGAACAATGCCAAGGAGATT

GGCAACGGCTGTTTCGAGTTTTACCACAAGTGCGACAACACCTGTATGGAGTCTGTG

AAGAATGGCACATACGATTATCCCAAGTATAGCGAGGAGGCCAAGCTGAATCGGGAG

GAAATCGATGGCGTGAAGCTGGAGAGCACCCGCATCTACCAGATCTAATAA

SEQ ID NO 140: UFV160664
ATGAAGGCCATCCTGGTCGTCCTGCTGTACACTTTCGCCACCGCCAACGCTGATACC

CTGTGCATCGGGTACCACGCTAACAACTCTACCGACACAGTGGATACCGTGCTGGAG

AAGAACGTGACCGTGACACACTCTGTGAATCTGCTGGAGGATAAGAAGTACGTCTGC

AGCACCAAGCTGAGGCTGGCCACAGGCCTGAGAAACAAGCCCAGCAAGCAGAGCCAG

GGCCTGTTTGGAGCAATTGCAGGCTTTACCGAGGGCGGCTGGACAGGCATGGTGGAT

GGCTGGTACGGCTATCACCACCAGAATGAGCAGGGATCTGGATATGCTGCTGACCTG

AAGTCTACCCAGAATGCCATTGATGAGATCACAAACAAGGTCAATAGCGTGATCGAG

AAGATGAACACCCAGCGGACAGCCATCGGCTGCGAGTACAATAAGTCCGAGAGGTGC

ATGAAGCAGATCGAGGACAAGATCGAGGAGATCGAGTCTAAGATCTGGTGCTATAAC

GCCGAGCTGCTGGTGCTGCTCGAGAATCAGCGGACCCTGGACTACCACGACAGCAAC

GTGAAGAATCTGTATGAGAAGGTGCGCTCCCAGCTGAAGAACAATGCCAAGGAGATC

-continued

```
GGCAACGGCTGTTTCGAGTTTTACCACAAGTGCGACAACACCTGTATGGAGTCTGTG

AAGAATGGCACATACGATTATCCCAAGTATAGCGAGGAGGCCAAGCTGAATAGGGAG

GAAATCGATGGCGTGAAGCTGGAGTCTACAAGAATCTACCAGATCTAATAA

SEQ ID NO 141: UFV160665
ATGAAGGCCATCCTGGTCGTCCTGCTGTACACTTTCGCCACCGCCAACGCTGATACC

CTGTGCATCGGGTACCACGCTAACAACTCTACCGACACAGTGGATACCGTGCTGGAG

AAGAACGTGACCGTGACACACTCTGTGAATCTGCTGGAGGATAAGAAGTACGTCTGC

AGCACCAAGCTGAGGCTGGCCACAGGCCTGAGAAACAAGCCCAGCAAGCAGAGCCAG

GGCCTGTTTGGAGCAATTGCAGGCTTTACCGAGGGCGGCTGGACAGGCATGGTGGAT

GGCTGGTACGGCTATCACCACCAGAATGAGCAGGGATCTGGATATGCTGCTGACCTG

AAGTCTACCCAGAATGCCATTGATGAGATCACAAACAAGGTCAATAGCGTGATCGAG

AAGATGAACACCCAGCCTACAGCCATCGGCTGCGAGTACAATAAGTCCGAGAGGTGC

ATGAAGCAGATCGAGGACAAGATCGAGGAGATCGAGTCTAAGATCTGGTGCTATAAC

GCCGAGCTGCTGGTGCTGCTCGAGAATCAGCGGACCCTGGACTACCACGACAGCAAC

GTGAAGAATCTGTATGAGAAGGTGCGCTCCCAGCTGAAGAACAATGCCAAGGAGATC

GGCAACGGCTGTTTCGAGTTTTACCACAAGTGCGACAACACCTGTATGGAGTCTGTG

AAGAATGGCACATACGATTATCCCAAGTATAGCGAGGAGGCCAAGCTGAATAGGGAG

GAAATCGATGGCGTGAAGCTGGAGTCTACAAGAATCTACCAGATCTAATAA

SEQ ID NO 142: UFV171588 (UFV160655 + TM))
ATGAAGGTCAAACTGCTGGTCCTGCTGTGCACTTTTACTGCCACCTACGCTGACACT

ATCTGTATCGGGTACCACGCAAACAACTCAACCGACACAGTGGATACCGTGCTGGAG

AAGAACGTGACCGTGACACACTCCGTGAACCTGCTGGAGAATAGCAAGTACGTCTGC

AGCGCCAAGCTGCGGATGGTGACAGGCCTGAGAAATAAGCCCTCTAAGCAGAGCCAG

GGACTGTTCGGAGCAATCGCAGGCTTTACCGAGGGAGGATGGACAGGAATGGTGGAC

GGATGGTACGGCTATCACCACCAGAACGAGCAGGGCAGCGGCTATGCCGCCGATCAG

AAGTCCACCCAGAACGCCATCAATGGCATCACAAACAAGGTGAACAGCGTGATCGAG

AAGATGAACACCCAGCCTACAGCCATCGGCTGCGAGTATAATAAGAGCGAGCAGTGT

ATGAAGCAGATCGAGGACAAGATCGAGGAGATCGAGTCCAAGATCTGGTGCTACAAC

GCCGAGCTGCTGGTGCTGCTGGAGAATCAGCGCACCCTGGACTTCCACGATGCCAAC

GTGAAGAATCTGTATGAGAAGGTGAAGAGCCAGCTGAAGAACAATGCCAAGGAGATC

GGCAACGGCTGTTTCGAGTTTTACCACAAGTGCAACGACGAGTGTATGGAGAGCGTG

AAGAATGGCACCTACGATTATCCTAAGTATTCCGAGGAGTCTAAGCTGAATCGGGAG

AAAATCGATGGCGTGAAGCTGGAGTCCATGGGCGTGTACCAGATCCTGGCCATCTAT

TCTACAGTGGCCAGCTCCCTGGTGCTGCTGGTGAGCCTGGGGGCTATTTCATTCTGG

ATGTGCTCTAACGGCTCTCTCCAGTGTCGCATTTGTATCTGATAA

SEQ ID NO 143: UFV171589 (UFV160656 + TM)
ATGAAGGCCATTCTGGTCGTGCTGCTGTACACTTTCGCCACCGCTAACGCTGACACC

CTGTGCATCGGGTACCACGCCAATAACTCCACCGACACAGTGGATACCGTGCTGGAG

AAGAACGTGACCGTGACACACTCTGTGAATCTGCTGGAGGACAAGAAGTACGTCTGC

AGCACCAAGCTGAGGCTGGCCACAGGCCTGAGAAACAAGCCCTCTAAGCAGAGCCAG

GGCCTGTTCGGAGCAATCGCAGGCTTTACCGAGGGAGGATGGACAGGCATGGTGGAT

GGCTGGTACGGCTATCACCACCAGAACGAGCAGGGATCCGGATATGCCGCCGACCTG
```

AAGTCTACCCAGAATGCCATCGACGAGATCACAAACAAGGTCAATTCTGTGATCGAG

AAGATGAACACCCAGCCTACAGCCATCGGCTGCGAGTACAATAAGAGCGAGCAGTGT

ATGAAGCAGATCGAGGACAAGATCGAGGAGATCGAGTCCAAGATCTGGTGCTATAAC

GCCGAGCTGCTGGTGCTGCTGGAGAATCAGAGGACCCTGGACTACCACGATGCCAAC

GTGAAGAATCTGTATGAGAAGGTGCGGTCCCAGCTGAAGAACAATGCCAAGGAGATC

GGCAACGGCTGTTTCGAGTTTTACCACAAGTGCGACAACACCTGTATGGAGTCCGTG

AAGAATGGCACATACGATTATCCCAAGTATTCTGAGGAGGCCAAGCTGAATCGGGAG

GAAATCGATGGCGTGAAGCTGGAGTCTACCCGCATCTACCAGATCCTGGCCATCTAT

AGCACAGTGGCCAGCTCCCTGGTGCTGGTGGTGTCCCTGGGGGCTATCTCTTTCTGG

ATGTGCTCAAATGGGTCCCTCCAGTGTCGCATCTGTATCTGATAA

SEQ ID NO 144: UFV171590 (UFV160664 + TM)
ATGAAGGCCATTCTGGTCGTGCTGCTGTACACTTTCGCCACCGCTAACGCTGACACC

CTGTGCATCGGGTACCACGCCAATAACTCCACCGACACAGTGGATACCGTGCTGGAG

AAGAACGTGACCGTGACACACTCTGTGAATCTGCTGGAGGACAAGAAGTACGTCTGC

AGCACCAAGCTGAGGCTGGCCACAGGCCTGAGAAACAAGCCCTCTAAGCAGAGCCAG

GGCCTGTTCGGAGCAATCGCAGGCTTTACCGAGGGAGGATGGACAGGCATGGTGGAT

GGCTGGTACGGCTATCACCACCAGAACGAGCAGGGATCCGGATATGCCGCCGACCTG

AAGTCTACCCAGAATGCCATCGACGAGATCACAAACAAGGTCAATTCTGTGATCGAG

AAGATGAACACCCAGAGGACAGCCATCGGCTGCGAGTACAATAAGAGCGAGAGGTGT

ATGAAGCAGATCGAGGACAAGATCGAGGAGATCGAGTCCAAGATCTGGTGCTATAAC

GCCGAGCTGCTGGTGCTGCTGGAGAATCAGAGGACCCTGGACTACCACGATAGCAAC

GTGAAGAATCTGTATGAGAAGGTGCGGTCCCAGCTGAAGAACAATGCCAAGGAGATC

GGCAACGGCTGTTTCGAGTTTTACCACAAGTGCGACAACACCTGTATGGAGTCCGTG

AAGAATGGCACATACGATTATCCCAAGTATTCTGAGGAGGCCAAGCTGAATCGGGAG

GAAATCGATGGCGTGAAGCTGGAGTCTACCCGCATCTACCAGATCCTGGCCATCTAT

AGCACAGTGGCCAGCTCCCTGGTGCTGGTGGTGTCCCTGGGGGCTATCTCTTTCTGG

ATGTGCTCAAATGGGTCCCTCCAGTGTCGCATCTGTATCTGATAA

SEQ ID NO 145: UFV171591 (UFV160665 + TM)
ATGAAGGCCATTCTGGTCGTGCTGCTGTACACTTTCGCCACCGCTAACGCTGACACC

CTGTGCATCGGGTACCACGCCAATAACTCCACCGACACAGTGGATACCGTGCTGGAG

AAGAACGTGACCGTGACACACTCTGTGAATCTGCTGGAGGACAAGAAGTACGTCTGC

AGCACCAAGCTGAGGCTGGCCACAGGCCTGAGAAACAAGCCCTCTAAGCAGAGCCAG

GGCCTGTTCGGAGCAATCGCAGGCTTTACCGAGGGAGGATGGACAGGCATGGTGGAT

GGCTGGTACGGCTATCACCACCAGAACGAGCAGGGATCCGGATATGCCGCCGACCTG

AAGTCTACCCAGAATGCCATCGACGAGATCACAAACAAGGTCAATTCTGTGATCGAG

AAGATGAACACCCAGCCTACAGCCATCGGCTGCGAGTACAATAAGAGCGAGAGGTGT

ATGAAGCAGATCGAGGACAAGATCGAGGAGATCGAGTCCAAGATCTGGTGCTATAAC

GCCGAGCTGCTGGTGCTGCTGGAGAATCAGAGGACCCTGGACTACCACGATAGCAAC

GTGAAGAATCTGTATGAGAAGGTGCGGTCCCAGCTGAAGAACAATGCCAAGGAGATC

GGCAACGGCTGTTTCGAGTTTTACCACAAGTGCGACAACACCTGTATGGAGTCCGTG

AAGAATGGCACATACGATTATCCCAAGTATTCTGAGGAGGCCAAGCTGAATCGGGAG

```
-continued
GAAATCGATGGCGTGAAGCTGGAGTCTACCCGCATCTACCAGATCCTGGCCATCTAT

AGCACAGTGGCCAGCTCCCTGGTGCTGGTGGTGTCCCTGGGGGCTATCTCTTTCTGG

ATGTGCTCAAATGGGTCCCTCCAGTGTCGCATCTGTATCTGATAA
```

SEQ ID NO: 146: MD3606 PROTEIN
EVQLVESGGGLVQPGGSLRLSCAVSISIFDIYAMDWYRQAPGKQRDLVATSFRDGST

NYADSVKGRFTISRDNAKNTLYLQMNSLKPEDTAVYLCHVSLYRDPLGVAGGMGVYW

GKGALVTVSSGGGGSGGGGSEVQLVESGGGLVQAGGSLKLSCAASGRTYAMGWFRQA

PGKEREFVAHINALGTRTYYSDSVKGRFTISRDNAKNTEYLEMNNLKPEDTAVYYCT

AQGQWRAAPVAVAAEYEFWGQGTQVTVSSGGGGSGGGGSEVQLVESGGGLVQPGGSL

RLSCAATGFTLENKAIGWFRQTPGSEREGVLCISKSGSWTYYTDSMRGRFTISRDNA

ENTVYLQMDSLKPEDTAVYYCATTTAGGGLCWDGTTFSRLASSWGQGTQVTVSSGGG

GSGGGGSEVQLVESGGGLVQPGGSLKLSCAASGFTFSTSWMYWLRQAPGKGLEWVSV

INTDGGTYYADSVKDRFTISRDNAKDTLYLQMSSLKSEDTAVYYCAKDWGGPEPTRG

QGTQVTVSSDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSN

KALPAPIEKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEALHNHYTQK

SLSLSPGK

SEQ ID NO: 147: UFV180496 H1 A/California/07/09
MKAILVVLLYTFATANADTLCIGYHANNSTDTVDTVLEKNVTVTHSVNLLEDKKYVC

STKLRLATGLRNKPSKQSQGLFGAIAGFTEGGWTGMVDGWYGYHHQNEQGSGYAADL

KSTQNAIDEITNKVNSVIEKMNTQRTAIGCEYNKSERCMKQIEDKIEEIESKIWCYN

AELLVLLENQRTLDYHDSNVKNLYEKVRSQLKNNAKEIGNGCFEFYHKCDNTCMESV

KNGTYDYPKYSEEAKLNREEIDGVKLESTRIYQIHHHHHH

SEQ ID NO: 148: UFV180497 H1 A/Michigan/45/2015
MKAILVVLLYTFTTANADTLCIGYHANNSTDTVDTVLEKNVTVTHSVNLLEDKKYVC

STKLRLATGLRNKPSKQSQGLFGAIAGFTEGGWTGMVDGWYGYHHQNEQGSGYAADL

KSTQNAIDKITNKVNSVIEKMNTQRTAIGCEYNKSEKCMKQIEDKIEEIESKIWCYN

AELLVLLENQRTLDYHDSNVKNLYEKVRNQLKNNAKEIGNGCFEFYHKCDNTCMESV

KNGTYDYPKYSEEAKLNREKIDGVKLESTRIYQIHHHHHH

SEQ ID NO: 149: UFV180498 H1 A/Puerto Rico/8/1934
MKANLLVLLCALAAADADTICIGYHANNSTDTVDTVLEKNVTVTHSVNLLEDSKYVC

SAKLRMVTGLRNKPSKQSQGLFGAIAGFTEGGWTGMIDGWYGYHHQNEQGSGYAADQ

KSTQNAINGITNKVNSVIEKMNIQRTAIGCEYNKSEKCMKQIEDKIEEIESKIWCYN

AELLVLLENQRTLDFHDSNVKNLYEKVKSQLKNNAKEIGNGCFEFYHKCDNECMESV

RNGTYDYPKYSEESKLNREKVDGVKLESMGIYQIHHHHHH

SEQ ID NO: 150: UFV180499 H5 A/Hong Kong/156/97
MEKTVLLLATVSLVKSDQICIGYHANNSTEQVDTIMEKNVTVTHAQDILERTKYVCS

NRLVLATGLRNKPQKESQGLFGAIAGFTEGGWQGMVDGWYGYHHSNEQGSGYAADKE

STQKAIDGVTNKVNSIINKMNTQREAIGCEYNKSERCMKQIEDKIEEIESKVWCYNA

ELLVLMENQRTLDFHDSNVKNLYDKVRLQLRDNAKELGNGCFEFYHKCDNECMESVK

NGTYDYPQYSEEARLNREEISGVKLESMGTYQIHHHHHH

-continued

SEQ ID NO: 151: UFV180500 H5 A/Vietnam/1203/04
MEKIVLLFAIVSLVKSDQICIGYHANNSTEQVDTIMEKNVTVTHAQDILEKKKYVCS

NRLVLATGLRNKPQKESQGLFGAIAGFTEGGWQGMVDGWYGYHHSNEQGSGYAADKE

STQKAIDGVTNKVNSIIDKMNTQREAIGCEYNKSERCMKQIEDKIEEIESKVWCYNA

ELLVLMENQRTLDFHDSNVKNLYDKVRLQLRDNAKELGNGCFEFYHKCDNECMESVR

NGTYDYPQYSEEARLKREEISGVKLESIGIYQIHHHHHH

SEQ ID NO: 152: UFV180501 H2 A/Singapore/1/57
MAIIYLILLFTAVRGDQICIGYHANNSTEKVDTILERNVTVTHAKDILEKTKYVCSE

KLVLATGLRNKPQKESQGLFGAIAGFTEGGWQGMVDGWYGYHHSNDQGSGYAADKES

TQKAFDGITNKVNSVIEKMNTQREAIGCEYSKSERCMKQIEDKIEEIESKVWCYNAE

LLVLMENQRTLDFHDSNVKNLYDKVRMQLRDNVKELGNGCFEFYHKCDDECMNSVKN

GTYDYPKYEEESKLNRNEIKGVKLSSMGVYQIHHHHHH

SEQ ID NO: 153: UFV171590 (UFV160664 + TM)
MKAILVVLLYTFATANADTLCIGYHANNSTDTVDTVLEKNVTVTHSVNLLEDKKYVC

STKLRLATGLRNKPSKQSQGLFGAIAGFTEGGWTGMVDGWYGYHHQNEQGSGYAADL

KSTQNAIDEITNKVNSVIEKMNTQRTAIGCEYNKSERCMKQIEDKIEEIESKIWCYN

AELLVLLENQRTLDYHDSNVKNLYEKVRSQLKNNAKEIGNGCFEFYHKCDNTCMESV

KNGTYDYPKYSEEAKLNREEIDGVKLESTRIYQILAIYSTVASSLVLVVSLGAISFW

MCSNGSLQCRICI

---

The invention claimed is:

1. A group 1 influenza A hemagglutinin (HA) stem polypeptide, comprising an HA1 and a HA2 domain, said HA stem polypeptide comprising an amino acid sequence comprising at least the amino acids 1-231 of SEQ ID NO: 103, 104, 109 or 110.

2. The polypeptide according to claim 1, wherein the amino acid sequence is selected from the group consisting of SEQ ID NOs: 103, 104, 109 and 110.

3. A nucleic acid encoding the polypeptide according to claim 1.

4. The nucleic acid according to claim 3, wherein said nucleic acid sequence comprises a sequence selected from SEQ ID NO: 138-145.

5. The nucleic acid according to claim 3, wherein said nucleic acid sequence comprises a sequence selected from the group consisting of SEQ ID NO: 142, SEQ ID NO: 143, SEQ ID NO: 144 and SEQ ID NO: 145.

6. A vector comprising the nucleic acid according to claim 3.

7. The vector according to claim 6, wherein the vector is a recombinant adenoviral vector.

8. A pharmaceutical composition comprising the vector according to claim 6 and a pharmaceutically acceptable carrier.

9. A pharmaceutical composition comprising the polypeptide according to claim 1 and a pharmaceutically acceptable carrier.

10. A pharmaceutical composition comprising the nucleic acid according to claim 3 and a pharmaceutically acceptable carrier.

11. A method of inducing an immune response against an influenza in a subject comprising administering the vector according to claim 6.

12. A method of inducing an immune response against an influenza in a subject comprising administering the polypeptide according to claim 1.

13. A method of inducing an immune response against an influenza in a subject comprising administering the nucleic acid according to claim 3.

14. A method of inducing an immune response against an influenza in a subject comprising administering the pharmaceutical composition according to claim 8.

15. A method of inducing an immune response against an influenza in a subject comprising administering the pharmaceutical composition according to claim 9.

16. A method of inducing an immune response against an influenza in a subject comprising administering the pharmaceutical composition according to claim 10.

* * * * *